(12) United States Patent
Wiener et al.

(10) Patent No.: US 12,329,437 B2
(45) Date of Patent: Jun. 17, 2025

(54) SURGICAL PROCEDURALIZATION VIA MODULAR ENERGY SYSTEM

(71) Applicant: Cilag GmbH International, Zug (CH)

(72) Inventors: Eitan T. Wiener, Loveland, OH (US); Brendan J. Oberkircher, Cincinnati, OH (US); Megan A. Broderick, Mason, OH (US); Ryan M. Asher, Cincinnati, OH (US); Leonardo N. Rossoni, Rahway, NJ (US); Amanda R. Stautberg, Cincinnati, OH (US); Jacob S. Childs, Huntington Beach, CA (US); Molly M F Petre, Cincinnati, OH (US); Lucas B. Elmer, Cincinnati, OH (US); Stephen M. Leuck, Milford, OH (US); Kristen G. Denzinger, Cincinnati, OH (US); James M. Vachon, West Chester, OH (US)

(73) Assignee: Cilag GmbH International, Zug (CH)

( * ) Notice: Subject to any disclaimer, the term of this patent is extended or adjusted under 35 U.S.C. 154(b) by 995 days.

(21) Appl. No.: 17/217,403

(22) Filed: Mar. 30, 2021

(65) Prior Publication Data
US 2022/0313341 A1 Oct. 6, 2022

(51) Int. Cl.
*A61B 18/12* (2006.01)
*A61B 18/14* (2006.01)
(Continued)

(52) U.S. Cl.
CPC .......... *A61B 18/1206* (2013.01); *A61B 18/14* (2013.01); *A61B 34/25* (2016.02);
(Continued)

(58) Field of Classification Search
CPC .............. A61B 34/25; A61B 2034/252; A61B 18/1206; A61B 18/14; A61B 2018/00178;
(Continued)

(56) References Cited

U.S. PATENT DOCUMENTS 4,171,700 A 10/1979 Farin
4,849,752 A 7/1989 Bryant
(Continued)

FOREIGN PATENT DOCUMENTS

EP 0408160 A1 1/1991
EP 0473987 A1 3/1992
(Continued)

OTHER PUBLICATIONS

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.
(Continued)

*Primary Examiner* — Mong-Shune Chung

(57) ABSTRACT

Systems, methods and devices for surgical procedurelization via a modular energy system are disclosed herein. In various aspects, the systems, methods and devices include an energy module, a header module communicably coupled to the energy module, and a display screen capable of rendering a graphical user interface (GUI). The GUI may be configured to display a plurality of steps that correspond with actions performed by a user while operating the modular energy system. In some aspects, the steps displayed are steps of a predetermined procedural checklist corresponding with a mental model followed by the user while performing a surgical procedure. In some aspects, the steps displayed are steps of an output verification process.

28 Claims, 64 Drawing Sheets

(51) Int. Cl.
   *A61B 34/00*   (2016.01)
   *A61B 18/00*   (2006.01)
   *A61B 90/00*   (2016.01)

(52) U.S. Cl.
   CPC ............... *A61B 2018/00178* (2013.01); *A61B 2018/00755* (2013.01); *A61B 2018/1253* (2013.01); *A61B 2018/126* (2013.01); *A61B 2034/252* (2016.02); *A61B 2034/254* (2016.02); *A61B 2034/256* (2016.02); *A61B 90/37* (2016.02); *A61B 2560/0443* (2013.01); *A61B 2560/0493* (2013.01)

(58) Field of Classification Search
   CPC .. A61B 2018/00755; A61B 2018/1253; A61B 2018/126; A61B 2560/0443; A61B 2560/0493; A61B 90/37
   See application file for complete search history.

(56) References Cited

U.S. PATENT DOCUMENTS

| | | |
|---|---|---|
| D303,787 S | 10/1989 | Messenger et al. |
| D327,061 S | 6/1992 | Soren et al. |
| 5,189,277 A | 2/1993 | Boisvert et al. |
| 5,204,669 A | 4/1993 | Dorfe et al. |
| 5,318,563 A | 6/1994 | Malis et al. |
| D379,346 S | 5/1997 | Mieki |
| 5,693,042 A | 12/1997 | Boiarski et al. |
| 5,724,468 A | 3/1998 | Leone et al. |
| 6,269,411 B1 | 7/2001 | Reasoner |
| 6,584,358 B2 | 6/2003 | Carter et al. |
| 6,611,793 B1 | 8/2003 | Burnside et al. |
| 6,731,514 B2 | 5/2004 | Evans |
| 6,913,471 B2 | 7/2005 | Smith |
| 7,009,511 B2 | 3/2006 | Mazar et al. |
| 7,044,949 B2 | 5/2006 | Orszulak et al. |
| 7,217,269 B2 | 5/2007 | El-Galley et al. |
| 7,252,664 B2 | 8/2007 | Nasab et al. |
| 7,344,532 B2 | 3/2008 | Goble et al. |
| 7,353,068 B2 | 4/2008 | Tanaka et al. |
| 7,408,439 B2 | 8/2008 | Wang et al. |
| D579,876 S | 11/2008 | Novotney et al. |
| D583,328 S | 12/2008 | Chiang |
| 7,496,418 B2 | 2/2009 | Kim et al. |
| D589,447 S | 3/2009 | Sasada et al. |
| 7,518,502 B2 | 4/2009 | Austin et al. |
| 7,563,259 B2 | 7/2009 | Takahashi |
| 7,637,907 B2 | 12/2009 | Blaha |
| 7,757,028 B2 | 7/2010 | Druke et al. |
| D631,252 S | 1/2011 | Leslie |
| 7,932,826 B2 | 4/2011 | Fritchie et al. |
| 7,945,065 B2 | 5/2011 | Menzl et al. |
| 7,945,342 B2 | 5/2011 | Tsai et al. |
| 7,982,776 B2 | 7/2011 | Dunki-Jacobs et al. |
| 7,995,045 B2 | 8/2011 | Dunki-Jacobs |
| 8,019,094 B2 | 9/2011 | Hsieh et al. |
| D655,678 S | 3/2012 | Kobayashi et al. |
| D657,368 S | 4/2012 | Magee et al. |
| 8,239,066 B2 | 8/2012 | Jennings et al. |
| D667,838 S | 9/2012 | Magee et al. |
| D675,164 S | 1/2013 | Kobayashi et al. |
| D676,392 S | 2/2013 | Gassauer |
| D678,196 S | 3/2013 | Miyauchi et al. |
| D678,304 S | 3/2013 | Yakoub et al. |
| 8,423,182 B2 | 4/2013 | Robinson et al. |
| D687,146 S | 7/2013 | Juzkiw et al. |
| 8,540,709 B2 | 9/2013 | Allen |
| 8,567,393 B2 | 10/2013 | Hickle et al. |
| D704,839 S | 5/2014 | Juzkiw et al. |
| 8,795,001 B1 | 8/2014 | Lam et al. |
| 8,819,581 B2 | 8/2014 | Nakamura et al. |
| D716,333 S | 10/2014 | Chotin et al. |
| 8,917,513 B1 | 12/2014 | Hazzard |
| 8,920,186 B2 | 12/2014 | Shishikura |
| 8,968,296 B2 | 3/2015 | McPherson |
| 8,986,288 B2 | 3/2015 | Konishi |
| D729,267 S | 5/2015 | Yoo et al. |
| 9,055,870 B2 | 6/2015 | Meador et al. |
| 9,160,853 B1 | 10/2015 | Daddi et al. |
| 9,168,054 B2 | 10/2015 | Turner et al. |
| 9,168,091 B2 | 10/2015 | Janssen et al. |
| 9,198,711 B2 | 12/2015 | Joseph |
| 9,226,766 B2 | 1/2016 | Aldridge et al. |
| 9,226,791 B2 | 1/2016 | McCarthy et al. |
| 9,237,921 B2 | 1/2016 | Messerly et al. |
| 9,265,429 B2 | 2/2016 | St. Pierre et al. |
| 9,277,961 B2 | 3/2016 | Panescu et al. |
| 9,277,969 B2 | 3/2016 | Brannan et al. |
| 9,320,646 B2 | 4/2016 | Todd et al. |
| 9,345,481 B2 | 5/2016 | Hall et al. |
| 9,345,900 B2 | 5/2016 | Wu et al. |
| 9,463,646 B2 | 10/2016 | Payne et al. |
| 9,474,565 B2 | 10/2016 | Shikhman et al. |
| D772,252 S | 11/2016 | Myers et al. |
| 9,486,271 B2 | 11/2016 | Dunning |
| 9,532,827 B2 | 1/2017 | Morgan et al. |
| 9,600,031 B2 | 3/2017 | Kaneko et al. |
| 9,603,277 B2 | 3/2017 | Morgan et al. |
| D783,675 S | 4/2017 | Yagisawa et al. |
| D784,270 S | 4/2017 | Bhattacharya |
| 9,713,503 B2 | 7/2017 | Goldschmidt |
| 9,750,563 B2 | 9/2017 | Shikhman et al. |
| 9,782,214 B2 | 10/2017 | Houser et al. |
| 9,867,670 B2 | 1/2018 | Brannan et al. |
| 9,907,196 B2 | 2/2018 | Susini et al. |
| 9,974,595 B2 | 5/2018 | Anderson et al. |
| 9,987,068 B2 | 6/2018 | Anderson et al. |
| 9,987,072 B2 | 6/2018 | McPherson |
| 10,028,402 B1 | 7/2018 | Walker |
| 10,039,589 B2 | 8/2018 | Virshek et al. |
| 10,098,527 B2 | 10/2018 | Weisenburgh et al. |
| 10,105,470 B2 | 10/2018 | Reasoner et al. |
| D834,541 S | 11/2018 | You et al. |
| 10,117,702 B2 | 11/2018 | Danziger et al. |
| 10,136,954 B2 | 11/2018 | Johnson et al. |
| 10,137,245 B2 | 11/2018 | Melker et al. |
| 10,147,148 B2 | 12/2018 | Wu et al. |
| 10,166,061 B2 | 1/2019 | Berry et al. |
| 10,170,205 B2 | 1/2019 | Curd et al. |
| 10,201,365 B2 | 2/2019 | Boudreaux et al. |
| 10,339,496 B2 | 7/2019 | Matson et al. |
| 10,357,184 B2 | 7/2019 | Crawford et al. |
| 10,386,990 B2 | 8/2019 | Shikhman et al. |
| 10,499,847 B2 | 12/2019 | Latimer et al. |
| 10,531,579 B2 | 1/2020 | Hsiao et al. |
| D876,466 S | 2/2020 | Kobayashi et al. |
| 10,561,753 B2 | 2/2020 | Thompson et al. |
| 10,602,007 B2 | 3/2020 | Takano |
| 10,624,667 B2 | 4/2020 | Faller et al. |
| 10,624,691 B2 | 4/2020 | Wiener et al. |
| 10,675,100 B2 | 6/2020 | Frushour |
| 10,687,884 B2 | 6/2020 | Wiener et al. |
| 10,743,872 B2 | 8/2020 | Leimbach et al. |
| 10,772,673 B2 | 9/2020 | Allen, IV et al. |
| 10,881,399 B2 | 1/2021 | Shelton, IV et al. |
| 10,898,256 B2 | 1/2021 | Yates et al. |
| 10,932,772 B2 | 3/2021 | Shelton, IV et al. |
| 10,950,982 B2 | 3/2021 | Regnier et al. |
| 10,987,176 B2 | 4/2021 | Poltaretskyi et al. |
| D924,139 S | 7/2021 | Jayme |
| D928,725 S | 8/2021 | Oberkircher et al. |
| D928,726 S | 8/2021 | Asher et al. |
| D939,545 S | 12/2021 | Oberkircher et al. |
| 11,857,252 B2 | 1/2024 | Geresy et al. |
| 11,950,860 B2 | 4/2024 | Morgan et al. |
| 11,963,727 B2 | 4/2024 | Morgan et al. |
| 11,968,776 B2 | 4/2024 | Jayme et al. |
| 11,969,216 B2 | 4/2024 | Shelton, IV et al. |
| 11,978,554 B2 | 5/2024 | Oberkircher et al. |
| 11,980,411 B2 | 5/2024 | Leuck et al. |
| 12,004,824 B2 | 6/2024 | Herman et al. |
| 12,040,749 B2 | 7/2024 | Samuel et al. |
| 2005/0165390 A1 | 7/2005 | Mauti et al. |

(56) References Cited

U.S. PATENT DOCUMENTS

| | | |
|---|---|---|
| 2005/0251233 A1 | 11/2005 | Kanzius |
| 2006/0136622 A1 | 6/2006 | Rouvelin et al. |
| 2006/0142657 A1* | 6/2006 | Quaid .................... A61B 90/37 |
| | | 600/424 |
| 2007/0282321 A1 | 12/2007 | Shah et al. |
| 2008/0129465 A1 | 6/2008 | Rao |
| 2009/0234352 A1 | 9/2009 | Behnke et al. |
| 2010/0069939 A1 | 3/2010 | Konishi |
| 2010/0120266 A1 | 5/2010 | Rimborg |
| 2010/0198200 A1 | 8/2010 | Horvath |
| 2011/0125149 A1 | 5/2011 | El-Galley et al. |
| 2011/0273465 A1 | 11/2011 | Konishi et al. |
| 2011/0306840 A1 | 12/2011 | Allen et al. |
| 2012/0179155 A1* | 7/2012 | Strul ................. A61B 18/1206 |
| | | 606/33 |
| 2013/0185093 A1* | 7/2013 | Wittliff, III ............ G16H 50/20 |
| | | 705/2 |
| 2013/0197510 A1* | 8/2013 | Heckel ............... A61B 18/1206 |
| | | 606/41 |
| 2013/0268283 A1 | 10/2013 | Vann et al. |
| 2014/0009894 A1 | 1/2014 | Yu |
| 2014/0226572 A1 | 8/2014 | Thota et al. |
| 2014/0263552 A1 | 9/2014 | Hall et al. |
| 2016/0287312 A1 | 10/2016 | Tegg et al. |
| 2017/0202595 A1 | 7/2017 | Shelton, IV |
| 2017/0296213 A1 | 10/2017 | Swensgard et al. |
| 2018/0042659 A1 | 2/2018 | Rupp et al. |
| 2018/0065248 A1 | 3/2018 | Barral et al. |
| 2018/0221005 A1 | 8/2018 | Hamel et al. |
| 2018/0250093 A1* | 9/2018 | Frushour ............... A61B 90/98 |
| 2018/0333207 A1 | 11/2018 | Moctezuma De La Barrera |
| 2019/0000478 A1 | 1/2019 | Messerly et al. |
| 2019/0183591 A1* | 6/2019 | Johnson ................. B25J 9/1666 |
| 2019/0201104 A1* | 7/2019 | Shelton, IV ........... A61B 90/98 |
| 2019/0224434 A1 | 7/2019 | Silver et al. |
| 2019/0278262 A1 | 9/2019 | Taylor et al. |
| 2019/0314088 A1* | 10/2019 | Kemper ................ A61B 34/10 |
| 2019/0380792 A1* | 12/2019 | Poltaretskyi ............ G06F 30/20 |
| 2020/0038120 A1 | 2/2020 | Ziraknejad et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0273575 A1* | 8/2020 | Wolf ..................... A61B 5/1032 |
| 2020/0305924 A1 | 10/2020 | Carroll |
| 2020/0305945 A1 | 10/2020 | Morgan et al. |
| 2020/0314569 A1 | 10/2020 | Morgan et al. |
| 2021/0212717 A1 | 7/2021 | Yates et al. |
| 2022/0313338 A1 | 10/2022 | Carroll et al. |
| 2022/0313369 A1 | 10/2022 | Oberkircher et al. |
| 2022/0313373 A1 | 10/2022 | Morgan et al. |
| 2022/0317750 A1 | 10/2022 | Jayme et al. |
| 2022/0317751 A1 | 10/2022 | Samuel et al. |
| 2022/0318179 A1 | 10/2022 | Morgan et al. |
| 2022/0319685 A1 | 10/2022 | Vachon et al. |
| 2024/0167895 A1* | 5/2024 | Greenhalgh ......... A61B 18/1815 |

FOREIGN PATENT DOCUMENTS

| | | | |
|---|---|---|---|
| EP | 0929263 B1 | 7/1999 | |
| EP | 2942023 A2 | 11/2015 | |
| GB | 2604920 A * | 9/2022 | ............. A61B 18/18 |
| JP | 2001029353 A | 2/2001 | |
| WO | WO-0112089 A1 | 2/2001 | |
| WO | WO-2008053485 A1 | 5/2008 | |
| WO | WO-2014031800 A1 | 2/2014 | |
| WO | WO-2014071184 A1 | 5/2014 | |
| WO | WO-2017058617 | 4/2017 | |
| WO | WO-2018116247 A1 | 6/2018 | |

OTHER PUBLICATIONS

IEEE Std 802.3-2012 (Revision of IEEE Std 802.3-2008, published Dec. 28, 2012.

"ATM-MPLS Network Interworking Version 2.0, af-aic-0178.001" ATM Standard, The ATM Forum Technical Committee, published Aug. 2003.

* cited by examiner

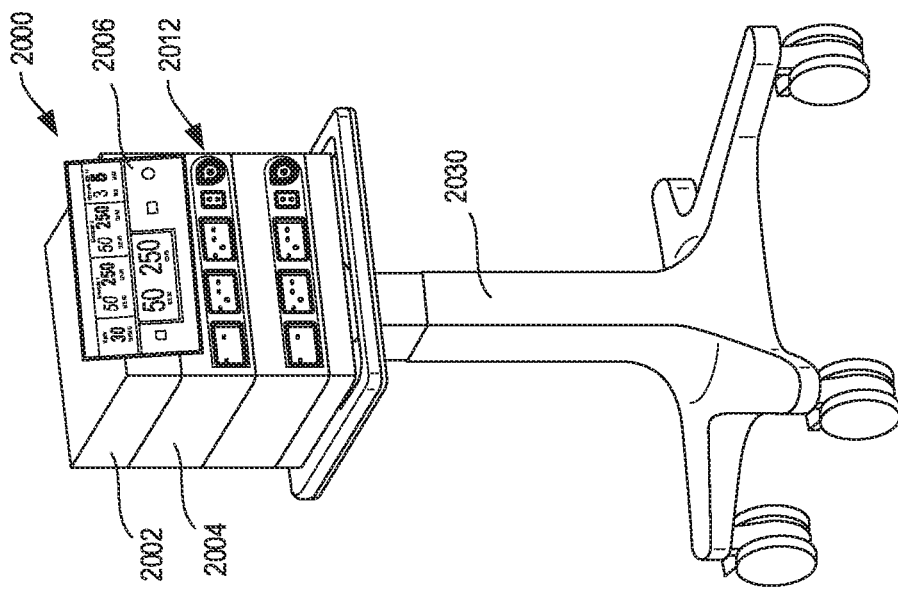
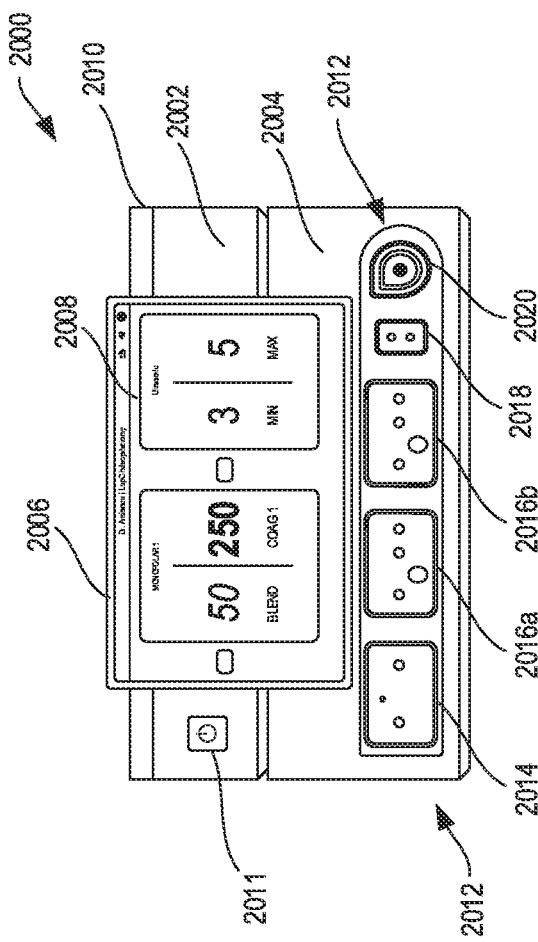
FIG. 7B
FIG. 7A

SURGICAL PROCEDURALIZATION VIA MODULAR ENERGY SYSTEM

BACKGROUND

The present disclosure relates to various surgical systems, including modular electrosurgical and/or ultrasonic surgical systems. Operating rooms (ORs) are in need of streamlined capital solutions because ORs are a tangled web of cords, devices, and people due to the number of different devices that are needed to complete each surgical procedure. This is a reality of every OR in every market throughout the globe. Capital equipment is a major offender in creating clutter within ORs because most capital equipment performs one task or job, and each type of capital equipment requires unique techniques or methods to use and has a unique user interface. Accordingly, there are unmet consumer needs for capital equipment and other surgical technology to be consolidated in order to decrease the equipment footprint within the OR, streamline the equipment's interfaces, and improve surgical staff efficiency during a surgical procedure by reducing the number of devices that surgical staff members need to interact with.

SUMMARY

In various aspects, a modular energy system for use in a surgical environment is disclosed. The system comprises: an energy module configured to generate at least one energy modality for driving an electrosurgical and/or ultrasonic surgical instrument connected thereto; a header module communicably coupled to the energy module, the header module comprising a display screen capable of rendering a graphical user interface (GUI); wherein the GUI is configured to display a plurality of steps that correspond with actions performed by a user while operating the modular energy system.

In various aspects a modular energy system for use in a surgical environment is disclosed. The system comprises: an energy module configured to generate at least one energy modality for driving an electrosurgical and/or ultrasonic surgical instrument connected thereto; a header module communicably coupled to the energy module, the header module comprising a display screen capable of rendering a GUI; a storage device configured to record event data related to operation of the energy module; wherein the modular energy system is able to detect which events of the event data are related to a surgical procedure based on a detection of a predetermined series of events; and wherein the event data is organized in an event log based on the detection of events related to the surgical procedure.

In various aspects, an output verification key device is disclosed. The device comprises: a first side comprising: a neutral electrode plug that connects to a neutral electrode port of the energy module: an advanced energy plug that connects to an advanced energy port of the energy module; and a second side comprising: a neutral key port that accepts a lead of an electrical surgical unit analyzer to create a connection with the neutral electrode port; a monopolar key port that accepts a lead of an electrical surgical unit analyzer to create a connection with a monopolar energy modality of the advanced energy port; a bipolar key port that accepts a lead of an electrical surgical unit analyzer to create a connection with a bipolar energy modality of the advanced energy port; and an ultrasonic key port that accepts a lead of an electrical surgical unit analyzer to create a connection with an ultrasonic energy modality of the advanced energy port.

FIGURES

The various aspects described herein, both as to organization and methods of operation, together with further objects and advantages thereof, may best be understood by reference to the following description, taken in conjunction with the accompanying drawings as follows.

FIG. 7A is a first illustrative modular energy system configuration including a header module and a display screen that renders a graphical user interface (GUI) for relaying information regarding modules connected to the header module, in accordance with at least one aspect of the present disclosure.

FIG. 7B is the modular energy system shown in FIG. 7A mounted to a cart, in accordance with at least one aspect of the present disclosure.

FIG. 47 is an illustrative graphical user interface utilities second bipolar test mode screen, in accordance with at least one aspect of the present disclosure.

FIG. 48 is an illustrative graphical user interface final bipolar test mode screen, in accordance with at least one aspect of the present disclosure.

Figure 90:
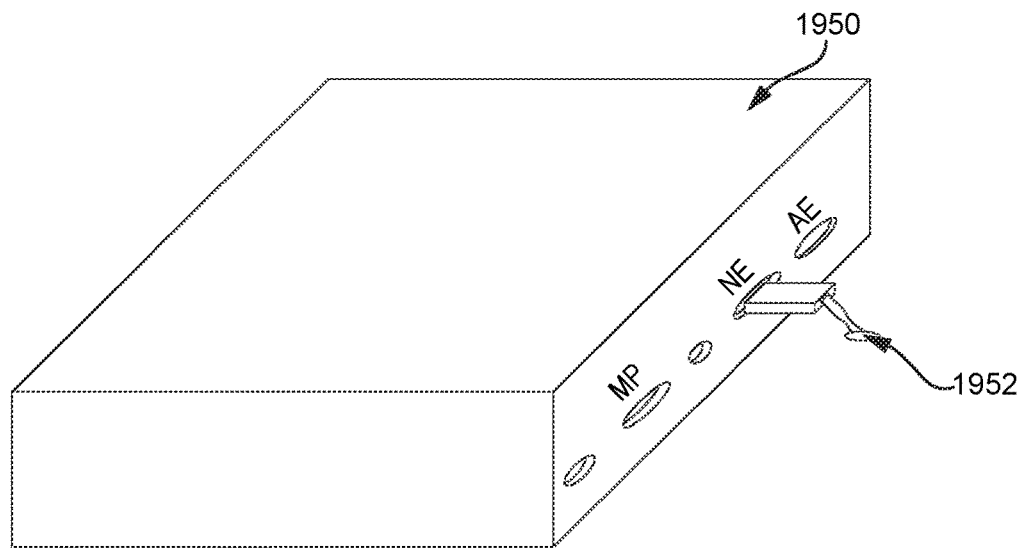

FIG. 90 a perspective view of an electrosurgical generator with a makeshift electrosurgical unit (ESU) analyzer connection, in accordance with at least one aspect of the present disclosure.

Figure 91:
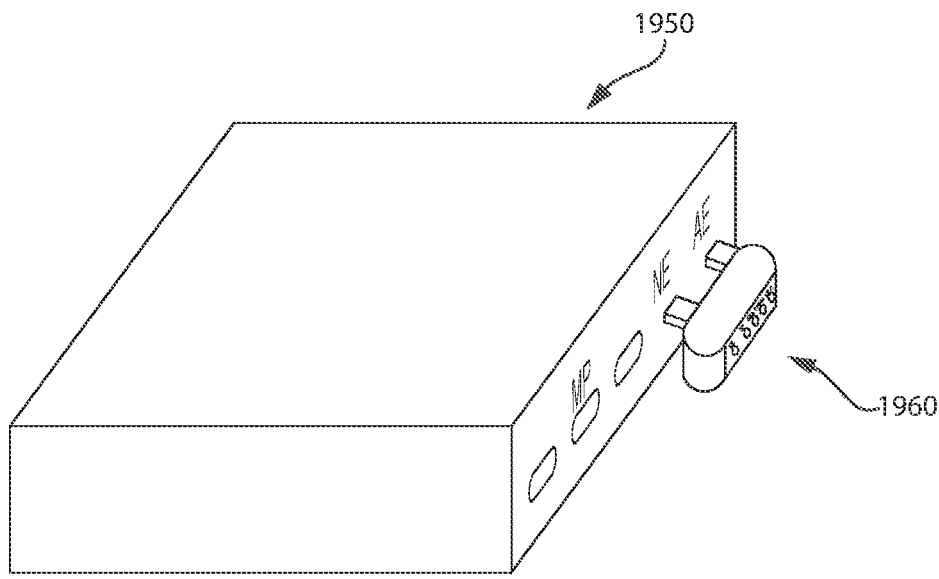

FIG. 91 is a perspective view of an electrosurgical generator connected to an output verification key, in accordance with at least one aspect of the present disclosure.

Figure 92:
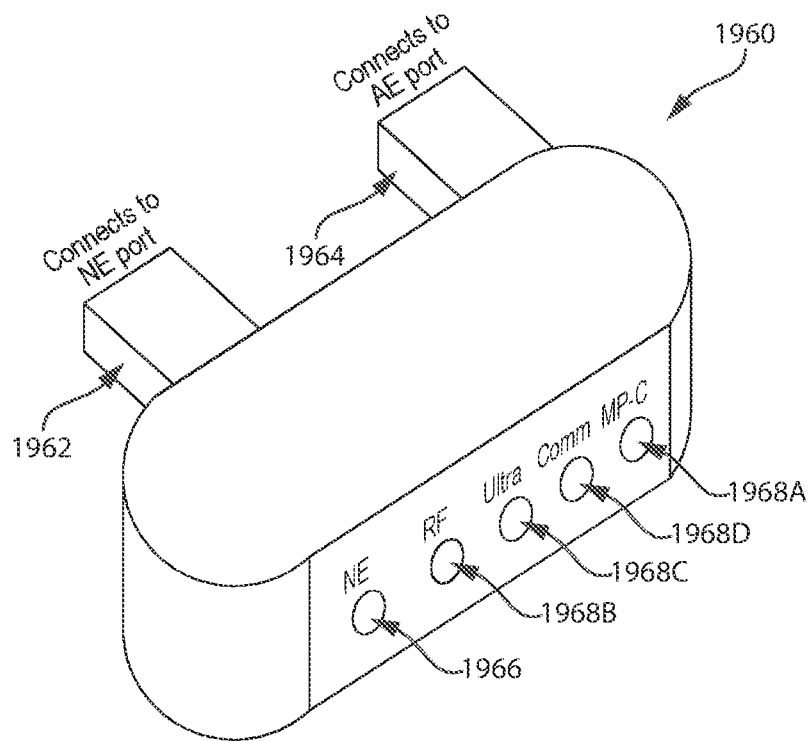

FIG. 92 is a perspective view of an illustrative output verification key, in accordance with at least one aspect of the present disclosure.

Figure 93:
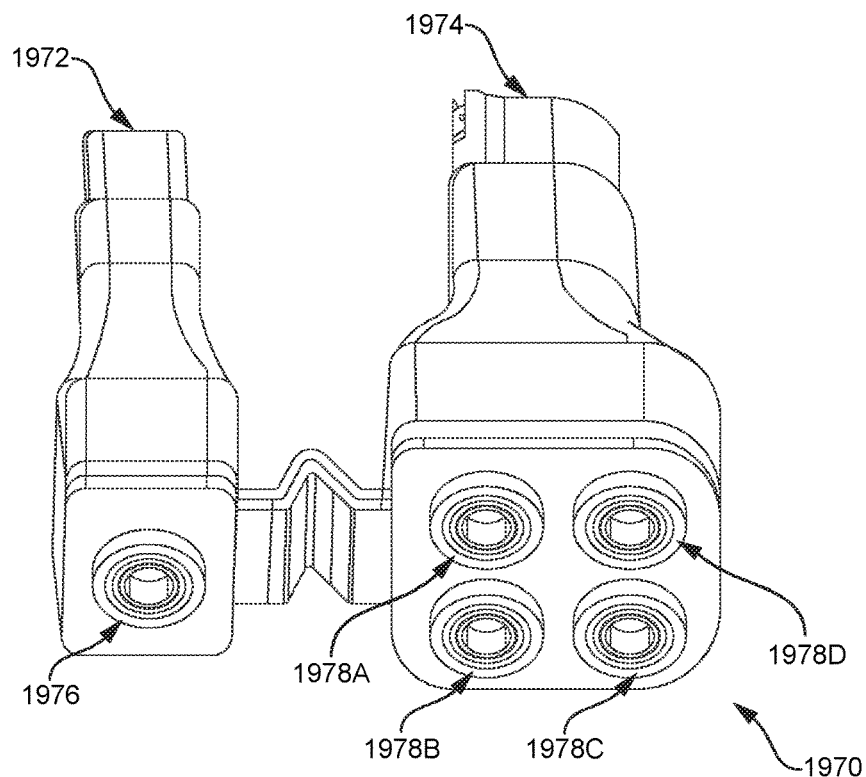

FIG. 93 is a perspective view of an alternative illustrative output verification key, in accordance with at least one aspect of the present disclosure.

Figure 94:
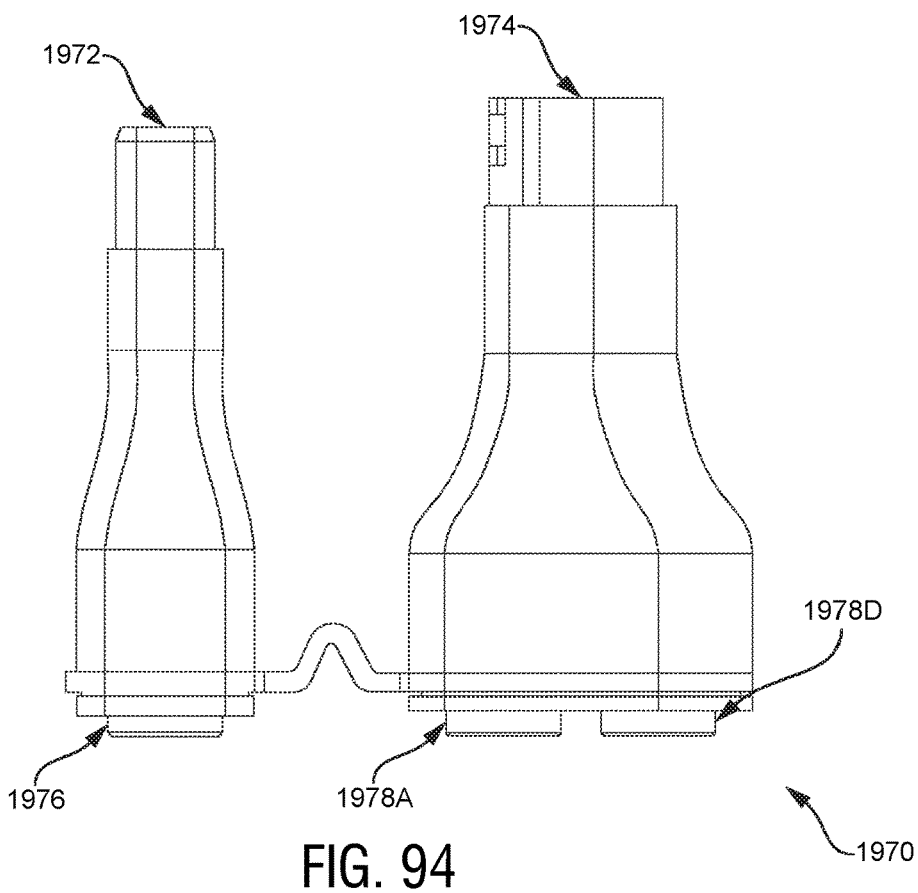

FIG. 94 is a top view of the output verification key shown in FIG. 93, in accordance with at least one aspect of the present disclosure.

Figure 95:
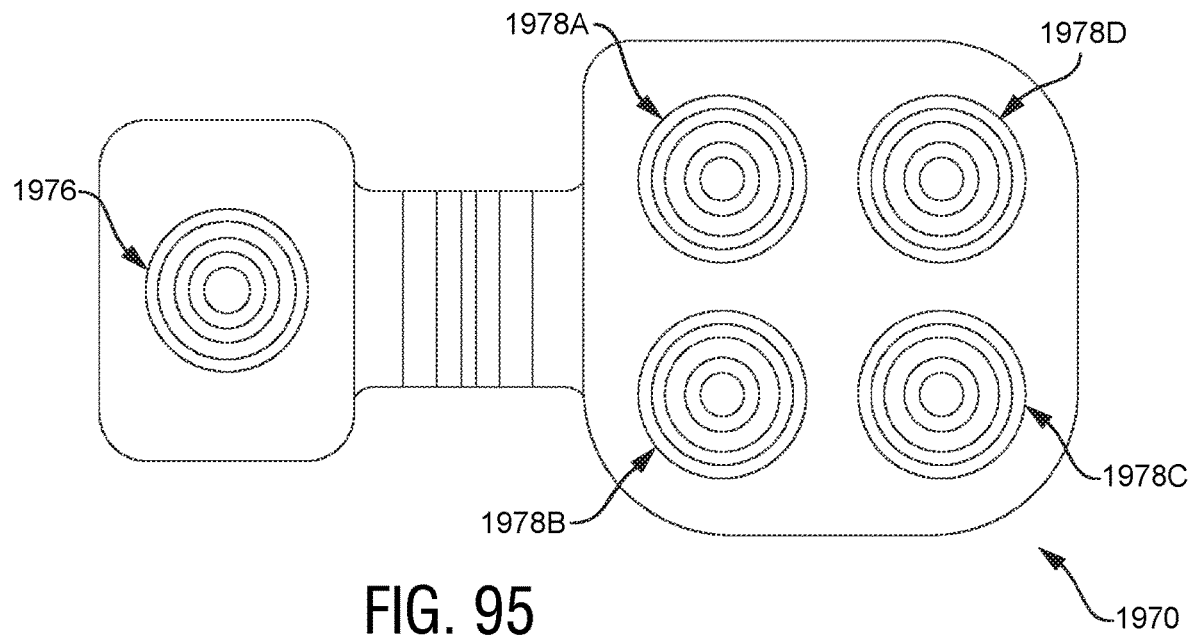

FIG. 95 is a front view of the output verification key shown in FIG. 93, in accordance with at least one aspect of the present disclosure.

Figure 96:
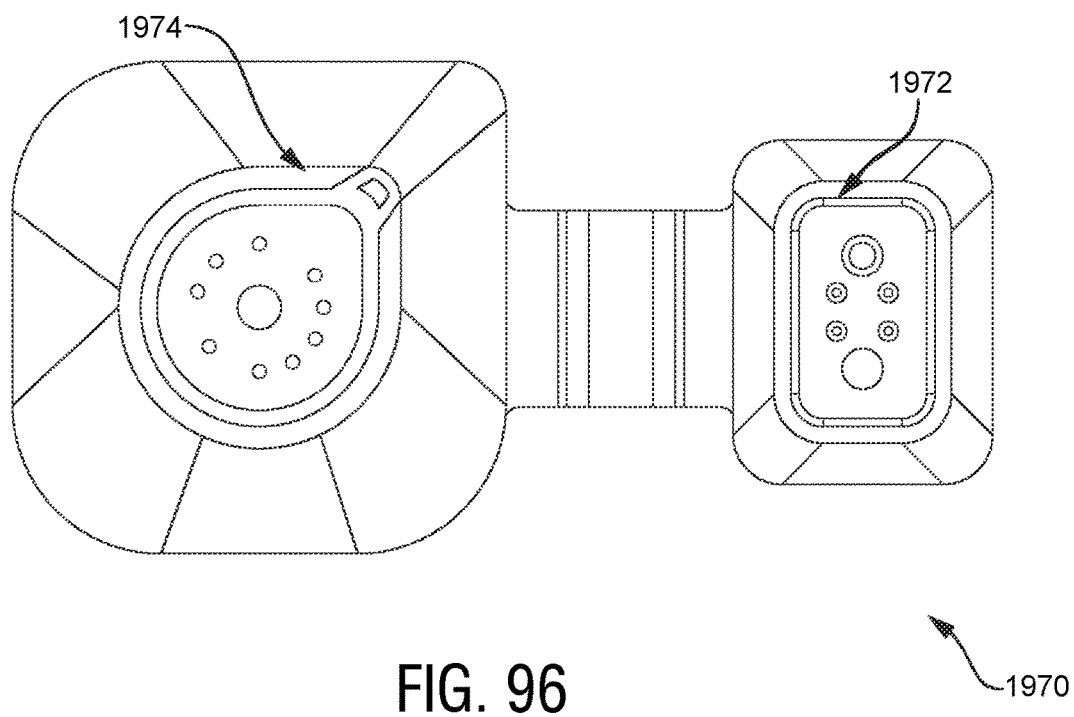

FIG. 96 is a back view of the output verification key shown in FIG. 93, in accordance with at least one aspect of the present disclosure.

Figure 97:
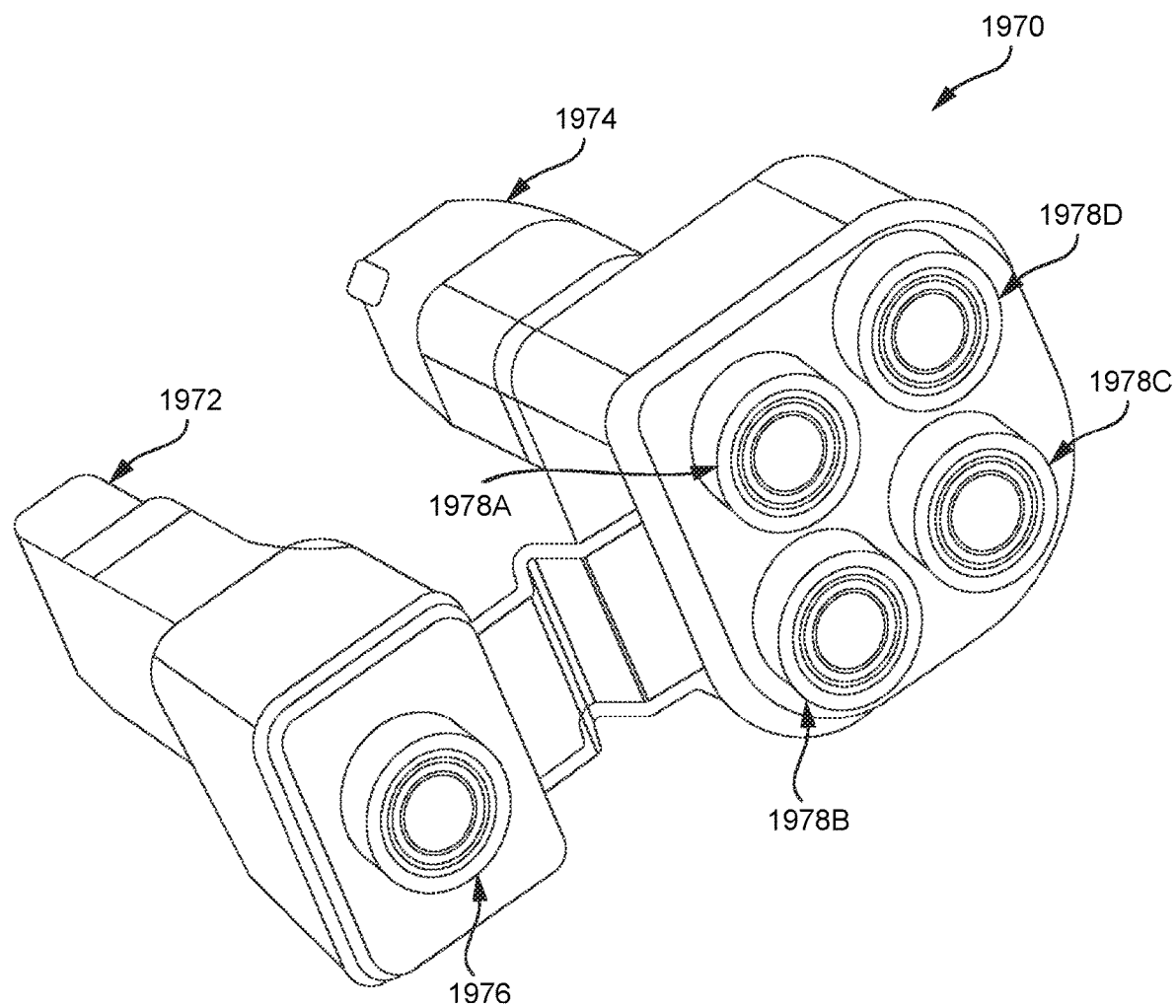

FIG. 97 is an alternate perspective view of the output verification key shown in FIG. 93, in accordance with at least one aspect of the present disclosure.

Corresponding reference characters indicate corresponding parts throughout the several views. The exemplifications set out herein illustrate various disclosed aspects, in one form, and such exemplifications are not to be construed as limiting the scope thereof in any manner.

DESCRIPTION

Applicant of the present application owns the following U.S. Patent Applications filed Mar. 30, 2021, the disclosure of each of which is herein incorporated by reference in its entirety:

U.S. patent application Ser. No. 17/217,394, titled METHOD FOR MECHANICAL PACKAGING FOR MODULAR ENERGY SYSTEM, now U.S. Pat. No. 11,968,776;

U.S. patent application Ser. No. 17/217,402, titled BACKPLANE CONNECTOR ATTACHMENT MECHANISM FOR MODULAR ENERGY SYSTEM, now U.S. Patent Application Publication No. 2022/0317750;

U.S. patent application Ser. No. 17/217,436, titled BEZEL WITH LIGHT BLOCKING FEATURES FOR MODULAR ENERGY SYSTEM, now U.S. Pat. No. 11,857,252;

U.S. patent application Ser. No. 17/217,446, titled HEADER FOR MODULAR ENERGY SYSTEM, now U.S. Pat. No. 11,980,411;

U.S. patent application Ser. No. 17/217,424, titled METHOD FOR ENERGY DELIVERY FOR MODULAR ENERGY SYSTEM, now U.S. Patent Application Publication No. 2022/0317751;

U.S. patent application Ser. No. 17/217,439, titled MODULAR ENERGY SYSTEM WITH DUAL AMPLIFIERS AND TECHNIQUES FOR UPDATING PARAMETERS THEREOF, now U.S. Pat. No. 12,040,749;

U.S. patent application Ser. No. 17/217,471, titled MODULAR ENERGY SYSTEM WITH MULTI-ENERGY PORT SPLITTER FOR MULTIPLE ENERGY DEVICES, now U.S. Patent Application Publication No. 2022/0313373;

U.S. patent application Ser. No. 17/217,385, titled METHOD FOR INTELLIGENT INSTRUMENTS FOR MODULAR ENERGY SYSTEM, now U.S. Patent Application Publication No. 2022/0313369;

U.S. patent application Ser. No. 17/217,392, titled RADIO FREQUENCY IDENTIFICATION TOKEN FOR WIRELESS SURGICAL INSTRUMENTS, now U.S. Pat. No. 11,978,554;

U.S. patent application Ser. No. 17/217,397, titled INTELLIGENT DATA PORTS FOR MODULAR ENERGY SYSTEMS, now U.S. Patent Application Publication No. 2022/0318179;

U.S. patent application Ser. No. 17/217,405, titled METHOD FOR SYSTEM ARCHITECTURE FOR MODULAR ENERGY SYSTEM, now U.S. Pat. No. 11,963,727;

U.S. patent application Ser. No. 17/217,423, titled USER INTERFACE MITIGATION TECHNIQUES FOR MODULAR ENERGY SYSTEMS, now U.S. Pat. No. 11,950,860;

U.S. patent application Ser. No. 17/217,429, titled ENERGY DELIVERY MITIGATIONS FOR MODULAR ENERGY SYSTEMS, now U.S. Patent Application Publication No. 2022/0313338;

U.S. patent application Ser. No. 17/217,449, titled ARCHITECTURE FOR MODULAR ENERGY SYSTEM, now U.S. Pat. No. 12,004,824; and.

U.S. patent application Ser. No. 17/217,461, titled MODULAR ENERGY SYSTEM WITH HARDWARE MITIGATED COMMUNICATION, now U.S. Patent Application Publication No. 2022/0319685.

Applicant of the present application owns the following U.S. patent applications filed Sep. 5, 2019, the disclosure of each of which is herein incorporated by reference in its entirety:

U.S. patent application Ser. No. 16/562,144, titled METHOD FOR CONTROLLING A MODULAR ENERGY SYSTEM USER INTERFACE, now U.S. Patent Application Publication No. 2020/0078106;

U.S. patent application Ser. No. 16/562,151, titled PASSIVE HEADER MODULE FOR A MODULAR ENERGY SYSTEM, now U.S. Patent Application Publication No. 2020/0078110;

U.S. patent application Ser. No. 16/562,157, titled CONSOLIDATED USER INTERFACE FOR MODULAR ENERGY SYSTEM, now U.S. Patent Application Publication No. 2020/0081585;

U.S. patent application Ser. No. 16/562,159, titled AUDIO TONE CONSTRUCTION FOR AN ENERGY MODULE OF A MODULAR ENERGY SYSTEM, now U.S. Patent Application Publication No. 2020/0314569;

U.S. patent application Ser. No. 16/562,163, titled ADAPTABLY CONNECTABLE AND REASSIGNABLE SYSTEM ACCESSORIES FOR MODULAR ENERGY SYSTEM, now U.S. Patent Application Publication No. 2020/0078111;

U.S. patent application Ser. No. 16/562,123, titled METHOD FOR CONSTRUCTING AND USING A MODULAR SURGICAL ENERGY SYSTEM WITH MULTIPLE DEVICES, now U.S. Patent Application Publication No. 2020/0100830;

U.S. patent application Ser. No. 16/562,135, titled METHOD FOR CONTROLLING AN ENERGY MODULE OUTPUT, now U.S. Patent Application Publication No. 2020/0078076;

U.S. patent application Ser. No. 16/562,180, titled ENERGY MODULE FOR DRIVING MULTIPLE ENERGY MODALITIES, now U.S. Patent Application Publication No. 2020/0078080;

U.S. patent application Ser. No. 16/562,184, titled GROUNDING ARRANGEMENT OF ENERGY MODULES, now U.S. Patent Application Publication No. 2020/0078081;

U.S. patent application Ser. No. 16/562,188, titled BACKPLANE CONNECTOR DESIGN TO CONNECT STACKED ENERGY MODULES, now U.S. Patent Application Publication No. 2020/0078116;

U.S. patent application Ser. No. 16/562,195, titled ENERGY MODULE FOR DRIVING MULTIPLE ENERGY MODALITIES THROUGH A PORT, now U.S. Patent Application Publication No. 2020/0078117;

U.S. patent application Ser. No. 16/562,202 titled SURGICAL INSTRUMENT UTILIZING DRIVE SIGNAL TO POWER SECONDARY FUNCTION, now U.S. Patent Application Publication No. 2020/0078082;

U.S. patent application Ser. No. 16/562,142, titled METHOD FOR ENERGY DISTRIBUTION IN A SURGICAL MODULAR ENERGY SYSTEM, now U.S. Patent Application Publication No. 2020/0078070;

U.S. patent application Ser. No. 16/562,169, titled SURGICAL MODULAR ENERGY SYSTEM WITH A SEGMENTED BACKPLANE, now U.S. Patent Application Publication No. 2020/0078112;

U.S. patent application Ser. No. 16/562,185, titled SURGICAL MODULAR ENERGY SYSTEM WITH FOOTER MODULE, now U.S. Patent Application Publication No. 2020/0078115;

U.S. patent application Ser. No. 16/562,203, titled POWER AND COMMUNICATION MITIGATION ARRANGEMENT FOR MODULAR SURGICAL ENERGY SYSTEM, now U.S. Patent Application Publication No. 2020/0078118;

U.S. patent application Ser. No. 16/562,212, titled MODULAR SURGICAL ENERGY SYSTEM WITH MODULE POSITIONAL AWARENESS SENSING WITH VOLTAGE DETECTION, now U.S. Patent Application Publication No. 2020/0078119;

U.S. patent application Ser. No. 16/562,234, titled MODULAR SURGICAL ENERGY SYSTEM WITH MODULE POSITIONAL AWARENESS SENSING WITH TIME COUNTER, now U.S. Patent Application Publication No. 2020/0305945;

U.S. patent application Ser. No. 16/562,243, titled MODULAR SURGICAL ENERGY SYSTEM WITH MODULE POSITIONAL AWARENESS WITH DIGITAL LOGIC, now U.S. Patent Application Publication No. 2020/0078120;

U.S. patent application Ser. No. 16/562,125, titled METHOD FOR COMMUNICATING BETWEEN MODULES AND DEVICES IN A MODULAR SURGICAL SYSTEM, now U.S. Patent Application Publication No. 2020/0100825;

U.S. patent application Ser. No. 16/562,137, titled FLEXIBLE HAND-SWITCH CIRCUIT, now U.S. Patent Application Publication No. 2020/0106220;

U.S. patent application Ser. No. 16/562,143, titled FIRST AND SECOND COMMUNICATION PROTOCOL ARRANGEMENT FOR DRIVING PRIMARY AND SECONDARY DEVICES THROUGH A SINGLE PORT, now U.S. Patent Application Publication No. 2020/0090808;

U.S. patent application Ser. No. 16/562,148, titled FLEXIBLE NEUTRAL ELECTRODE, now U.S. Patent Application Publication No. 2020/0078077;

U.S. patent application Ser. No. 16/562,154, titled SMART RETURN PAD SENSING THROUGH MODULATION OF NEAR FIELD COMMUNICATION AND CONTACT QUALITY MONITORING SIGNALS, now U.S. Patent Application Publication No. 2020/0078089;

U.S. patent application Ser. No. 16/562,162, titled AUTOMATIC ULTRASONIC ENERGY ACTIVATION CIRCUIT DESIGN FOR MODULAR SURGICAL SYSTEMS, now U.S. Patent Application Publication No. 2020/0305924;

U.S. patent application Ser. No. 16/562,167, titled COORDINATED ENERGY OUTPUTS OF SEPARATE BUT CONNECTED MODULES, now U.S. Patent Application Publication No. 2020/0078078;

U.S. patent application Ser. No. 16/562,170, titled MANAGING SIMULTANEOUS MONOPOLAR OUTPUTS USING DUTY CYCLE AND SYNCHRONIZATION, now U.S. Patent Application Publication No. 2020/0078079;

U.S. patent application Ser. No. 16/562,172, titled PORT PRESENCE DETECTION SYSTEM FOR MODULAR ENERGY SYSTEM, now U.S. Patent Application Publication No. 2020/0078113;

U.S. patent application Ser. No. 16/562,175, titled INSTRUMENT TRACKING ARRANGEMENT BASED ON REAL TIME CLOCK INFORMATION, now U.S. Patent Application Publication No. 2020/0078071;

U.S. patent application Ser. No. 16/562,177, titled REGIONAL LOCATION TRACKING OF COMPONENTS OF A MODULAR ENERGY SYSTEM, now U.S. Patent Application Publication No. 2020/0078114;

U.S. Design patent application Ser. No. 29/704,610, titled ENERGY MODULE;

U.S. Design patent application Ser. No. 29/704,614, titled ENERGY MODULE MONOPOLAR PORT WITH FOURTH SOCKET AMONG THREE OTHER SOCKETS;

U.S. Design patent application Ser. No. 29/704,616, titled BACKPLANE CONNECTOR FOR ENERGY MODULE; and U.S. Design patent application Ser. No. 29/704,617, titled ALERT SCREEN FOR ENERGY MODULE.

Applicant of the present application owns the following U.S. Patent Provisional Applications filed Mar. 29, 2019, the disclosure of each of which is herein incorporated by reference in its entirety:

U.S. Provisional Patent Application Ser. No. 62/826,584, titled MODULAR SURGICAL PLATFORM ELECTRICAL ARCHITECTURE;

U.S. Provisional Patent Application Ser. No. 62/826,587, titled MODULAR ENERGY SYSTEM CONNECTIVITY;

U.S. Provisional Patent Application Ser. No. 62/826,588, titled MODULAR ENERGY SYSTEM INSTRUMENT COMMUNICATION TECHNIQUES; and U.S. Provisional Patent Application Ser. No. 62/826,592, titled MODULAR ENERGY DELIVERY SYSTEM.

Applicant of the present application owns the following U.S. Patent Provisional Application filed Sep. 7, 2018, the disclosure of which is herein incorporated by reference in its entirety:

U.S. Provisional Patent Application Ser. No. 62/728,480, titled MODULAR ENERGY SYSTEM AND USER INTERFACE.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Various aspects are directed to improved ultrasonic surgical devices, electrosurgical devices and generators for use therewith. Aspects of the ultrasonic surgical devices can be configured for transecting and/or coagulating tissue during surgical procedures, for example. Aspects of the electrosurgical devices can be configured for transecting, coagulating, scaling, welding and/or desiccating tissue during surgical procedures, for example.

Surgical System Hardware

Figure 1:
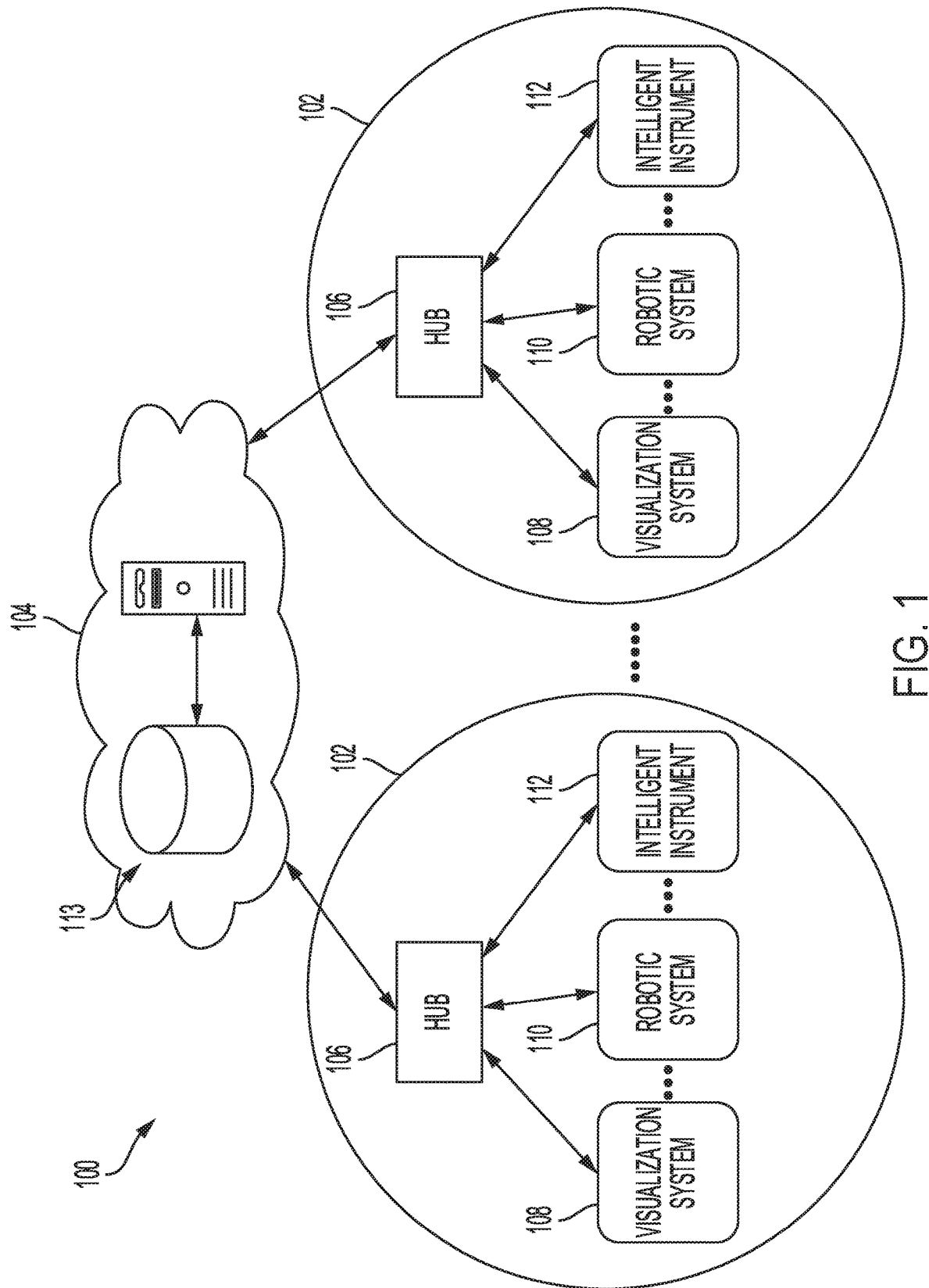
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
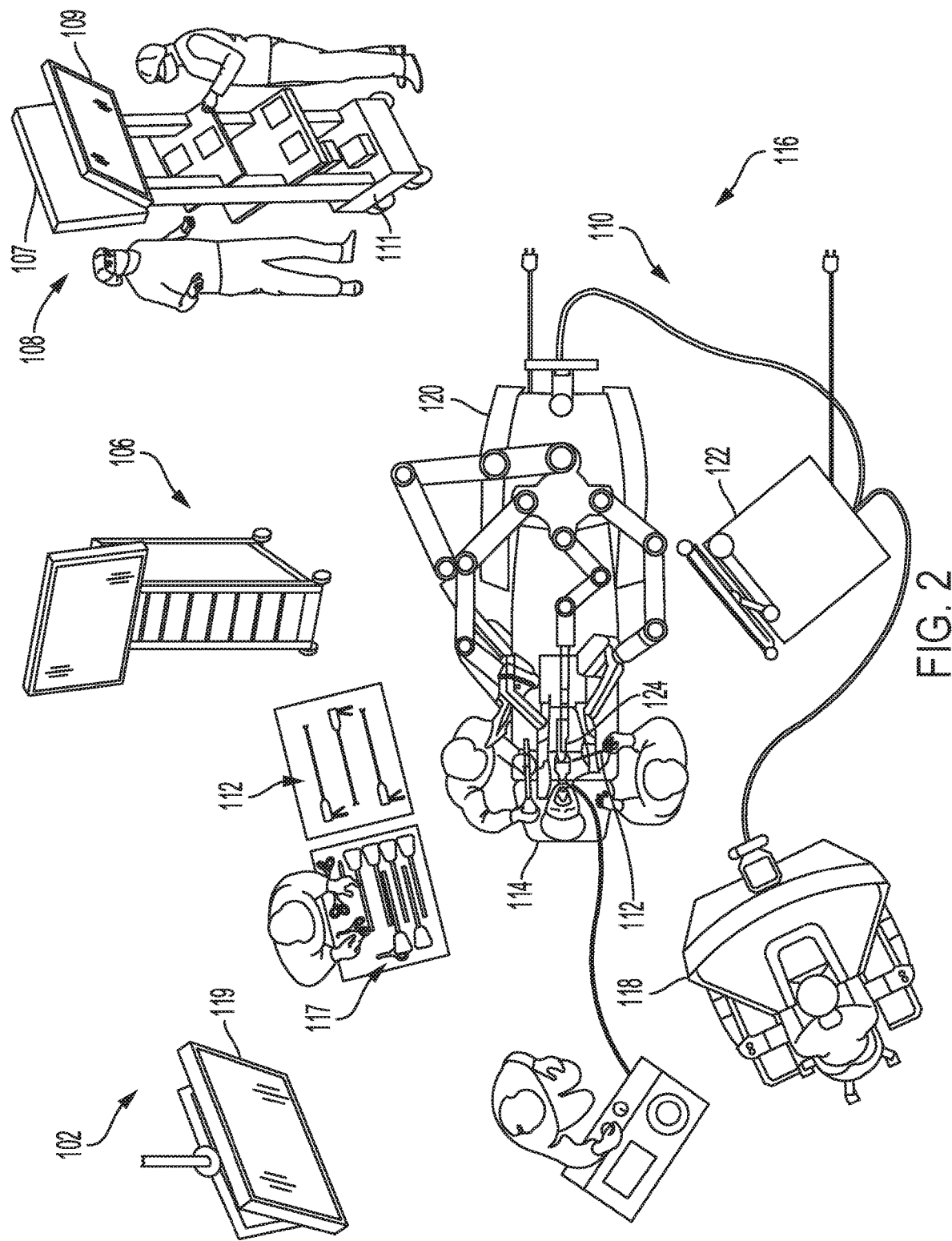
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading SURGICAL INSTRUMENT HARDWARE and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
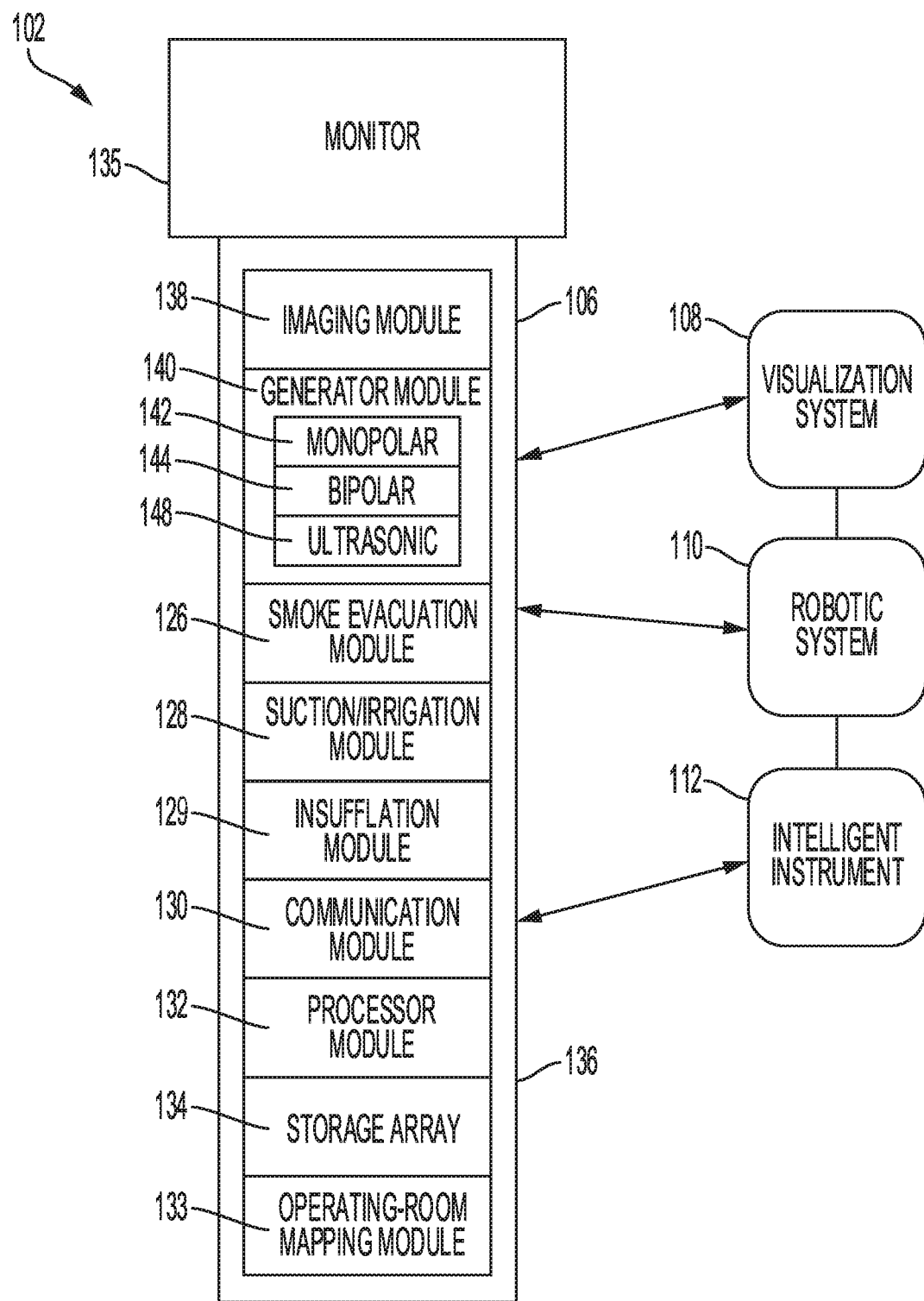
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. In some aspects, the visualization system 108 may be a separable piece of equipment. In alternative aspects, the visualization system 108 could be contained within the hub 106 as a functional module. The hub 106 includes a hub display 135, an imaging module 138, a generator module 140, a communication module 130, a processor module 132, a storage array 134, and an operating room mapping module 133. In certain aspects, as illustrated in FIG. 3, the hub 106 further includes a smoke evacuation module 126, a suction/irrigation module 128, and/or an insufflation module 129. In certain aspects, any of the modules in the hub 106 may be combined with each other into a single module.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes one or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts. In one aspect, the first energy-generator module is slidably movable into an electrical engagement with the power and data contacts and wherein the first energy-generator module is slidably movable out of the electrical engagement with the first power and data contacts. In an alternative aspect, the first energy-generator module is stackably movable into an electrical engagement with the power and data contacts and wherein the first energy-generator module is stackably movable out of the electrical engagement with the first power and data contacts.

Further to the above, the modular surgical enclosure also includes a second energy-generator module configured to generate a second energy, either the same or different than the first energy, for application to the tissue, and a second docking station comprising a second docking port that includes second data and power contacts. In one aspect, the second energy-generator module is slidably movable into an electrical engagement with the power and data contacts, and wherein the second energy-generator module is slidably movable out of the electrical engagement with the second power and data contacts. In an alternative aspect, the second energy-generator module is stackably movable into an electrical engagement with the power and data contacts, and wherein the second energy-generator module is stackably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, a suction/irrigation module 128, and an insufflation module 129. The hub modular enclosure 136 further facilitates interactive communication between the modules 140, 126, 128, 129. The generator module 140 can be a generator module with integrated monopolar, bipolar, and ultrasonic components supported in a single housing unit slidably insertable into the hub modular enclosure 136. The generator module 140 can be configured to connect to a monopolar device 142, a bipolar device 144, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128, 129 and interactive communication therebetween.

Generator Hardware

As used throughout this description, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some aspects they might not. The communication module may implement any of a number of wireless or wired communication standards or protocols, including but not limited to Wi-Fi (IEEE 802.11 family), WiMAX (IEEE 802.16 family), IEEE 802.20, long term evolution (LTE), Ev-DO, HSPA+, HSDPA+, HSUPA+, EDGE, GSM, GPRS, CDMA, TDMA, DECT, Bluetooth, Ethernet derivatives thereof, as well as any other wireless and wired protocols that are designated as 3G, 4G, 5G, and beyond. The computing module may include a plurality of communication modules. For instance, a first communication module may be dedicated to shorter range wireless communications such as Wi-Fi and Bluetooth and a second communication module may be dedicated to longer range wireless communications such as GPS, EDGE, GPRS, CDMA, WiMAX, LTE, Ev-DO, and others.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (SoC or SOC) is an integrated circuit (also known as an "IC" or "chip") that integrates all components of a computer or other electronic systems. It may contain digital, analog, mixed-signal, and often radio-frequency functions—all on a single substrate. A SoC integrates a microcontroller (or microprocessor) with advanced peripherals like graphics processing unit (GPU), Wi-Fi module, or coprocessor. A SoC may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a SoC; a SoC may include a microcontroller as one of its components. A microcontroller may contain one or more core processing units (CPUs) along with memory and programmable input/output peripherals. Program memory in the form of Ferro-electric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

Modular devices include the modules (as described in connection with FIG. 3, for example) that are receivable within a surgical hub and the surgical devices or instruments that can be connected to the various modules in order to connect or pair with the corresponding surgical hub. The modular devices include, for example, intelligent surgical instruments, medical imaging devices, suction/irrigation devices, smoke evacuators, energy generators, ventilators, insufflators, and displays. The modular devices described herein can be controlled by control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the devices based on data sensed by the modular device itself (i.e., by sensors in, on, or connected to the modular device). This data can be related to the patient being operated on (e.g., tissue properties or insufflation pressure) or the modular device itself (e.g., the rate at which a knife is being advanced, motor current, or energy levels). For example, a control algorithm for a surgical stapling and cutting instrument can control the rate at which the instrument's motor drives its knife through tissue according to resistance encountered by the knife as it advances.

Figure 4:
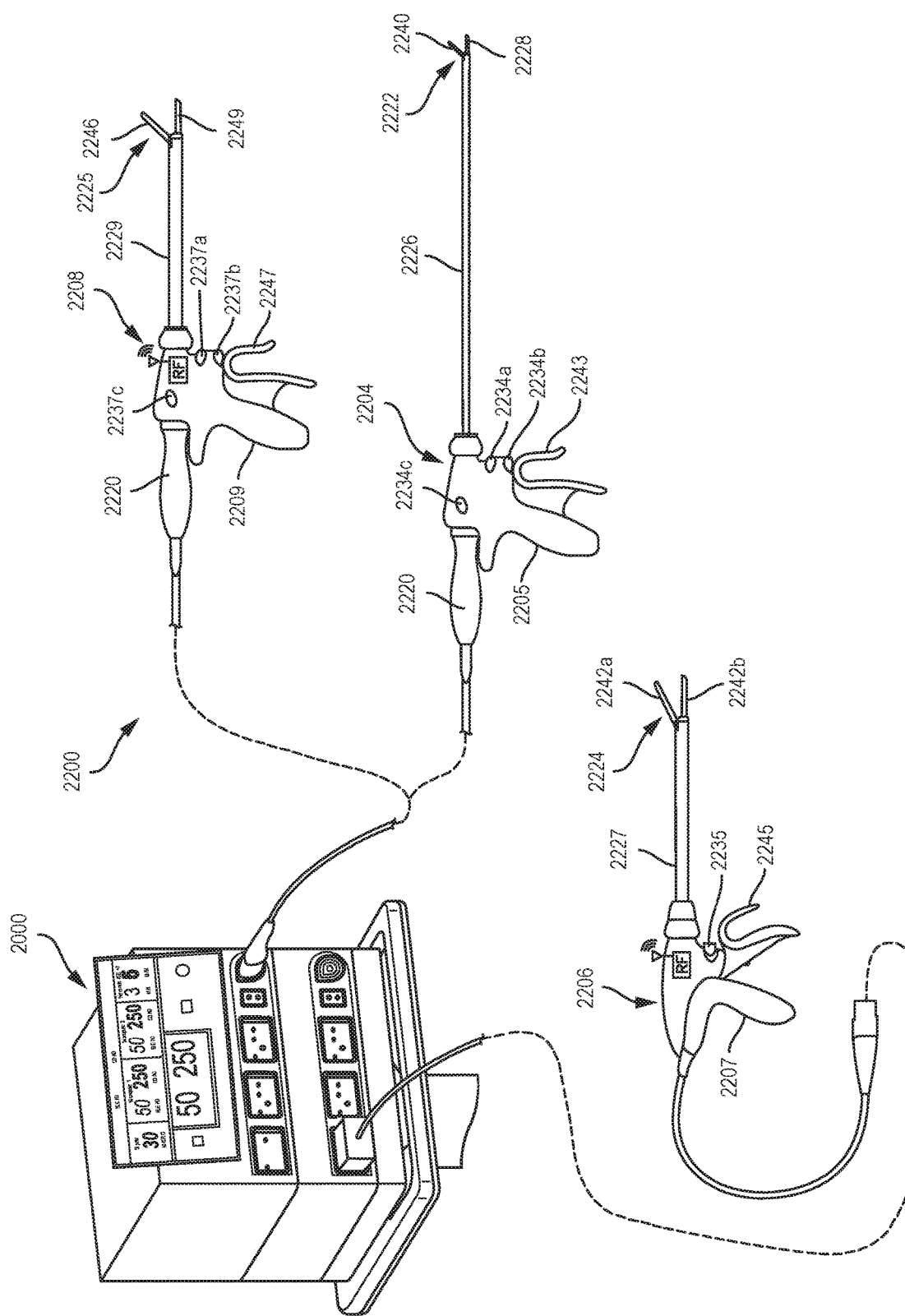
FIG. 4 is a surgical system comprising a generator and various surgical instruments usable therewith, in accordance with at least one aspect of the present disclosure.

FIG. 4 illustrates one form of a surgical system 2200 comprising a modular energy system 2000 and various surgical instruments 2204, 2206, 2208 usable therewith, where the surgical instrument 2204 is an ultrasonic surgical instrument, the surgical instrument 2206 is an RF electrosurgical instrument, and the multifunction surgical instrument 2208 is a combination ultrasonic/RF electrosurgical instrument. The modular energy system 2000 is configurable for use with a variety of surgical instruments. According to various forms, the modular energy system 2000 may be configurable for use with different surgical instruments of different types including, for example, ultrasonic surgical instruments 2204, RF electrosurgical instruments 2206, and multifunction surgical instruments 2208 that integrate RF and ultrasonic energies delivered individually or simultaneously from the modular energy system 2000. Although in the form of FIG. 4 the modular energy system 2000 is shown separate from the surgical instruments 2204, 2206, 2208 in one form, the modular energy system 2000 may be formed integrally with any of the surgical instruments 2204, 2206, 2208 to form a unitary surgical system. The modular energy system 2000 may be configured for wired or wireless communication.

The modular energy system 2000 is configured to drive multiple surgical instruments 2204, 2206, 2208. The first surgical instrument is an ultrasonic surgical instrument 2204 and comprises a handpiece 2205 (HP), an ultrasonic transducer 2220, a shaft 2226, and an end effector 2222. The end effector 2222 comprises an ultrasonic blade 2228 acoustically coupled to the ultrasonic transducer 2220 and a clamp arm 2240. The handpiece 2205 comprises a trigger 2243 to operate the clamp arm 2240 and a combination of the toggle buttons 2234a, 2234b, 2234c to energize and drive the ultrasonic blade 2228 or other function. The toggle buttons 2234a, 2234b, 2234c can be configured to energize the ultrasonic transducer 2220 with the modular energy system 2000.

The modular energy system 2000 also is configured to drive a second surgical instrument 2206. The second surgical instrument 2206 is an RF electrosurgical instrument and comprises a handpiece 2207 (HP), a shaft 2227, and an end effector 2224. The end effector 2224 comprises electrodes in clamp arms 2242a, 2242b and return through an electrical conductor portion of the shaft 2227. The electrodes are coupled to and energized by a bipolar energy source within the modular energy system 2000. The handpiece 2207 comprises a trigger 2245 to operate the clamp arms 2242a, 2242b and an energy button 2235 to actuate an energy switch to energize the electrodes in the end effector 2224.

The modular energy system 2000 also is configured to drive a multifunction surgical instrument 2208. The multifunction surgical instrument 2208 comprises a handpiece 2209 (HP), a shaft 2229, and an end effector 2225. The end effector 2225 comprises an ultrasonic blade 2249 and a clamp arm 2246. The ultrasonic blade 2249 is acoustically coupled to the ultrasonic transducer 2220. The ultrasonic transducer 2220 may be separable from or integral to the handpiece 2209. The handpiece 2209 comprises a trigger 2247 to operate the clamp arm 2246 and a combination of the toggle buttons 2237a, 2237b, 2237c to energize and drive the ultrasonic blade 2249 or other function. The toggle buttons 2237a, 2237b, 2237c can be configured to energize the ultrasonic transducer 2220 with the modular energy system 2000 and energize the ultrasonic blade 2249 with a bipolar energy source also contained within the modular energy system 2000.

The modular energy system 2000 is configurable for use with a variety of surgical instruments. According to various forms, the modular energy system 2000 may be configurable for use with different surgical instruments of different types including, for example, the ultrasonic surgical instrument 2204, the RF electrosurgical instrument 2206, and the multifunction surgical instrument 2208 that integrates RF and ultrasonic energies delivered individually or simultaneously from the modular energy system 2000. Although in the form of FIG. 4 the modular energy system 2000 is shown separate from the surgical instruments 2204, 2206, 2208, in another form the modular energy system 2000 may be formed integrally with any one of the surgical instruments 2204, 2206, 2208 to form a unitary surgical system. Further aspects of generators for digitally generating electrical signal waveforms and surgical instruments are described in U.S. Patent Application Publication No. 2017/0086914, which is herein incorporated by reference in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or sub optimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 5:
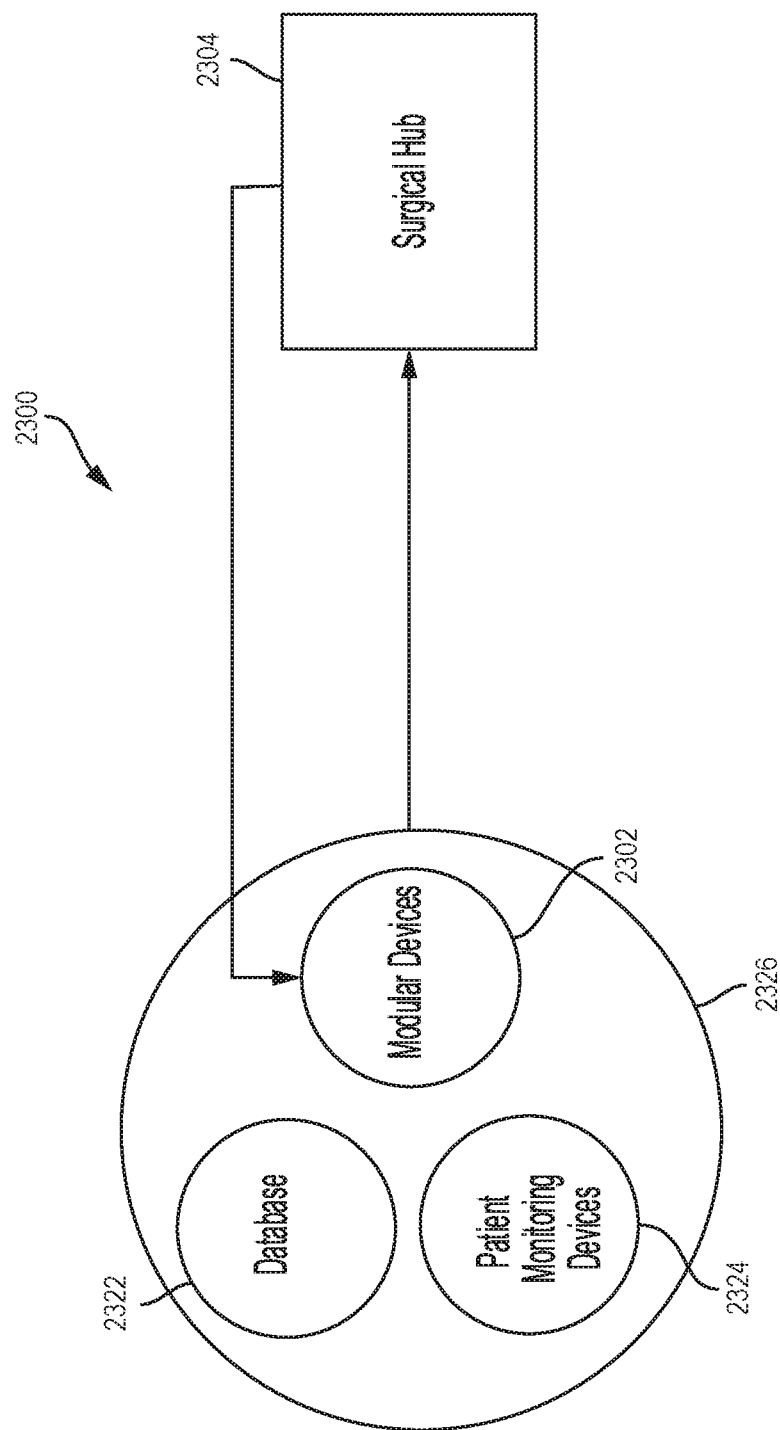
FIG. 5 is a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 5 illustrates a diagram of a situationally aware surgical system 2300, in accordance with at least one aspect of the present disclosure. In some exemplifications, the data sources 2326 include, for example, the modular devices 2302 (which can include sensors configured to detect parameters associated with the patient and/or the modular device itself), databases 2322 (e.g., an EMR database containing patient records), and patient monitoring devices 2324 (e.g., a blood pressure (BP) monitor and an electrocardiography (EKG) monitor). The surgical hub 2304 can be configured to derive the contextual information pertaining to the surgical procedure from the data based upon, for example, the particular combination(s) of received data or the particular order in which the data is received from the data sources 2326. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 2304 to derive or infer information related to the surgical procedure from received data can be referred to as "situational awareness." In one exemplification, the surgical hub 2304 can incorporate a situational awareness system, which is the hardware and/or programming associated with the surgical hub 2304 that derives contextual information pertaining to the surgical procedure from the received data.

The situational awareness system of the surgical hub 2304 can be configured to derive the contextual information from the data received from the data sources 2326 in a variety of different ways. In one exemplification, the situational awareness system includes a pattern recognition system, or machine learning system (e.g., an artificial neural network), that has been trained on training data to correlate various inputs (e.g., data from databases 2322, patient monitoring devices 2324, and/or modular devices 2302) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 2302. In one exemplification, the contextual information received by the situational awareness system of the surgical hub 2304 is associated with a particular control adjustment or set of control adjustments for one or more modular devices 2302. In another exemplification, the situational awareness system includes a further machine learning system, lookup table, or other such system, which generates or retrieves one or more control adjustments for one or more modular devices 2302 when provided the contextual information as input.

A surgical hub 2304 incorporating a situational awareness system provides a number of benefits for the surgical system 2300. One benefit includes improving the interpretation of sensed and collected data, which would in turn improve the processing accuracy and/or the usage of the data during the course of a surgical procedure. To return to a previous example, a situationally aware surgical hub 2304 could determine what type of tissue was being operated on; therefore, when an unexpectedly high force to close the surgical instrument's end effector is detected, the situationally aware surgical hub 2304 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 2304 could infer whether a surgical procedure being performed is a thoracic or an abdominal procedure, allowing the surgical hub 2304 to determine whether the tissue clamped by an end effector of the surgical stapling and cutting instrument is lung (for a thoracic procedure) or stomach (for an abdominal procedure) tissue. The surgical hub 2304 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 2304 could determine whether the surgical site is under pressure (by determining that the surgical procedure is utilizing insufflation) and determine the procedure type. As a procedure type is generally performed in a specific body cavity, the surgical hub 2304 could then control the motor rate of the smoke evacuator appropriately for the body cavity being operated in. Thus, a situationally aware surgical hub 2304 could provide a consistent amount of smoke evacuation for both thoracic and abdominal procedures.

As yet another example, the type of procedure being performed can affect the optimal energy level at which an ultrasonic surgical instrument or radio frequency (RF) electrosurgical instrument operates. Arthroscopic procedures, for example, require higher energy levels because the end effector of the ultrasonic surgical instrument or RF electrosurgical instrument is immersed in fluid. A situationally aware surgical hub 2304 could determine whether the surgical procedure is an arthroscopic procedure. The surgical hub 2304 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 2304 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 2304 can be configured to adjust the energy level for the ultrasonic surgical instrument or RF electrosurgical instrument throughout the course of a surgical procedure, rather than just on a procedure-by-procedure basis. A situationally aware surgical hub 2304 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 2326 to improve the conclusions that the surgical hub 2304 draws from one data source 2326. A situationally aware surgical hub 2304 could augment data that it receives from the modular devices 2302 with contextual information that it has built up regarding the surgical procedure from other data sources 2326. For example, a situationally aware surgical hub 2304 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 2304 can be further configured to compare a physiologic measurement (e.g., blood pressure sensed by a BP monitor communicably connected to the surgical hub 2304) with the visual or image data of hemostasis (e.g., from a medical imaging device 124 (FIG. 2) communicably coupled to the surgical hub 2304) to make a determination on the integrity of the staple line or tissue weld. In other words, the situational awareness system of the surgical hub 2304 can consider the physiological measurement data to provide additional context in analyzing the visualization data. The additional context can be useful when the visualization data may be inconclusive or incomplete on its own.

Another benefit includes proactively and automatically controlling the paired modular devices 2302 according to the particular step of the surgical procedure that is being performed to reduce the number of times that medical personnel are required to interact with or control the surgical system 2300 during the course of a surgical procedure. For example, a situationally aware surgical hub 2304 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 2304 could determine whether the current or subsequent step of the surgical procedure requires a different view or degree of magnification on the display according to the feature(s) at the surgical site that the surgeon is expected to need to view. The surgical hub 2304 could then proactively change the displayed view (supplied by, e.g., a medical imaging device for the visualization system 108) accordingly so that the display automatically adjusts throughout the surgical procedure.

As yet another example, a situationally aware surgical hub 2304 could determine which step of the surgical procedure is being performed or will subsequently be performed and whether particular data or comparisons between data will be required for that step of the surgical procedure. The surgical hub 2304 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 2304 could determine whether the operating theater is setup properly or optimally for the surgical procedure to be performed. The surgical hub 2304 can be configured to determine the type of surgical procedure being performed, retrieve the corresponding checklists, product location, or setup needs (e.g., from a memory), and then compare the current operating theater layout to the standard layout for the type of surgical procedure that the surgical hub 2304 determines is being performed. In one exemplification, the surgical hub 2304 can be configured to compare the list of items for the procedure (scanned by a scanner, for example) and/or a list of devices paired with the surgical hub 2304 to a recommended or anticipated manifest of items and/or devices for the given surgical procedure. If there are any discontinuities between the lists, the surgical hub 2304 can be configured to provide an alert indicating that a particular modular device 2302, patient monitoring device 2324, and/or other surgical item is missing. In one exemplification, the surgical hub 2304 can be configured to determine the relative distance or position of the modular devices 2302 and patient monitoring devices 2324 via proximity sensors, for example. The surgical hub 2304 can compare the relative positions of the devices to a recommended or anticipated layout for the particular surgical procedure. If there are any discontinuities between the layouts, the surgical hub 2304 can be configured to provide an alert indicating that the current layout for the surgical procedure deviates from the recommended layout.

As another example, a situationally aware surgical hub 2304 could determine whether the surgeon (or other medical personnel) was making an error or otherwise deviating from the expected course of action during the course of a surgical procedure. For example, the surgical hub 2304 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 2304 determined is being performed. In one exemplification, the surgical hub 2304 can be configured to provide an alert indicating that an unexpected action is being performed or an unexpected device is being utilized at the particular step in the surgical procedure.

Overall, the situational awareness system for the surgical hub 2304 improves surgical procedure outcomes by adjusting the surgical instruments (and other modular devices 2302) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 2302 in the surgical theater according to the specific context of the procedure.

Modular Energy System

ORs everywhere in the world are a tangled web of cords, devices, and people due to the amount of equipment required to perform surgical procedures. Surgical capital equipment tends to be a major contributor to this issue because most surgical capital equipment performs a single, specialized task. Due to their specialized nature and the surgeons' needs to utilize multiple different types of devices during the course of a single surgical procedure, an OR may be forced to be stocked with two or even more pieces of surgical capital equipment, such as energy generators. Each of these pieces of surgical capital equipment must be individually plugged into a power source and may be connected to one or more other devices that are being passed between OR personnel, creating a tangle of cords that must be navigated. Another issue faced in modern ORs is that each of these specialized pieces of surgical capital equipment has its own user interface and must be independently controlled from the other pieces of equipment within the OR. This creates complexity in properly controlling multiple different devices in connection with each other and forces users to be trained on and memorize different types of user interfaces (which may further change based upon the task or surgical procedure being performed, in addition to changing between each piece of capital equipment). This cumbersome, complex process can necessitate the need for even more individuals to be present within the OR and can create danger if multiple devices are not properly controlled in tandem with each other. Therefore, consolidating surgical capital equipment technology into singular systems that are able to flexibly address surgeons' needs to reduce the footprint of surgical capital equipment within ORs would simplify the user experience, reduce the amount of clutter in ORs, and prevent difficulties and dangers associated with simultaneously controlling multiple pieces of capital equipment. Further, making such systems expandable or customizable would allow for new technology to be conveniently incorporated into existing surgical systems, obviating the need to replace entire surgical systems or for OR personnel to learn new user interfaces or equipment controls with each new technology.

As described in FIGS. 1-3, a surgical hub 106 can be configured to interchangeably receive a variety of modules, which can in turn interface with surgical devices (e.g., a surgical instrument or a smoke evacuator) or provide various other functions (e.g., communications). In one aspect, a surgical hub 106 can be embodied as a modular energy system 2000, which is illustrated in connection with FIGS. 6-12. The modular energy system 2000 can include a variety of different modules 2001 that are connectable together in a stacked configuration. In one aspect, the modules 2001 can be both physically and communicably coupled together when stacked or otherwise connected together into a singular assembly. Further, the modules 2001 can be interchangeably connectable together in different combinations or arrangements. In one aspect, each of the modules 2001 can include a consistent or universal array of connectors disposed along their upper and lower surfaces, thereby allowing any module 2001 to be connected to another module 2001 in any arrangement (except that, in some aspects, a particular module type, such as the header module 2002, can be configured to serve as the uppermost module within the stack, for example). In an alternative aspect, the modular energy system 2000 can include a housing that is configured to receive and retain the modules 2001, as is shown in FIG. 3. The modular energy system 2000 can also include a variety of different components or accessories that are also connectable to or otherwise associatable with the modules 2001. In another aspect, the modular energy system 2000 can be embodied as a generator module 140 (FIG. 3) of a surgical hub 106. In yet another aspect, the modular energy system 2000 can be a distinct system from a surgical hub 106. In such aspects, the modular energy system 2000 can be communicably couplable to a surgical hub 206 for transmitting and/or receiving data therebetween.

Figure 6:
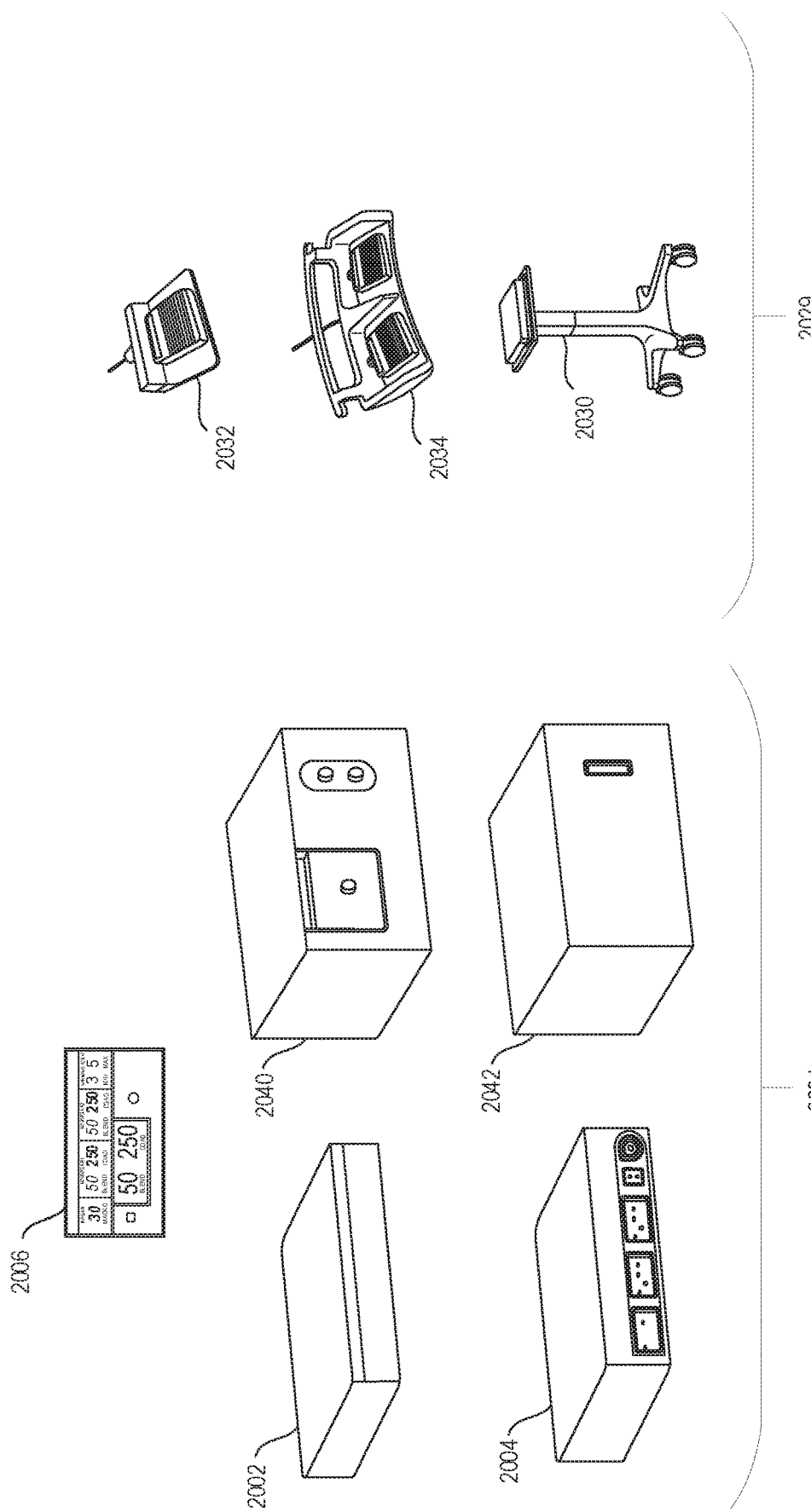
FIG. 6 is a diagram of various modules and other components that are combinable to customize modular energy systems, in accordance with at least one aspect of the present disclosure.

The modular energy system 2000 can be assembled from a variety of different modules 2001, some examples of which are illustrated in FIG. 6. Each of the different types of modules 2001 can provide different functionality, thereby allowing the modular energy system 2000 to be assembled into different configurations to customize the functions and capabilities of the modular energy system 2000 by customizing the modules 2001 that are included in each modular energy system 2000. The modules 2001 of the modular energy system 2000 can include, for example, a header module 2002 (which can include a display screen 2006), an energy module 2004, a technology module 2040, and a visualization module 2042. In the depicted aspect, the header module 2002 is configured to serve as the top or uppermost module within the modular energy system stack and can thus lack connectors along its top surface. In another aspect, the header module 2002 can be configured to be positioned at the bottom or the lowermost module within the modular energy system stack and can thus lack connectors along its bottom surface. In yet another aspect, the header module 2002 can be configured to be positioned at an intermediate position within the modular energy system stack and can thus include connectors along both its bottom and top surfaces. The header module 2002 can be configured to control the system-wide settings of each module 2001 and component connected thereto through physical controls 2011 thereon and/or a graphical user interface (GUI) 2008 rendered on the display screen 2006. Such settings could include the activation of the modular energy system 2000, the volume of alerts, the footswitch settings, the settings icons, the appearance or configuration of the user interface, the surgeon profile logged into the modular energy system 2000, and/or the type of surgical procedure being performed. The header module 2002 can also be configured to provide communications, processing, and/or power for the modules 2001 that are connected to the header module 2002. The energy module 2004, which can also be referred to as a generator module 140 (FIG. 3), can be configured to generate one or multiple energy modalities for driving electrosurgical and/or ultrasonic surgical instruments connected thereto. The technology module 2040 can be configured to provide additional or expanded control algorithms (e.g., electrosurgical or ultrasonic control algorithms for controlling the energy output of the energy module 2004). The visualization module 2042 can be configured to interface with visualization devices (i.e., scopes) and accordingly provide increased visualization capabilities.

The modular energy system 2000 can further include a variety of accessories 2029 that are connectable to the modules 2001 for controlling the functions thereof or that are otherwise configured to work on conjunction with the modular energy system 2000. The accessories 2029 can include, for example, a single-pedal footswitch 2032, a dual-pedal footswitch 2034, and a cart 2030 for supporting the modular energy system 2000 thereon. The footswitches 2032, 2034 can be configured to control the activation or function of particular energy modalities output by the energy module 2004, for example.

By utilizing modular components, the depicted modular energy system 2000 provides a surgical platform that grows with the availability of technology and is customizable to the needs of the facility and/or surgeons. Further, the modular energy system 2000 supports combo devices (e.g., dual electrosurgical and ultrasonic energy generators) and supports software-driven algorithms for customized tissue effects. Still further, the surgical system architecture reduces the capital footprint by combining multiple technologies critical for surgery into a single system.

The various modular components utilizable in connection with the modular energy system 2000 can include monopolar energy generators, bipolar energy generators, dual electrosurgical/ultrasonic energy generators, display screens, and various other modules and/or other components, some of which are also described above in connection with FIGS. 1-3.

Figure 11:
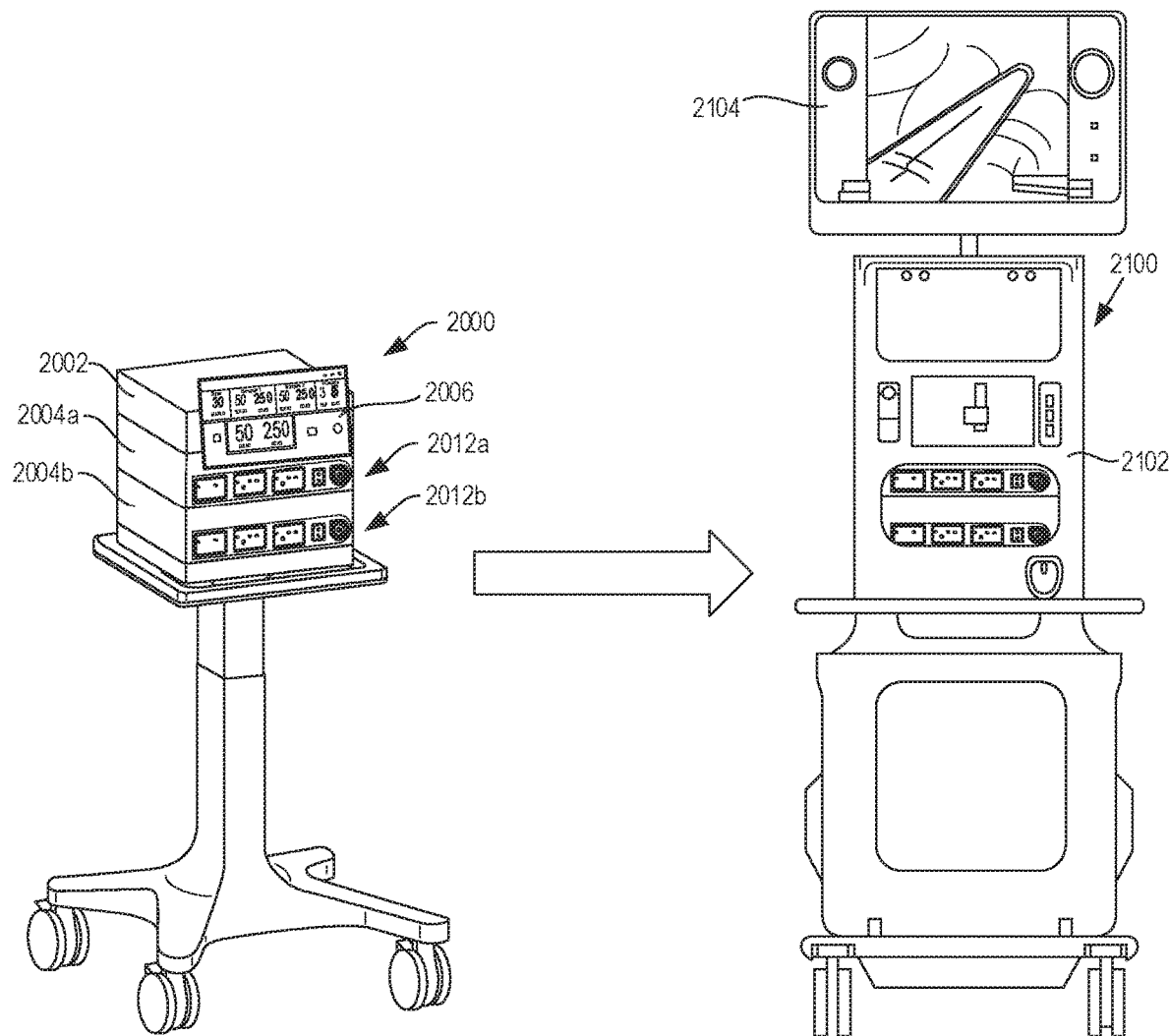
FIG. 11 is a diagram of a modular energy system including communicably connectable surgical platforms, in accordance with at least one aspect of the present disclosure.

Referring now to FIG. 7A, the header module 2002 can, in some aspects, include a display screen 2006 that renders a GUI 2008 for relaying information regarding the modules 2001 connected to the header module 2002. In some aspects, the GUI 2008 of the display screen 2006 can provide a consolidated point of control of all of the modules 2001 making up the particular configuration of the modular energy system 2000. Various aspects of the GUI 2008 are discussed in fuller detail below in connection with FIG. 12. In alternative aspects, the header module 2002 can lack the display screen 2006 or the display screen 2006 can be detachably connected to the housing 2010 of the header module 2002. In such aspects, the header module 2002 can be communicably couplable to an external system that is configured to display the information generated by the modules 2001 of the modular energy system 2000. For example, in robotic surgical applications, the modular energy system 2000 can be communicably couplable to a robotic cart or robotic control console, which is configured to display the information generated by the modular energy system 2000 to the operator of the robotic surgical system. As another example, the modular energy system 2000 can be communicably couplable to a mobile display that can be carried or secured to a surgical staff member for viewing thereby. In yet another example, the modular energy system 2000 can be communicably couplable to a surgical hub 2100 or another computer system that can include a display 2104, as is illustrated in FIG. 11. In aspects utilizing a user interface that is separate from or otherwise distinct from the modular energy system 2000, the user interface can be wirelessly connectable with the modular energy system 2000 as a whole or one or more modules 2001 thereof such that the user interface can display information from the connected modules 2001 thereon.

Referring still to FIG. 7A, the energy module 2004 can include a port assembly 2012 including a number of different ports configured to deliver different energy modalities to corresponding surgical instruments that are connectable thereto. In the particular aspect illustrated in FIGS. 6-12, the port assembly 2012 includes a bipolar port 2014, a first monopolar port 2016a, a second monopolar port 2016b, a neutral electrode port 2018 (to which a monopolar return pad is connectable), and a combination energy port 2020. However, this particular combination of ports is simply provided for illustrative purposes and alternative combinations of ports and/or energy modalities may be possible for the port assembly 2012.

As noted above, the modular energy system 2000 can be assembled into different configurations. Further, the different configurations of the modular energy system 2000 can also be utilizable for different surgical procedure types and/or different tasks. For example, FIGS. 7A and 7B illustrate a first illustrative configuration of the modular energy system 2000 including a header module 2002 (including a display screen 2006) and an energy module 2004 connected together. Such a configuration can be suitable for laparoscopic and open surgical procedures, for example.

Figure 8A:
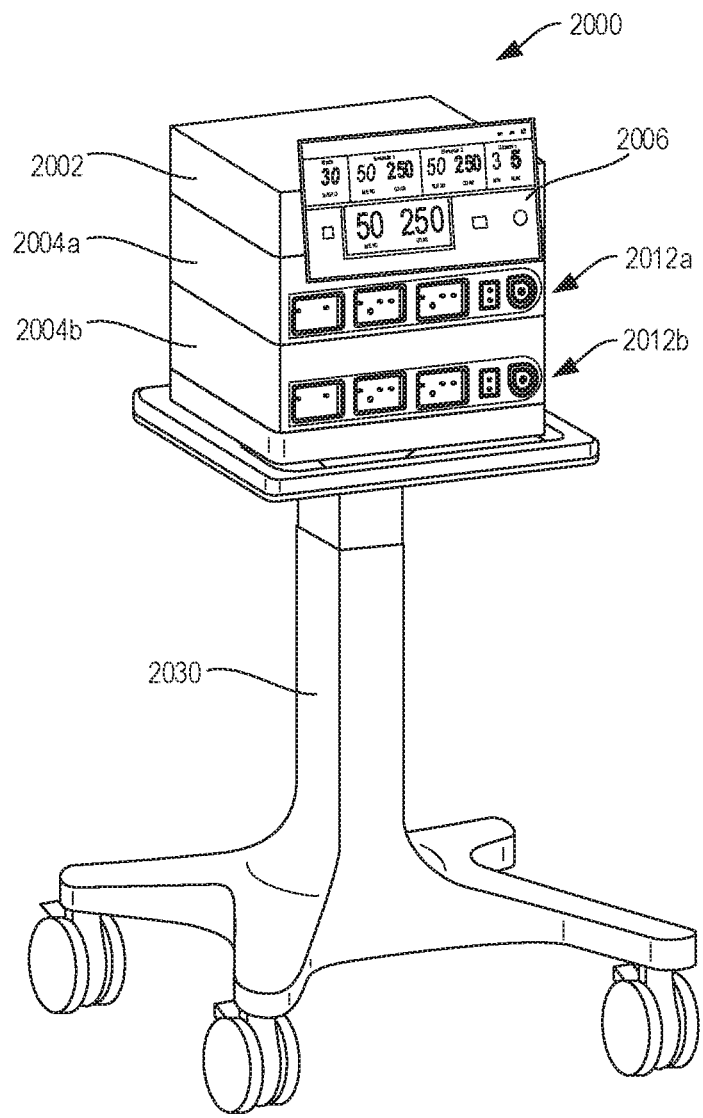
FIG. 8A is a second illustrative modular energy system configuration including a header module, a display screen, an energy module, and an expanded energy module connected together and mounted to a cart, in accordance with at least one aspect of the present disclosure.
Figure 8B:
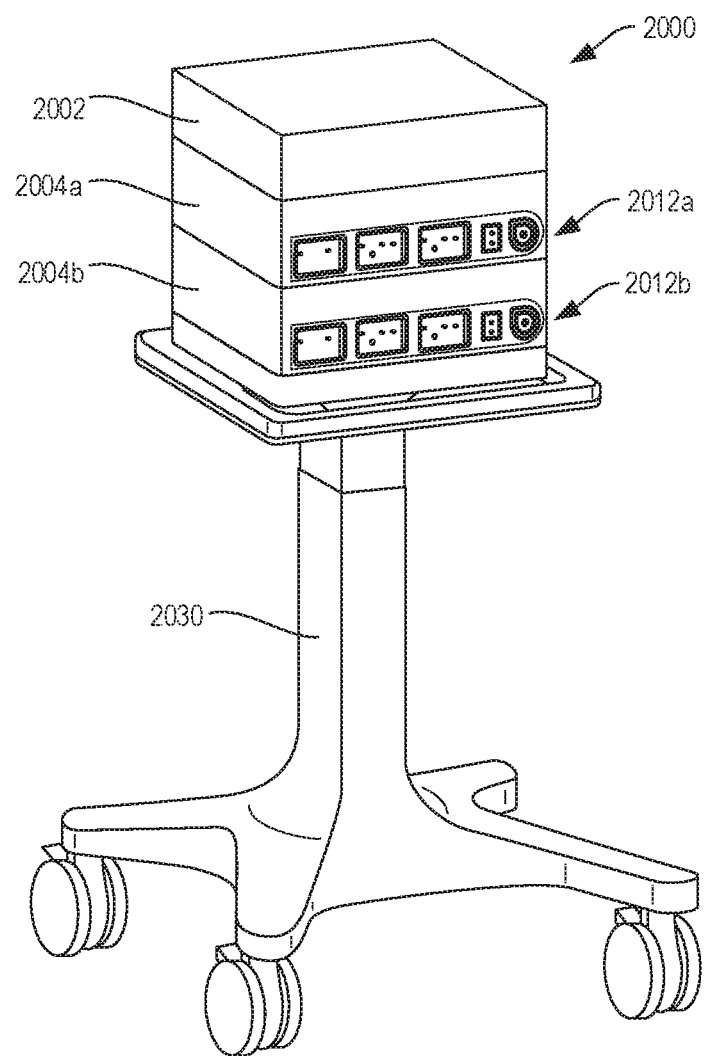
FIG. 8B is a third illustrative modular energy system configuration that is similar to the second configuration shown in FIG. 7A, except that the header module lacks a display screen, in accordance with at least one aspect of the present disclosure.

FIG. 8A illustrates a second illustrative configuration of the modular energy system 2000 including a header module 2002 (including a display screen 2006), a first energy module 2004a, and a second energy module 2004b connected together. By stacking two energy modules 2004a, 2004b, the modular energy system 2000 can provide a pair of port assemblies 2012a, 2012b for expanding the array of energy modalities deliverable by the modular energy system 2000 from the first configuration. The second configuration of the modular energy system 2000 can accordingly accommodate more than one bipolar/monopolar electrosurgical instrument, more than two bipolar/monopolar electrosurgical instruments, and so on. Such a configuration can be suitable for particularly complex laparoscopic and open surgical procedures. FIG. 8B illustrates a third illustrative configuration that is similar to the second configuration, except that the header module 2002 lacks a display screen 2006. This configuration can be suitable for robotic surgical applications or mobile display applications, as noted above.

Figure 9:
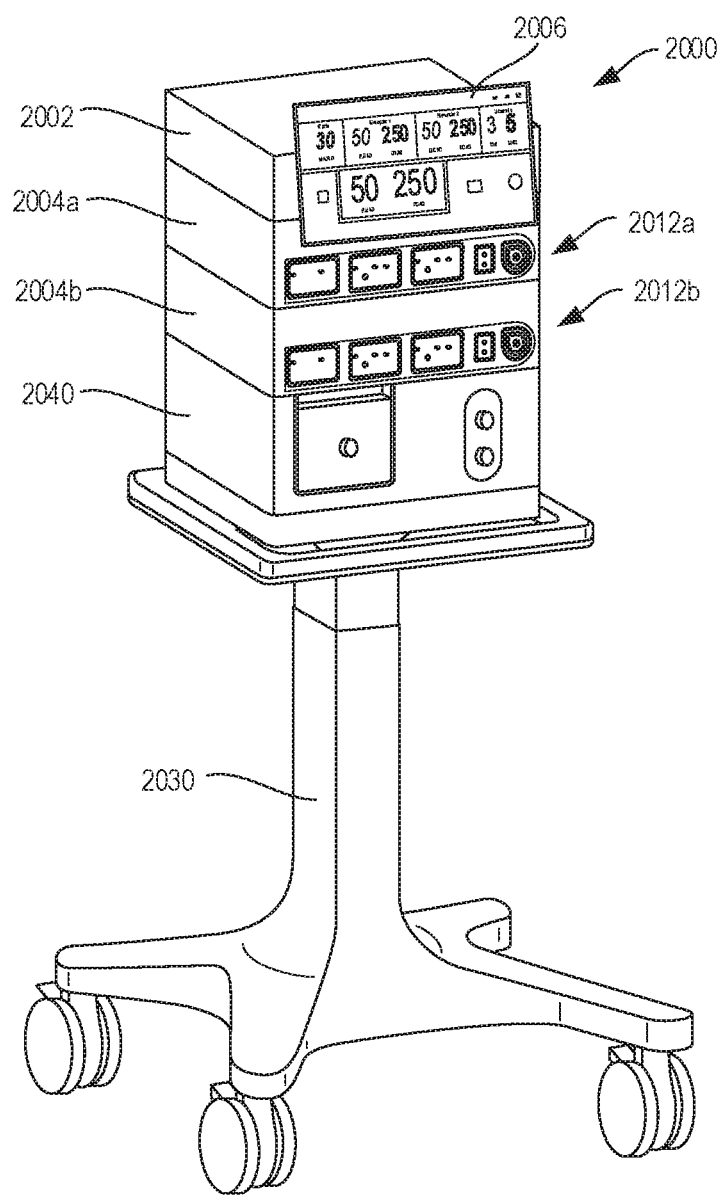
FIG. 9 is a fourth illustrative modular energy system configuration including a header module, a display screen, an energy module, an expanded energy module, and a technology module connected together and mounted to a cart, in accordance with at least one aspect of the present disclosure.

FIG. 9 illustrates a fourth illustrative configuration of the modular energy system 2000 including a header module 2002 (including a display screen 2006), a first energy module 2004a, a second energy module 2004b, and a technology module 2040 connected together. Such a configuration can be suitable for surgical applications where particularly complex or computation-intensive control algorithms are required. Alternatively, the technology module 2040 can be a newly released module that supplements or expands the capabilities of previously released modules (such as the energy module 2004).

Figure 10:
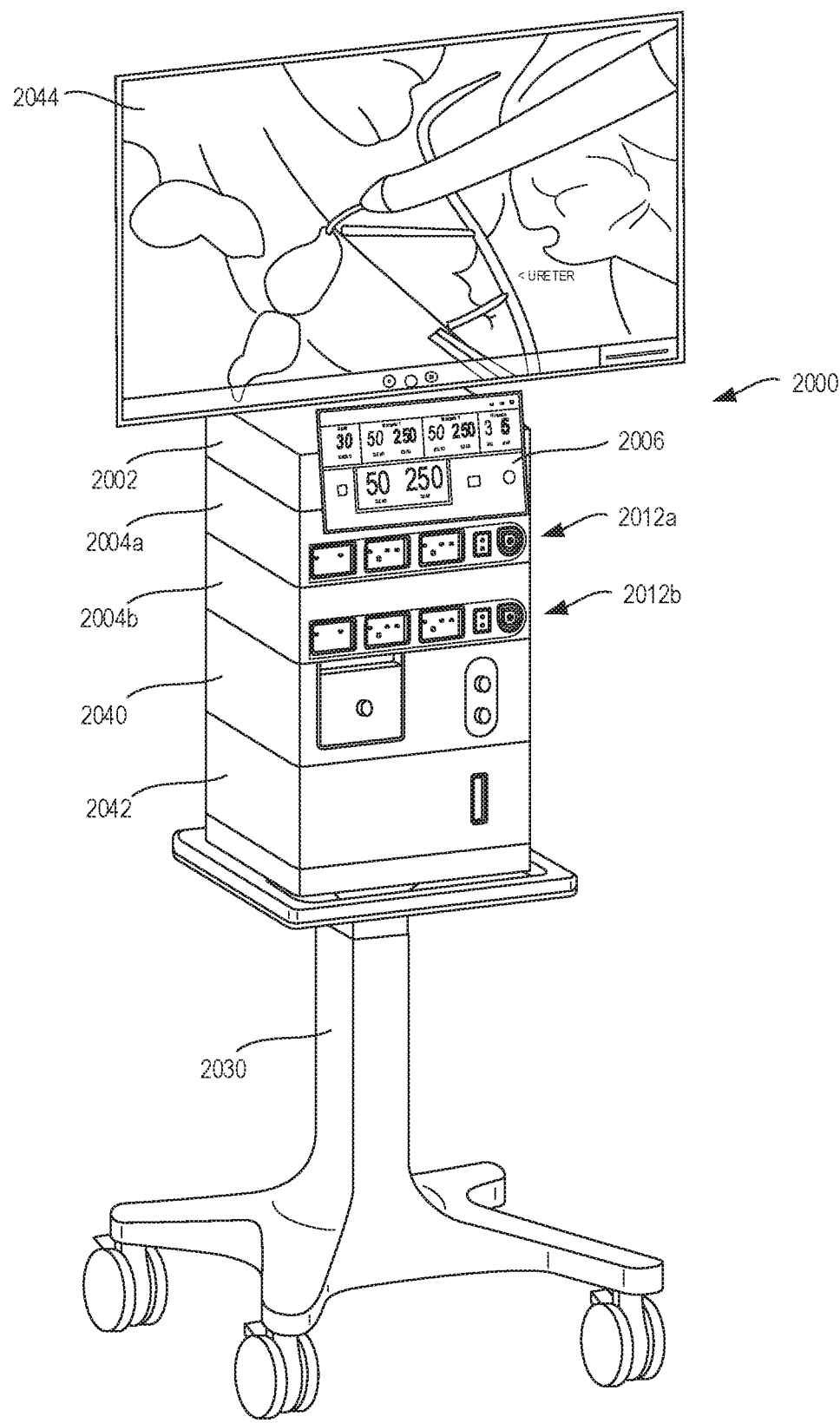
FIG. 10 is a fifth illustrative modular energy system configuration including a header module, a display screen, an energy module, an expanded energy module, a technology module, and a visualization module connected together and mounted to a cart, in accordance with at least one aspect of the present disclosure.

FIG. 10 illustrates a fifth illustrative configuration of the modular energy system 2000 including a header module 2002 (including a display screen 2006), a first energy module 2004a, a second energy module 2004b, a technology module 2040, and a visualization module 2042 connected together. Such a configuration can be suitable for endoscopic procedures by providing a dedicated surgical display 2044 for relaying the video feed from the scope coupled to the visualization module 2042. It should be noted that the configurations illustrated in FIGS. 7A-11 and described above are provided simply to illustrate the various concepts of the modular energy system 2000 and should not be interpreted to limit the modular energy system 2000 to the particular aforementioned configurations.

As noted above, the modular energy system 2000 can be communicably couplable to an external system, such as a surgical hub 2100 as illustrated in FIG. 11. Such external systems can include a display screen 2104 for displaying a visual feed from an endoscope (or a camera or another such visualization device) and/or data from the modular energy system 2000. Such external systems can also include a computer system 2102 for performing calculations or otherwise analyzing data generated or provided by the modular energy system 2000, controlling the functions or modes of the modular energy system 2000, and/or relaying data to a cloud computing system or another computer system. Such external systems could also coordinate actions between multiple modular energy systems 2000 and/or other surgical systems (e.g., a visualization system 108 and/or a robotic system 110 as described in connection with FIGS. 1 and 2).

Figure 12:
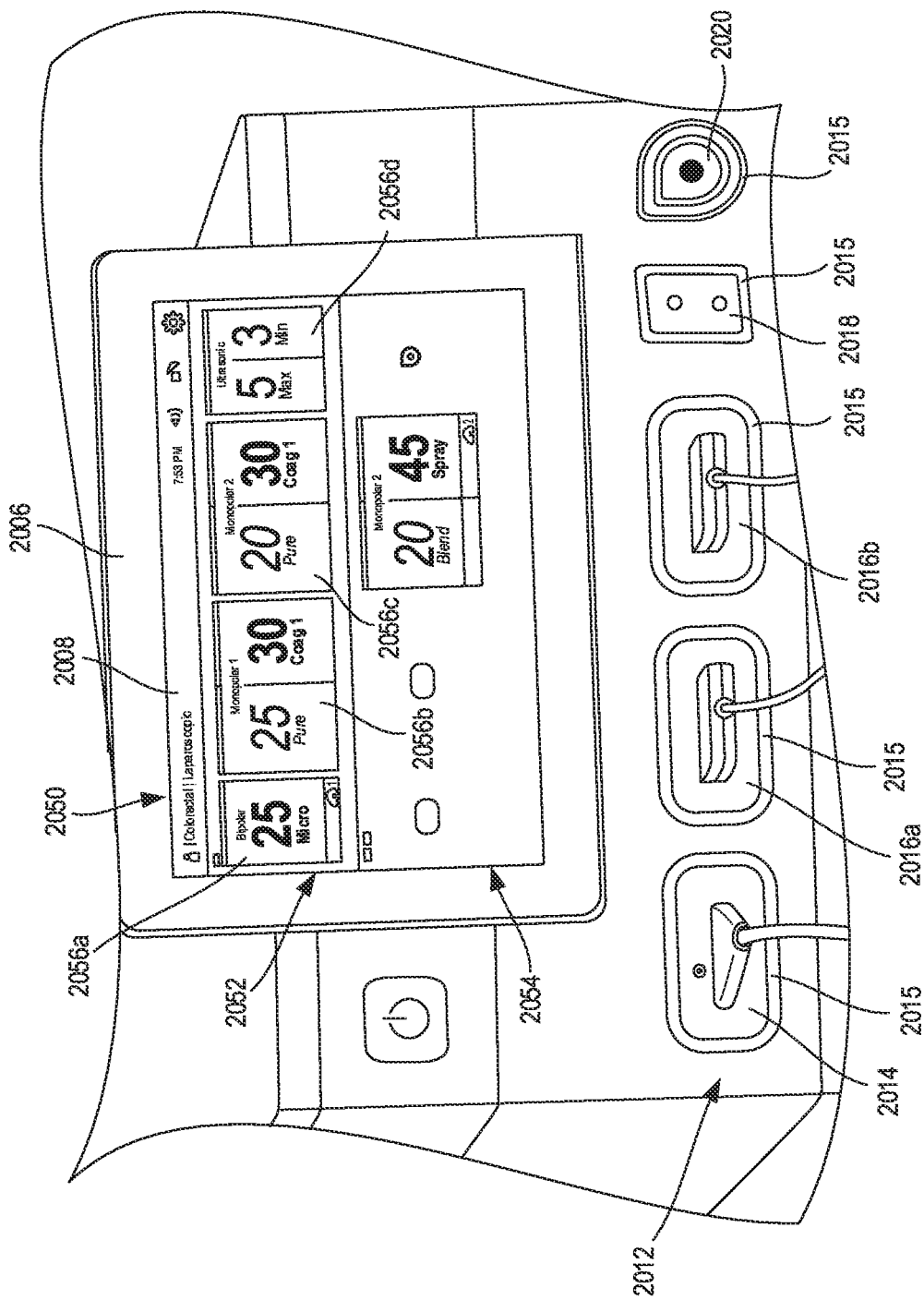
FIG. 12 is a perspective view of a header module of a modular energy system including a user interface, in accordance with at least one aspect of the present disclosure.

Referring now to FIG. 12, in some aspects, the header module 2002 can include or support a display 2006 configured for displaying a GUI 2008, as noted above. The display screen 2006 can include a touchscreen for receiving input from users in addition to displaying information. The controls displayed on the GUI 2008 can correspond to the module(s) 2001 that are connected to the header module 2002. In some aspects, different portions or areas of the GUI 2008 can correspond to particular modules 2001. For example, a first portion or area of the GUI 2008 can correspond to a first module and a second portion or area of the GUI 2008 can correspond to a second module. As different and/or additional modules 2001 are connected to the modular energy system stack, the GUI 2008 can adjust to accommodate the different and/or additional controls for each newly added module 2001 or remove controls for each module 2001 that is removed. Each portion of the display corresponding to a particular module connected to the header module 2002 can display controls, data, user prompts, and/or other information corresponding to that module. For example, in FIG. 12, a first or upper portion 2052 of the depicted GUI 2008 displays controls and data associated with an energy module 2004 that is connected to the header module 2002. In particular, the first portion 2052 of the GUI 2008 for the energy module 2004 provides first widget 2056a corresponding to the bipolar port 2014, a second widget 2056b corresponding to the first monopolar port 2016a, a third widget 2056c corresponding to the second monopolar port 2016b, and a fourth widget 2056d corresponding to the combination energy port 2020. Each of these widgets 2056a-d provides data related to its corresponding port of the port assembly 2012 and controls for controlling the modes and other features of the energy modality delivered by the energy module 2004 through the respective port of the port assembly 2012. For example, the widgets 2056a-d can be configured to display the power level of the surgical instrument connected to the respective port, change the operational mode of the surgical instrument connected to the respective port (e.g., change a surgical instrument from a first power level to a second power level and/or change a monopolar surgical instrument from a "spray" mode to a "blend" mode), and so on.

In one aspect, the header module 2002 can include various physical controls 2011 in addition to or in lieu of the GUI 2008. Such physical controls 2011 can include, for example, a power button that controls the application of power to each module 2001 that is connected to the header module 2002 in the modular energy system 2000. Alternatively, the power button can be displayed as part of the GUI 2008. Therefore, the header module 2002 can serve as a single point of contact and obviate the need to individually activate and deactivate each individual module 2001 from which the modular energy system 2000 is constructed.

In one aspect, the header module 2002 can display still images, videos, animations, and/or information associated with the surgical modules 2001 of which the modular energy system 2000 is constructed or the surgical devices that are communicably coupled to the modular energy system 2000. The still images and/or videos displayed by the header module 2002 can be received from an endoscope or another visualization device that is communicably coupled to the modular energy system 2000. The animations and/or information of the GUI 2008 can be overlaid on or displayed adjacent to the images or video feed.

In one aspect, the modules 2001 other than the header module 2002 can be configured to likewise relay information to users. For example, the energy module 2004 can include light assemblies 2015 disposed about each of the ports of the port assembly 2012. The light assemblies 2015 can be configured to relay information to the user regarding the port according to their color or state (e.g., flashing). For example, the light assemblies 2015 can change from a first color to a second color when a plug is fully seated within the respective port. In one aspect, the color or state of the light assemblies 2015 can be controlled by the header module 2002. For example, the header module 2002 can cause the light assembly 2015 of each port to display a color corresponding to the color display for the port on the GUI 2008.

Figure 13:
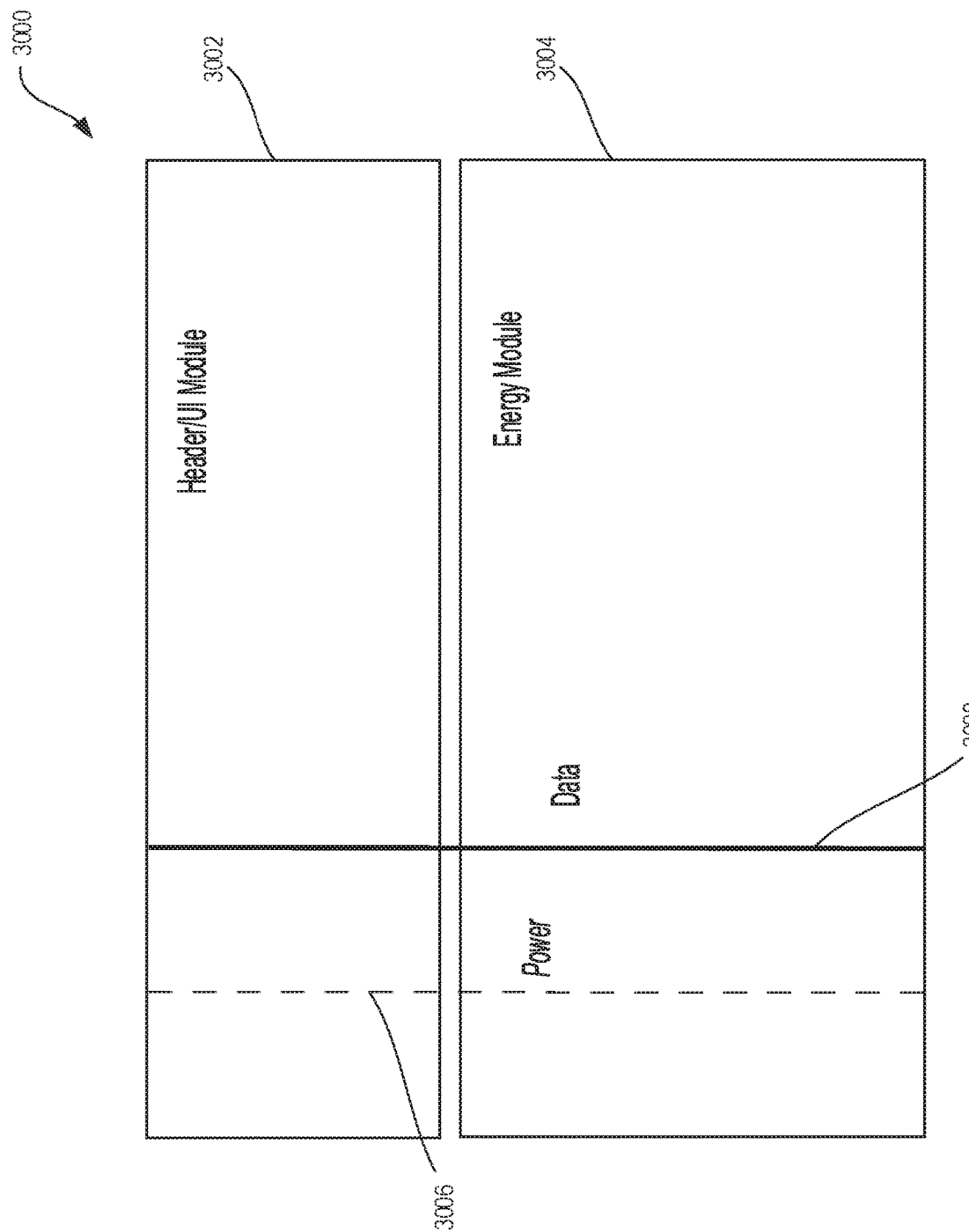
FIG. 13 is a block diagram of a stand-alone hub configuration of a modular energy system, in accordance with at least one aspect of the present disclosure.
Figure 14:
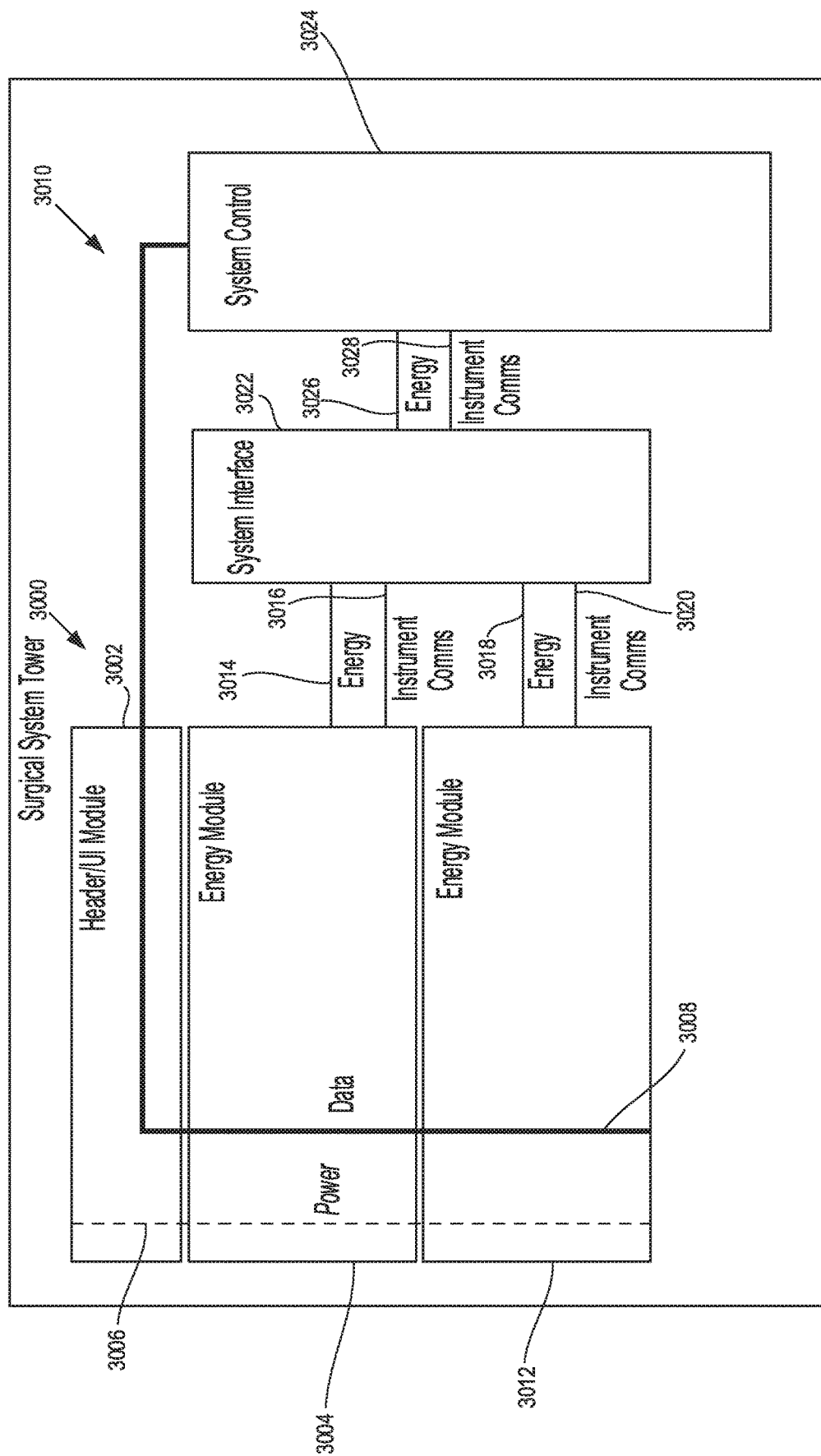
FIG. 14 is a block diagram of a hub configuration of a modular energy system integrated with a surgical control system, in accordance with at least one aspect of the present disclosure.

FIG. 13 is a block diagram of a stand-alone hub configuration of a modular energy system 3000, in accordance with at least one aspect of the present disclosure and FIG. 14 is a block diagram of a hub configuration of a modular energy system 3000 integrated with a surgical control system 3010, in accordance with at least one aspect of the present disclosure. As depicted in FIGS. 13 and 14, the modular energy system 3000 can be either utilized as stand-alone units or integrated with a surgical control system 3010 that controls and/or receives data from one or more surgical hub units. In the examples illustrated in FIGS. 13 and 14, the integrated header/UI module 3002 of the modular energy system 3000 includes a header module and a UI module integrated together as a singular module. In other aspects, the header module and the UI module can be provided as separate components that are communicatively coupled though a data bus 3008.

As illustrated in FIG. 13, an example of a stand-alone modular energy system 3000 includes an integrated header module/user interface (UI) module 3002 coupled to an energy module 3004. Power and data are transmitted between the integrated header/UI module 3002 and the energy module 3004 through a power interface 3006 and a data interface 3008. For example, the integrated header/UI module 3002 can transmit various commands to the energy module 3004 through the data interface 3008. Such commands can be based on user inputs from the UI. As a further example, power may be transmitted to the energy module 3004 through the power interface 3006.

In FIG. 14, a surgical hub configuration includes a modular energy system 3000 integrated with a control system 3010 and an interface system 3022 for managing, among other things, data and power transmission to and/or from the modular energy system 3000. The modular energy system depicted in FIG. 14 includes an integrated header module/UI module 3002, a first energy module 3004, and a second energy module 3012. In one example, a data transmission pathway is established between the system control unit 3024 of the control system 3010 and the second energy module 3012 through the first energy module 3004 and the header/UI module 3002 through a data interface 3008. In addition, a power pathway extends between the integrated header/UI module 3002 and the second energy module 3012 through the first energy module 3004 through a power interface 3006. In other words, in one aspect, the first energy module 3004 is configured to function as a power and data interface between the second energy module 3012 and the integrated header/UI module 3002 through the power interface 3006 and the data interface 3008. This arrangement allows the modular energy system 3000 to expand by seamlessly connecting additional energy modules to energy modules 3004, 3012 that are already connected to the integrated header/UI module 3002 without the need for dedicated power and energy interfaces within the integrated header/UI module 3002.

The system control unit 3024, which may be referred to herein as a control circuit, control logic, microprocessor, microcontroller, logic, or FPGA, or various combinations thereof, is coupled to the system interface 3022 via energy interface 3026 and instrument communication interface 3028. The system interface 3022 is coupled to the first energy module 3004 via a first energy interface 3014 and a first instrument communication interface 3016. The system interface 3022 is coupled to the second energy module 3012 via a second energy interface 3018 and a second instrument communication interface 3020. As additional modules, such as additional energy modules, are stacked in the modular energy system 3000, additional energy and communications interfaces are provided between the system interface 3022 and the additional modules.

The energy modules 3004, 3012 are connectable to a hub and can be configured to generate electrosurgical energy (e.g., bipolar or monopolar), ultrasonic energy, or a combination thereof (referred to herein as an "advanced energy" module) for a variety of energy surgical instruments. Generally, the energy modules 3004, 3012 include hardware/software interfaces, an ultrasonic controller, an advanced energy RF controller, bipolar RF controller, and control algorithms executed by the controller that receives outputs from the controller and controls the operation of the various energy modules 3004, 3012 accordingly. In various aspects of the present disclosure, the controllers described herein may be implemented as a control circuit, control logic, microprocessor, microcontroller, logic, or FPGA, or various combinations thereof.

In one aspect, with reference to FIGS. 13 and 14, the modules of the modular energy system 3000 can include an optical link allowing high speed communication (10-50 Mb/s) across the patient isolation boundary. This link would carry device communications, mitigation signals (watchdog, etc.), and low bandwidth run-time data. In some aspects, the optical link(s) will not contain real-time sampled data, which can be done on the non-isolated side.

In one aspect, with reference to FIGS. 13 and 14, the modules of the modular energy system 3000 can include a multi-function circuit block which can: (i) read presence resistor values via A/D and current source, (ii) communicate with legacy instruments via hand switch Q protocols, (iii) communicate with instruments via local bus 1-Wire protocols, and (iv) communicate with CAN FD-enabled surgical instruments. When a surgical instrument is properly identified by an energy generator module, the relevant pin functions and communications circuits are enabled, while the other unused functions are disabled or disconnected, and set to a high impedance state.

In one aspect, with reference to FIGS. 13 and 14, the modules of the modular energy system 3000 can include a pulse/stimulation/auxiliary amplifier. This is a flexible-use amplifier based on a full-bridge output and incorporates functional isolation. This allows its differential output to be referenced to any output connection on the applied part (except, in some aspects, a monopolar active electrode). The amplifier output can be either small signal linear (pulse/stim) with waveform drive provided by a DAC or a square wave drive at moderate output power for DC applications such as DC motors, illumination, FET drive, etc. The output voltage and current are sensed with functionally isolated voltage and current feedback to provide accurate impedance and power measurements to the FPGA. Paired with a CAN FD-enabled instrument, this output can offer motor/motion control drive, while position or velocity feedback is provided by the CAN FD interface for closed loop control.

As described in greater detail herein, a modular energy system comprises a header module and one or more functional or surgical modules. In various instances, the modular energy system is a modular energy system. In various instances, the surgical modules include energy modules, communication modules, user interface modules; however, the surgical modules are envisioned to be any suitable type of functional or surgical module for use with the modular energy system.

Figure 15:
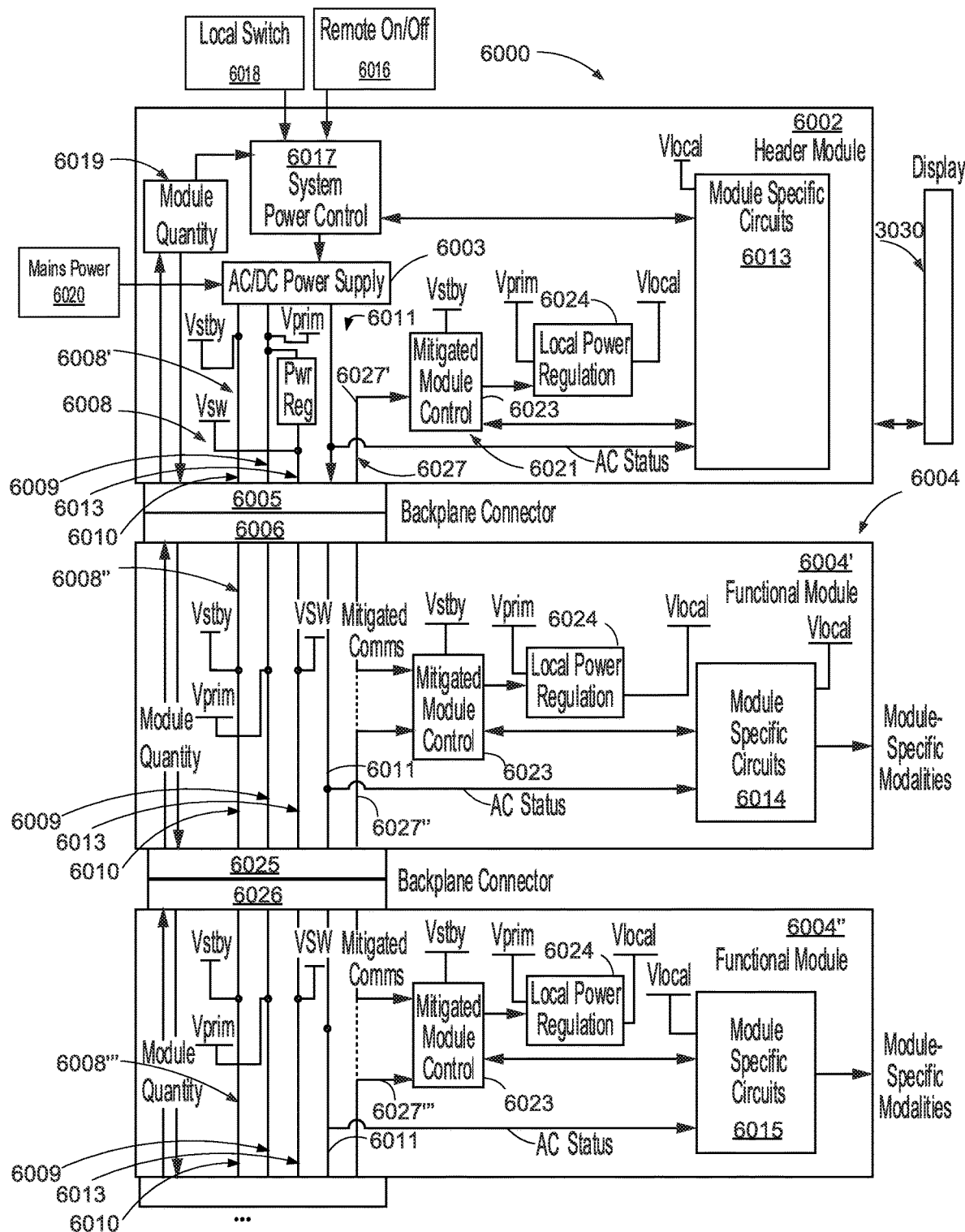
FIG. 15 is a schematic diagram of a modular energy system stack illustrating a power backplane, in accordance with at least one aspect of the present disclosure.

Modular energy system offers many advantages in a surgical procedure, as described above in connection with the modular energy systems 2000 (FIGS. 6-12), 3000 (FIGS. 13-15). However, cable management and setup/teardown time can be a significant deterrent. Various aspects of the present disclosure provide a modular energy system with a single power cable and a single power switch to control startup and shutdown of the entire modular energy system, which obviated the need to individually activate and deactivate each individual module from which the modular energy system is constructed. Also, various aspects of the present disclosure provide a modular energy system with power management schemes that facilitate a safe and, in some instances, concurrent delivery of power to the modules of a modular energy system.

In various aspects, as illustrated in FIG. 15, a modular energy system 6000 that is similar in many respects to the modular energy systems 2000 (FIGS. 6-12), 3000 (FIGS. 13-15). For the sake of brevity, various details of the modular energy system 6000, which are similar to the modular energy system 2000 and/or the modular energy system 3000, are not repeated herein.

The modular energy system 6000 comprises a header module 6002 and an "N" number of surgical modules 6004, where "N" is an integer greater than or equal to one. In various examples, the modular energy system 6000 includes a UI module such as, for example, the UI module 3030 and/or a communication module such as, for example, the communication module 3032. Furthermore, pass-through hub connectors couple individual modules to one another in a stack configuration. In the example of FIG. 15, the header module 6002 is coupled to a surgical module 6004 via pass-through hub connectors 6005, 6006.

The modular energy system 6000 comprises an example power architecture that consists of a single AC/DC power supply 6003 that provides power to all the surgical modules in the stack. The AC/DC power supply 6003 is housed in the header module 6002, and utilizes a power backplane 6008 to distribute power to each module in the stack. The example of FIG. 15 demonstrates three separate power domains on the power backplane 6008: a primary power domain 6009, a standby power domain 6010, and an Ethernet switch power domain 6013.

In the example illustrated in FIG. 15, the power backplane 6008 extends from the header module 6002 through a number of intermediate modules 6004 to a most bottom, or farthest, module in the stack. In various aspects, the power backplane 6008 is configured to deliver power to a surgical module 6004 through one or more other surgical modules 6004 that are ahead of it in the stack. The surgical module 6004 receiving power from the header module 6002 can be coupled to a surgical instrument or tool configured to deliver therapeutic energy to a patient.

The primary power domain 6009 is the primary power source for the functional module-specific circuits 6013, 6014, 6015 of the modules 6002, 6004. It consists of a single voltage rail that is provided to every module. In at least one example, a nominal voltage of 60V can be selected to be higher than the local rails needed by any module, so that the modules can exclusively implement buck regulation, which is generally more efficient than boost regulation.

In various aspects, the primary power domain 6009 is controlled by the header module 6002. In certain instances, as illustrated in FIG. 15, a local power switch 6018 is positioned on the header module 6002. In certain instances, a remote on/off interface 6016 can be configured to control a system power control 6017 on the header module 6002, for example. In at least one example, the remote on/off interface 6016 is configured to transmit pulsed discrete commands (separate commands for On and Off) and a power status telemetry signal. In various instances, the primary power domain 6009 is configured to distribute power to all the modules in the stack configuration following a user-initiated power-up.

Figure 16:
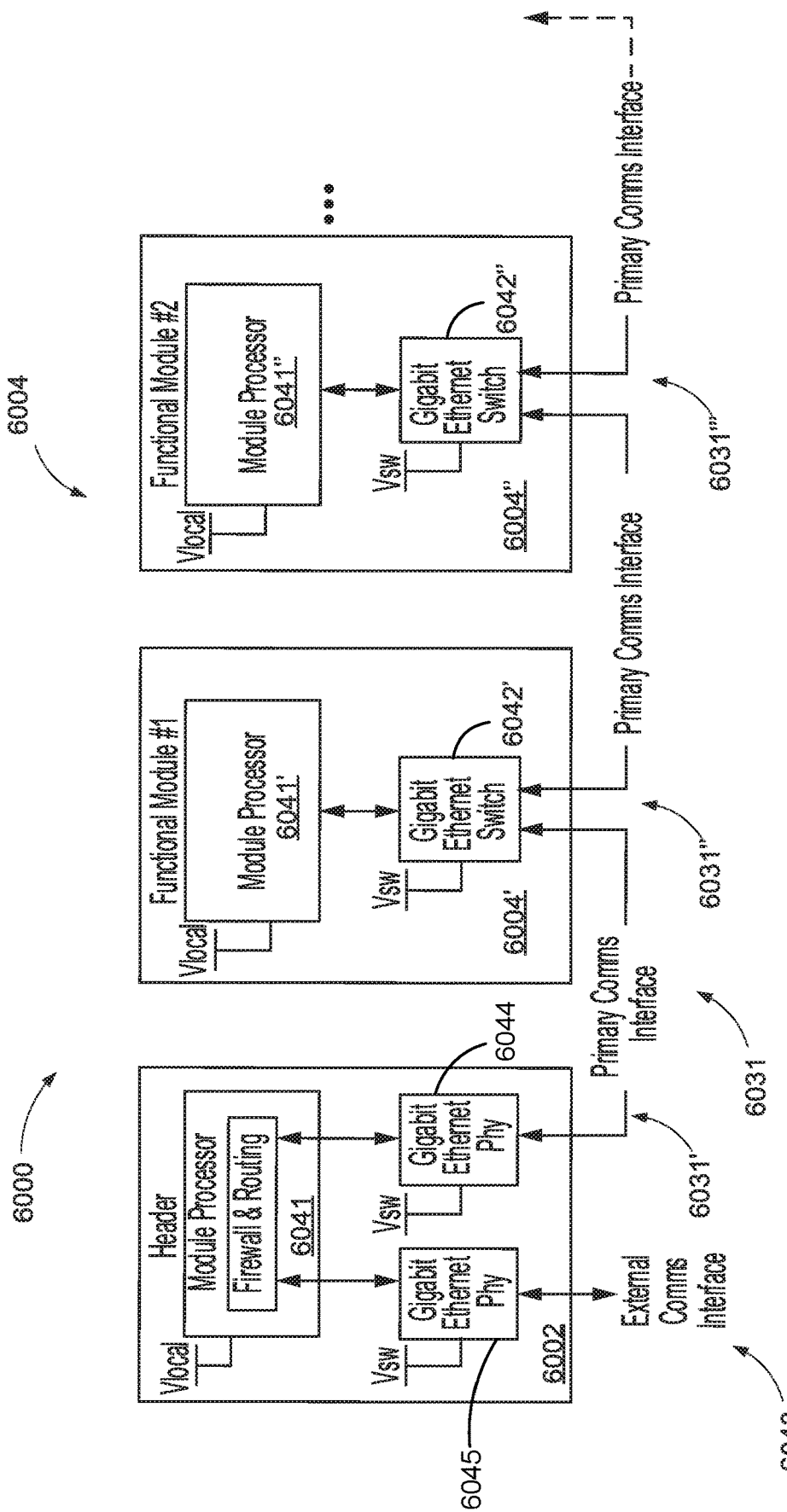
FIG. 16 is a schematic diagram of a modular energy system, in accordance with at least one aspect of the present disclosure.

In various aspects, as illustrated in FIG. 16, the modules of the modular energy system 6000 can be communicably coupled to the header module 6002 and/or to each other via a communication (Serial bus/Ethernet) interface 6040 such that data or other information is shared by and between the modules of which the modular energy system is constructed. An Ethernet switch domain 6013 can be derived from the primary power domain 6009, for example. The Ethernet switch power domain 6013 is segregated into a separate power domain, which is configured to power Ethernet switches within each of the modules in the stack configuration, so that the primary communications interface 6040 will remain alive when local power to a module is removed. In at least one example, the primary communication interface 6040 comprises a 1000BASE-T Ethernet network, where each module represents a node on the network, and each module downstream from the header module 6002 contains a 3-port Ethernet switch for routing traffic to the local module or passing the data up or downstream as appropriate.

Furthermore, in certain examples, the modular energy system 6000 includes secondary, low speed, communication interface between modules for critical, power related functions including module power sequencing and module power status. The secondary communications interface can, for example, be a multi-drop Local Interconnect Network (LIN), where the header module is the master and all downstream modules are slaves.

In various aspects, as illustrated in FIG. 15, a standby power domain 6010 is a separate output from the AC/DC power supply 6003 that is always live when the supply is connected to mains power 6020. The standby power domain 6010 is used by all the modules in the system to power circuitry for a mitigated communications interface, and to control the local power to each module. Further, the standby power domain 6010 is configured to provide power to circuitry that is critical in a standby mode such as, for example, on/off command detection, status LEDs, secondary communication bus, etc.

In various aspects, as illustrated in FIG. 15, the individual surgical modules 6004 lack independent power supplies and, as such, rely on the header module 6002 to supply power in the stack configuration. Only the header module 6002 is directly connected to the mains power 6020. The surgical modules 6004 lack direct connections to the mains power 6020, and can receive power only in the stack configuration. This arrangement improves the safety of the individual surgical modules 6004, and reduces the overall footprint of the modular energy system 6000. This arrangement further reduces the number of cords required for proper operation of the modular energy system 6000, which can reduce clutter and footprint in the operating room.

Accordingly, a surgical instrument connected to surgical modules 6004 of a modular energy system 6000, in the stack configuration, receives therapeutic energy for tissue treatment that is generated by the surgical module 6004 from power delivered to the surgical module 6004 from the AC/DC power supply 6003 of the header module 6002.

In at least one example, while a header module 6002 is assembled in a stack configuration with a first surgical module 6004', energy can flow from the AC/DC power supply 6003 to the first surgical module 6004'. Further, while a header module 6002 is assembled in a stack configuration with a first surgical module 6004' (connected to the header module 6002) and a second surgical module 6004" (connected to the first surgical module 6004'), energy can flow from the AC/DC power supply 6003 to the second surgical module 6004" through the first surgical module 6004'.

The energy generated by the AC/DC power supply 6003 of the header module 6002 is transmitted through a segmented power backplane 6008 defined through the modular energy system 6000. In the example of FIG. 15, the header module 6002 houses a power backplane segment 6008', the first surgical module 6004' houses a power backplane segment 6008", and the second surgical module 6004" houses a power backplane segment 6008'''. The power backplane segment 6008' is detachably coupled to the power backplane segment 6008" in the stack configuration. Further, the power backplane 6008" is detachably coupled to the power backplane segment 6008''' in the stack configuration. Accordingly, energy flows from the AC/DC power supply 6003 to the power backplane segment 6008', then to the power backplane segment 6008", and then to the power backplane segment 6008'''.

In the example of FIG. 15, the power backplane segment 6008' is detachably connected to the power backplane segment 6008" via pass-through hub connectors 6005, 6006 in the stack configuration. Further, the power backplane segment 6008" is detachably connected to the power backplane segment 6008''' via pass-through hub connectors 6025, 6056 in the stack configuration. In certain instances, removing a surgical module from the stack configuration severs its connection to the power supply 6003. For example, separating the second surgical module 6004" from the first surgical module 6004' disconnects the power backplane segment 6008''' from the power backplane segment 6008". However, the connection between the power backplane segment 6008" and the power backplane segment 6008''' remains intact as long as the header module 6002 and the first surgical module 6004' remain in the stack configuration. Accordingly, energy can still flow to the first surgical module 6004' after disconnecting the second surgical module 6004" through the connection between the header module 6002 and the first surgical module 6004'. Separating connected modules can be achieved, in certain instances, by simply pulling the surgical modules 6004 apart.

In the example of FIG. 15, each of the modules 6002, 6004 includes a mitigated module control 6023. The mitigated module controls 6023 are coupled to corresponding local power regulation modules 6024 that are configured to regulate power based on input from the mitigated module controls 6023. In certain aspects, the mitigated module controls 6023 allow the header module 6002 to independently control the local power regulation modules 6024.

The modular energy system 6000 further includes a mitigated communications interface 6021 that includes a segmented communication backplane 6027 extending between the mitigated module controls 6023. The segmented communication backplane 6027 is similar in many respects to the segmented power backplane 6008. Mitigated Communication between the mitigated module controls 6023 of the header module 6002 and the surgical modules 6004 can be achieved through the segmented communication backplane 6027 defined through the modular energy system 6000. In the example of FIG. 15, the header module 6002 houses a communication backplane segment 6027', the first surgical module 6004' houses a communication backplane segment 6027", and the second surgical module 6004" houses a communication backplane segment 6027'". The communication backplane segment 6027' is detachably coupled to the communication backplane segment 6027" in the stack configuration via the pass-through hub connectors 6005, 6006. Further, the communication backplane 6027" is detachably coupled to the communication backplane segment 6027" in the stack configuration via the pass-through hub connectors 6025, 6026.

Although the example of FIG. 15 depicts a modular energy system 6000 includes a header module 6002 and two surgical modules 6004' 6004", this is not limiting. Modular energy systems with more or less surgical modules are contemplated by the present disclosure. In some aspects, the modular energy system 6000 includes other modules such as, for example, a communications module. In some aspects, the header module 6502 supports a display screen such as, for example, the display 2006 (FIG. 7A) that renders a GUI such as, for example, the GUI 2008 for relaying information regarding the modules connected to the header module 6002. The GUI 2008 of the display screen 2006 can provide a consolidated point of control all of the modules making up the particular configuration of a modular energy system.

FIG. 16 depicts a simplified schematic diagram of the modular energy system 6000, which illustrates a primary communications interface 6040 between the header module 6002 and the surgical modules 6004. The primary communications interface 6040 communicably connects module processors 6041, 6041', 6041" of the header module 6002 and the surgical modules 6004. Commands generated by the module processor 6041 of the header module are transmitted downstream to a desired functional surgical module via the primary communications interface 6040. In certain instances, the primary communications interface 6040 is configured to establish a two-way communication pathway between neighboring modules. In other instances, the primary communications interface 6040 is configured to establish a one-way communication pathway between neighboring modules.

Furthermore, the primary communications interface 6040 includes a segmented communication backplane 6031, which is similar in many respects to the segmented power backplane 6008. Communication between the header module 6002 and the surgical modules 6004 can be achieved through the segmented communication backplane 6031 defined through the modular energy system 6000. In the example of FIG. 16, the header module 6002 houses a communication backplane segment 6031', the first surgical module 6004' houses a communication backplane segment 6031", and the second surgical module 6004" houses a communication backplane segment 6031'". The communication backplane segment 6031' is detachably coupled to the communication backplane segment 6031" in the stack configuration via the pass-through hub connectors 6005, 6006. Further, the communication backplane 6031" is detachably coupled to the communication backplane segment 6031" in the stack configuration via the pass-through hub connectors 6025, 6026.

In at least one example, as illustrated in FIG. 16, the primary communications interface 6040 is implemented using the DDS framework running on a Gigabit Ethernet interface. The module processors 6041, 6041', 6041" are connected to Gigabit Ethernet Phy 6044, and Gigabit Ethernet Switches 6042', 6042". In the example of FIG. 16, the segmented communication backplane 6031 connects the Gigabit Ethernet Phy 6044 and the Gigabit Ethernet Switches 6042 of the neighboring modules.

In various aspects, as illustrated in FIG. 16, the header module 6002 includes a separate Gigabit Ethernet Phy 6045 for an external communications interface 6043 with the processor module 6041 of the header module 6002. In at least one example, the processor module 6041 of the header module 6002 handles firewalls and information routing.

Referring to FIG. 15, the AC/DC power supply 6003 may provide an AC Status signal 6011 that indicates a loss of AC power supplied by the AC/DC power supply 6003. The AC status signal 6011 can be provided to all the modules of the modular energy system 6000 via the segmented power backplane 6008 to allow each module as much time as possible for a graceful shutdown, before primary output power is lost. The AC status signal 6011 is received by the module specific circuits 6013, 6014, 6015, for example. In various examples, the system power control 6017 can be configured to detect AC power loss. In at least one example, the AC power loss is detected via one or more suitable sensors.

Referring to FIGS. 15 and 16, to ensure that a local power failure in one of the modules of the modular energy system 6000 does not disable the entire power bus, the primary power input to all modules can be fused or a similar method of current limiting can be used (e-fuse, circuit breaker, etc.). Further, Ethernet switch power is segregated into a separate power domain 6013 so that the primary communications interface 6040 remains alive when local power to a module is removed. In other words, primary power can be removed and/or diverted from a surgical module without losing its ability to communicate with other surgical modules 6004 and/or the header module 6002.

Surgical Procedurelization Via Modular Energy System

Having described a general implementation the header and modules of modular energy systems 2000, 3000, 6000, the disclosure now turns to describe various aspects of other modular energy systems. The other modular energy systems are substantially similar to the modular energy system 2000, the modular energy system 3000, and/or the modular energy system 6000. For the sake of brevity, various details of the other modular energy systems being described in the following sections, which are similar to the modular energy system 2000, the modular energy system 3000, and/or the modular energy system 6000, are not repeated herein. Any aspect of the other modular energy systems described below can be brought into the modular energy system 2000, the modular energy system 3000, or the modular energy system 6000.

Case Proceduralization Via the Modular Energy System

As surgical procedures are performed using various aspects of the modular energy system disclosed above, data related to the procedures may be collected and stored. For example, the modular energy system may collect and store data corresponding to when an energy port is activated, the energy modality provided by the activated port, the power level provided by the activated port, the activation time, and the method by which the port was activated (e.g., a first single-pedal footswitch, a second single-pedal footswitch, a dual-pedal foot switch, etc.). By reviewing and analyzing the data collected, surgeons and other users can gain valuable insight related to their performance during a surgical procedure. However, as with any integrated visualization system, there are challenges related to sorting the large amount of data that is collected. For example, it may not be meaningful for surgeons to compare unsorted data collected across multiple surgical procedures because the complexity of each surgical procedure may vary. Accordingly, there is a need for systems and methods to organize the data collected by modular energy systems based on the specific surgical procedure that is being performed.

In one aspect of the present disclosure, data collected by the modular energy system during a surgical procedure is organized based on predefined procedural checklists. Further, the steps of each predetermined checklist correspond with the mental model that a surgeon may follow during a given procedure. The predetermined checklist may be displayed by a display screen of the modular energy system. Throughout the procedure, the surgeon interacts with the modular energy system to identify when each step of the checklist is complete.

For example, as the surgeon carries out a surgical procedure, the display screen may display a current expected step of the procedure based on a predefined procedural checklist. In alternate aspects, the display screen may display the current expected step in addition to all of the expected steps of the surgical procedure. The surgeon then indicates when the current step of the procedure is complete by "flagging" the step. Flagging may be carried out by interacting with a touch screen graphical user interface (GUI) rendered on the display screen, by voice command, by using a keyboard connected to the modular energy system, or by other means. If while performing the surgical procedure, the surgeon determines that a step of the predefined checklist will not be carried out, the surgeon may manually skip or override the step. The process of flagging each step continues until all steps of the predefined checklist are complete. In other cases, a surgical procedure may require multiple checklists (e.g., a sleeve gastrectomy with a cholecystectomy), in which case, each checklist is displayed and flagged by the surgeon unit the entire procedure is complete. The modular energy system organizes the collected data based on the corresponding flagged step of the surgical procedure. The organized data is logged into an event log for future use. As a result, by accessing the event log, surgeons and other users are beneficially able to review data related to the surgical procedure based on which low-level step of the procedure the data is associated with.

In another aspect of the present disclosure, surgeons may choose to not use a predefined checklist. In this case, a surgeon performing a surgical procedure is able to freely flag steps of the procedure as they are completed. These flagged steps are timestamped by the modular energy system. Further, a description of the step may be added by the surgeon or another user (e.g., via touchscreen GUI, voice command, keyboard, etc.). Similar to the description above, the modular energy system organizes the collected data based on the corresponding flagged steps of the surgical procedure and logs the data into an event log for future use. If neither the use of a predefined checklist nor manual flagging is desired, surgical procedures may be performed without utilizing either method.

There are numerous benefits associated with utilizing predetermined procedural checklists. First, the use of checklists bring standardization to surgery. The use of standard checklists have been a growing trend in the medical field, especially related to what are considered routine procedures. Using a predetermined checklist is helpful to the entire operating room staff because it informs them as to which step of the surgical procedure is currently being performed. This is especially helpful for staff who are in training and for complicated procedures with many steps.

Further, the use of predetermined checklists with user-flagged steps beneficially allows for data segregation. Segregated data is easily reviewable by surgeons. Moreover, by reviewing the segregated data, surgeons are better able to analyze their performance during a procedure. For example, a surgeon may discover that he or she is slow during access but very fast during resection, in comparison to some other group (e.g., surgeons worldwide, surgeons nationally, or surgeons at the same hospital). This type of data organization also provides insight related to how surgeons' techniques differ. Moreover, the data stored may be paired with visual recordings of surgical procedures. This pairing beneficially allows for the visual recordings to be segregated into sub-videos based on each procedural step, allowing for a more organized and quicker review of the recording. Information about the specific step may also be displayed with the sub-videos. This could be especially useful for training surgeons and other staff.

Additionally, segregation of data based on predetermined procedural checklists may be useful to modular energy system manufacturers. For example, segregated data allows for easier comparison across multiple procedures. Because data can be more easier compared, users may me more willing to share data with the manufacturer.

Figure 17:
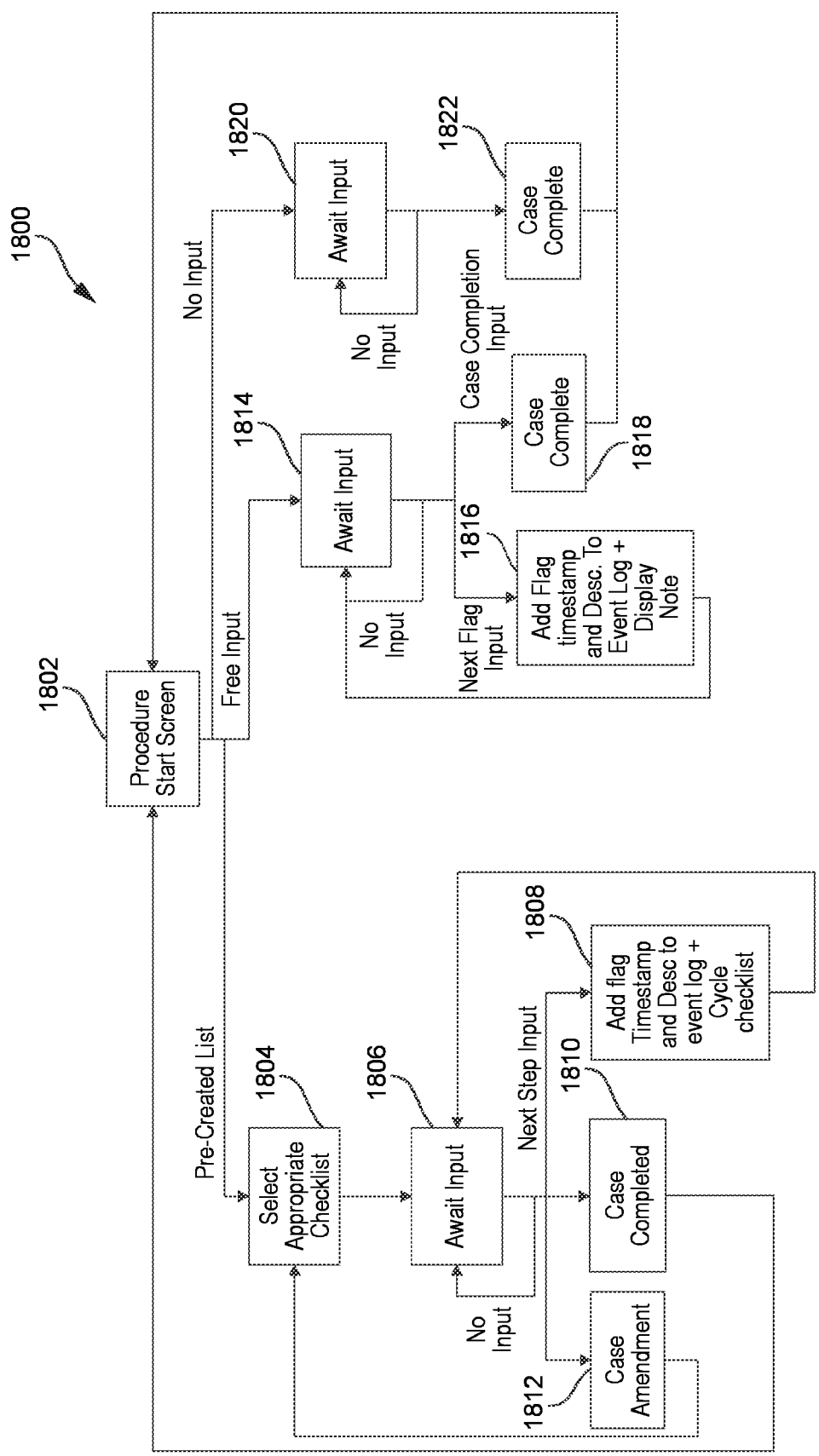
FIG. 17 is a flowchart of a process for organizing data collected during a surgical procedure, in accordance with at least one aspect of the present disclosure.

Referring to FIG. 17, a process for organizing data collected during a surgical procedure 1800 begins at a procedure start screen 1802. At procedure start screen 1802, the display screen of the modular energy system prompts the user (e.g., surgeon) to select whether a pre-created list, free input, or no input will be used. If a pre-created list (or predetermined checklist) is selected, the user is then prompted to select the appropriate checklist for the procedure at 1804. Once the checklist is selected, the user may start performing the surgical procedure, at which point the modular energy system awaits input at 1806. As the user completes a first step of the surgical procedure, which is associated with the first step of the checklist, the user provides an input instructing the system to flag the first step at 1808. At this point, the system associates a timestamp and description with the data collected during the first step of the procedure. The modular energy system also causes the display screen to display the next step of the predetermined checklist and awaits further input at 1806. This process repeats for every step of the checklist. If the user wishes to change or amend the checklist used, the user may provide an input for case amendment at 1812. The user is then prompted to select the appropriate checklist at 1804 and the process continues. Upon completion of the surgical procedure, the user provides an input indicating the case is complete at 1810 and the process returns to procedure start screen 1802.

If instead the user selects the free input option at procedure start screen 1802, the user may start performing the surgical procedure, at which point the modular energy system awaits input at 1814. As the user completes a first step of the surgical procedure, the user provides an input instructing the system to flag the first step at 1816. At this point, the system associates a timestamp with the data collected during the first step of the procedure. The user may also be prompted to provide a description for the completed step. The system then awaits further input at 1814. As the user completes the next step of the procedure, the user again provides an input instructing the system to flag the step at 1816. This process repeats until the user provides an input indicating the case is complete at 1818 and the process returns to procedure start screen 1802.

If the user selects the no input option at procedure start screen 1802, the user may start performing the surgical procedure, at which point the modular energy system awaits input at 1820. The process will remain at 1820 unit the user provides an input indicating the case is complete at 1822 and the process returns to procedure start screen 1802.

Figure 18:
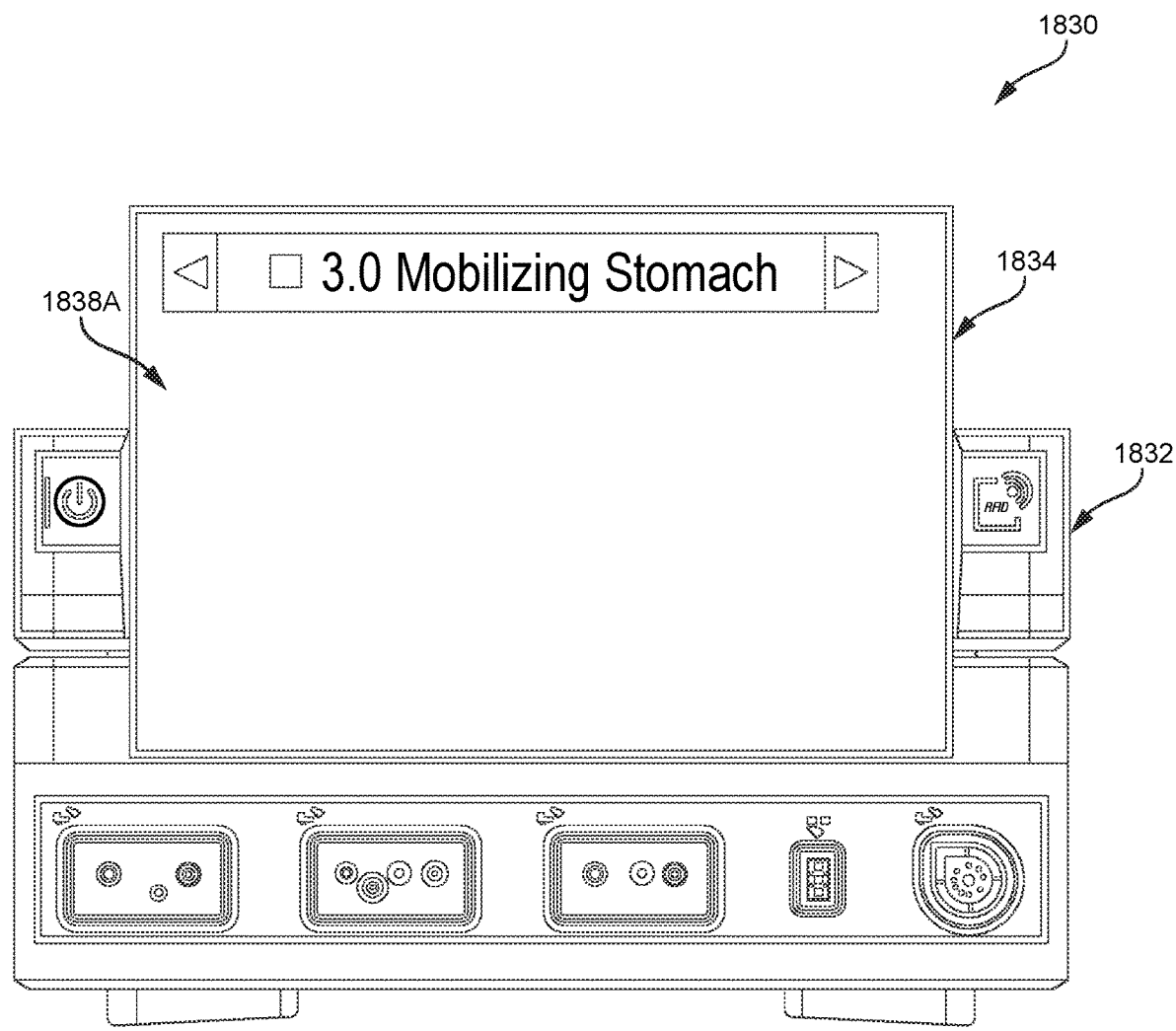
FIG. 18 is an illustrative modular energy system displaying a current step of a predefined checklist, in accordance with at least one aspect of the present disclosure.
Figure 19:
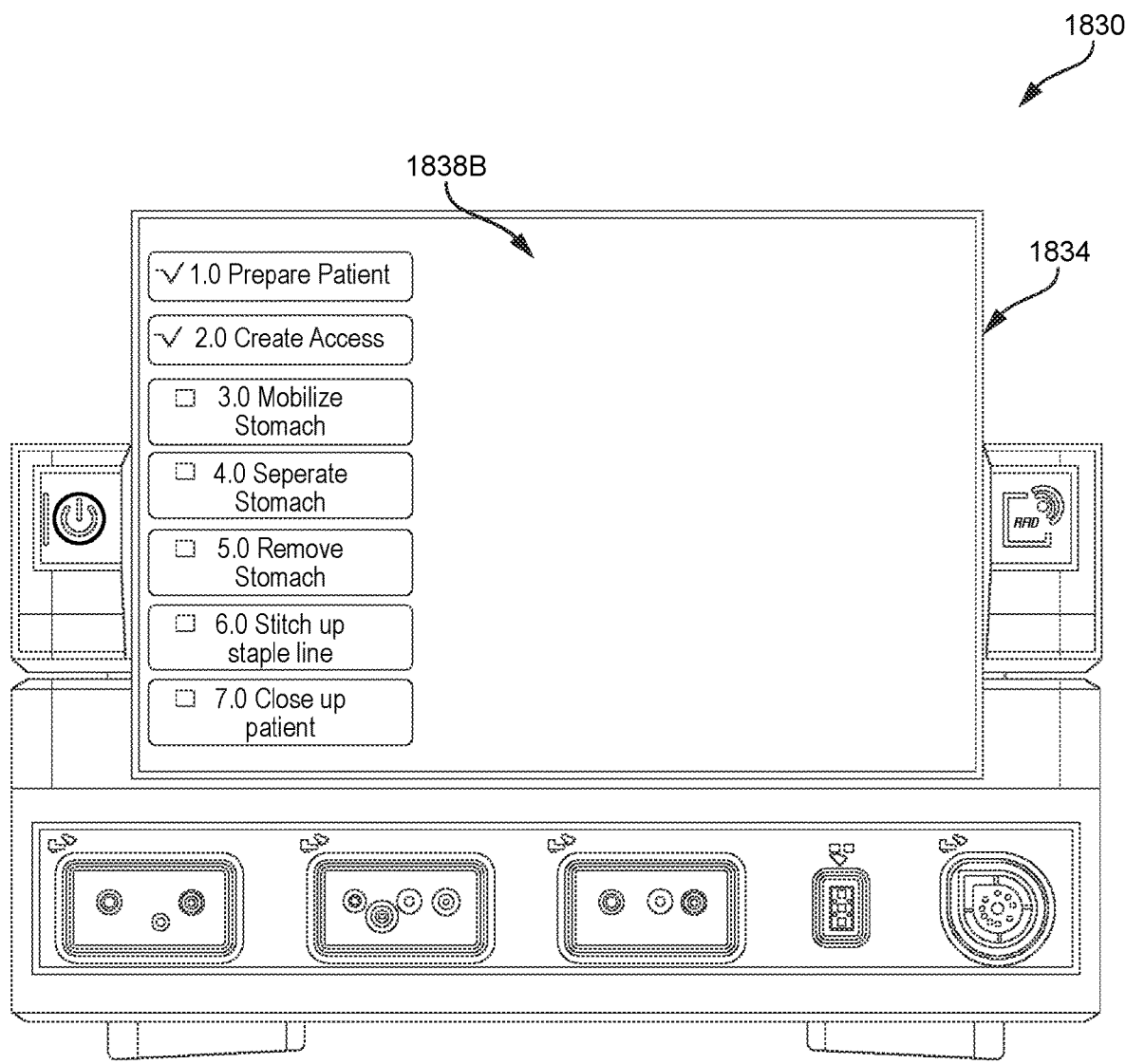
FIG. 19 is an illustrative modular energy system displaying all steps of a predefined checklist, in accordance with at least one aspect of the present disclosure.

FIG. 18 depicts a modular energy system displaying a current step of a predetermined checklist. Modular energy system 1830 includes a header module 1832 with a display screen 1834. In this example, GUI 1838A is rendered on the display screen 1834 and is displaying a current step of a predefined checklist (e.g., 3.0 Mobilizing Stomach). Alternatively, as depicted in FIG. 19, the modular energy system may display all steps of a predetermined checklist. In this example, GUI 1838B is rendered on the display screen 1834 and is displaying not only the current step of the procedure (e.g., 3.0 Mobilizing Stomach), but also the completed steps (e.g., 1.0 Prepare Patient, 2.0 Create Access) as well as future steps (e.g., 4.0 Separate Stomach, 5.0 Remove Stomach, 6.0 Stich Up Staple Line, 7.0 Close Up Patient).

Figure 20:
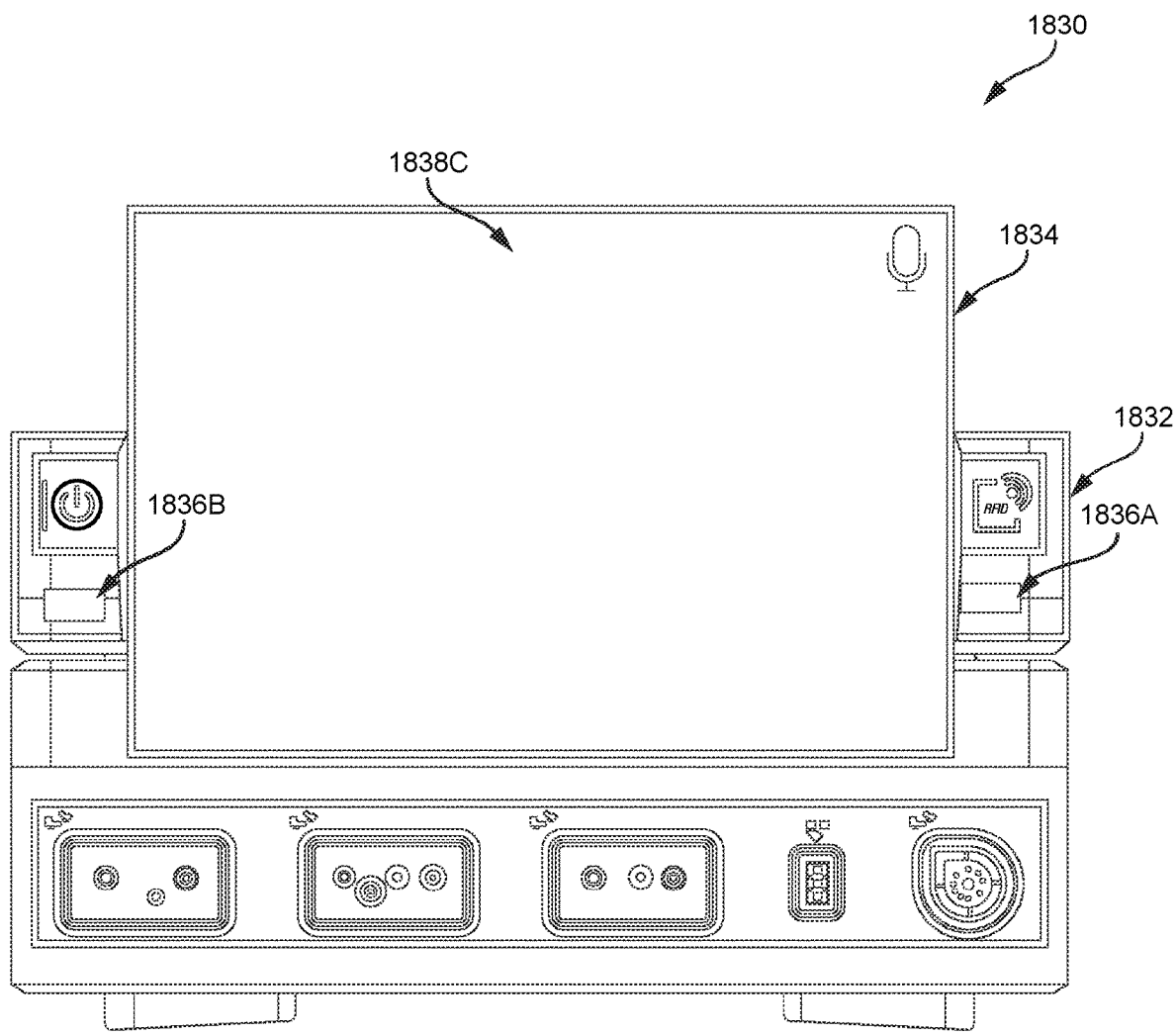
FIG. 20 is an illustrative modular energy system configured for voice activation, in accordance with at least one aspect of the present disclosure.
Figure 21:
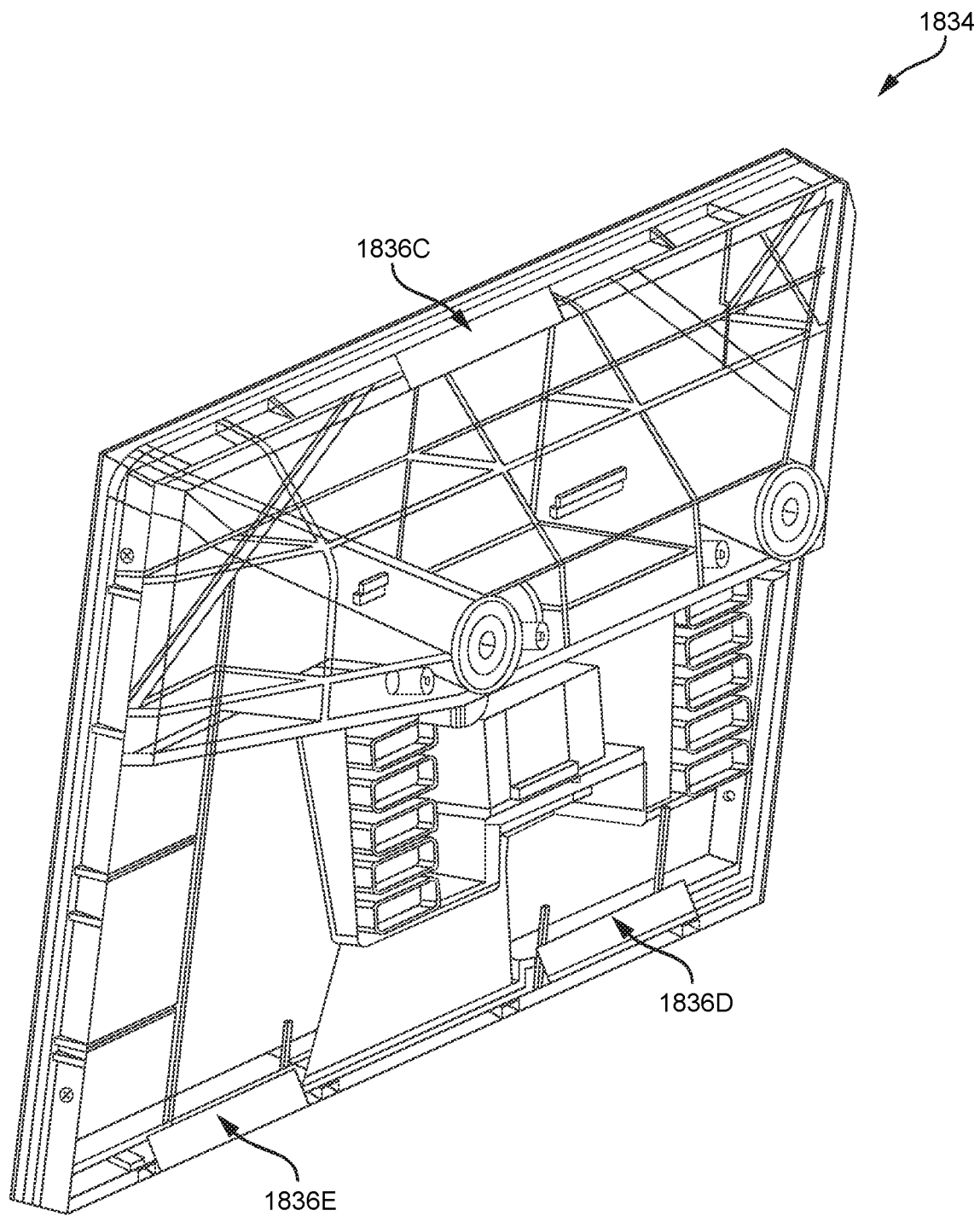
FIG. 21 is an illustrative a display screen configured for voice activation, in accordance with at least one aspect of the present disclosure.

FIG. 20 depicts a modular energy system configured for voice activation. Modular energy system 1830 includes a header module 1832 and a display screen 1834 with touchscreen capability. In this example, GUI 1838C is rendered on display screen 1834 and is displaying a microphone symbol. As a user completes a step of a surgical procedure, the user touches the microphone symbol indicating that a voice command will be entered. Via voice command, the user indicates that a step of the surgical procedure has been completed. If the user is performing a procedure using the free input option described above, the user may also provide a voice command that includes a description of the completed step. A microphone installed on modular energy system 1830 captures the voice command. For example, modular energy system 1830 may include microphone(s) 1836A and/or 1836B located on the header module 1832. Alternatively, referring to FIG. 21, microphone(s) 1836C, 1836D and/or 1836E may be located on display screen 1834. Locating the microphone(s) on the display screen 1834 beneficially allows for the upgrade of existing modular energy systems to include a microphone without the need to change the entire header module. Similarly, to accommodate users who may be concerned about having a microphone in the operating room, locating the microphone on the display screen allows for easy construction of non-microphone versions of the modular energy system by simply using a different display screen.

Surgeon Profile Case Data Feedback

As explained above, by reviewing and analyzing data collected by the modular energy system, surgeons and other users can gain valuable insight related to their performance during a surgical procedure. For example, a surgeon may benefit by comparing his or her instrument usage patterns to other surgeons in order to identify areas for improvement. Technicians, engineers, and sales representatives may also use collected data to assist with troubleshooting equipment issues. However, because a large amount of data is collected by modular energy systems, quickly and easily accessing the most meaningful data is challenging. Accordingly, there is a need for systems and methods that provide users with streamlined access to relevant information related to surgical procedures performed using modular energy systems.

In one aspect of the present disclosure, the modular energy system provides feedback to users (e.g., surgeons) by presenting information related to the users' usage patterns. Each user of the modular energy system may have a unique user profile. As described above, data is collected during surgical procedures as the user "flags" or tags specific steps performed throughout the procedure. As the user inputs these flags, the collected data is organized based on the procedural step it is corresponds to. The modular energy system is configured to present this organized data in a streamlined manner. For example, users may view a summary of their usage patterns for a specific procedure or a summary of their usage patterns across multiple procedures. Usage pattern data related to specific procedures may also be organized chronologically and displayed with video recorded during the procedure. As discussed in more detail related to FIGS. 22 through 24, each of these methods of data presentation may be viewed as a chart rendered on a display screen of the modular energy system.

Figure 22:
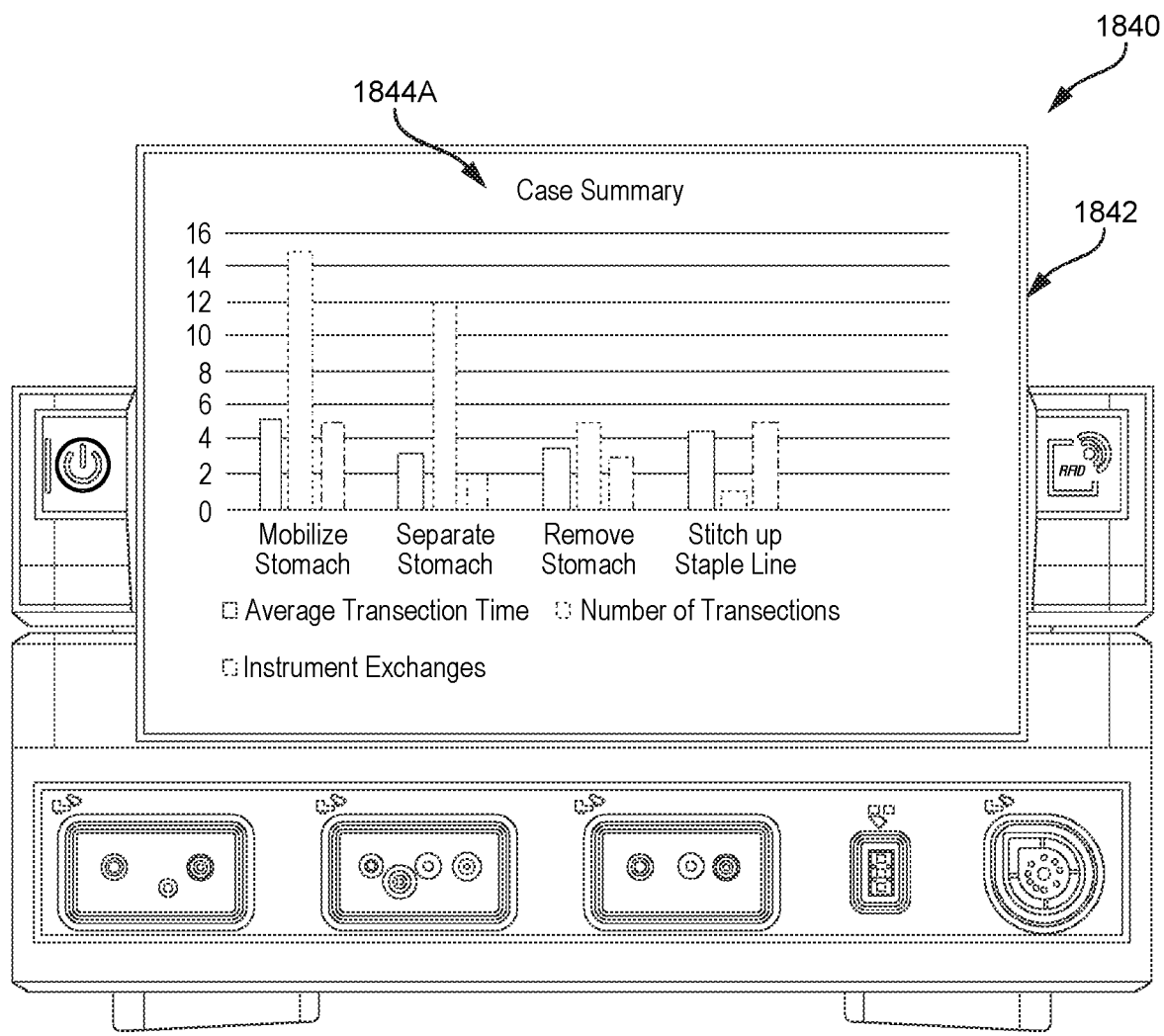
FIG. 22 is an illustrative display screen of a modular energy system displaying usage pattern data related to a specific surgical procedure, in accordance with at least one aspect of the present disclosure.

FIG. 22 depicts a display screen 1842 of a modular energy system 1840 displaying usage pattern data related to an exemplary surgical procedure. The usage data shown on screen 1844A of display screen 1842 is organized using a bar graph. In this example, the surgical procedural summary (or case summary) being displayed includes four steps: Mobilize Stomach; Separate Stomach; Remove Stomach; and Stich Up Staple Line. For each step, the average transection time, number of transactions, and number of instrument exchanges is visually displayed on the bar graph. Other types of usage pattern data and methods of visual presentation (e.g., line graphs, charts, etc.) may similarly be implemented using the modular energy system. This type of information presentation beneficially allows for users to easily visualize their instrument utilization patterns and assess their performance related to a specific surgical procedure.

Figure 23:
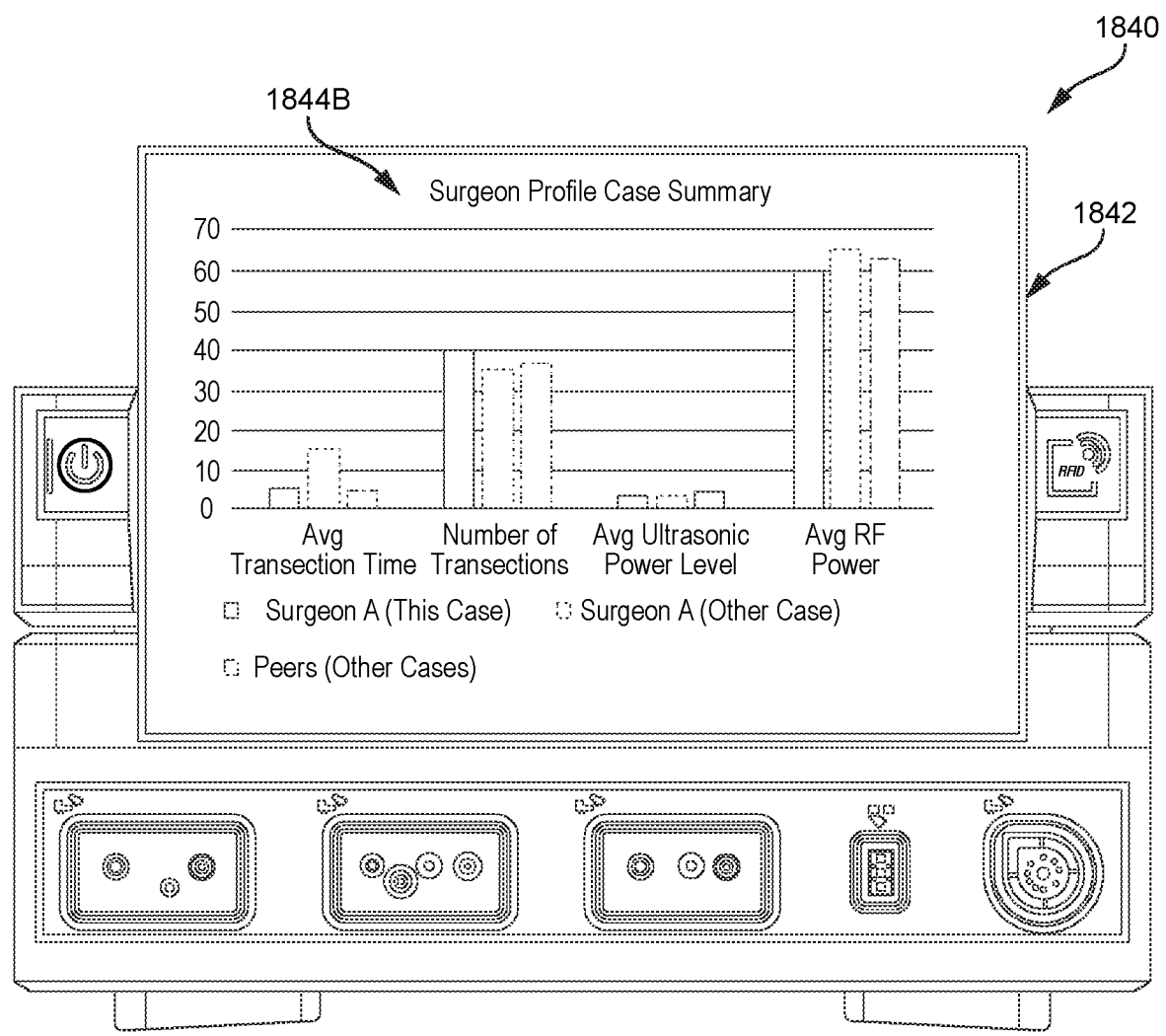
FIG. 23 is an illustrative display screen of a modular energy system displaying usage pattern data of an exemplary user profile across multiple surgical procedures, in accordance with at least one aspect of the present disclosure.

FIG. 23 depicts a display screen 1842 of a modular energy system 1840 displaying usage pattern data based on an exemplary user profile across multiple surgical procedures. The usage data shown on screen 1844B of display screen 1842 is organized using on a bar graph. In this example, the user's (e.g., surgeon's) average transection time, number of transactions, average ultrasonic power level used, and average RF power level used for a specific surgical procedure (case) is compared to other procedures (cases) performed by that user, as well as to the average values corresponding to usage data of that user's peers (e.g., other surgeons). By viewing screen 1844B, a surgeon is able to, for example, quickly identify that their average transection time for the procedure that was just performed (this case) is lower than their average transection time for other procedures (other cases), and similar to the average transection time of his or her peers. Other types of usage pattern data and methods of visual presentation (e.g., line graphs, charts, etc.) may similarly be implemented using the modular energy system. This type of comparison is beneficial because it allows users to anticipate their future needs and behaviors by comparing their usage patterns to their peers. As described above, peer groups may be defined and sorted geographically (e.g., surgeons worldwide, surgeons nationally, or surgeons at the same hospital).

Figure 24:
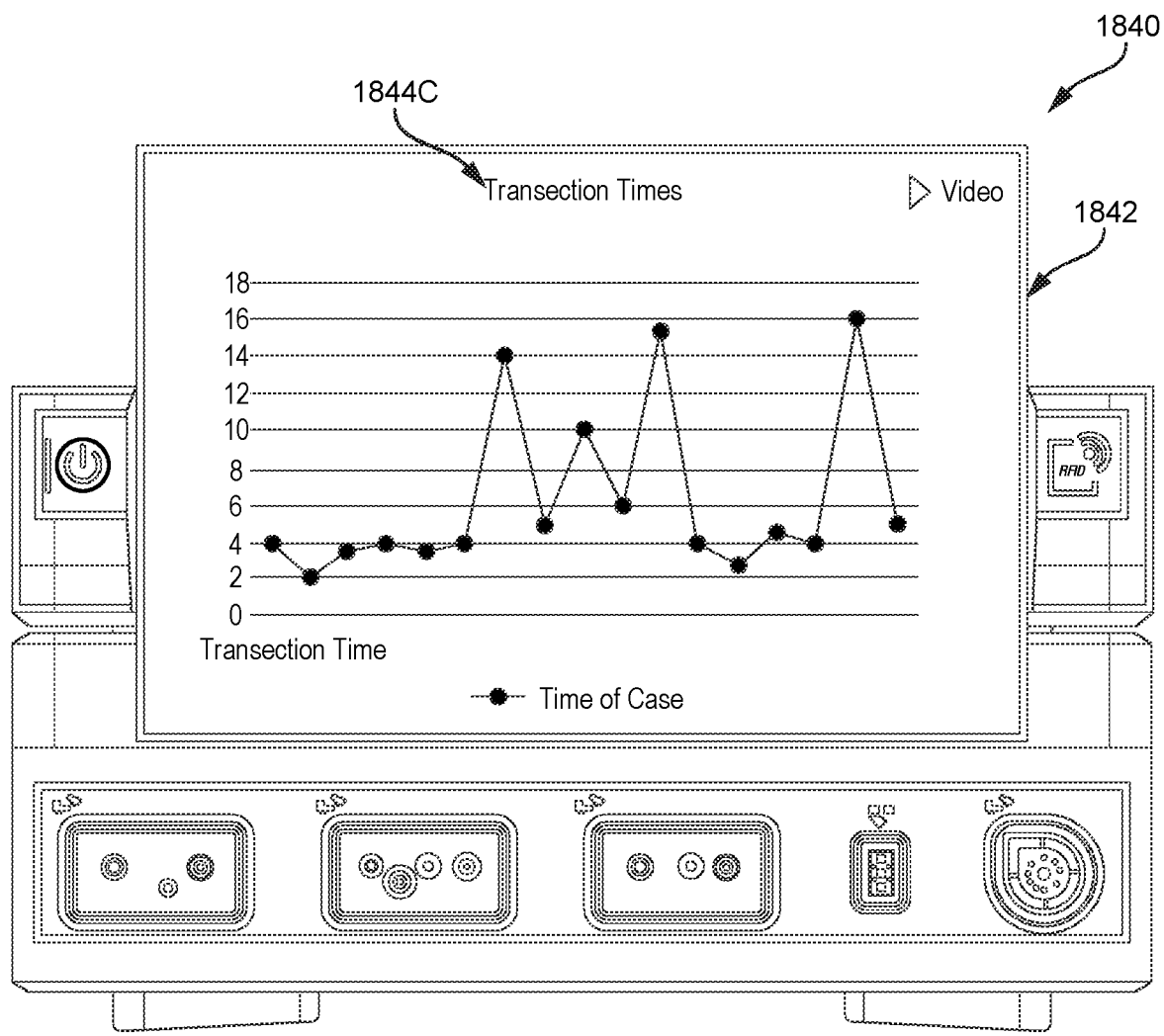
FIG. 24 is an illustrative display screen of a modular energy system displaying transection times of an exemplary surgical procedure, in accordance with at least one aspect of the present disclosure.

FIG. 24 depicts a display screen 1842 of a modular energy system 1840 displaying the transection times of an exemplary surgical procedure. The transection time data shown on screen 1844C of display screen 1842 is organized using a line graph. In this example, the time required to perform each transection of the procedure (case) is displayed from left to right across the line graph, corresponding to when the transections occurred chronologically. Again, other types of usage pattern data and methods of visual presentation (e.g., line graphs, charts, etc.) may similarly be implemented using the modular energy system. Further, screen 1844C also includes a video icon that, when selected by the user, allows the user to view a video recording of the procedure. This type of data organization beneficially allows for users to troubleshoot complaints. For example, if a surgeon complains that he or she consistently has longer transection times than others, and pad burn-throughs are observed, comparing the data displayed on screen 1844C with instrument usage beneficially enables a quicker complaint analysis. A technician, sales representative, or engineer troubleshooting the complaint may be able to identify issues while on-site, or remotely, by accessing a summary similar that of screen 1844C. To gain further insight related to the complaint, the technician, engineer, or sales representative may also access paired video from the visualization system that the modular energy system has correlated with the captured data.

Figure 25:
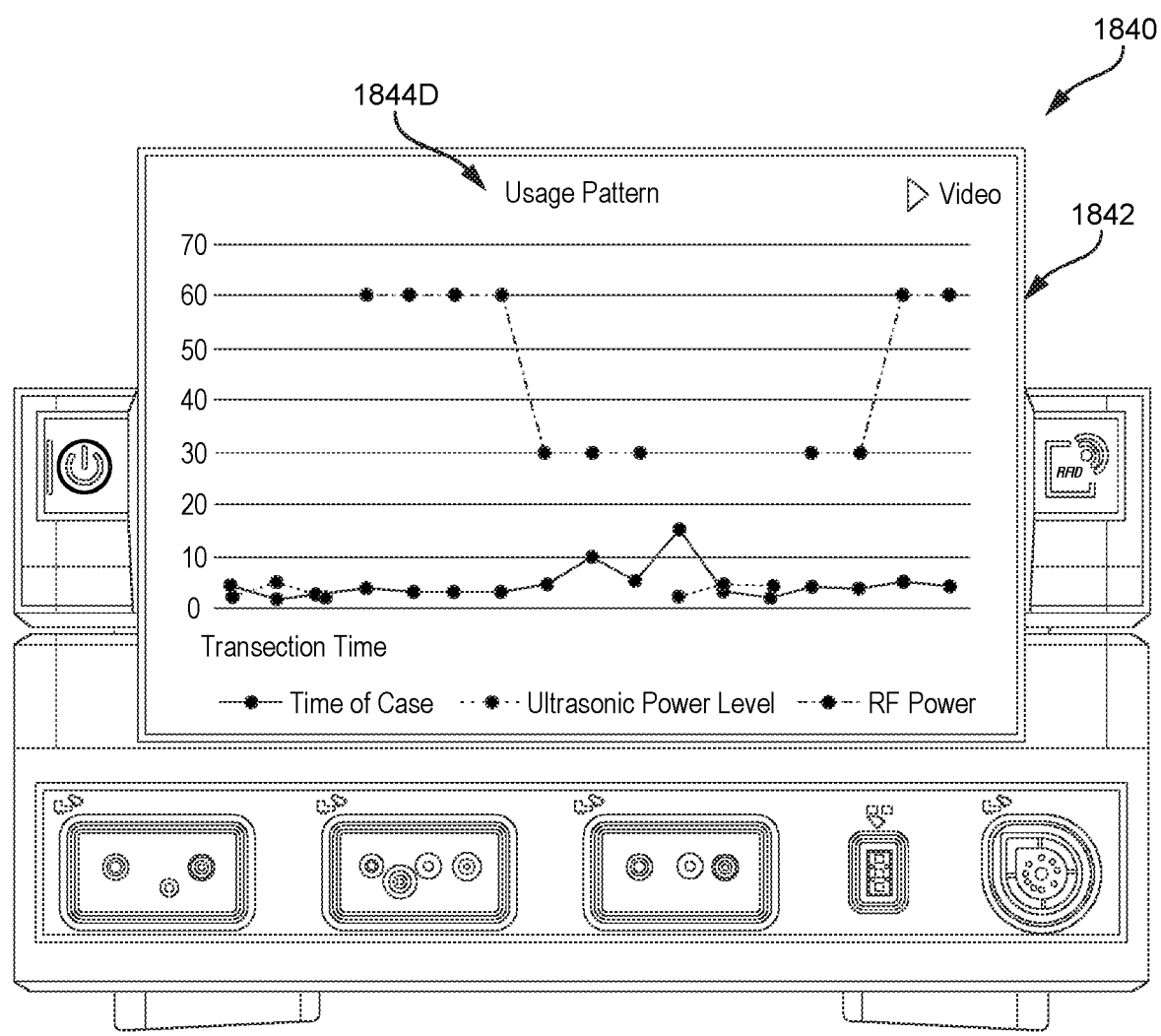
FIG. 25 is an illustrative display screen of a modular energy system displaying various usage patterns of an exemplary surgical procedure, in accordance with at least one aspect of the present disclosure.

FIG. 25 depicts a display screen 1842 of a modular energy system 1840 displaying various usage patterns of an exemplary surgical procedure. The usage pattern data shown on screen 1844D of display screen 1842 is organized using a line graph. In this example, the time required to perform each transection during the procedure (case) is displayed from left to right across the line graph, corresponding to when the transactions occurred chronologically. Also displayed is the harmonic or RF power level used for each transection. Again, other types of usage pattern data and methods of visual presentation (e.g., line graphs, charts, etc.) may similarly be implemented using the modular energy system. Further, screen 1844D also includes a video icon that, when selected by the user, allows the user to view a video recording of the procedure. Using one or several screens similar to screen 1844D, users may postoperatively analyze transection times compared against the corresponding the harmonic and RF power parameters used for the transections and determine how to better optimize transection time based on power level. Additionally, users may use this chart as a basis for which to analyze what happened during a long transection, or other data trends identified on the screen. Further, if the data was tied to a flagged step of the procedure, users may review video captured by the visualization system based on a timestamp corresponding to the flagged step.

The modular energy system may also be configured to analyze core instrument usage patterns against instrument presets (e.g., power level) and display data in a similar format to that depicted in screens 1844A-D. The modular energy system may be further configured to identify when usage patterns related to a given user profile change. Based on this identification, the modular energy system may prompt the user to update his or her instrument presets.

Enhanced Event Log Viewer

In various aspects of the present disclosure, the modular energy system may collect and store data related to events that occur while the system is in use. Events may be related to, for example, instrument usage (e.g., when an energy port is activated, the energy modality provided by the activated port, the power level provided by the activated port, the activation time, and the method by which the port was activated). Events may also be related to instrument and other system hardware errors (e.g., when a hand piece is no longer functioning, when communication to a footswitch has been lost, etc.). However, the modular energy system may also store and collect data related to numerous other events that do not occur during a surgical procedure (e.g., events related to output verification). Because of the large amount of data that is collected, navigating all of the events logged by the system is challenging. Accordingly, there is a need for systems and methods that allow users to easily access an event log that is comprised of a subset of all the stored events, such that the event log improves user experience related to event navigation and troubleshooting.

In one aspect of the present disclosure, the modular energy system is able to determine which events are related to a surgical procedure based on the detection of a predetermined series of events. For example, specific actions such as connecting various instruments, activating instruments, and disconnecting instruments may cause the modular energy system to recognize all events occurring between this predetermined series of events as events related to a specific procedure. Based on this recognition, the modular energy system may categorize and group these events as a surgical procedure. The modular energy system may also recognize when a series events are related to something other than a surgical procedure. For example, inserting a verification key and proceeding to activate various energy ports may trigger the system to recognize a series of events as relating to output verification. Using a graphical user interface rendered on a display screen of the modular energy system, users are able to access an event log wherein the event log displays only a subset of all stored events, and wherein the events in the event log are grouped based on different categories of system activity (e.g., surgical procedure, output verification, software update, etc). This easy-to-read, graphic display of information related to categorized events beneficially enables users (e.g., surgeons, technical support staff, etc.) to quickly assess and diagnose issues related to the modular energy system after they arise. Moreover, the organization of the event log, for example, as disclosed in the description accompanying FIGS. 26-31, beneficially makes it easier for users to find and access relevant event information. The various graphical user interface (GUI) screens shown in FIGS. 26-31 may be rendered by a display screen of the modular energy system, for example, similar to display screen 2006 and graphical user 2008 interface shown in FIG. 7A. The specific procedural event details shown in FIGS. 26-31 are illustrative examples and have been provided to assist in explaining the general layout, organization, user interaction, and function of the event log, in accordance with at least one aspect of the present disclosure.

Figure 26:
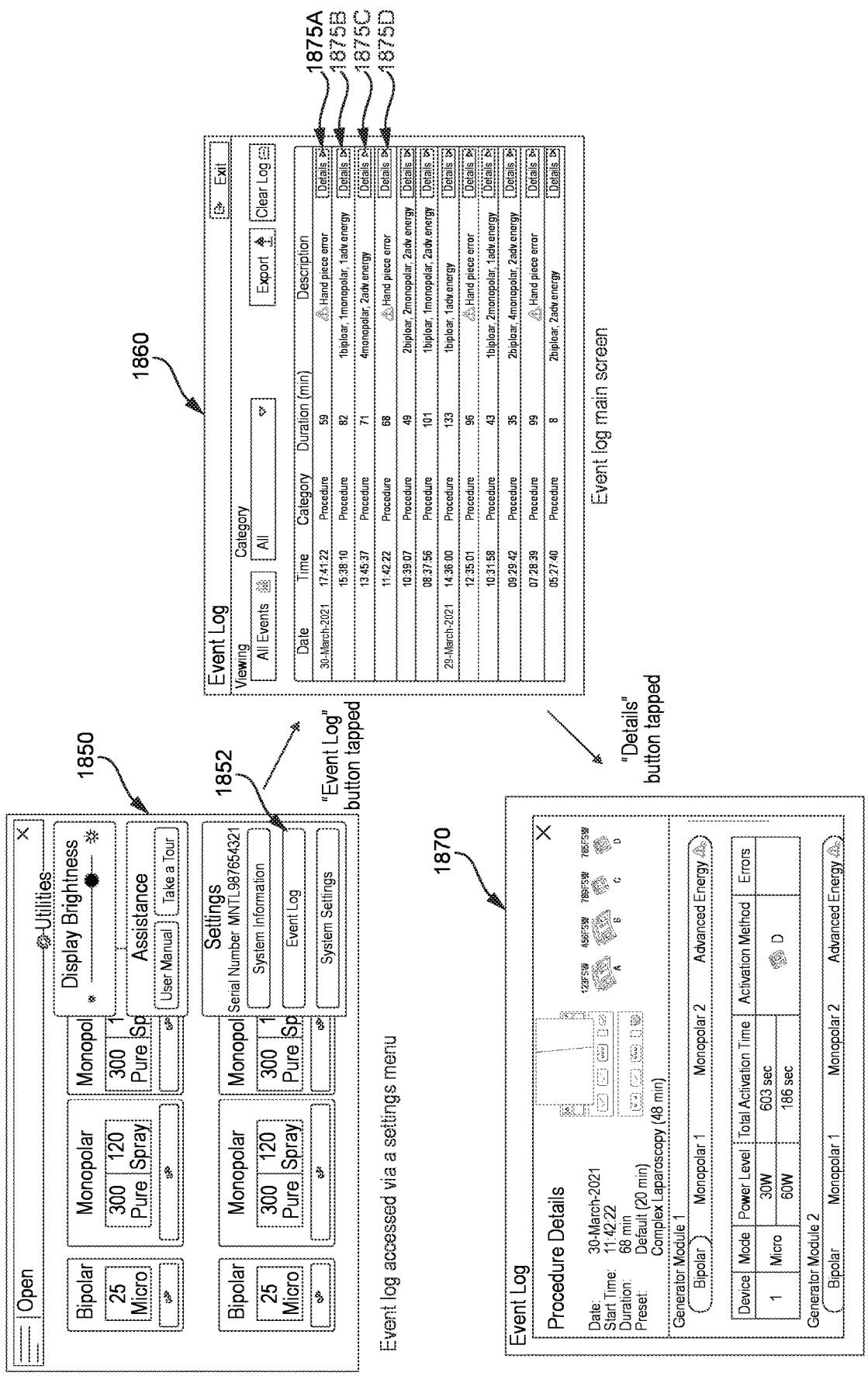
FIG. 26 is an illustrative series of graphical user interface screens that depict a general architecture of a modular energy system event log, in accordance with at least one aspect of the present disclosure.

FIG. 26 is an illustrative series of GUI screens that depict a general architecture of a modular energy system event log. Settings menu screen 1850 depicts a settings menu of the modular energy system GUI. Settings menu screen 1850 may be accessed by tapping a utilities or settings button displayed on the GUI main screen (GUI main screen not shown). To access the event log main screen 1860 from the settings menu screen 1850, the user taps the event log button 1852. Event log main screen 1860 displays groupings of events recorded and/or stored by the modular energy system based on category (e.g., procedure, output verification, etc.). The table shown on event log main screen 1860 includes rows related to each grouping of events (i.e. each procedure, output verification, etc.). The end of each row includes a details button (e.g., details button 1875A, 1875B, 1875C, 1875D, etc.). When the user taps on one of the details buttons, the GUI displays an event log details modal related to the specific grouping (i.e. procedure) that was selected. For example, tapping details button 1875D, which corresponds to the fourth procedure listed on event log main screen 1860, causes the modular energy system to display event log details modal 1870.

Figure 27:
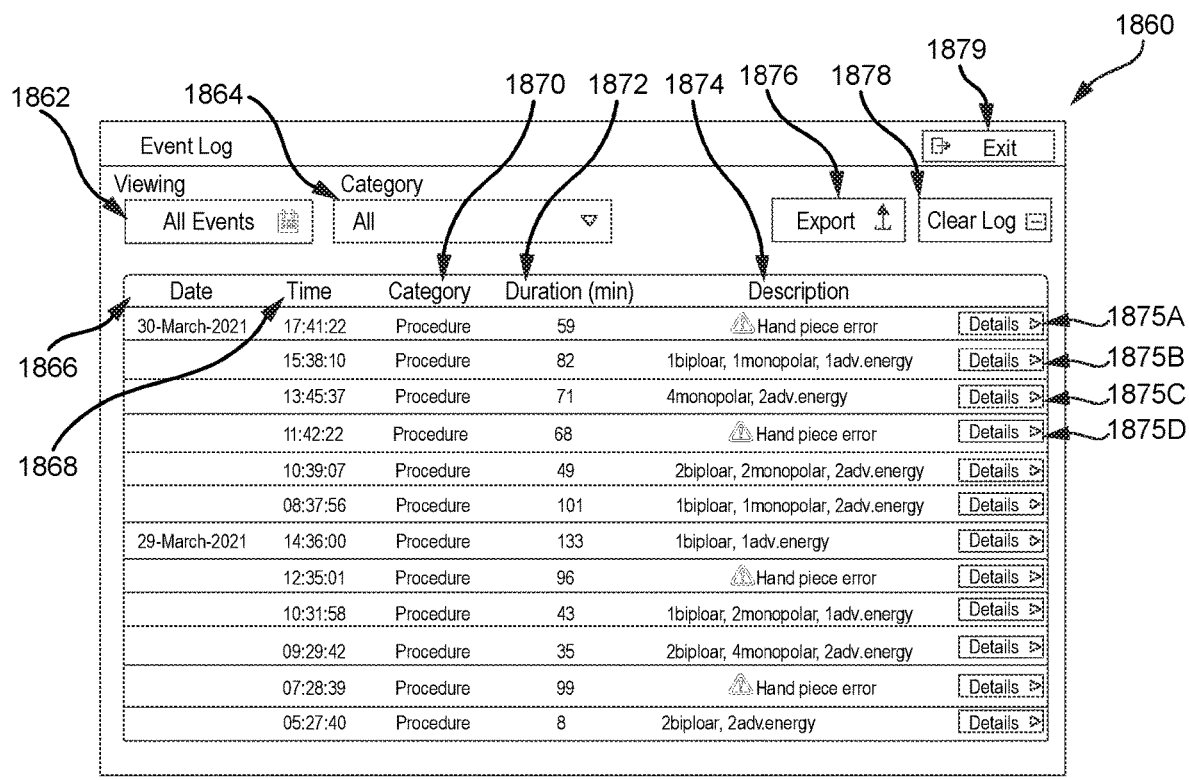
FIG. 27 is an illustrative graphical user interface event log main screen of a modular energy system event log, in accordance with at least one aspect of the present disclosure.

FIG. 27 is an illustrative GUI event log main screen of the modular energy system event log. At the top left of the event log main screen 1860, filtering options are included. For example, the user may filter which events are displayed by event log main screen 1860 based on date by tapping on date filter button 1862. Similarly, the user may select which category of events are shown (e.g., procedures, output verifications, etc.) by tapping on category filter drop down menu 1864. Below the filter buttons is a table displaying information related to each grouping of events. For the example shown on event log main screen 1860, only procedures are being displayed. The top right of the event log main screen 1860 includes an export button 1876, a clear log button 1878, and an exit button 1879. By tapping on export button 1876, the user is able to cause the modular energy system to export the event log data to an external source. By tapping on clear log button 1878, the user is able to cause the modular energy system to clear the event log. And by tapping on exit button 1879, the user is able to exit the event log main screen 1860 and return to the GUI main screen.

Still referring to FIG. 27, the procedures are sorted in chronologically in ascending, as shown under table headings for date 1866 and time 1868. A table heading for category 1870 is also included, below which the category for each grouping of events is displayed (e.g., procedure, output verification, software update, etc.). In one aspect of the present disclosure, if multiple grouping categories were displayed on event log main screen 1860, the user could tap on the category heading 1870 to sort the table based on category (i.e. procedure, output verification, etc.). The table shown on event log main screen 1860 also includes a duration 1872 and description 1874 for each procedure. For example, by looking at event log main screen 1860, a user would be able to identify that the fourth procedure listed, which occurred on Mar. 30, 2021 at 11:42:22, lasted for 68 minutes. Further, the user would be able to identify that a hand piece error occurred during the procedure. If desired, the user could tap details button 1875D to access an event log details modal and view additional details related to events recorded during the procedure.

Figure 28:
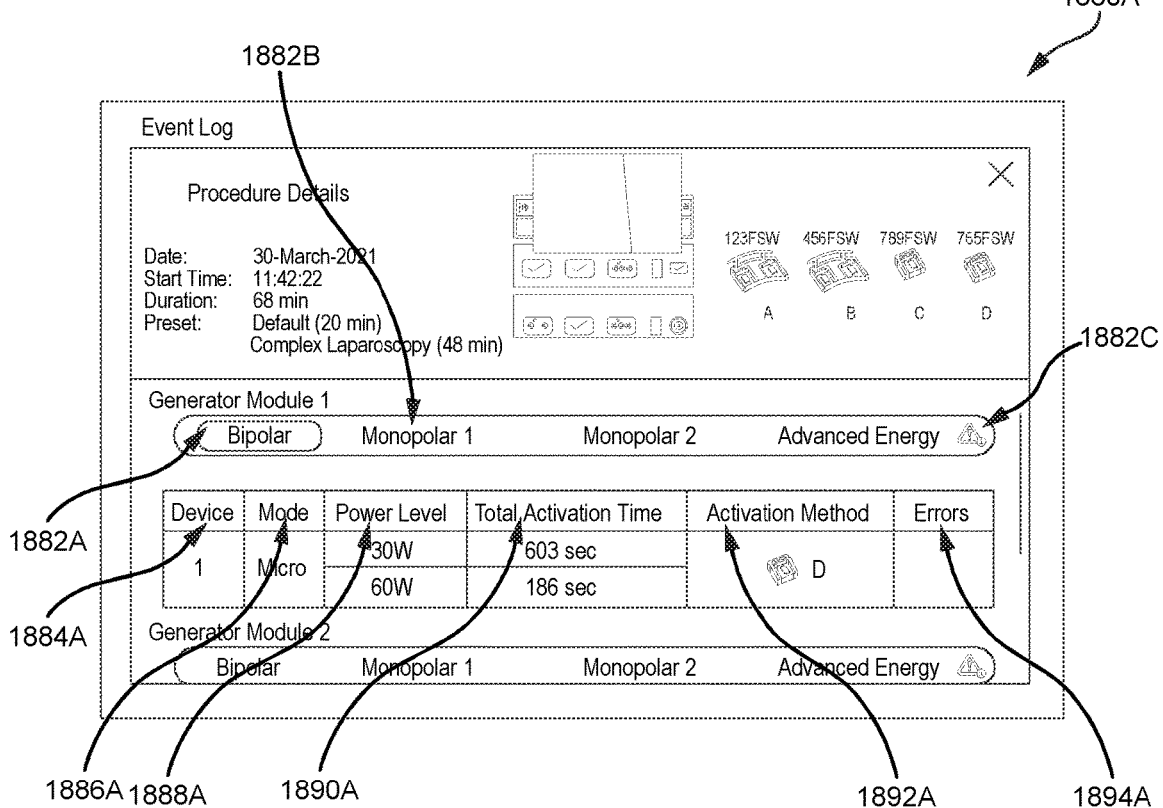
FIG. 28 is an illustrative graphical user interface event log details modal where information related to a bipolar energy modality is displayed, in accordance with at least one aspect of the present disclosure.

FIG. 28 is an illustrative GUI event log details modal where information related to the bipolar energy modality is displayed. The top portion of event log details modal 1880A includes a summary of details related to this exemplary procedure. For example, the date, start time, duration, and presets used (i.e. Default 20 min; Complex Laparoscopy 48 min) for the procedure are summarized at the top left portion of the screen. At the top center portion of event log details modal 1880A, a graphic representation of the energy ports used during the procedure are displayed. Based on this modal screen, a user can identify that, for this exemplary procedure, ports from two generator modules were utilized: the bipolar, monopolar 1, and advanced energy ports of generator 1; and the monopolar 1 port of generator 2. And at the top right portion of event log details modal 1880A, each footswitch used during the procedure (identified graphically and with a serial number or unique ID of each footswitch), and the plugs to which each footswitch was connected, is displayed. Below the procedural details summary, at the middle and bottom portion of the screen, the user has the option to select any of the energy ports used during the procedure to view a summary of events related to that port. For example, on event log details modal 1880A, below the heading for generator module 1, the bipolar button 1882A has been selected. Because this button was selected, event log details modal 1880A is displaying a device number 1884A, a mode 1886A, power levels 1888A, total activation times 1890A, an activation method 1892A, and any errors 1894A related to this energy modality. To view similar summaries for the other energy modalities of generator 1 used during this exemplary procedure, the user may tap on may tap on the monopolar 1 button 1882B or advanced energy button 1882C. Further, the user has the ability to scroll within the modal to view other content. For example, by scrolling down, summaries for energy modalities used during the procedure related to generator 2 are viewable.

Figure 29:
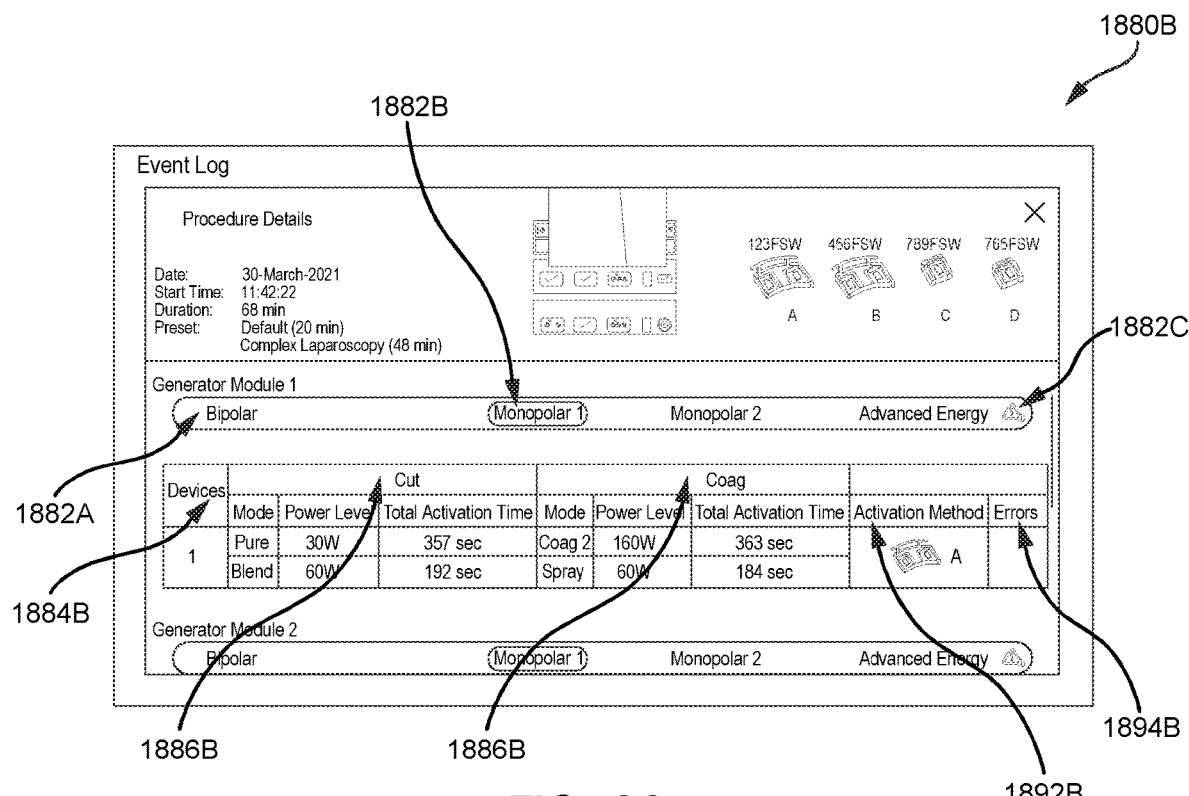
FIG. 29 is an illustrative graphical user interface event log details modal where information related to a monopolar 1 energy modality is displayed, in accordance with at least one aspect of the present disclosure.

FIG. 29 is an illustrative GUI event log details modal where information related to the monopolar 1 energy modality is displayed. The top portion of event log details modal 1880B includes the same summary of details related to this exemplary procedure as show in event log details modal 1880A. On event log details modal 1880B, below the heading for generator module 1, the monopolar 1 button 1882B has been selected. Because this button was selected, event log details modal 1880B is displaying a device number 1884B, cut information 1886B (including the mode, power level, and activation time), coagulation (coag) information 1888B (including the mode, power level, and activation time), an activation method 1892B, and any errors 1894B related to this energy modality. To view similar summaries for the other energy modalities used during the exemplary procedure related to generator 1, the user may tap on may tap on the bipolar button 1882A or advanced energy button 1882C.

Figure 30:
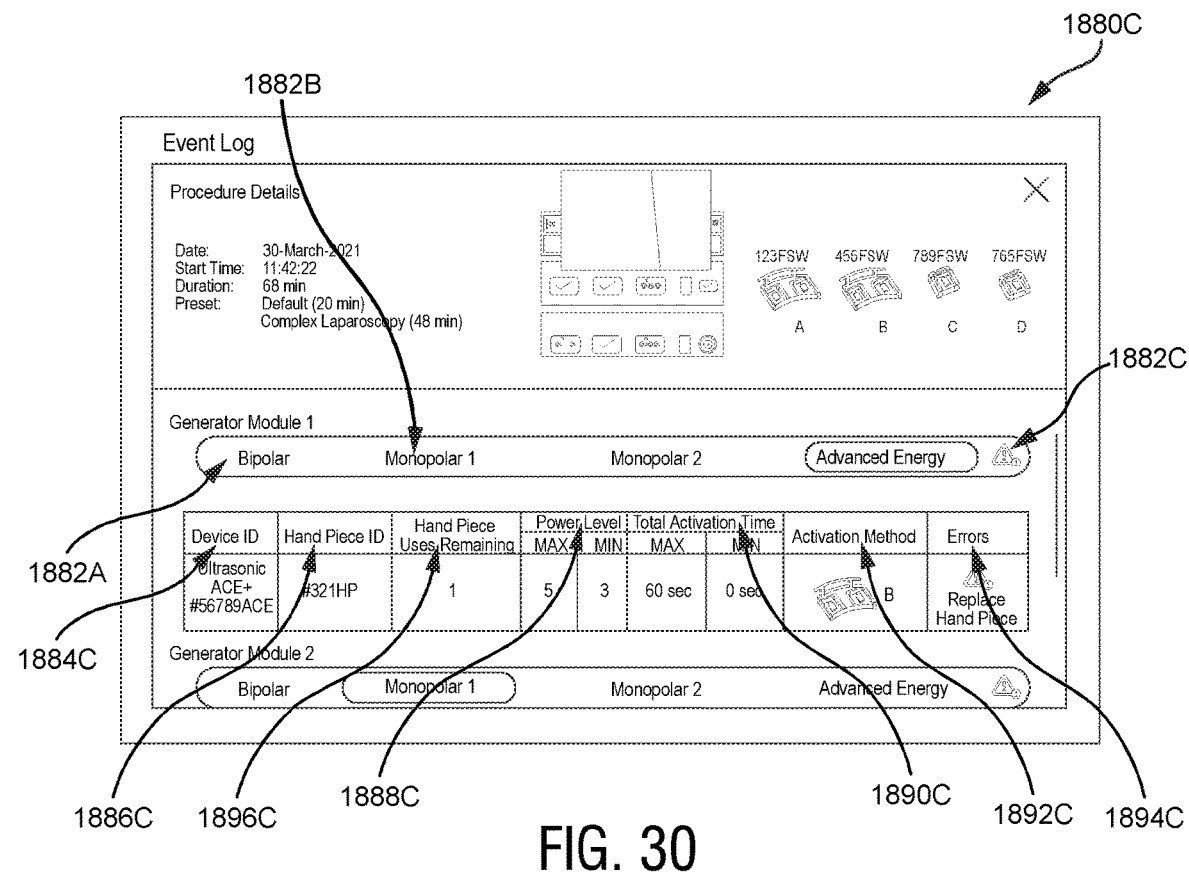
FIG. 30 is an illustrative graphical user interface event log details modal where information related to an advanced energy modality is displayed, in accordance with at least one aspect of the present disclosure.

FIG. 30 is an illustrative GUI event log details modal where information related to the advanced energy modality is displayed. The top portion of event log details modal 1880C includes the same summary of details related to this exemplary procedure as show in event log details modal 1880A and B. On event log details modal 1880C, below the heading for generator module 1, the advanced energy button 1882C has been selected. Because this button was selected, event log details modal 1880C is displaying a device ID 1884C, hand piece ID 1886B, number of had piece uses remaining 1896C, max and min power level 1888C, total activation time 1890C, activation method 1892C, and any errors 1894C related to this energy modality. The user may tap on buttons related to other energy modalities of generator 1 (1882A and 1882B) to return to each respective energy modality's summary, or the user may scroll down to view summaries for energy modalities related to generator 2 used during the procedure. Event log details modal 1880C also indicates that there was an error related to the advanced energy modality during this exemplary procedure. Specifically, advanced energy button 1882C has an alert symbol (in this example, the alert symbol is an exclamation point surrounded by a triangle) and an error description is included under error heading 1894C. Further, the number of errors (in this example, one error) is displayed in a bubble associated with the alert symbol. If one or more errors occurred during the procedure related to one or more of the other energy modalities used, the error(s) would similarly be displayed in association with the other energy modality buttons (e.g., 1882A and 1882B) and error descriptions (e.g., 1894A and 1894B). By tapping on a given error description, a pop-up window within the event log details modal presents details related to the error.

Figure 31:
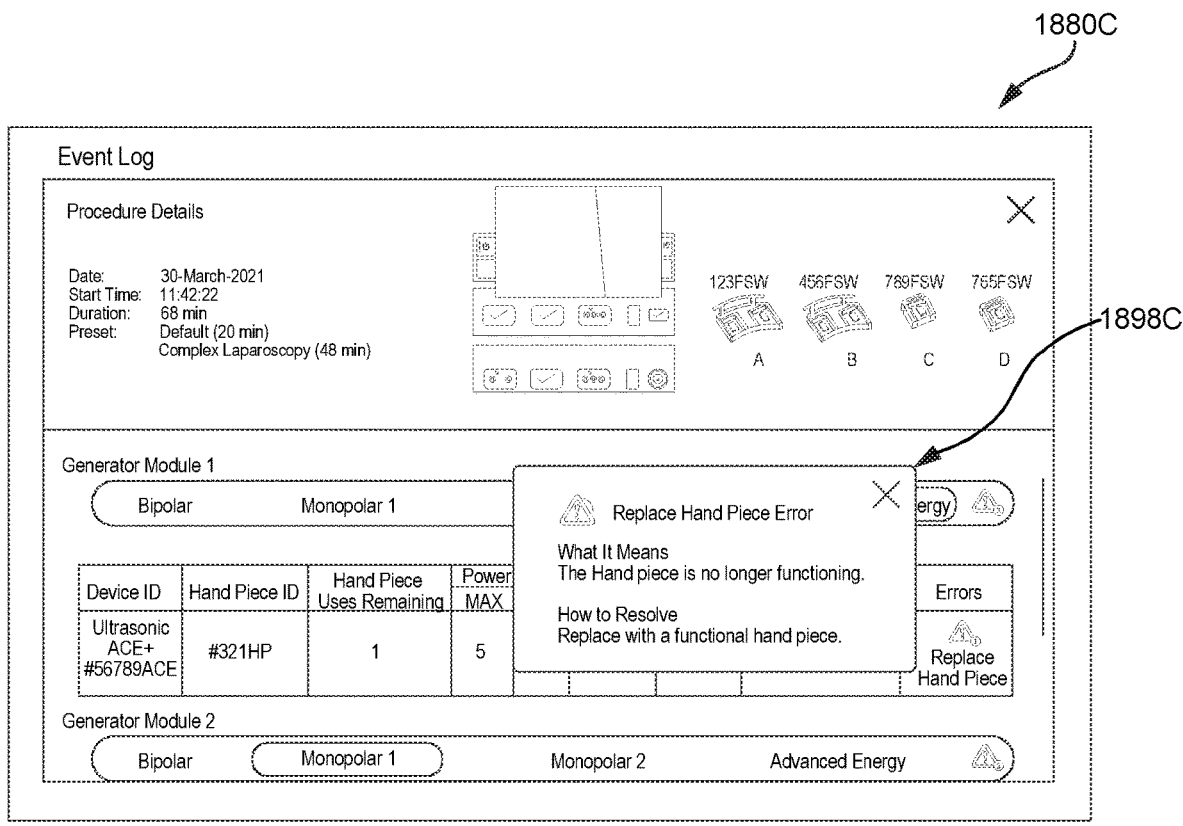
FIG. 31 is an illustrative graphical user interface event log details modal where error state information related to a advanced energy modality is displayed via a pop-up window, in accordance with at least one aspect of the present disclosure.

FIG. 31 is an illustrative GUI event log details modal where error state information related to the advanced energy modality is displayed via a pop-up window. When viewing event log details modal 1880C, tapping on the error description in the table under error heading 1894C causes error pop-up window 1898C to appear. Generally, in the error pup-up window, a title of the error state, a description of the error state, and instructions for how the user can resolve the error state are displayed. For example, error pop-up window 1898C indicates that a hand piece error occurred during the procedure. Further, pop-up window 1898C explains that this error state means that the hand piece is no longer functioning, and to resolve this error, the current hand piece should be replaced with a functional hand piece.

QR Code Display for Simple Transmission of System Event Data

When issues or other events arise related to the use of capital equipment, for example, equipment related to various aspects of the modular energy system disclosed herein, it can sometimes be difficult for the user to communicate information related to the events in order assist with troubleshooting. Similarly, it can sometimes be difficult for equipment support staff to gather information related to the events from the user. Therefore, there is a need for systems and methods to easily transmit system event data related to the modular energy system.

In one aspect of the present disclosure, the modular energy system may display unique QR codes (Quick Response codes) when a system event (e.g., system error) occurs. When the event occurs, users are notified of both the event and the associated QR code (e.g., with a notification on a display screen of the modular energy system). Next, users may take a picture of the QR code and send it to support staff (e.g., customer service, sales representatives, etc.). For example, a user may use a smartphone to capture the image and email or text it to support staff. Alternatively, a smartphone application may be used to capture and interpret or transmit the code (see Surgeon Cellphone Application for Recording and Monitoring Surgery section below). The data conveyed by the QR code may be encrypted to protect any sensitive information. After receiving an image of the QR code, support staff may then extract information related to the event. For example, the QR code may contain addition information useful for further diagnosing the event. Because QR codes may capture and convey up to 3 KB of data in a simple manner, support staff are beneficially able to receive this diagnostic information quickly and easily. As a result, they may offer better support to users.

Surgeon Cellphone Application for Recording and Monitoring Surgery

As explained above, various aspects of the modular energy system collect and store data as surgical procedures are performed. Further, the information derived from that data may be presented to users via a graphical user interface (GUI) rendered on a display screen, via a dedicated surgical display, and/or via various other modules of the modular energy system. However, surgeons may still desire additional ways to access clinical and record data. Therefore, there is a need to further improve user connectivity and enhance access to information using cellphone applications that interacts with the modular energy system.

In at least one aspect of the present disclosure, the modular energy system is configured to communicate with users' smartphones via a smartphone applications. The smartphone applications may include several features to improve user connectivity and access to information related to the modular energy system. Each application may securely connect with the modular energy system. Further, different applications may be specifically configured based on a type of surgery or medical specialty. For example, there may be one application dedicated to general surgery and several other applications dedicated to different specialty areas. Within each application, the user (e.g., surgeon) would be able to select the type of surgical procedure he or she wishes to perform. In other cases, users may also be able to view data related to past procedures.

While performing a surgical procedure, users may be able to view a graphical flow representing steps of the procedure via the smartphone application. For example, the step or steps shown on the application may be similar to the checklist steps described related to FIGS. 17-19. Further, by tapping icons displayed by the application, users may be able to identify or flag the completion of procedure steps, thereby causing the steps to be timestamped by the modular energy system. Users may also request that the modular energy system capture a picture of what is currently being displayed by one or more display screens of the modular energy system and associate the captured picture with a specific step of the procedure. Further, users may use the application to record audio. Additionally, users may request that other data related to the modular energy system be transmitted to their smartphone. For example, during a procedure, a surgeon may view real-time measurements of a patient's abdominal pressure. The application may also have the ability to access the smartphone's camera to capture an image of a QR code generated by other equipment of the modular energy system in response to an event (e.g., system error), and either send that code to support staff or provide instructions to the user based on the code.

During a procedure, it is intended that the smartphone applications only be used for personal monitoring and recording of data by users and not be used to control the operation of equipment used to perform surgery, with the exception that the application may submit a request to the modular energy system to transmit data to the user's smartphone.

Guided Output Verification

Standard hospital procedure requires that output verification testing be performed on electrosurgical generators, often on an annual or biannual basis. The output verification process involves connecting an electrosurgical unit (ESU) analyzer to various ports of the generator (e.g., port assembly 2012 of energy module 2004 shown in FIG. 7A). Once the ESU analyzer is connected, users (e.g., biomedical technicians) cause the electrosurgical generator to activate the connected port at various power settings while the ESU analyzer is set to various resistance levels. The user cycles through different combinations of power and resistance settings and records the results. The user uses these results to determine whether the power output of the electrosurgical generator conforms with the manufacture's specifications. On systems with multiple power modalities, such as the modular energy system described in various aspects of the present disclosure, output verification testing may involve significant complexity. For example, the user may be required to cycle through multiple power and resistance settings for multiple ports on multiple generators (e.g., port assemblies 2012a and 2012b of energy modules 2004a and 2004b shown in FIG. 8A). This complexity can lead to errors during the output verification process. Further, output verification can be a time consuming process for users, such as biomedical technicians, who often have wide-ranging responsibilities. Therefore, there is a need for systems and methods to improve the efficiency and reliability of the output verification process.

In one aspect of the present disclosure, systems an methods for guided output verification are disclosed. By displaying step-by-step instructions via a graphical user interface (GUI) of the modular energy system, users are guided through the output verification process. And as part of this step-by-step process, users are also able to activate energy ports at the appropriate mode and power level settings by simply tapping a button displayed by the GUI.

Users may cause the modular energy system to initiate guided output verification (output verification mode) by accessing the appropriate output verification button from the settings screen of the GUI. Alternatively, the modular energy system may automatically enter output verification mode when the user inserts an output verification key into the appropriate energy ports of the modular energy system. The output verification key is a device that serves as an adaptor that allows leads of the ESU analyzer to be connected to the neutral electrode port and various power modalities of the advanced energy port (see Output Verification Key section below). Once in output verification mode, the GUI displays a menu from which the user can select any port of the energy module for testing. Once a port is select, a pop-up display instructs the user to insert the leads of the ESU analyzer into the appropriate port of the energy module and/or output verification key. After the user confirms this action has been taken, the modular energy system guides the user, step-by-step, as to which resistance levels of the ESU analyzer and accompanying modes and power levels of the selected energy modality to verify. Unlike other electrosurgical generators that require users to manually select the appropriate power levels and modes, the guided output verification process disclosed herein causes the modular energy system to select and display the correct settings for users as they advance through the required testing. This beneficially improves efficiency of the output verification process and reduces the likelihood of error. Further, the sequence followed by the guided output verification process may be configured to match that of a process described in an output verification chart included in a service manual of the modular energy system. This beneficially enhances user comprehension which may reduce the time required to complete output verification testing. Moreover, the guided output verification process may be configured such that, at each point where the user must change the resistance on the ESU analyzer, a very clear stage-gate ensures that the user does not advance without making the change. Usability testing has shown that this guided output verification approach is highly intuitive and significantly reduces the time needed to complete output verification.

Figure 32:
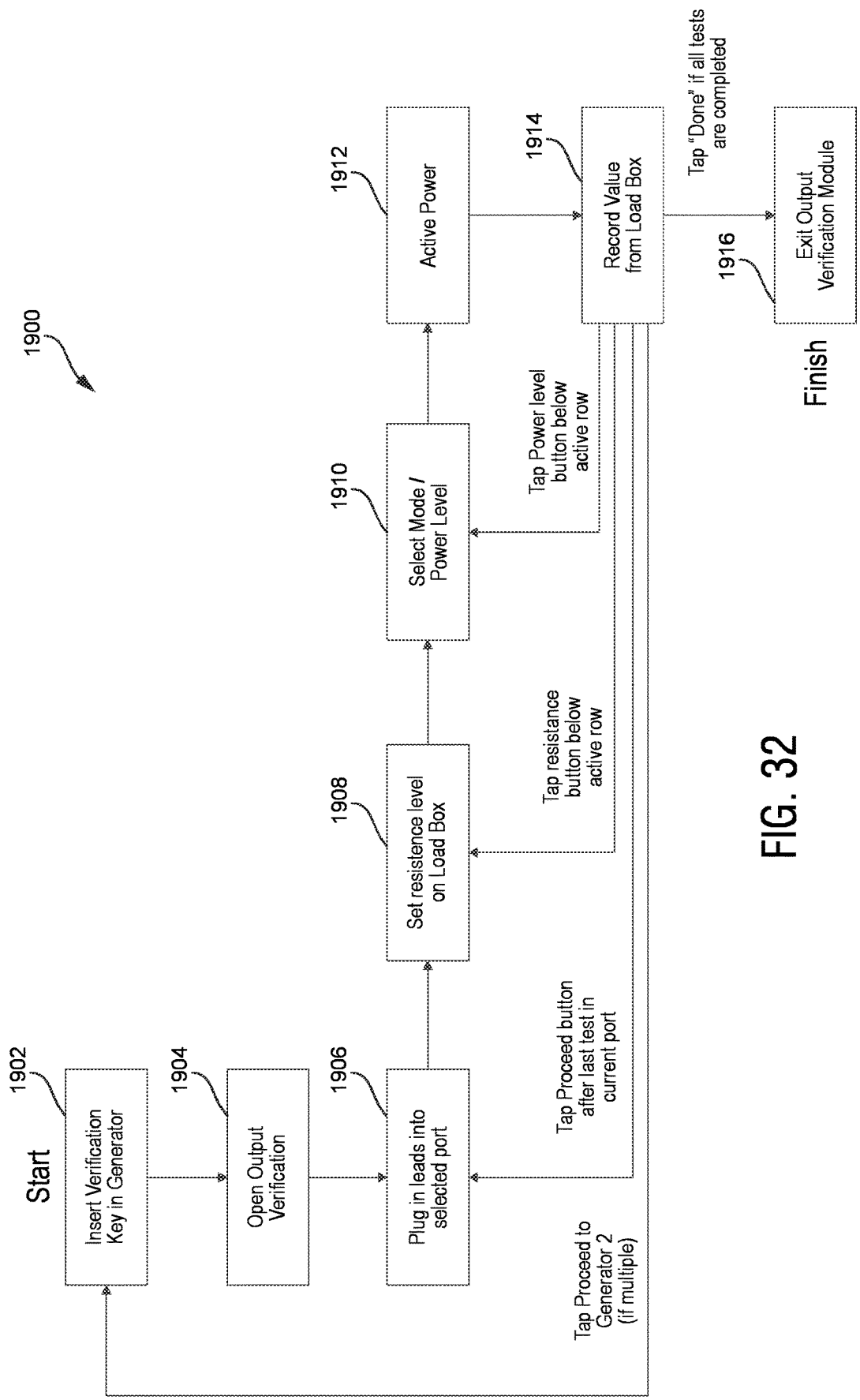
FIG. 32 is a flowchart of a process for guided output verification, in accordance with at least one aspect of the present disclosure.

Referring to FIG. 32, a illustrative process for guided output verification 1900 begins upon insertion of an output verification key into the appropriate energy ports of the modular energy system at step 1902. Insertion of the output verification key causes the modular energy system to open output verification mode at step 1904. As part of opening output verification mode, a GUI of the modular energy system displays an output verification mode menu screen. Upon selecting an energy modality to test from the menu screen, at step 1906, the user is instructed to plug leads of the ESU analyzer into the ports of the generator and/or verification key that correspond with the selected energy modality. Next, at step 1908, the GUI instructs the user to set the appropriate resistance level on the ESU analyzer (or load box). Once the user has set the appropriate resistance level, the user is instructed to select a mode and/or power level for the energy port at step 1910. The user then taps the appropriate button on the GUI to activate the energy port at step 1912, and viewing the ESU analyzer (load box), the user records the measured value at step 1914. In alternate aspects, the user may activate power using a foot pedal connected to the modular energy system. The modular energy system instructs the user to repeat steps 1910, 1912, and 1914 until all required modes and power levels for the selected port, at the selected resistance, have been tested. Upon completion of testing of all modes and levels at the selected resistance, the modular energy system may instruct the user to adjust the ESU analyzer to an additional resistance level at step 1908, and repeat steps 1910, 1912, and 1914 again until all required modes and power levels at the new resistance level are tested. If additional ports need to be tested, the modular energy system instructs the user to plug leads of the ESU analyzer into next port at step 1906 and the process repeats steps 1908 through 1914 as required for that port. If ports associated with a different energy module (i.e. generator) need to be tested, the process returns to step 1902 and the modular energy system instructs the user insert the output verification key into the appropriate ports of the next energy module. Again, the process repeats steps 1906 through 1914 as required for that energy module. After all of the ports associated with all of the energy modules have been tested, the process ends at step 1916, and the modular energy system exits output verification mode.

Figure 33:
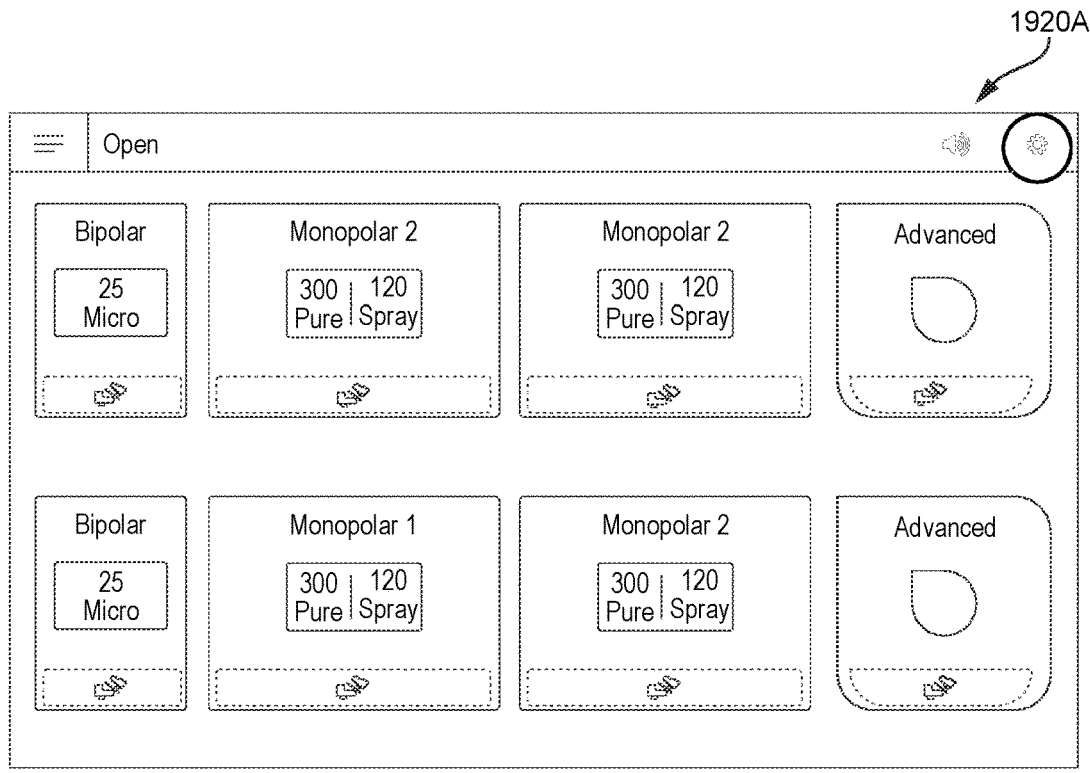
FIG. 33 is an illustrative graphical user interface main screen of a modular energy system, in accordance with at least one aspect of the present disclosure.
Figure 34:
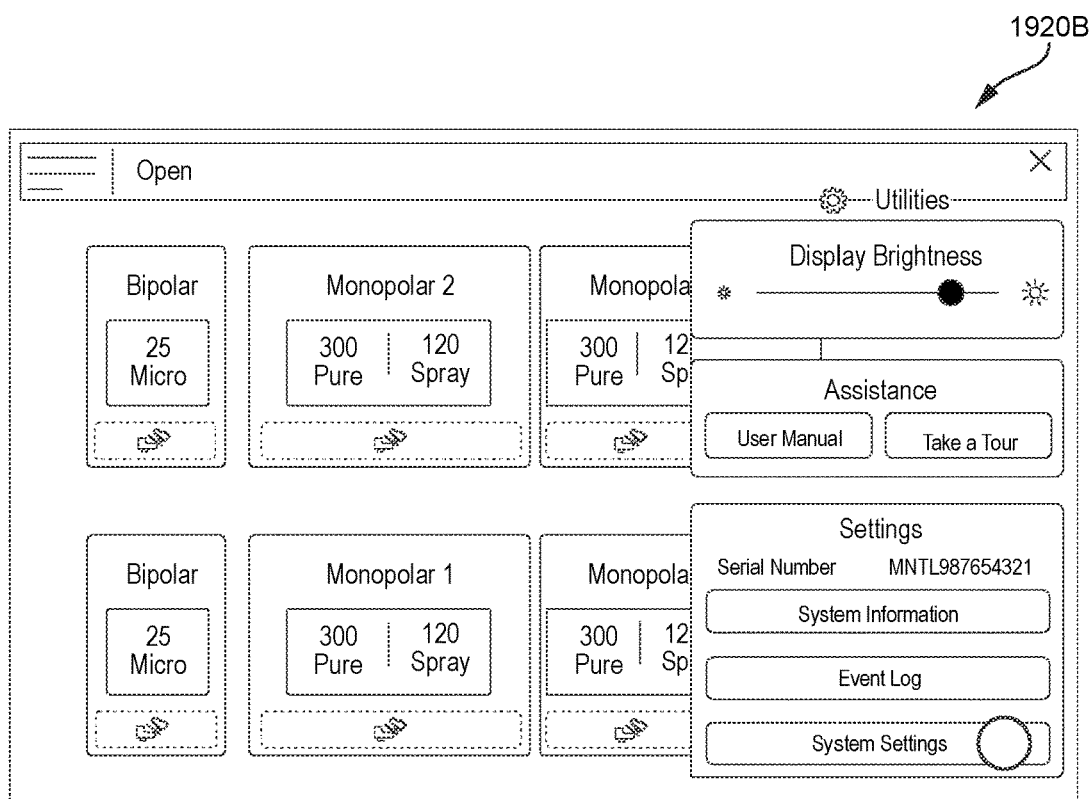
FIG. 34 is an illustrative graphical user interface utilities menu screen of a modular energy system, in accordance with at least one aspect of the present disclosure.
Figure 35:
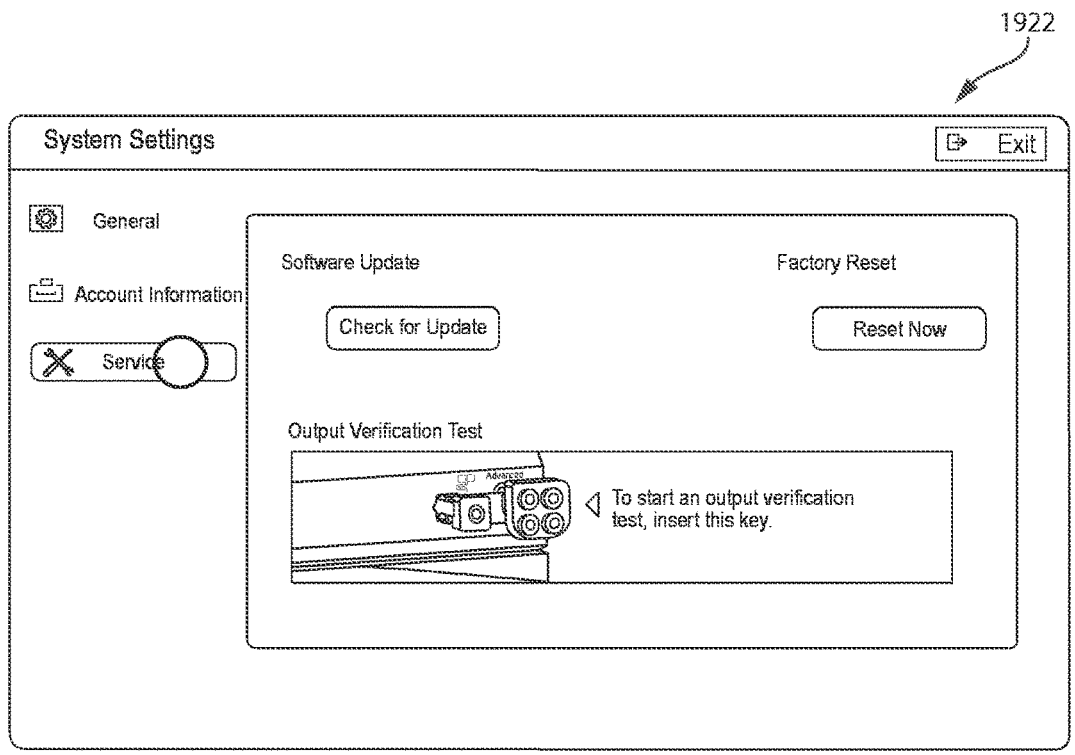
FIG. 35 is an illustrative graphical user interface system settings screen of a modular energy system, in accordance with at least one aspect of the present disclosure.
Figure 36:
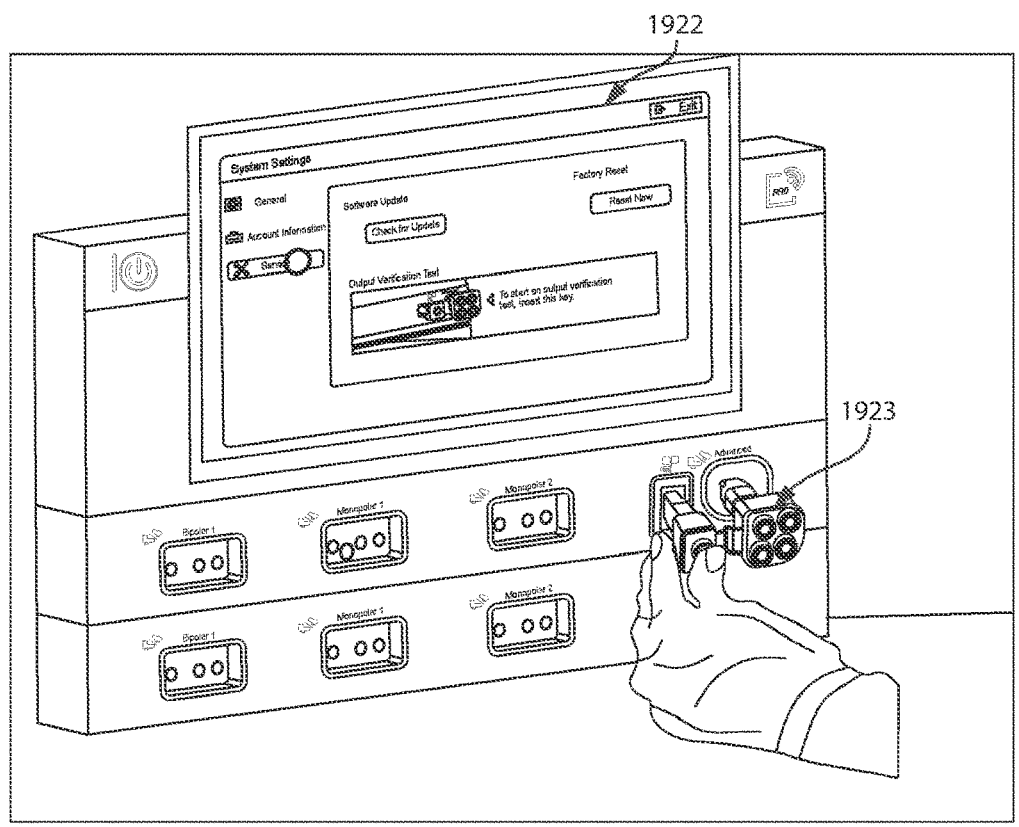
FIG. 36 is a perspective view of a graphical user interface of a modular energy system displaying the system settings screen of FIG. 35, in accordance with at least one aspect of the present disclosure.

In at least one aspect of the present disclosure, FIGS. 33 through 65 are illustrative GUI screens displayed by the modular energy system during the guided output verification process. FIG. 33 is an illustrative GUI main screen 1920A of the modular energy system. To begin accessing output verification mode, a user taps on the utilities button (gear icon) at the top right of GUI main screen 1920A, which causes a utilities menu screen to appear. FIG. 34 is an illustrative GUI utilities menu screen 1920B. By tapping on the system settings button at the bottom right of utilities menu screen 1920B, the user causes the modular energy system to display a system settings screen. FIG. 35 is an illustrative GUI system settings screen 1922. From the system settings screen 1922, the user next taps on the service button located to the left. Tapping the service button causes various service options to be displayed, including "Output Verification Test," as show on the middle portion system settings screen 1922. Under the "Output Verification Test" header, an image of the output verification key being inserted into the appropriate energy ports is displayed. System settings screen 1922 instructs the user to insert the output verification key as shown to begin output verification testing. FIG. 36 is a perspective view of a modular energy system displaying GUI system settings screen 1922 while a user inserts output verification key 1923 into neutral electrode and advanced energy ports of an energy module (i.e. generator). If the user inserts output verification key 1923 into the appropriate energy ports while system settings screen 1922 is displayed, it causes the modular energy system to enter output verification mode. In other aspects of the present disclosure, inserting the output verification key 1923 at any time may cause the modular energy system to enter output verification mode.

Figure 37:
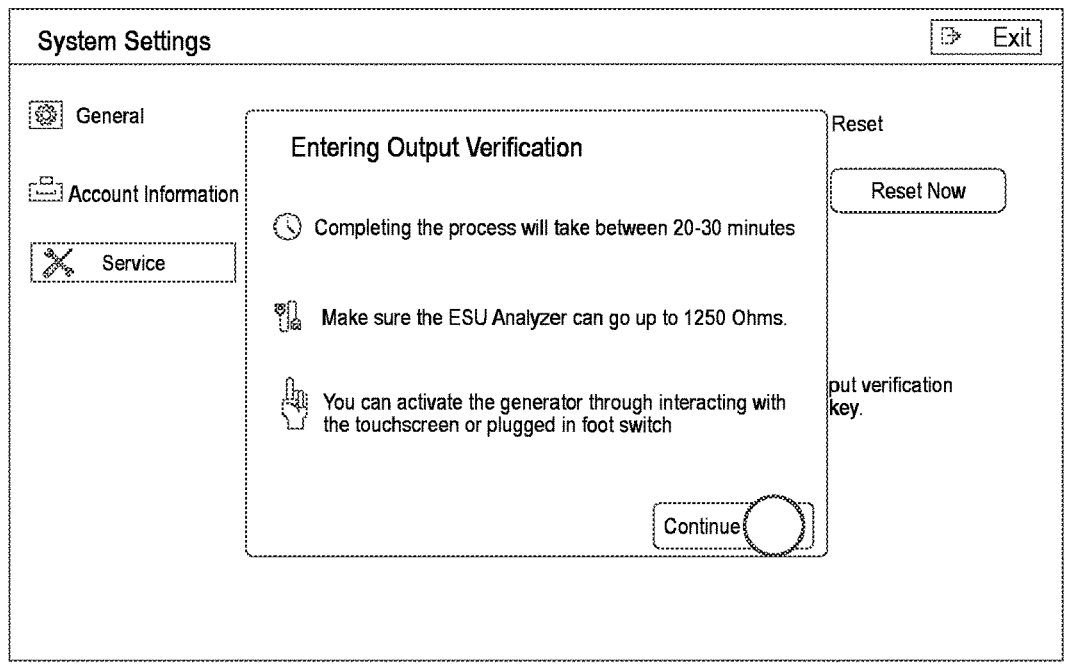
FIG. 37 is an illustrative graphical user interface screen for entering output verification, in accordance with at least one aspect of the present disclosure.

FIG. 37 is an illustrative GUI screen for entering output verification 1924. Screen for entering output verification 1924 displays a notice to users indicating the estimated length of time it will take to complete the output verification testing. The notice also asks users to ensure that they possess an ESU analyzer with the appropriate resistance capabilities (e.g., that it can reach a resistance of 1250 Ohms). Users are also notified that they can activate the generator (i.e. various modalities of the energy module) by interacting with the GUI touchscreen or the appropriate foot switch. Tapping on the continue button located at the bottom right of the screen for entering output verification 1924 causes the modular energy system to display the output verification mode main screen.

Figure 38:
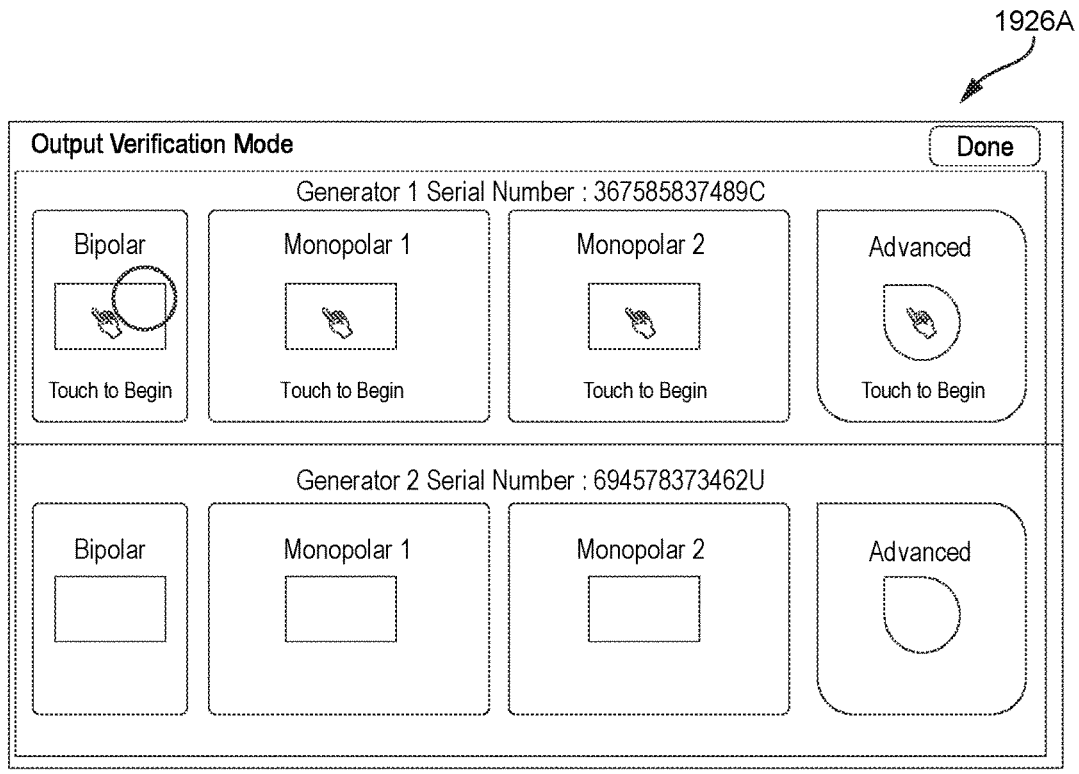
FIG. 38 is an illustrative graphical user interface output verification mode main screen, in accordance with at least one aspect of the present disclosure.

FIG. 38 is an illustrative GUI output verification mode main screen 1926A. Output verification mode main screen 1926A displays buttons representing the various energy ports associated with the modular energy system. The top row of buttons (i.e. bipolar, monopolar, 1, monopolar 2, and advanced) represent ports associated with a first energy module (i.e. generator 1) of the modular energy system. Output verification mode main screen 1926A may also display a serial number related to the first energy module above the top row of buttons. If there are more than one energy modules (more than one generators) associated with the modular energy system, output verification mode main screen 1926A may display additional rows of energy port buttons corresponding to energy ports of the additional energy modules. The user may begin output verification of a specific port by tapping on the appropriate energy port button. In the example show on output verification mode main screen 1926A, the bipolar energy port button is being tapped. This causes the bipolar ESU analyzer connection screen to appear.

Figure 39:
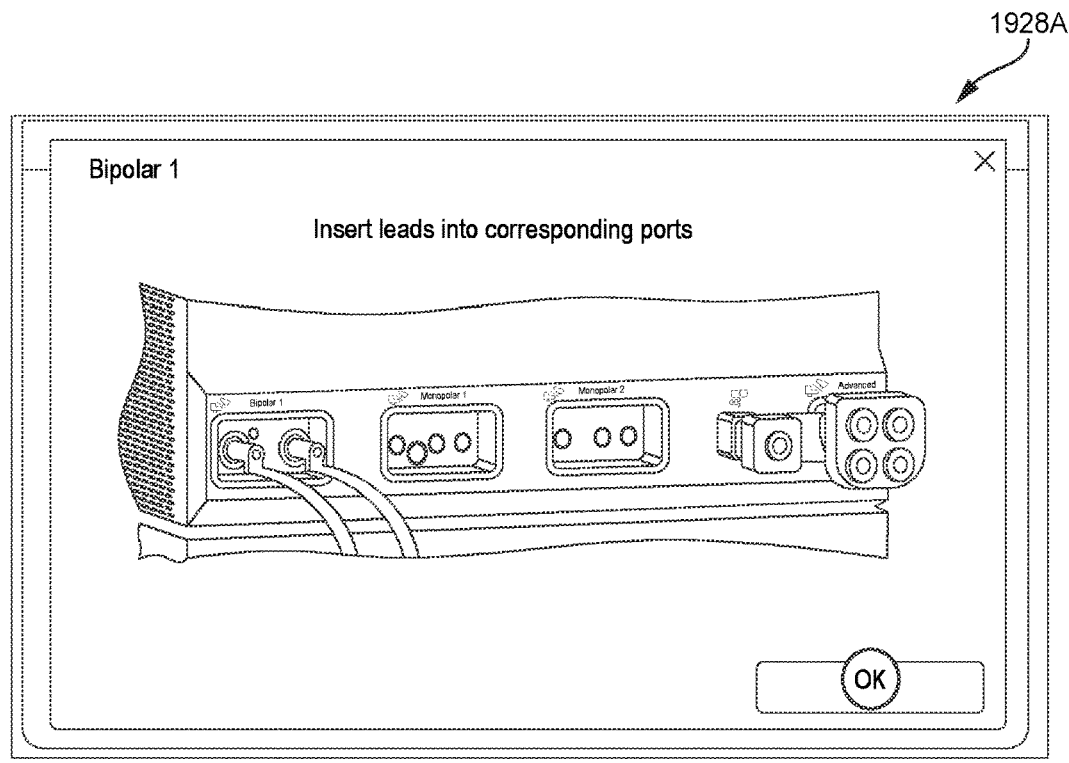
FIG. 39 is an illustrative graphical user interface bipolar ESU analyzer connection screen, in accordance with at least one aspect of the present disclosure.
Figure 40:
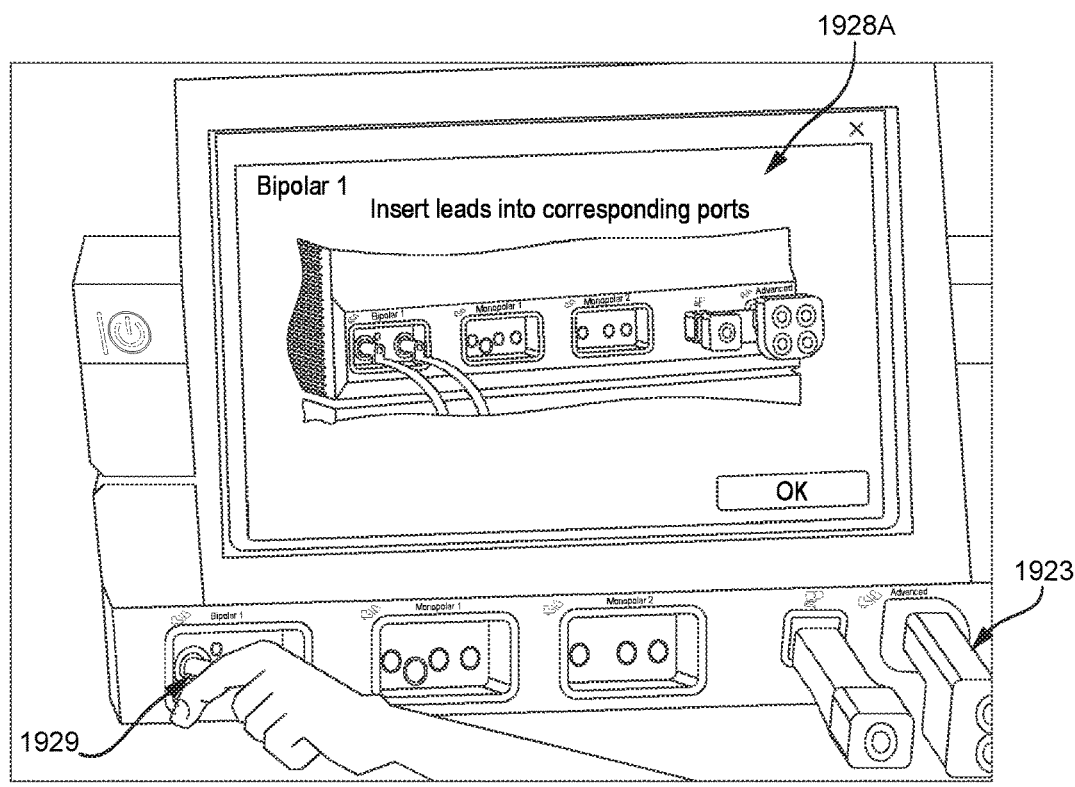
FIG. 40 is a perspective view of a graphical user interface of a modular energy system displaying the bipolar ESU analyzer connection screen of FIG. 39, in accordance with at least one aspect of the present disclosure.

FIG. 39 is an illustrative GUI bipolar ESU analyzer connection screen 1928A. Bipolar ESU analyzer connection screen 1928A instructs the user to insert the leads of the ESU analyzer into the appropriate ports for testing the bipolar energy modality. These instructions include a visual depiction of the leads connected to the appropriate ports. FIG. 40 is a perspective view a modular energy system displaying GUI bipolar ESU analyzer connection screen 1928A while a user inserts ESU analyzer leads 1929 into the bipolar energy port. After the leads are connected as shown, the user taps on the okay button to proceed to the bipolar set resistance screen.

Figure 41:
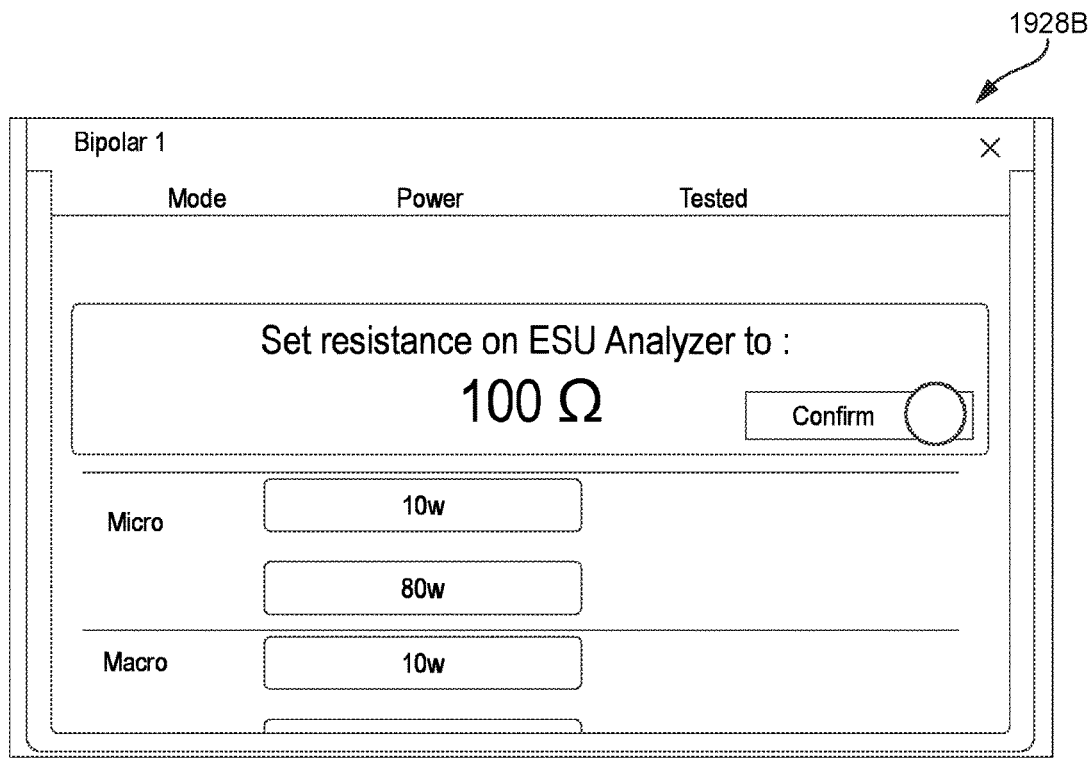
FIG. 41 is an illustrative graphical user interface bipolar set resistance screen, in accordance with at least one aspect of the present disclosure.
Figure 42:
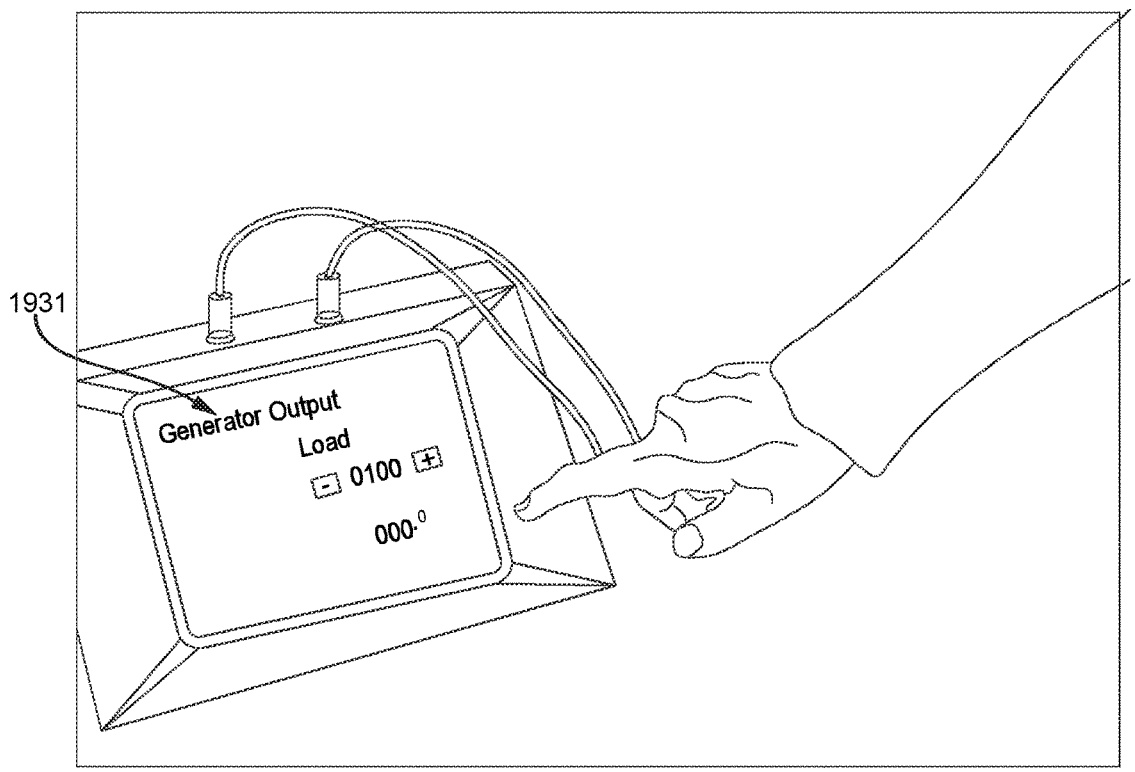
FIG. 42 is a perspective view a user adjusting a resistance level of an ESU analyzer, in accordance with at least one aspect of the present disclosure.

FIG. 41 is an illustrative GUI bipolar set resistance screen 1928B. At bipolar set resistance screen 1928B, the user is instructed to adjust the resistance of the ESU analyzer to the appropriate setting (e.g., 100 Ohms). Setting the resistance of the ESU analyzer must be done manually by the user. For example, FIG. 42 is a perspective view a user adjusting the resistance level of ESU analyzer 1931. Returning to FIG. 41, once the user has appropriately adjusted the resistance of the ESU analyzer as instructed, tapping the confirm button causes a first bipolar test mode screen to appear.

Figure 43:
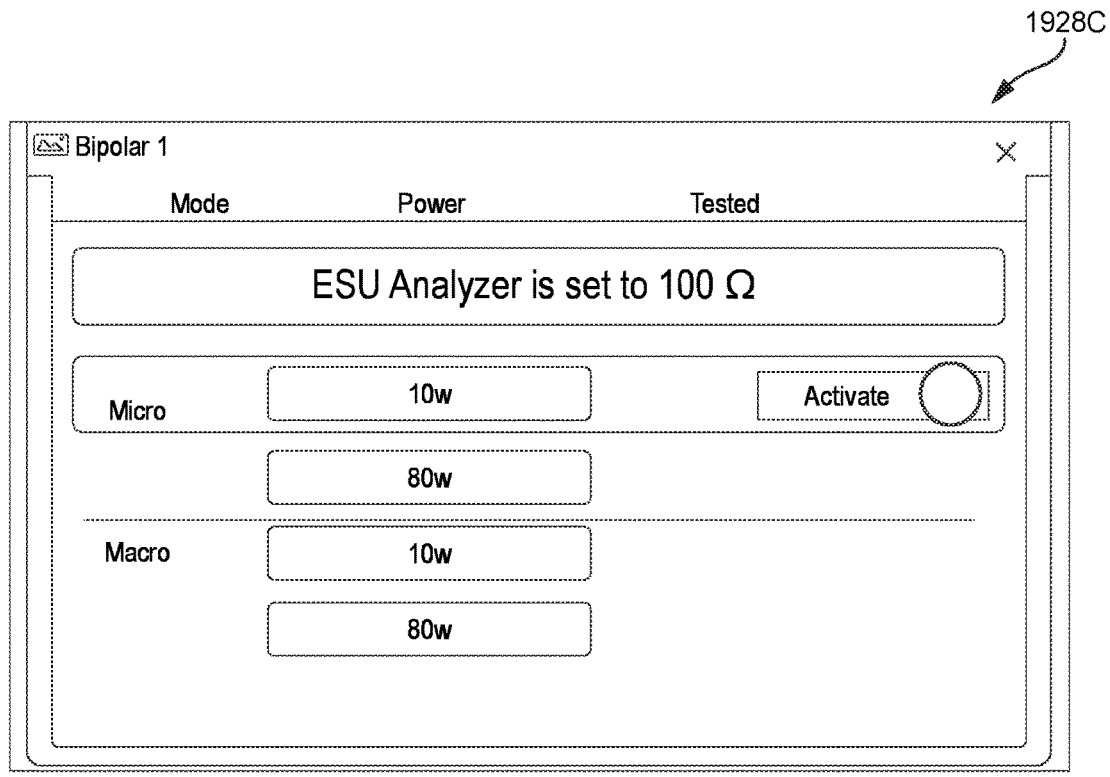
FIG. 43 is an illustrative graphical user interface first bipolar test mode screen, in accordance with at least one aspect of the present disclosure.
Figure 44:
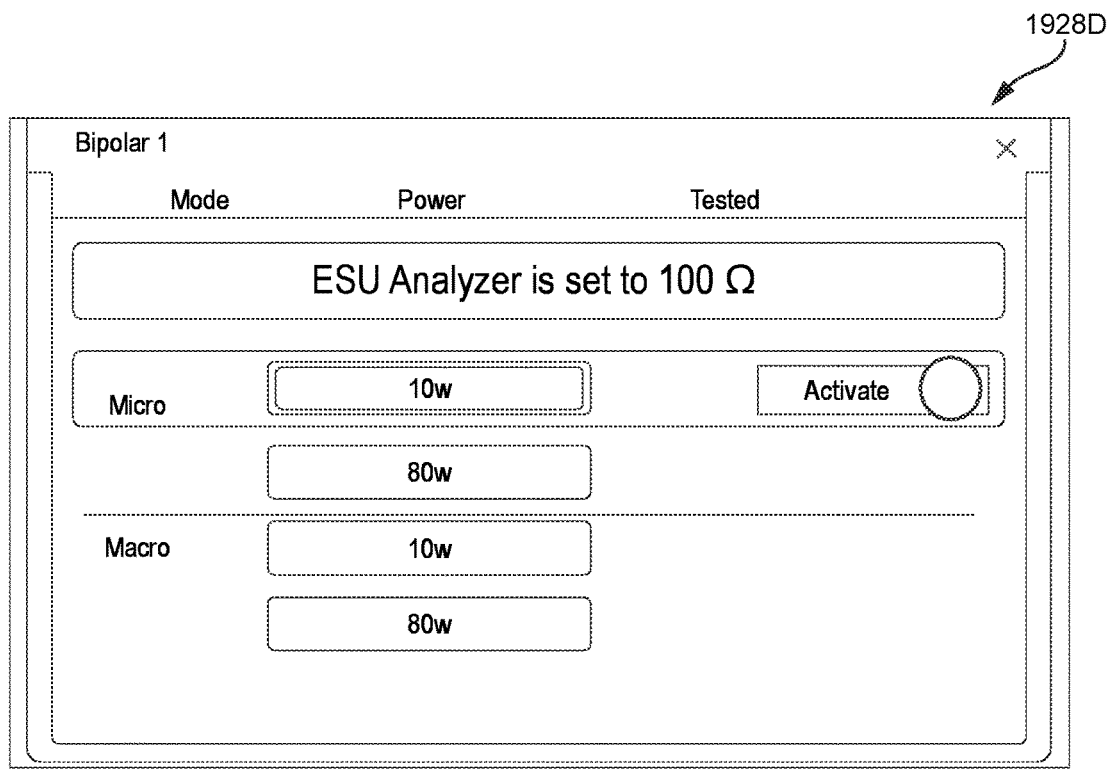
FIG. 44 is an illustrative graphical user interface first bipolar mode test screen, in accordance with at least one aspect of the present disclosure.
Figure 45:
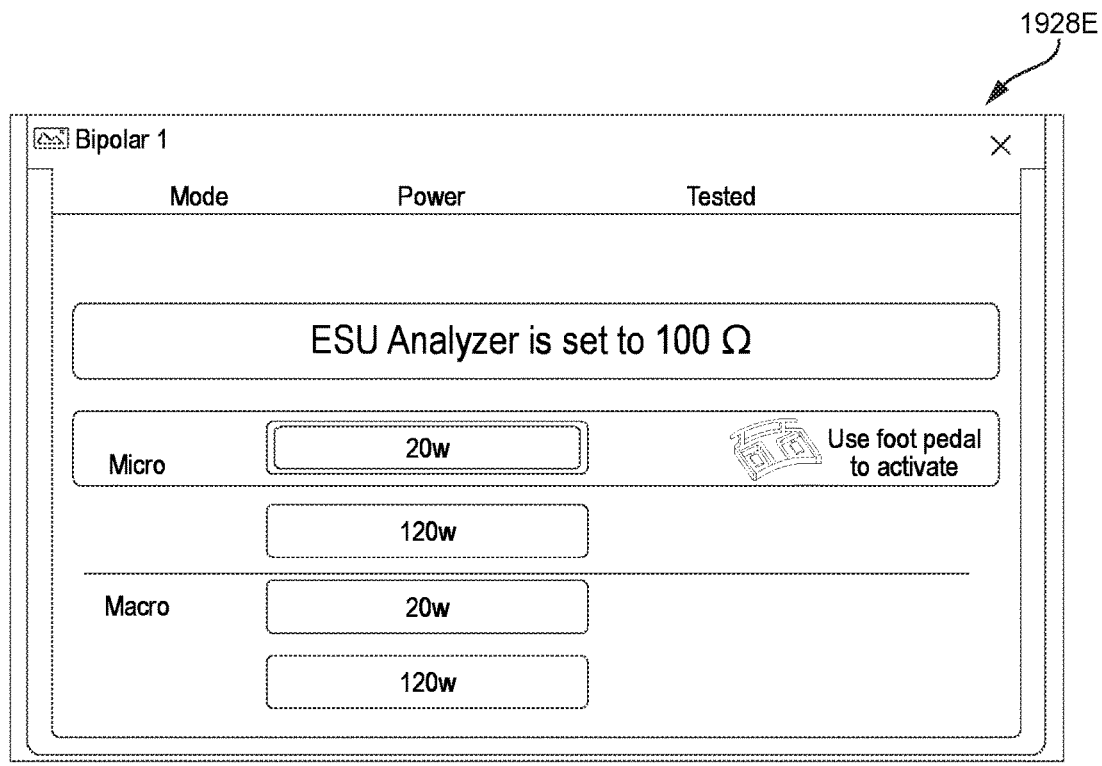
FIG. 45 is an illustrative graphical user interface first bipolar test mode screen, in accordance with at least one aspect of the present disclosure.
Figure 46:
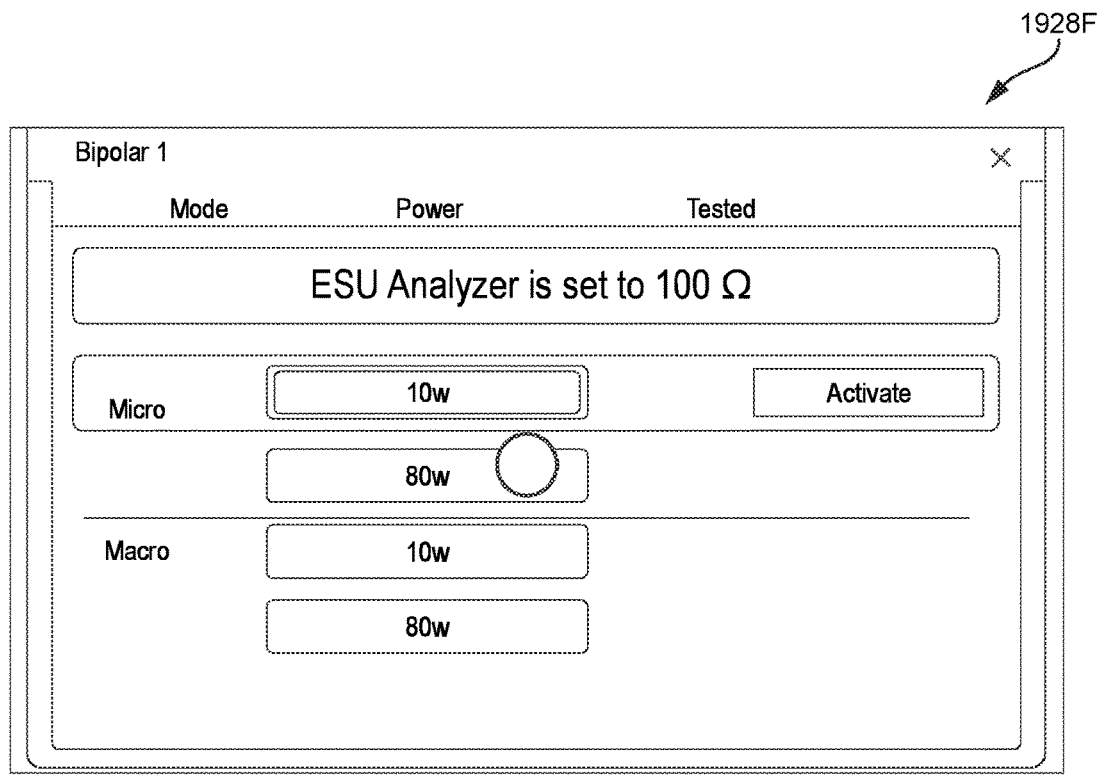
FIG. 46 is an illustrative graphical user interface first bipolar test mode screen, in accordance with at least one aspect of the present disclosure.

FIG. 43 is an illustrative GUI first bipolar test mode screen 1928C. The first bipolar test mode screen 1928C displays all modes and power levels that need to be tested for the bipolar energy modality. The first mode and power level to be tested (i.e. Micro 10w) are highlighted on the first bipolar test mode screen 1928C. Also, next to the first power mode and power level is an activate button. This activate button only appears next to the current mode and power level being tested. Referring now to the first bipolar mode test screen 1928D of FIG. 44, pressing and holding the activate button causes the modular energy system to deliver energy at the corresponding mode and power level of the active row. As energy is delivered, the power level displayed in the active row becomes highlighted. With the energy activated, the user can take the appropriate measurements using the ESU analyzer. Releasing the activate button causes the modular energy system to stop delivering energy through the bipolar port. In another aspect of the present disclosure, a foot pedal, instead of a GUI touchscreen button, may be used to cause the modular energy system to deliver energy. Referring to first bipolar test mode screen 1928E shown in FIG. 45, a foot pedal image is displayed instead of an activate button. First bipolar mode test screen 1928E instructs the user to activate power using the foot pedal. Similar to the activate button described above, pressing the foot pedal causes the modular energy system to deliver energy at the corresponding mode and power level of the active row. As energy is delivered, the power level displayed in the active row may become highlighted. With the energy activated, the user can take the appropriate measurements using the ESU analyzer. Releasing the foot pedal causes the modular energy system to stop delivering energy through the bipolar port. Referring now to first bipolar test mode screen 1928F of FIG. 46, the user may continue to activate bipolar energy at the first mode and power level (i.e. Micro 10w) by pressing the activate button as needed. When the user is ready to proceed to the second mode and power level, he or she may press the next power level button (i.e. 80w).

Figures 47, 48:
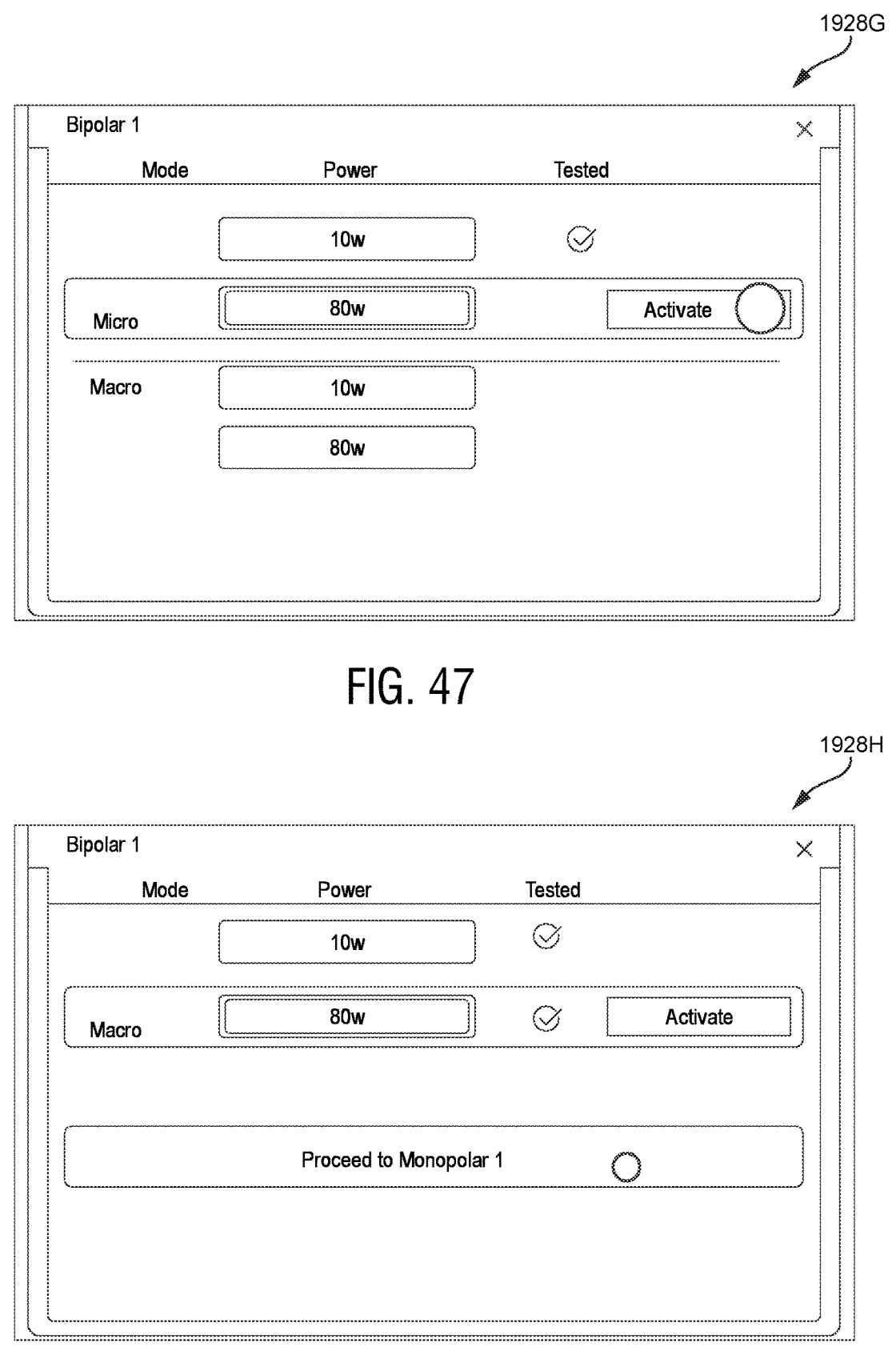

FIG. 47 is an illustrative GUI second bipolar test mode screen 1928G. Similar to the first bipolar test mode screen 1928C, the second bipolar test mode screen 1928G displays all modes and power levels that need to be tested for the bipolar energy modality. However, the second mode and power level to be tested (i.e. Micro 80w) are highlighted, the activate button has moved to that row, and there is now a check mark indicating that the first mode and level test has been completed. To test the second power level, the user proceeds similarly as explained above related to the first power level. The modular energy system instructs the user to proceed until all power modes and levels have been tested, at which point the final bipolar test mode screen 1928H of FIG. 48 is displayed. The final bipolar test mode screen 1928H confirms that testing of all modes and power levels is complete with check marks displayed at each row under the tested column. At this point, a proceed to monopolar 1 button appears at the bottom of the screen. Clicking the proceed to monopolar button causes the modular energy system to return to the output verification mode main screen.

Figure 49:
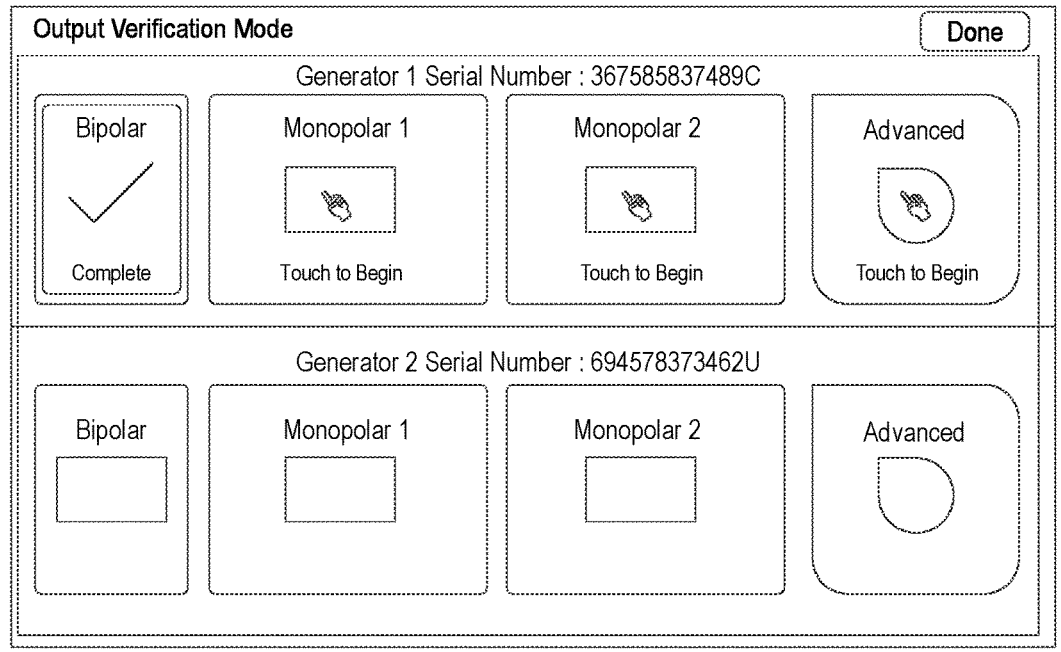
FIG. 49 is an illustrative graphical user interface output verification mode main screen, in accordance with at least one aspect of the present disclosure.

FIG. 49 is an illustrative GUI output verification mode main screen 1926B. Similar to output verification mode main screen 1926A, output verification mode main screen 1926B displays buttons representing the various energy ports associated with the modular energy system. However, because output verification of the bipolar port is complete, this button is now highlighted and displays a checkmark. To proceed to testing the monopolar 1 port, the user taps on the monopolar 1 button. This causes the monopolar 1 ESU analyzer connection screen to appear.

Figure 50:
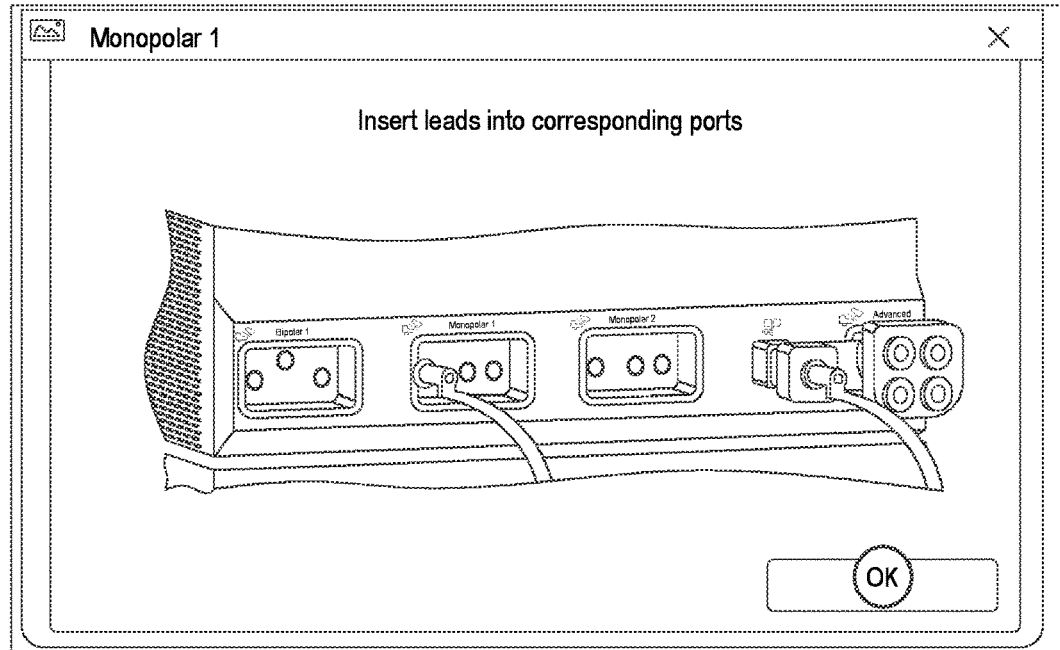
FIG. 50 is an illustrative graphical user interface monopolar 1 ESU analyzer connection screen, in accordance with at least one aspect of the present disclosure.

FIG. 50 is an illustrative GUI monopolar 1 ESU analyzer connection screen 1930A. Monopolar 1 ESU analyzer connection screen 1930A instructs the user to insert leads of the ESU analyzer into the appropriate ports for testing the monopolar 1 energy modality. These instructions include a visual depiction of the leads connected to the appropriate ports. After the leads are connected as shown, the user taps on the okay button to proceed to the first monopolar 1 set resistance screen.

Figure 51:
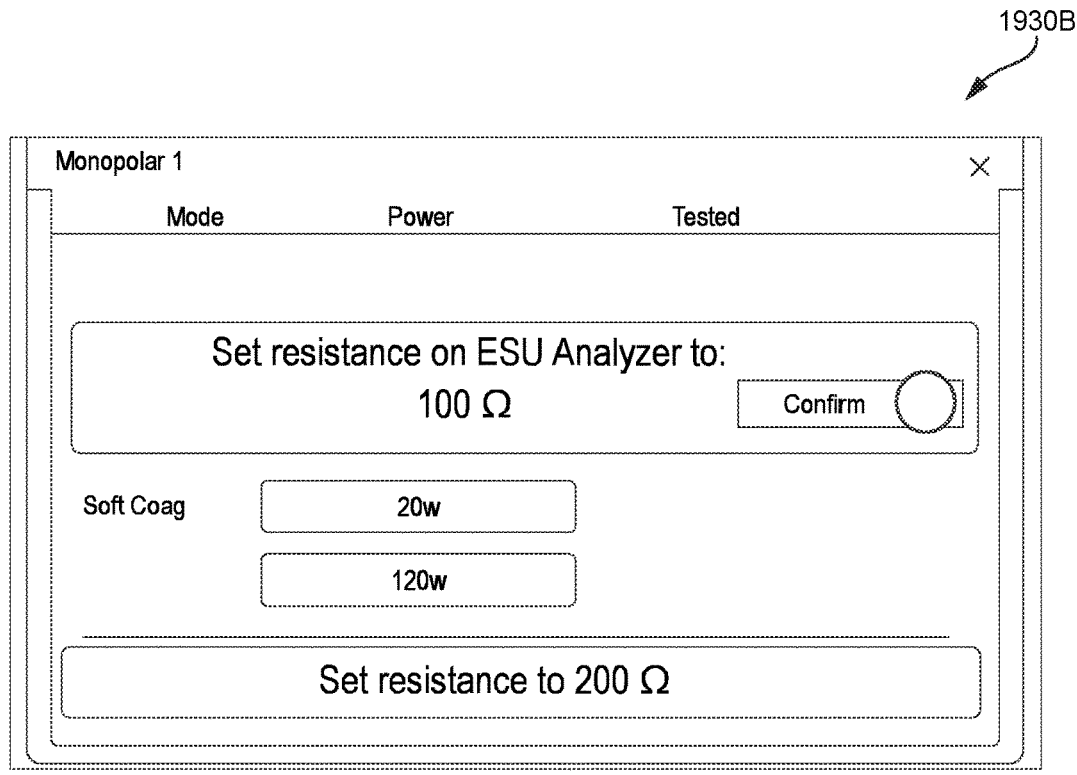
FIG. 51 is an illustrative graphical user interface first monopolar 1 set resistance screen, in accordance with at least one aspect of the present disclosure.

FIG. 51 is an illustrative GUI first monopolar 1 set resistance screen 1930B. At the first monopolar set resistance screen 1930B, the user is instructed to adjust the resistance of the ESU analyzer to the appropriate setting (e.g., 100 Ohms). Once the user has appropriately adjusted the resistance of the ESU analyzer as instructed, tapping the confirm button causes a first monopolar 1 test mode screen to appear.

Figure 52:
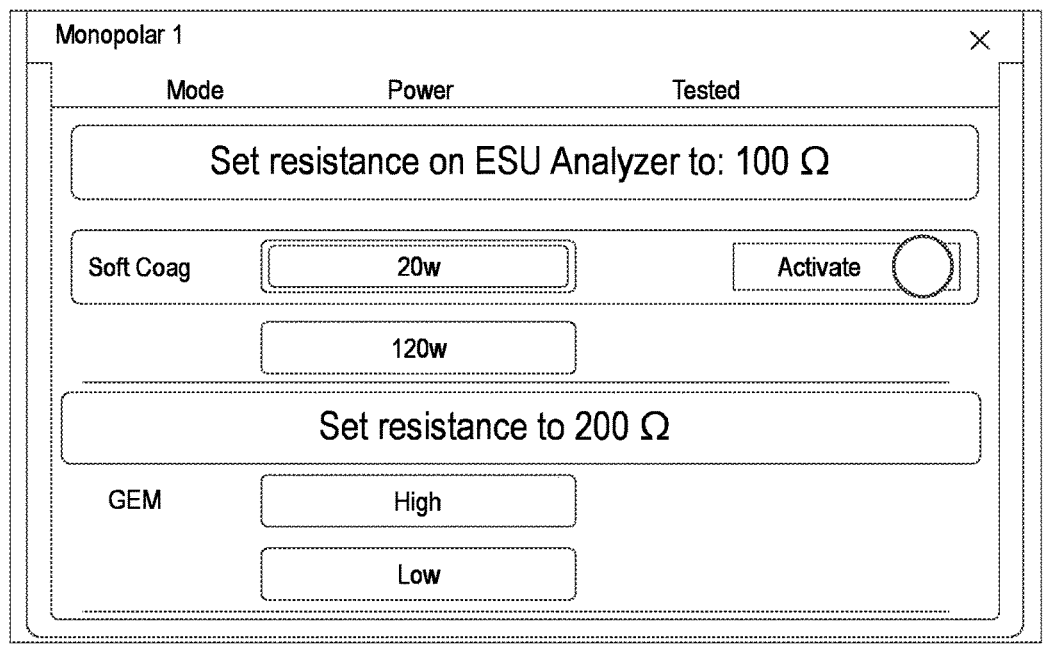
FIG. 52 is an illustrative graphical user interface first monopolar 1 set resistance screen, in accordance with at least one aspect of the present disclosure.
Figure 53:
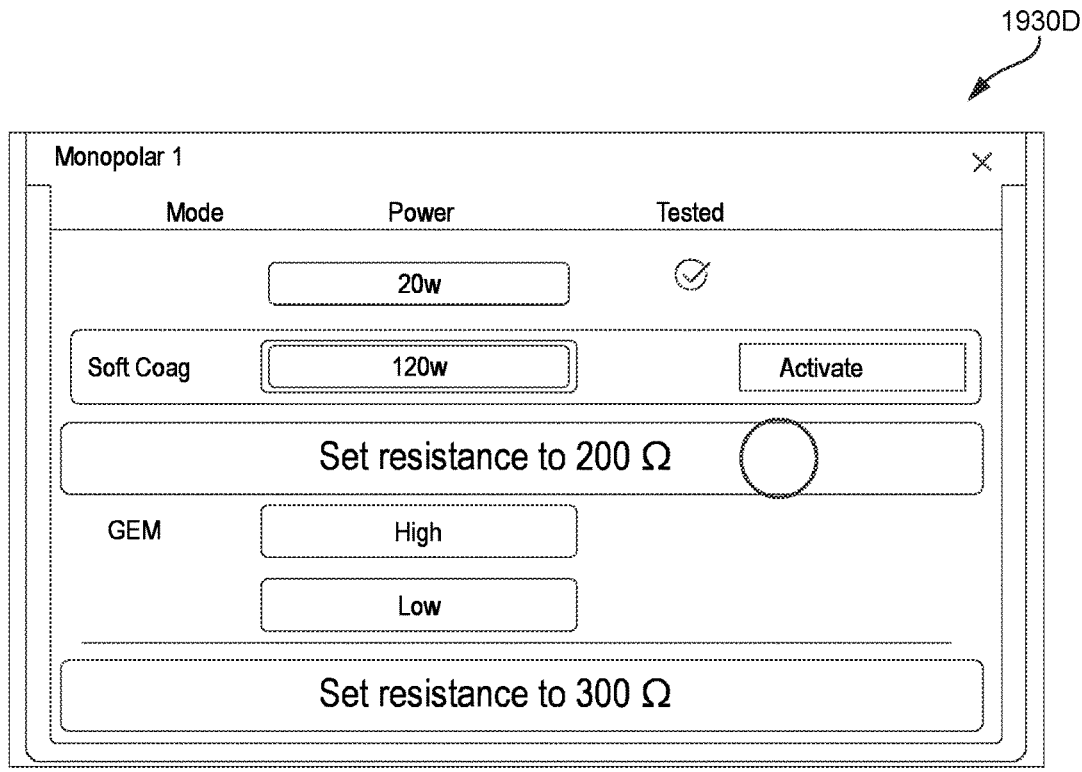
FIG. 53 is an illustrative graphical user interface second monopolar 1 test mode screen, in accordance with at least one aspect of the present disclosure.

FIG. 52 is an illustrative GUI first monopolar 1 test mode screen 1930C. The first monopolar 1 test mode screen 1930C displays all modes and power levels that need to be tested for the monopolar 1 energy modality (with the ability to scroll down if required). The first mode and power level to be tested (i.e. Soft Coag 20w) are highlighted on the first monopolar 1 test mode screen 1930C. Similar to the bipolar test mode screen described above, an activate button is displayed next to the highlighted row. Pressing and holding the activate button causes the modular energy system to deliver energy at the corresponding mode and power level of the active row. As energy is delivered, the power level displayed in the active row becomes highlighted. With the energy activated, the user can take the appropriate measurements using the ESU analyzer. When the user is ready to proceed to the second mode and power level, he or she may press the next mode and power level button (i.e. Soft Coag 20w). However, as the user proceeds through the modes and power levels required for output verification of the monopolar 1 port, the resistance level of the ESU analyzer may need to be adjusted. Referring to the second monopolar 1 test mode screen 1930D of FIG. 53, a set resistance button (i.e. set resistance to 200 Ohms) is displayed instructing the user to change the resistance. Tapping this button causes a second monopolar 1 set resistance screen to appear.

Figure 54:
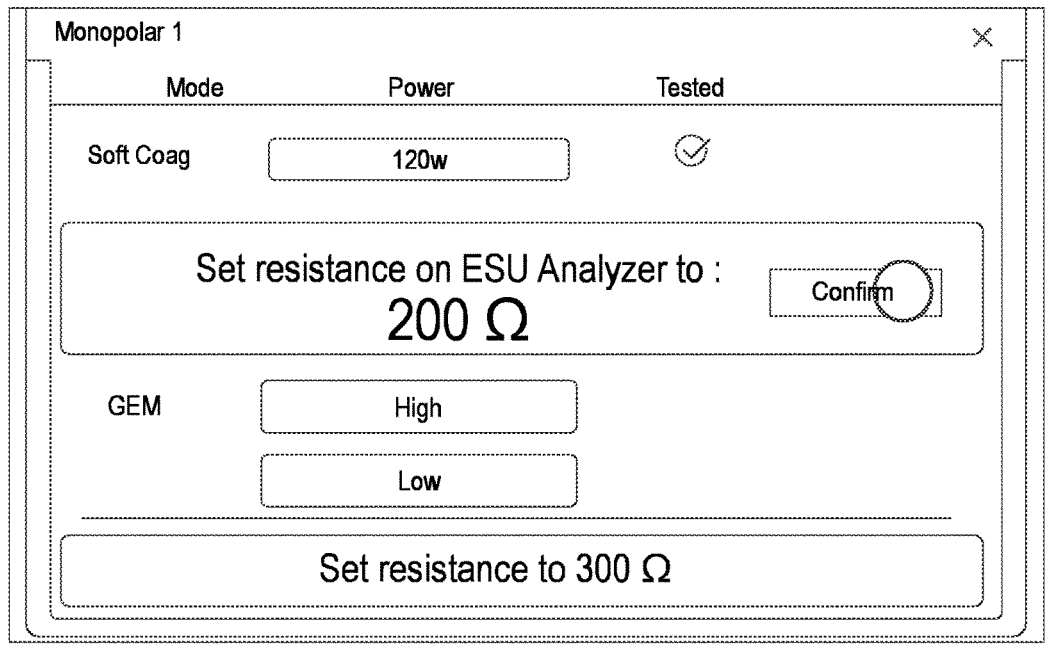
FIG. 54 is an illustrative graphical user interface second monopolar 1 test mode screen, in accordance with at least one aspect of the present disclosure.
Figure 55:
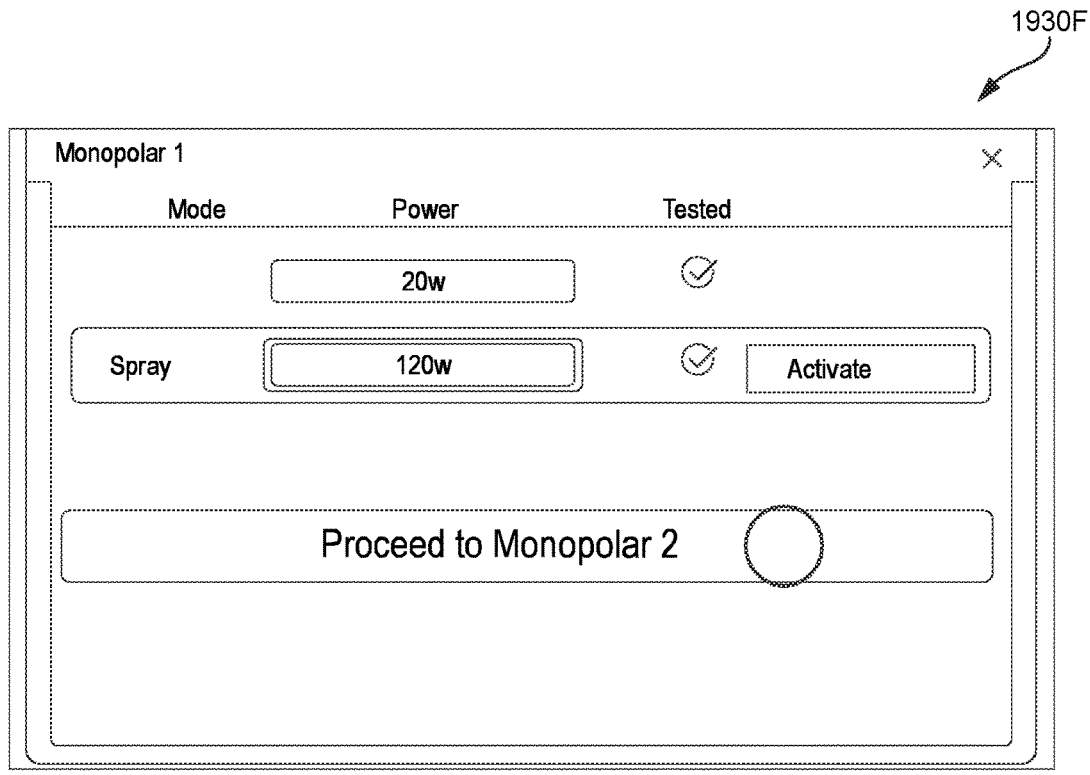
FIG. 55 is an illustrative graphical user interface final monopolar 1 test mode screen, in accordance with at least one aspect of the present disclosure.

FIG. 54 is an illustrative GUI second monopolar 1 set resistance screen 1930E. At the second monopolar set resistance screen 1930E, the user is again instructed to adjust the resistance of the ESU analyzer to the appropriate setting (e.g., 200 Ohms). Once the user has appropriately adjusted the resistance of the ESU analyzer, tapping the confirm button causes the next monopolar 1 test mode screen to appear. From the next test screen, the modular energy system instructs the user to proceed until all power modes and levels have been tested. Referring now to FIG. 55, after all modes and power levels have been tested, the final monopolar 1 test mode screen 1930F is displayed. At this point, a button to proceed to monopolar 2 output verification appears at the bottom of the screen. Clicking the proceed to monopolar 2 button causes the modular energy system to return to the output verification mode main screen where the user can then select the monopolar 2 port for testing. This causes a monopolar 2 ESU analyzer connection screen to appear.

Figure 56:
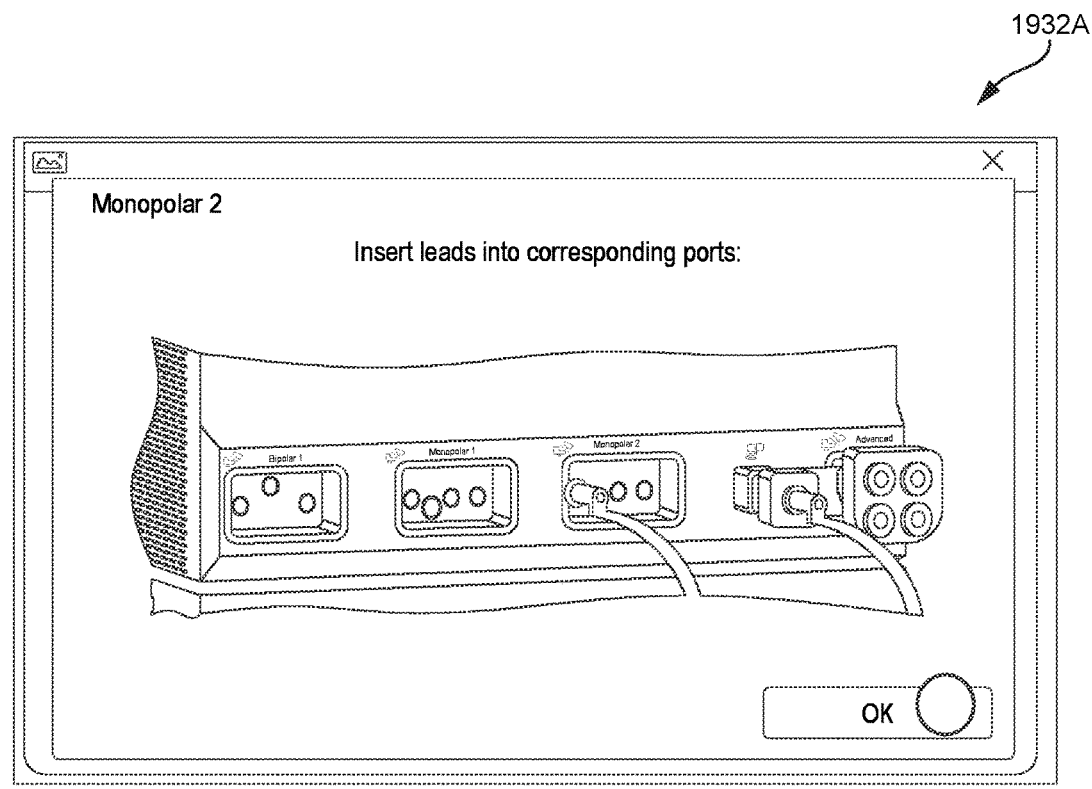
FIG. 56 is an illustrative graphical user interface monopolar 2 ESU analyzer connection screen, in accordance with at least one aspect of the present disclosure.
Figure 57:
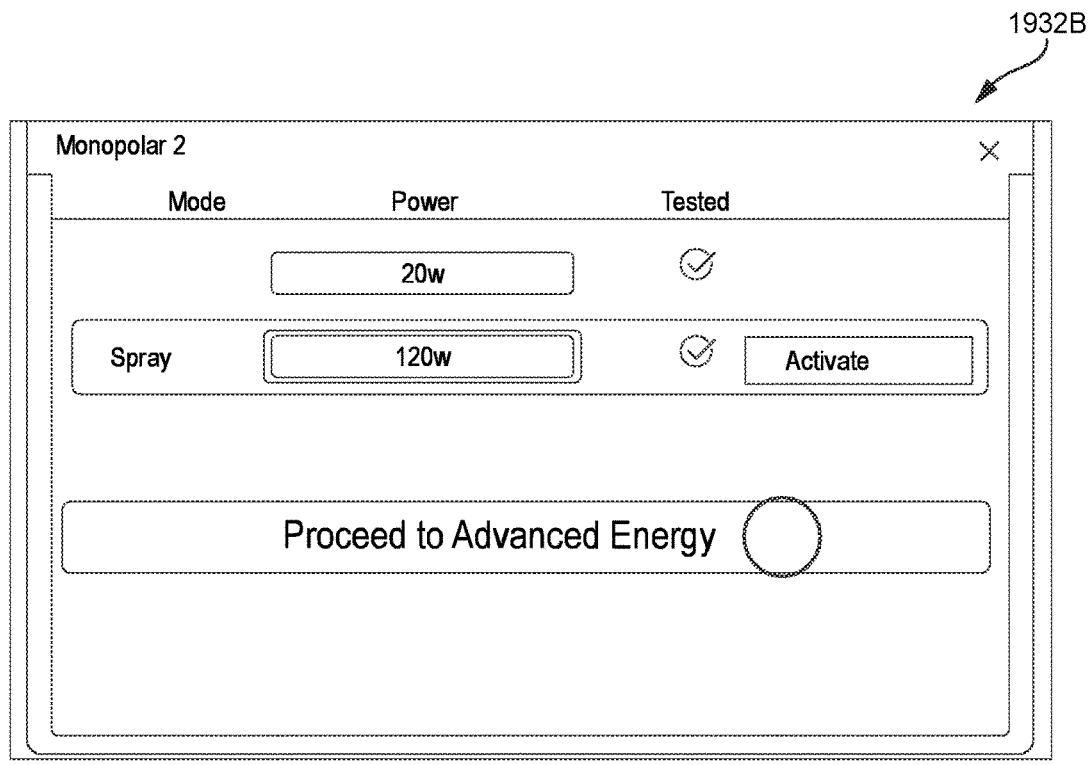
FIG. 57 is an illustrative graphical user interface final monopolar 2 test mode screen, in accordance with at least one aspect of the present disclosure.

FIG. 56 is an illustrative GUI monopolar 2 ESU analyzer connection screen 1932A. Monopolar 2 ESU analyzer connection screen 1932A instructs the user to insert leads of the ESU analyzer into the appropriate ports for testing the monopolar 2 energy modality. These instructions include a visual depiction of the leads connected to the appropriate ports. After the leads are connected as shown, the user taps on the okay button to proceed to the first monopolar 2 set resistance screen. Similar to the other ports described above, the modular energy system instructs the user to test each of the required modes and power levels for the monopolar 2 port. Referring now to FIG. 57, after all modes and power levels have been tested, the final monopolar 2 test mode screen 1934B is displayed. At this point, a button to proceed to advanced energy output verification appears at the bottom of the screen. Clicking the proceed to advanced energy button causes the modular energy system to return to the output verification mode main screen where the user can then select the advanced energy port for testing. Testing for the advanced energy port begins at the advanced energy: monopolar ESU analyzer connection screen.

Figure 58:
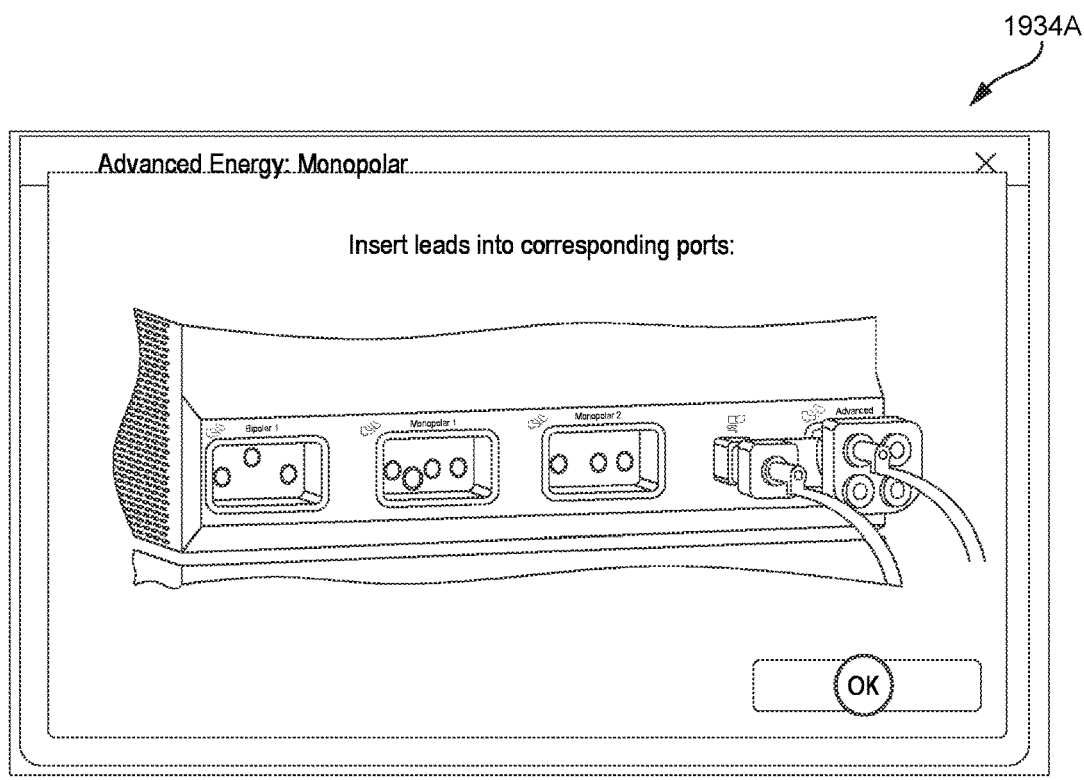
FIG. 58 is an illustrative graphical user interface advanced energy:monopolar ESU analyzer connection screen, in accordance with at least one aspect of the present disclosure.
Figure 59:
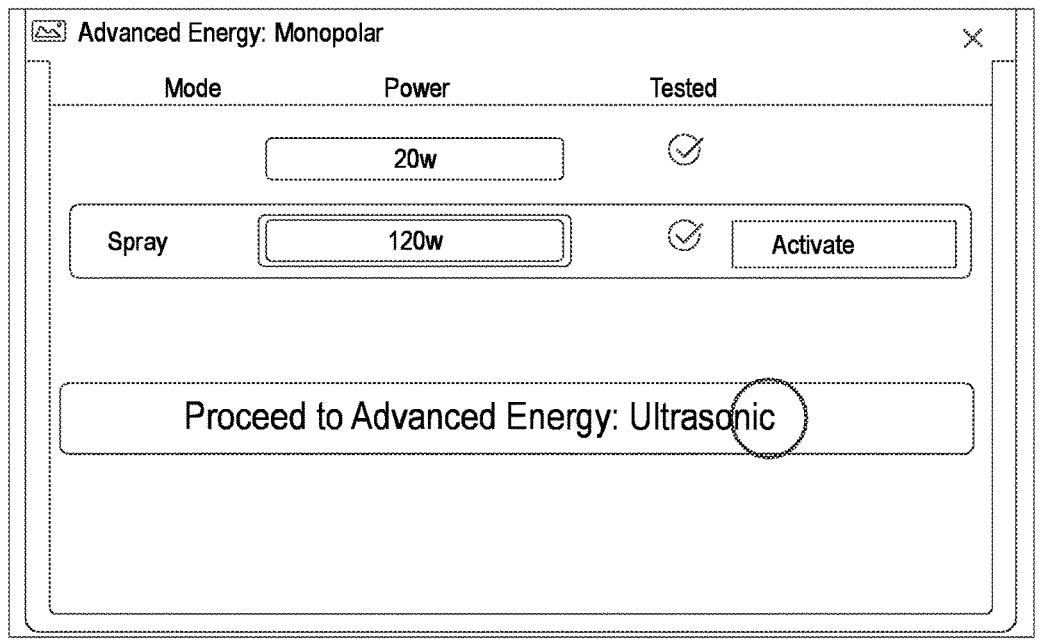
FIG. 59 is an illustrative graphical user interface final advanced energy:monopolar test mode screen, in accordance with at least one aspect of the present disclosure.

FIG. 58 is an illustrative GUI advanced energy: monopolar ESU analyzer connection screen 1934A. Advanced energy: monopolar ESU analyzer connection screen 1934A instructs the user to insert the leads of the ESU analyzer into the appropriate ports (of the output verification key) for testing the advanced energy:monopolar energy modality. These instructions include a visual depiction of the leads connected to the appropriate ports. After the leads are connected as shown, the user taps on the okay button to proceed to testing screens related to the advanced energy: monopolar modality. Similar to the other ports described above, the modular energy system instructs the user to test each of the required modes and power levels of the advanced energy:monopolar energy modality. Referring now to FIG. 59, after all power modes and levels have been tested, the final advanced energy:monopolar test mode screen 1934B is displayed. At this point, a button to proceed to advanced energy: ultrasonic output verification appears at the bottom of the screen. Clicking the proceed to advanced energy: ultrasonic button causes the modular energy system to proceed to the advanced energy: ultrasonic ESU analyzer connection screen.

Figure 60:
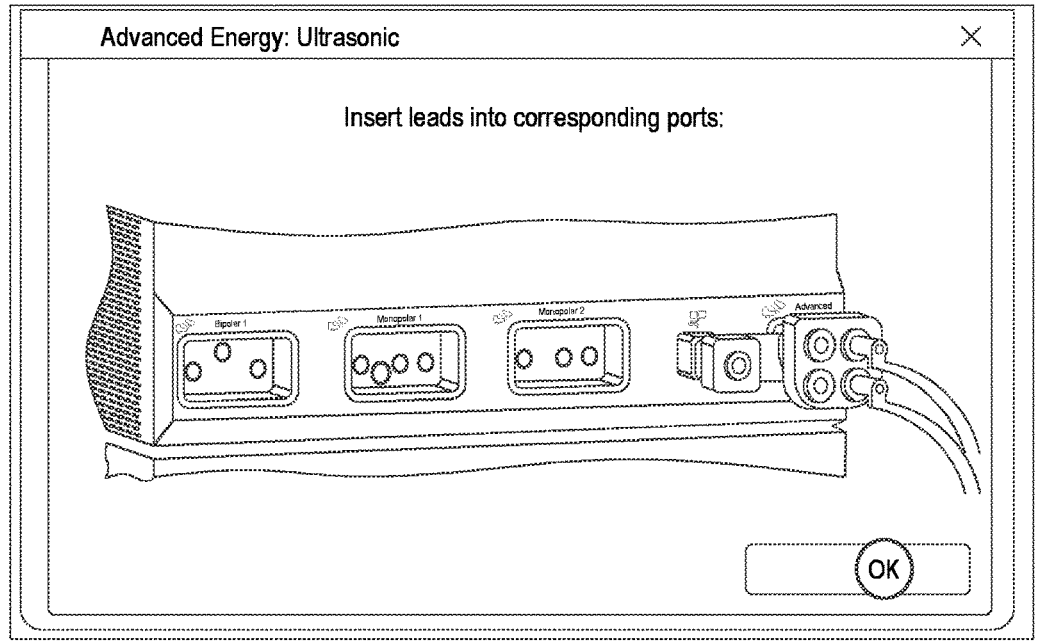
FIG. 60 is an illustrative graphical user interface advanced energy:ultrasonic ESU analyzer connection screen, in accordance with at least one aspect of the present disclosure.
Figure 61:
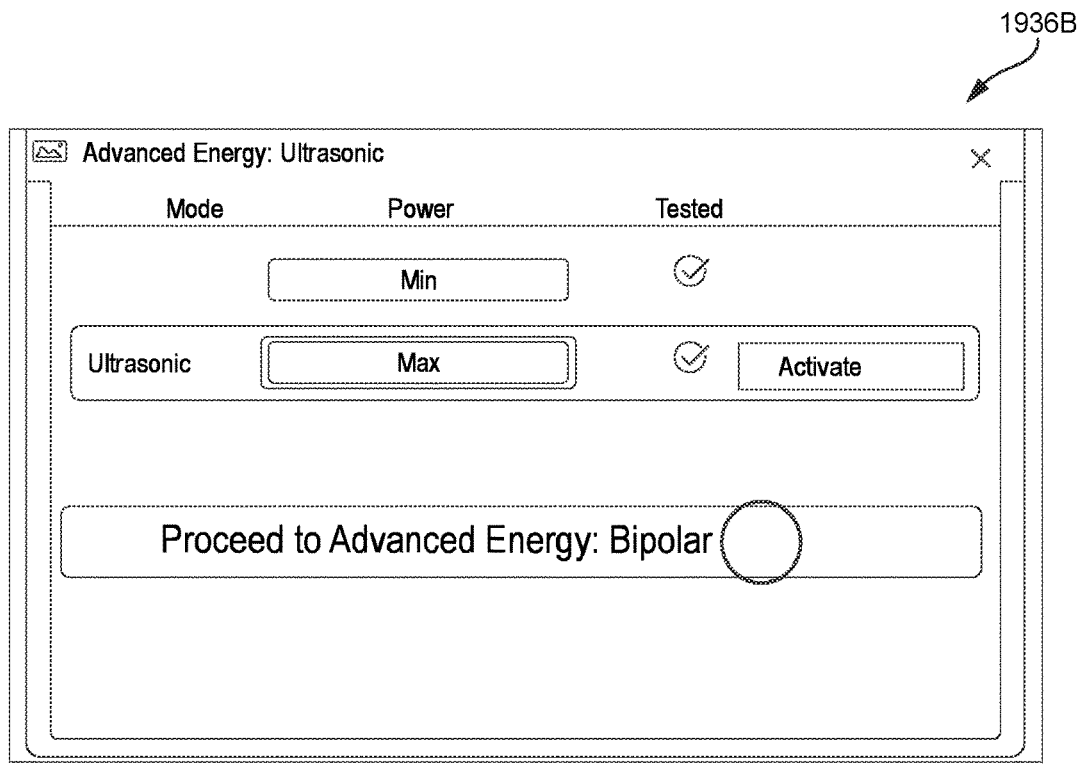
FIG. 61 is an illustrative graphical user interface final advanced energy:ultrasonic test mode screen, in accordance with at least one aspect of the present disclosure.

FIG. 60 is an illustrative GUI advanced energy: ultrasonic ESU analyzer connection screen 1936A. Advanced energy: ultrasonic ESU analyzer connection screen 1936A instructs the user to insert the leads of the ESU analyzer into the appropriate ports (of the output verification key) for testing the advanced energy: ultrasonic energy modality. These instructions include a visual depiction of the leads connected to the appropriate ports. After the leads are connected as shown, the user taps on the okay button to proceed to testing screens related to the advanced energy: ultrasonic modality. Similar to the other ports described above, the modular energy system instructs the user to test each of the required modes and power levels of the advanced energy: ultrasonic energy modality. Referring now to FIG. 61, after all modes and power levels have been tested, the final advanced energy: ultrasonic test mode screen 1936B is displayed. At this point, a button to proceed to advanced energy: bipolar output verification appears at the bottom of the screen. Clicking the proceed to advanced energy: bipolar button causes the modular energy system to proceed to the advanced energy: bipolar ESU analyzer connection screen.

Figure 62:
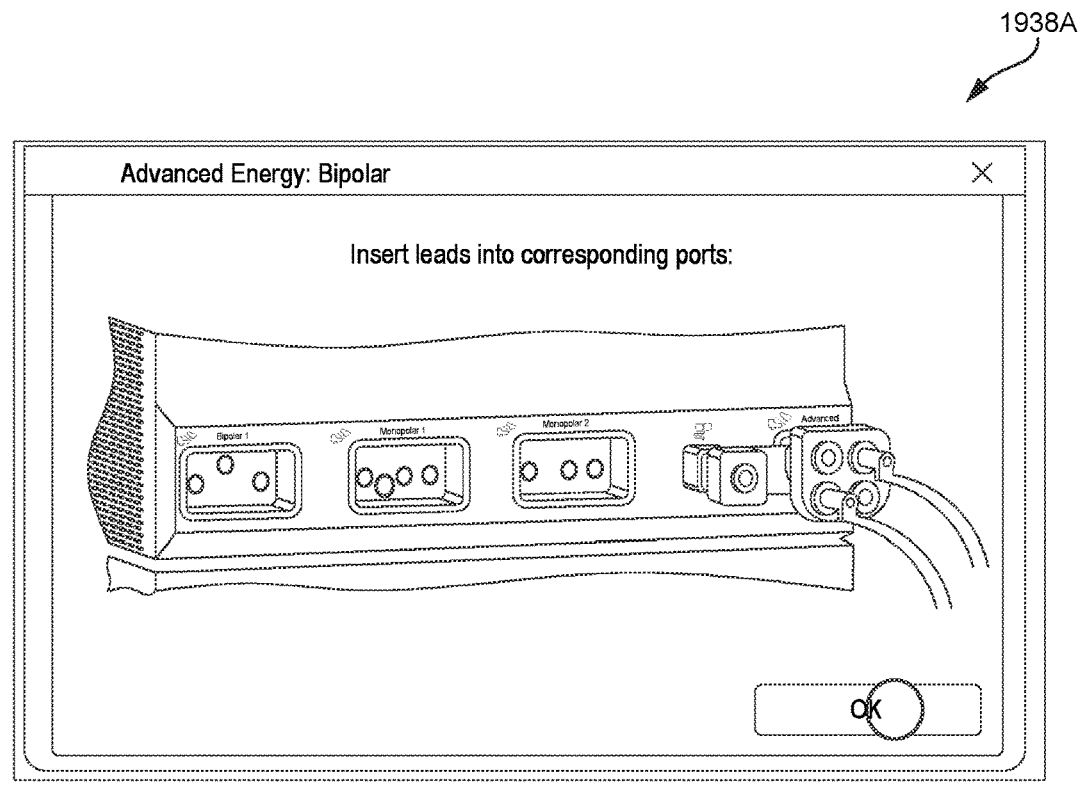
FIG. 62 is an illustrative graphical user interface advanced energy:bipolar ESU analyzer connection screen, in accordance with at least one aspect of the present disclosure.
Figure 63:
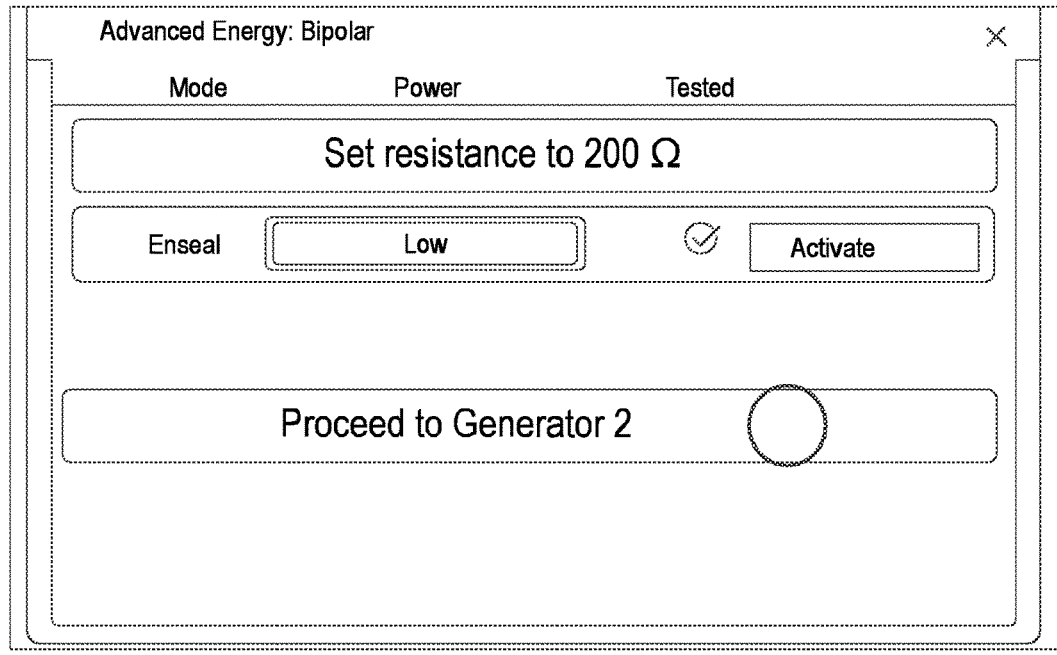
FIG. 63 is an illustrative graphical user interface final advanced energy:bipolar test mode screen, in accordance with at least one aspect of the present disclosure.

FIG. 62 is an illustrative GUI advanced energy: bipolar ESU analyzer connection screen 1938A. Advanced energy: bipolar ESU analyzer connection screen 1938A instructs the user to insert the leads of the ESU analyzer into the appropriate ports (of the output verification key) for testing the advanced energy: bipolar energy modality. These instructions include a visual depiction of the leads connected to the appropriate ports. After the leads are connected as shown, the user taps on the okay button to proceed to testing screens related to the advanced energy: bipolar modality. Similar to the other ports described above, the modular energy system instructs the user to test each of the required modes and power levels of the advanced energy: bipolar energy modality. Referring now to FIG. 63, after all power modes and levels have been tested, the final advanced energy: bipolar test mode screen 1938B is displayed. At this point, if the modular energy system includes an additional energy module (e.g., a second generator), a button to proceed to the next module (e.g., Generator 2) appears at the bottom of the screen. Clicking this button causes the modular energy system to proceed to the verification key connection screen.

Figure 64:
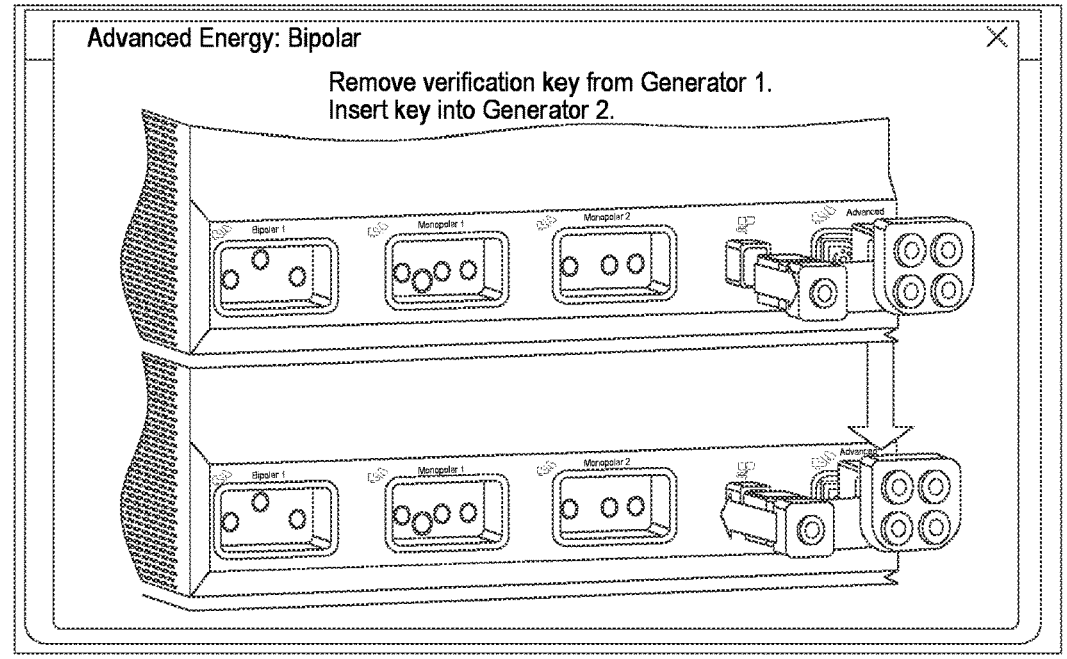
FIG. 64 is an illustrative graphical user interface verification key connection screen, in accordance with at least one aspect of the present disclosure.
Figure 65:
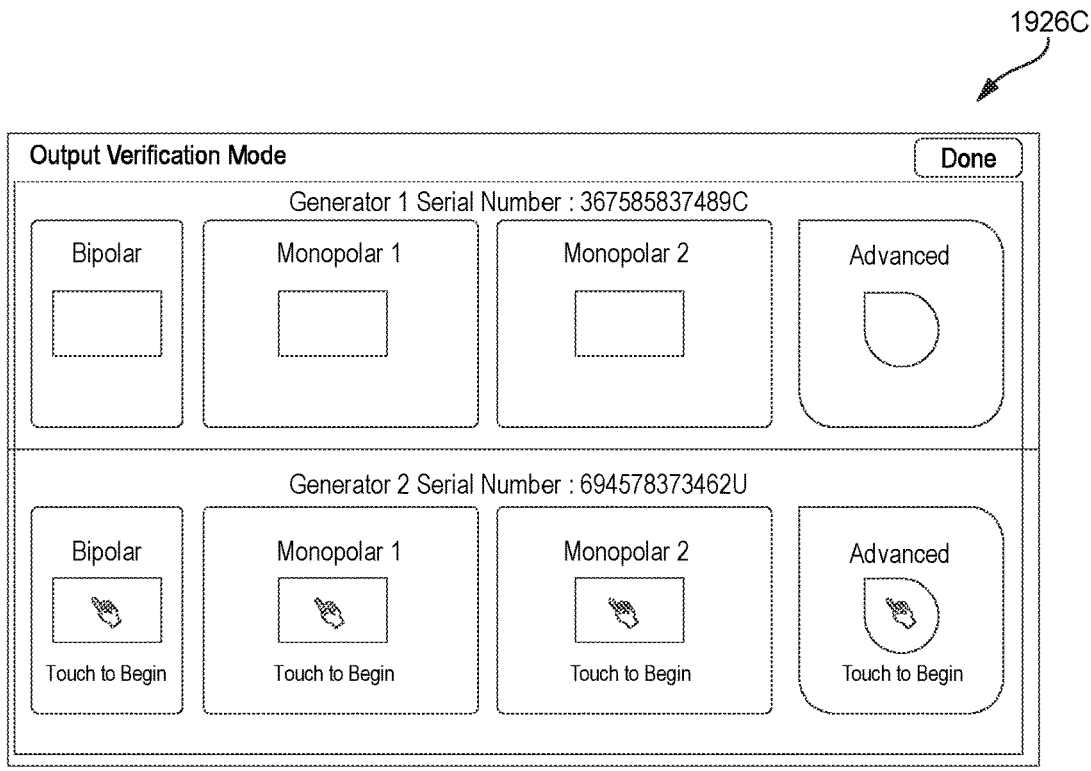
FIG. 65 is an illustrative graphical user interface output verification mode main screen, in accordance with at least one aspect of the present disclosure.

FIG. 64 is an illustrative GUI verification key connection screen 1940. Upon completion of output verification testing related to a first energy module (e.g., Generator 1), this screen instructs the user to remove the output verification key from the ports associated with the first energy module and insert them into the appropriate ports the second energy module (e.g., Generator 2). Included with these instructions are a visual depiction of the output verification key being removed from the ports of the first energy module and inserted into ports of the second energy module. Once the key is correctly inserted into the correct ports of the second energy module, the system may automatically recognize the connection and proceed to the output verification main screen FIG. 65 is an illustrative GUI output verification mode main screen 1926C. Output verification mode main screen 1926C displays buttons representing the various energy ports associated with the modular energy system. However, unlike verification mode main screen 1926A, output verification mode main screen 1926C displays a second row of available buttons (i.e. bipolar, monopolar, 1, monopolar 2, and advanced) representing ports associated with a second energy module (e.g., Generator 2) of the modular energy system. Output verification mode main screen 1926C may also display a serial number related to the second energy module above the second row of buttons. The user may begin output verification of a specific port of the second energy module by tapping on the appropriate energy port button. When the user has completed output verification, or if the user wishes to exit output verification mode and return to the system settings screen 1922, the user may tap the done button at the top right of the output verification mode menu screen.

Figure 66:
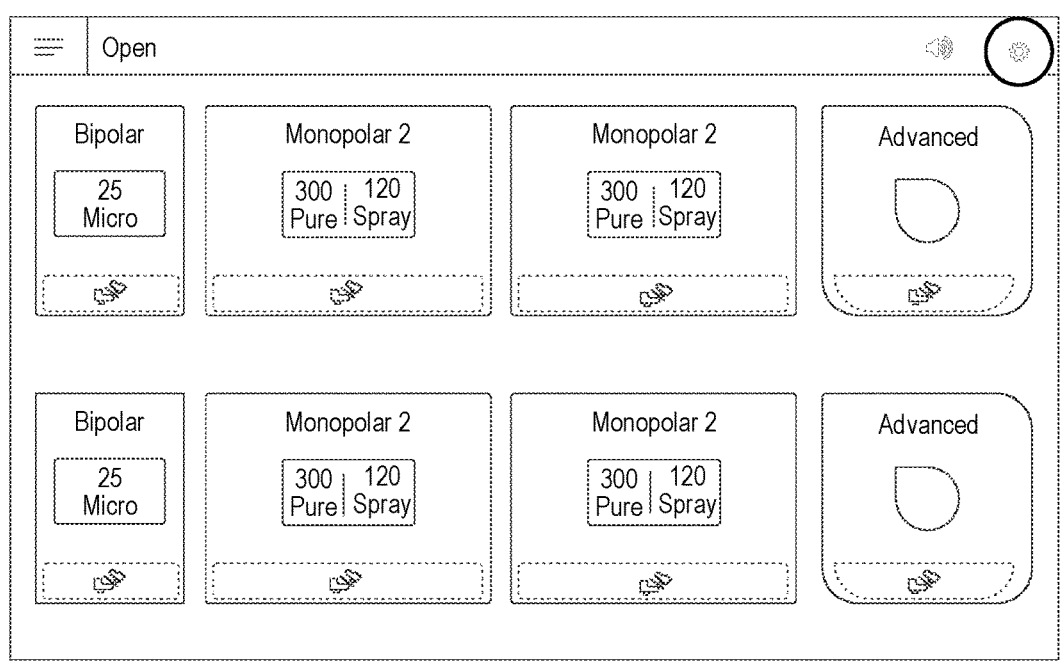
FIG. 66 is an illustrative graphical user interface main screen of a modular energy system, in accordance with at least one aspect of the present disclosure.
Figure 67:
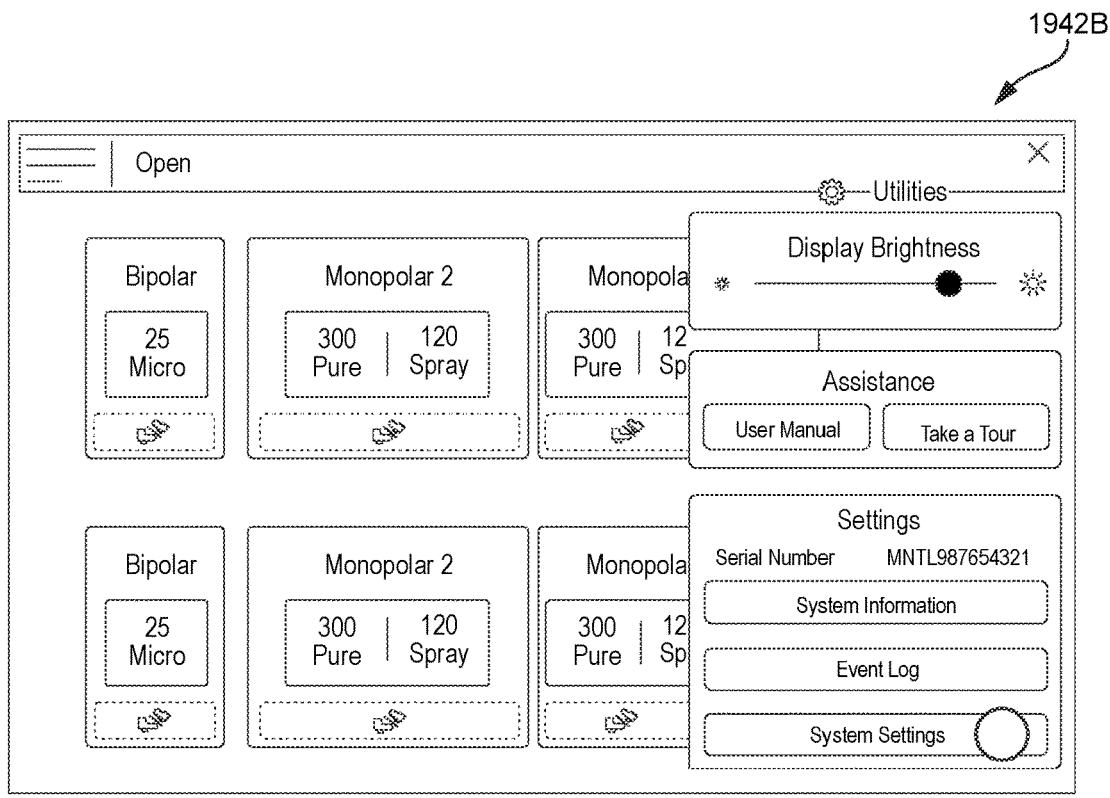
FIG. 67 is an illustrative graphical user interface utilities menu screen of a modular energy system, in accordance with at least one aspect of the present disclosure.
Figure 68:
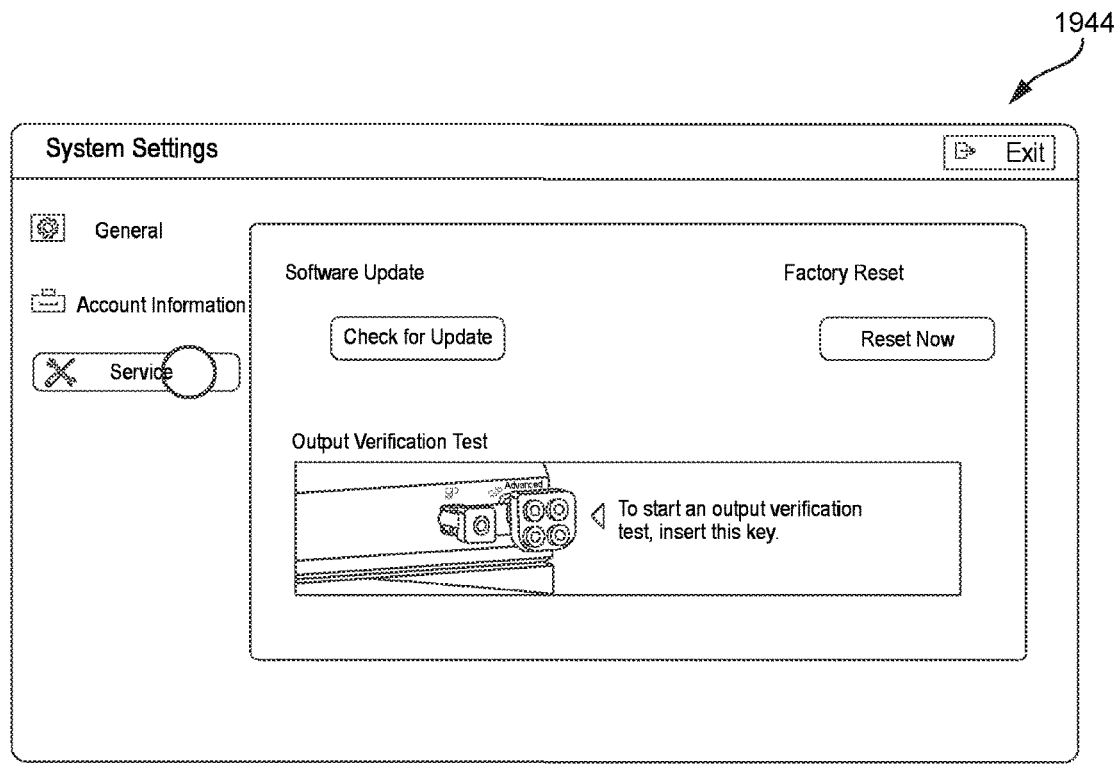
FIG. 68 is an illustrative graphical user interface system settings screen of a modular energy system, in accordance with at least one aspect of the present disclosure.

FIGS. 66 through 89 are illustrative GUI screens displayed by the modular energy system during a guided output verification process, in accordance with at least one other aspect of the current disclosure. FIG. 66 is an illustrative GUI main screen 1942A of the modular energy system. To begin accessing output verification mode, a user taps on the utilities button (gear icon) at the top right of GUI main screen 1942A, which causes a utilities menu screen to appear. FIG. 67 is an illustrative GUI utilities menu screen 1942B. By tapping on the system settings button at the bottom right of utilities menu screen 1942B, the user causes the modular energy system to display a system settings screen. FIG. 68 is an illustrative GUI system settings screen 1944. From the system settings screen 1944, the user next taps on the service button located to the left. Tapping the service button causes various service options to be displayed, including "Output Verification Test," as show on the middle portion system settings screen 1944. Under the "Output Verification Test" header, an image of the output verification key being inserted into the appropriate energy ports of an energy module (i.e. generator) is displayed. System settings screen 1944 instructs the user to insert the output verification key as shown to begin output verification testing. If the user inserts output verification key into the appropriate energy ports while system settings screen 1944 is displayed, it causes the modular energy system to enter output verification mode. In other aspects of the present disclosure, inserting the output verification key at any time may cause the modular energy system to enter output verification mode.

Figure 69:
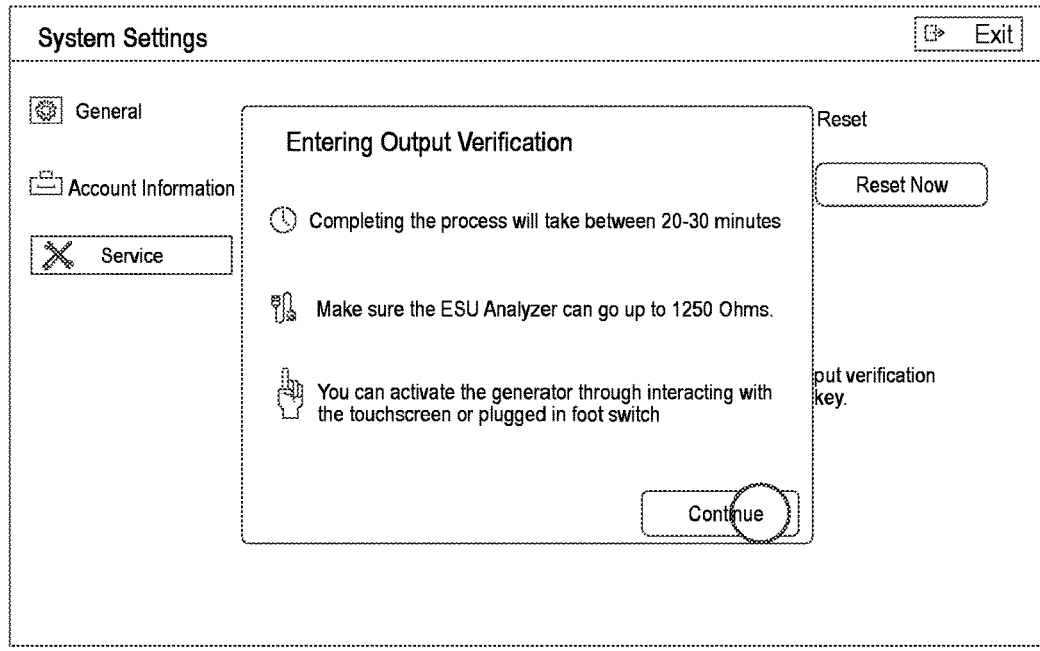
FIG. 69 is an illustrative graphical user interface screen for entering output verification, in accordance with at least one aspect of the present disclosure.

FIG. 69 is an illustrative GUI screen for entering output verification 1946. Screen for entering output verification 1946 displays a notice to users indicating the estimated length of time it will take to complete the output verification testing. The notice also asks users to ensure that they possess an ESU analyzer with the appropriate resistance capabilities (e.g., that it can reach a resistance of 1250 Ohms). Users are also notified that they can activate the generator (i.e. various modalities of the energy module) by interacting with the GUI touchscreen or the appropriate foot switch. Tapping on the continue button located at the bottom right of the screen for entering output verification 1946 causes the modular energy system to display the output verification mode main screen.

Figure 70:
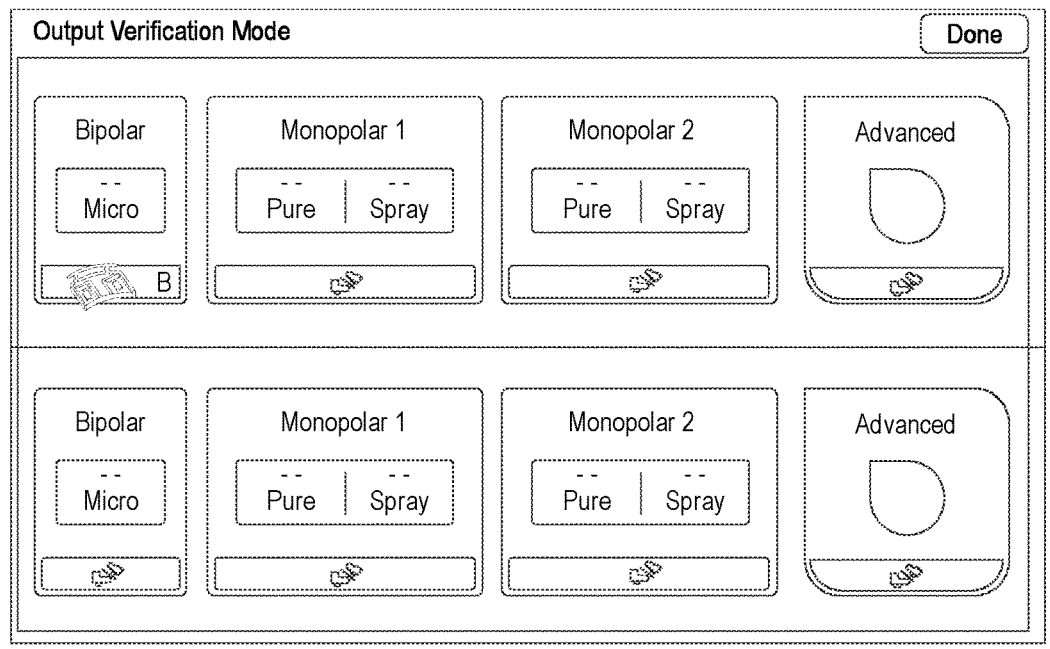
FIG. 70 is an illustrative graphical user interface output verification mode main screen, in accordance with at least one aspect of the present disclosure.

FIG. 70 is an illustrative GUI output verification mode main screen 1948A. Output verification mode main screen 1948A displays panels representing the various energy ports associated with the modular energy system. The top row of panels (i.e. bipolar, monopolar 1, monopolar 2, and advanced) represent ports associated with a first energy module (i.e. generator 1) of the modular energy system. If there are more than one energy modules (more than one generators) associated with the modular energy system, output verification mode main screen 1948A may display additional rows of energy port panels corresponding to energy ports of the additional energy modules. For example, output verification mode main screen 1948A includes a second row of panels (i.e. bipolar, monopolar 1, monopolar 2, and advanced) associated with a second energy module (i.e. generator 2) of the modular energy system. The user may begin output verification of a specific energy modality by inserting leads of the ESU analyzer into the appropriate ports associated with that energy modality. For example, inserting the ESU analyzer leads into the ports corresponding to the bipolar energy modality causes a first bipolar test mode screen to appear.

Figure 71:
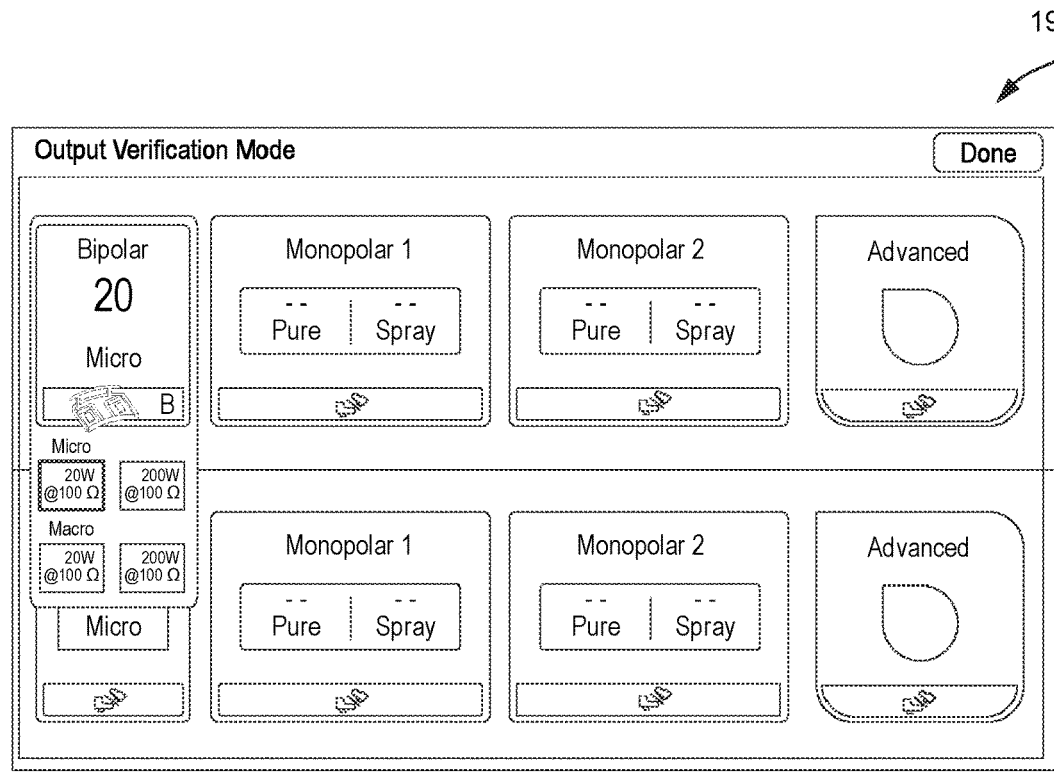
FIG. 71 is an illustrative graphical user interface first bipolar test mode screen, in accordance with at least one aspect of the present disclosure.

FIG. 71 is an illustrative GUI first bipolar test mode screen 1948B. The first bipolar test mode screen 1948B includes an expanded bipolar panel, wherein the expanded bipolar panel displays the available modes and power levels associated with the bipolar energy modality that are to be tested. For example, the expanded bipolar panel shown on first bipolar test mode screen 1948B includes buttons for 20w and 200w power levels to be tested using micro mode and buttons for 20w and 200w power levels to be tested using macro mode. Each of the buttons also displays the required ESU analyzer resistance level for each test. The button corresponding to the first power mode and power level to be tested (i.e. Micro 20w) is highlighted on the first bipolar test mode screen 1948B. Further, that same mode and power level is displayed in large font at the top of the expanded bipolar panel (i.e. 20 Micro). The foot pedal image displayed within the expanded bipolar panel of screen 1948B indicates that a foot pedal connected to the modular energy system may be used to activate power at the level/ mode corresponding to the highlighted button (i.e. Micro 20w). In various aspects of the present disclosure, an activate button displayed on the first bipolar test mode screen may be used to activate power instead of a foot pedal.

Figure 72:
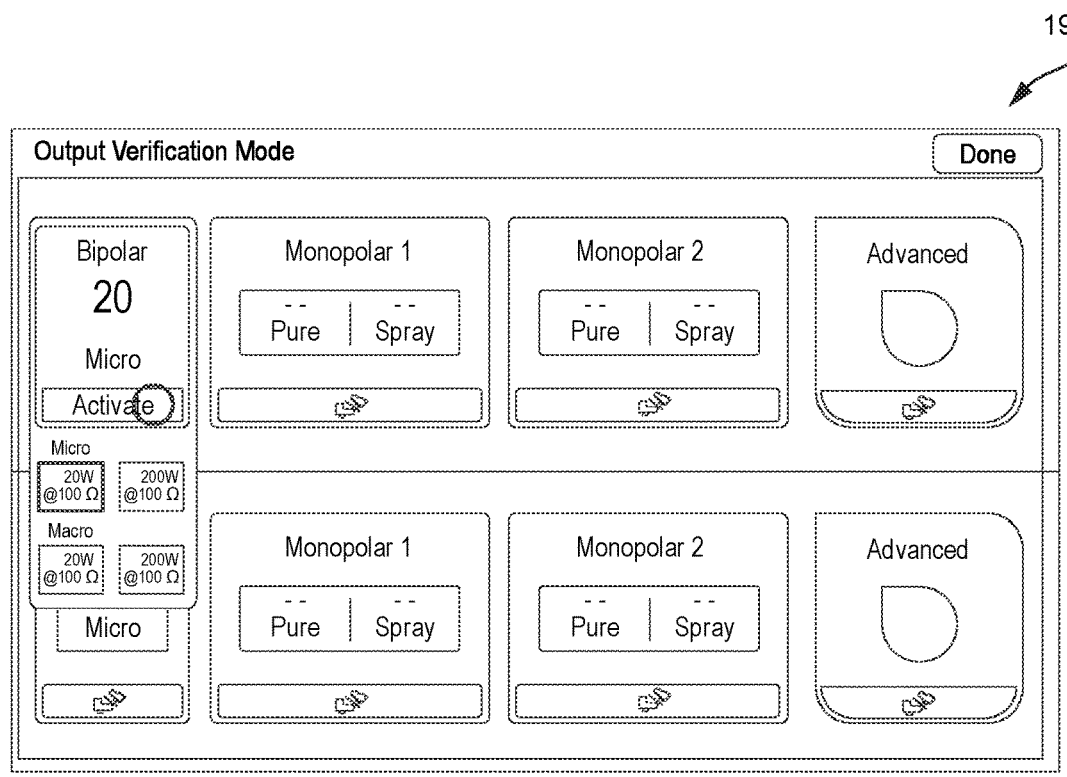
FIG. 72 is an illustrative graphical user interface first bipolar test mode screen, in accordance with at least one aspect of the present disclosure.

Referring now to FIG. 72, an illustrative GUI first bipolar test mode screen 1948C is depicted with activate button instead of a foot pedal. Pressing and holding the activate button causes the modular energy system to deliver energy at the mode and power level corresponding to the highlighted button within the expanded bipolar panel (i.e. Micro 20w). With the energy activated, the user can take the appropriate measurements using the ESU analyzer. Releasing the activate button causes the modular energy system to stop delivering energy through the bipolar port.

Figure 73:
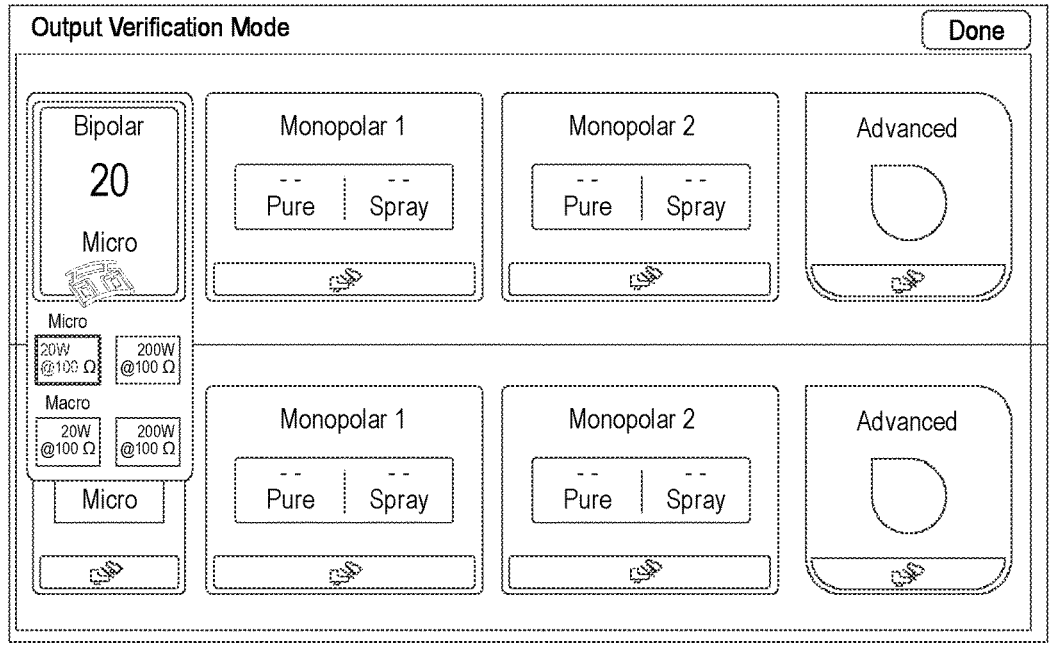
FIG. 73 is an illustrative graphical user interface first bipolar test mode screen, in accordance with at least one aspect of the present disclosure.
Figure 74:
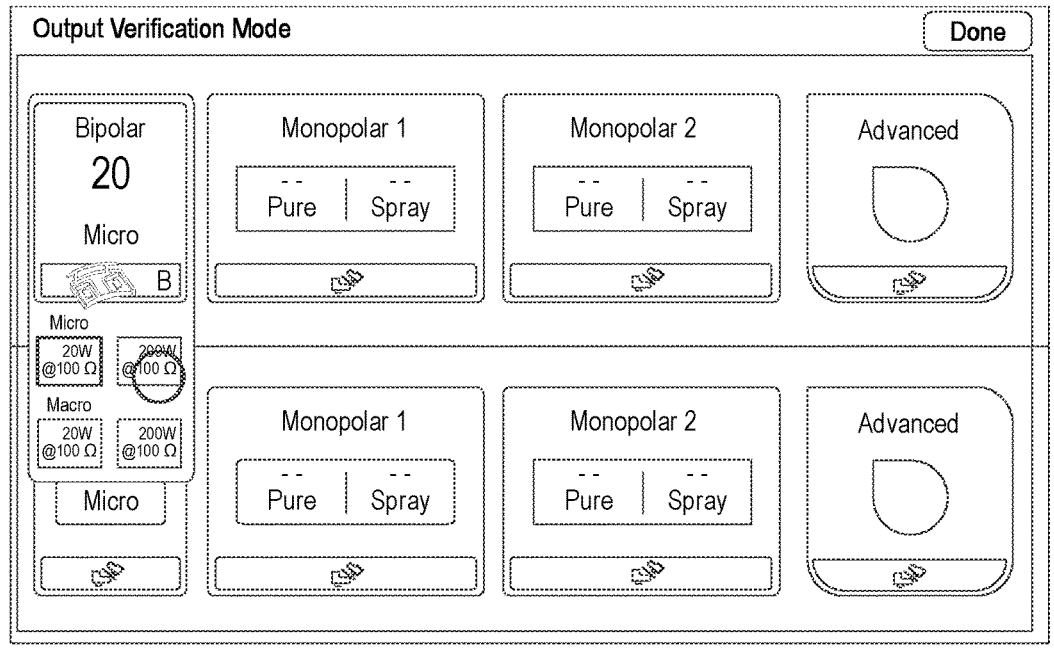
FIG. 74 is an illustrative graphical user interface first bipolar test mode screen, in accordance with at least one aspect of the present disclosure.

Referring now to first bipolar test mode screen 1948D of FIG. 73, the user activates bipolar energy at the first mode and power level (i.e. Micro 20w) by pressing the foot pedal. When power is activated, the top portion of the expanded bipolar panel becomes highlighted, as shown by screen 1948D. When the user is ready test a second mode and power level of the bipolar energy modality, he or she may tap the button within the expanded bipolar panel corresponding to that mode and level (e.g. Micro 200w), as illustrated by first bipolar test mode screen 1948E of FIG. 74. This causes a second bipolar test mode screen to appear.

Figure 75:
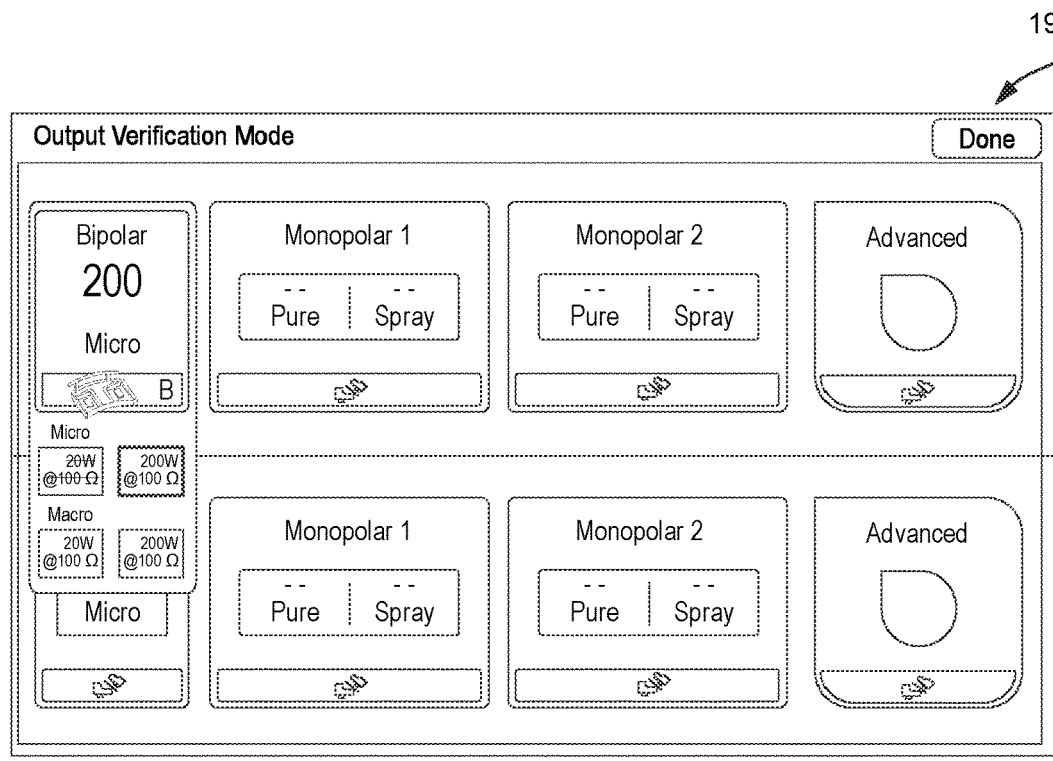
FIG. 75 is an illustrative graphical user interface second bipolar test mode screen, in accordance with at least one aspect of the present disclosure.
Figure 76:
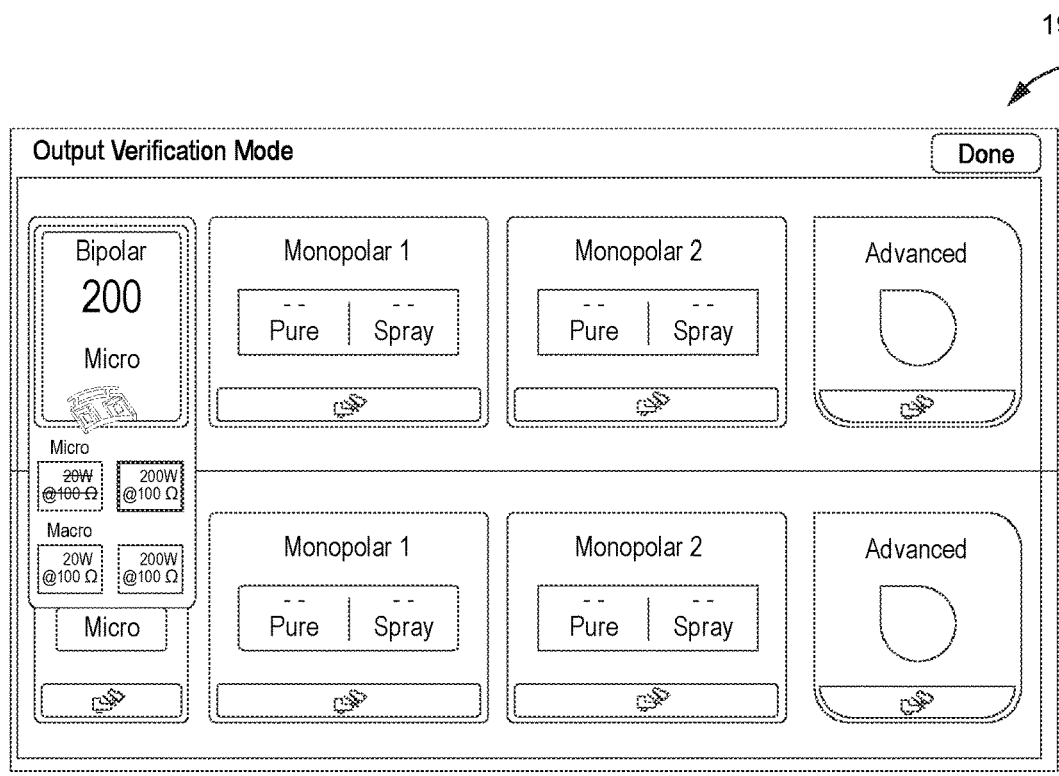
FIG. 76 is an illustrative graphical user interface second bipolar test mode screen, in accordance with at least one aspect of the present disclosure.
Figure 77:
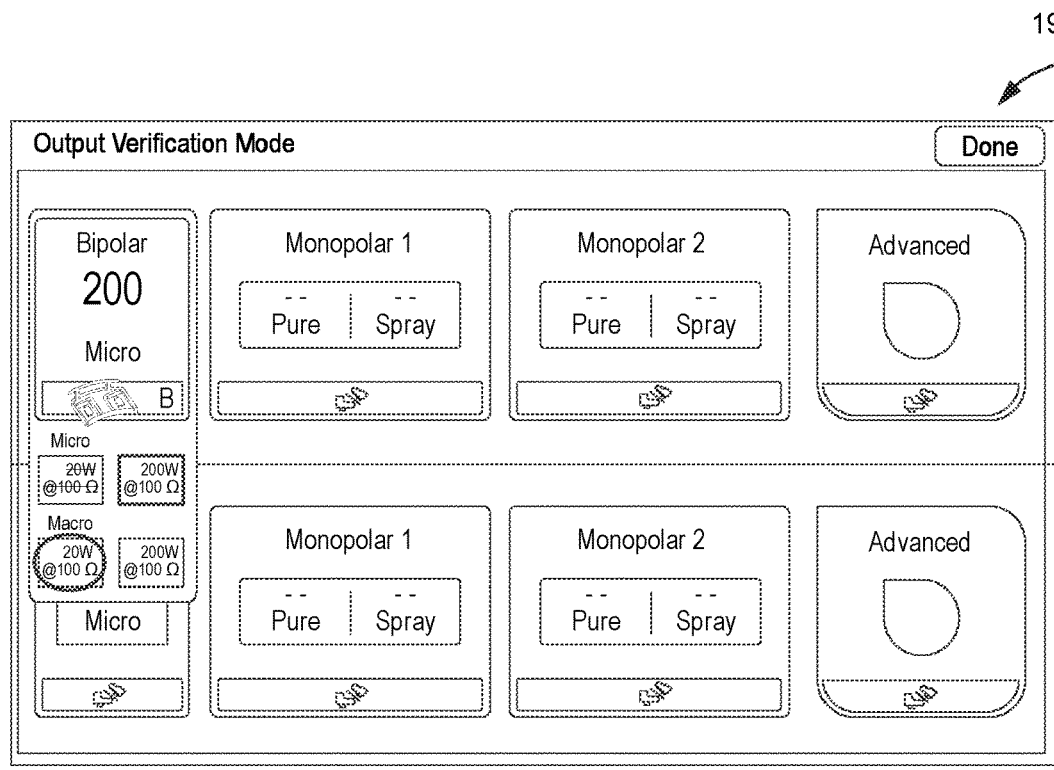
FIG. 77 is an illustrative graphical user interface second bipolar test mode screen, in accordance with at least one aspect of the present disclosure.
Figure 78:
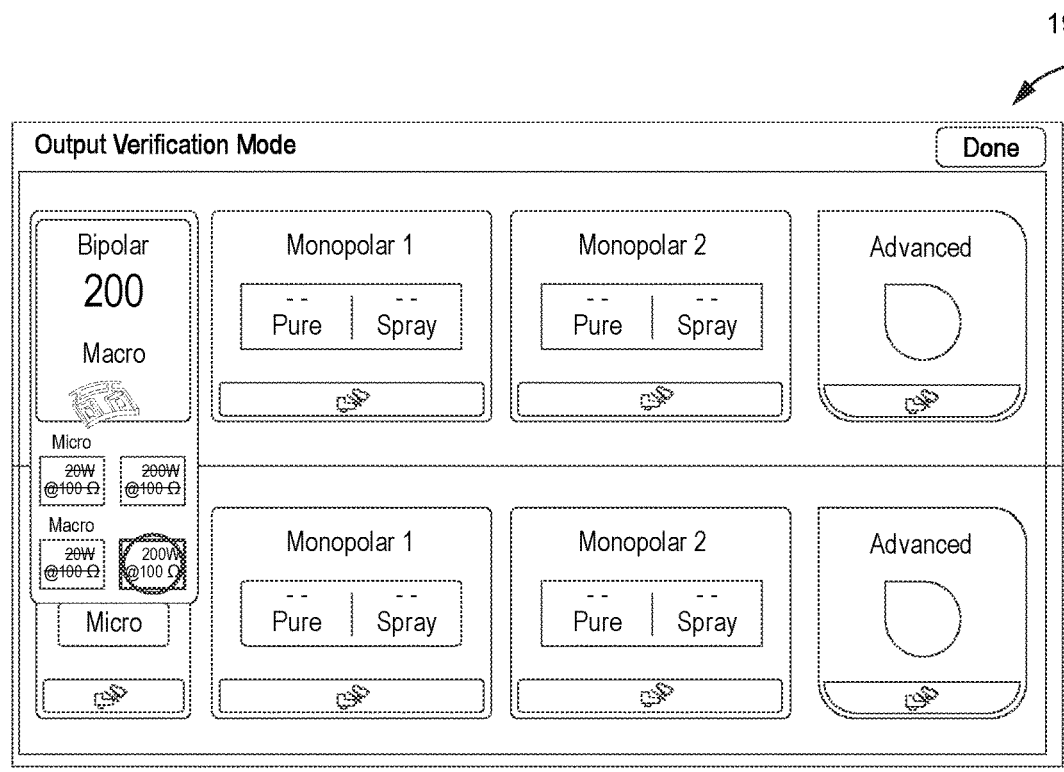
FIG. 78 is an illustrative graphical user interface final bipolar test mode screen, in accordance with at least one aspect of the present disclosure.

FIG. 75 is an illustrative GUI second bipolar test mode screen 1948F. Similar to the first bipolar test mode screen 1948B, the second bipolar test mode screen 1948F includes an expanded bipolar panel that displays the available modes and power levels associated with the bipolar energy modality that are to be tested. However, the text within the button corresponding to the first mode and power level tested now appears with strikethrough, indicated that testing at that setting has been completed. Further, the button corresponding to the second power mode and level to be tested (i.e. Micro 200w) is highlighted and the large text at the top of the expanded bipolar panel now is updated based on that mode and level (i.e. 200 Micro). To test the second power level, the user proceeds similarly as explained above related to the first power level. When power is activated, the top portion of the expanded bipolar panel becomes highlighted, as illustrated by second bipolar test mode screen 1948G of FIG. 76. When the user is ready test the next mode and power level of the bipolar energy modality, he or she may tap the button within the expanded bipolar panel corresponding to that mode and level (e.g. Macro 20w), as illustrated by second bipolar test mode screen 1948H of FIG. 77. This process continues for all available modes and power levels shown in the expanded bipolar panel. For example, FIG. 78 is an illustrative GUI final bipolar test mode screen 1948J indicating that testing at Micro 20w, Micro 200w, and Macro 20w have been completed and Macro 200w is currently being tested. After testing at the final mode and power level is complete, the user may remove the ESU analyzer leads from the ports corresponding to the bipolar energy modality. Removing the leads causes the modular energy system return to the output verification mode main screen.

Figure 79:
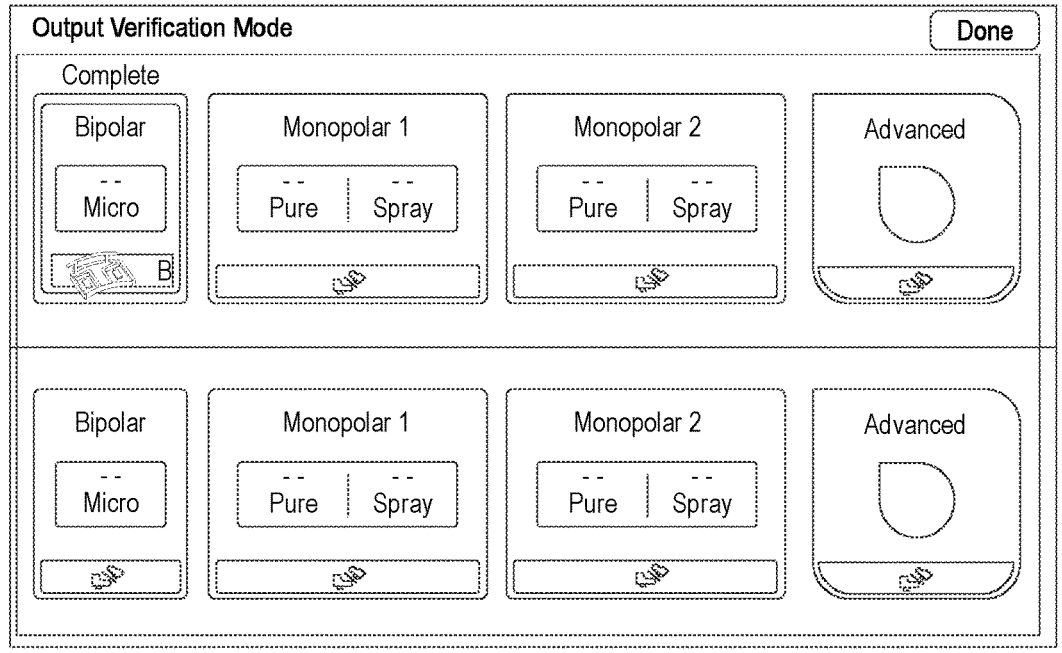
FIG. 79 is an illustrative graphical user interface output verification mode main screen, in accordance with at least one aspect of the present disclosure.

FIG. 79 is an illustrative GUI output verification mode main screen 1948K. Similar to output verification mode main screen 1948A, output verification mode main screen 1948K displays panels representing the various energy ports associated with the modular energy system. However, the panel corresponding to the bipolar energy modality of the first energy module is now highlighted, indicating that output verification testing for that modality has been completed. The user may begin output verification of the monopolar 1 energy modality by inserting the ESU analyzer leads into the corresponding ports of the energy module and output verification key. This causes a first monopolar 1 test mode screen to appear.

Figure 80:
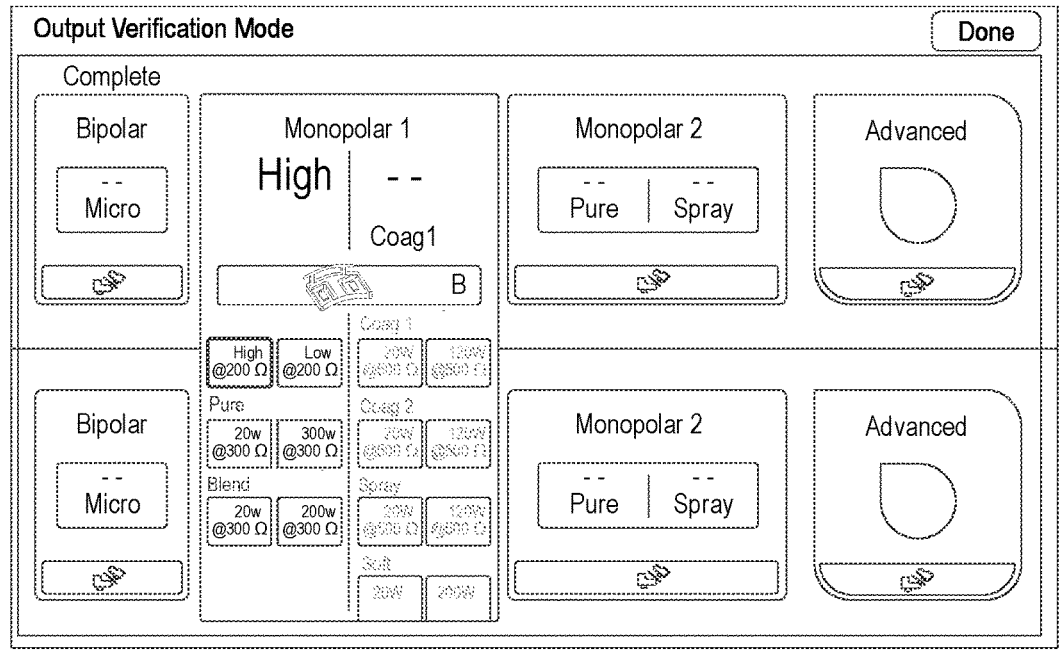
FIG. 80 is an illustrative graphical user interface first monopolar 1 test mode screen, in accordance with at least one aspect of the present disclosure.
Figure 81:
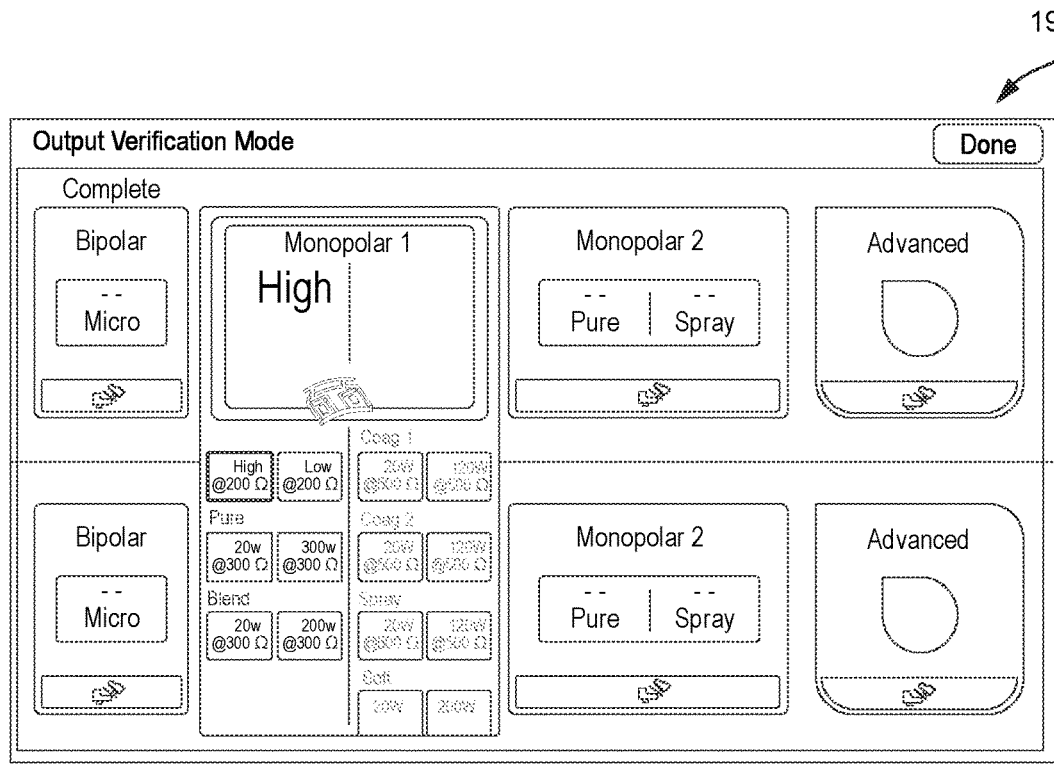
FIG. 81 is an illustrative graphical user interface first monopolar 1 test mode screen, in accordance with at least one aspect of the present disclosure.

FIG. 80 is an illustrative GUI first monopolar 1 test mode screen 1948L. The first monopolar 1 test mode screen 1948L includes an expanded monopolar 1 panel, wherein the expanded monopolar 1 panel displays the available modes and power levels associated with the monopolar 1 energy modality that are to be tested. Each of the buttons also displays the required ESU analyzer resistance level for each test. The button corresponding to the first power mode and power level to be tested is highlighted on screen 1948L. An indication such as monopolar modulation technique high may be displayed. Further, that same mode and power level may be displayed in large font at the top of the expanded monopolar 1 panel (e.g., High monopolar modulation technique). Referring now to first bipolar test mode screen 1948M of FIG. 81, the user activates the monopolar 1 energy port at the first mode and power level (i.e. monopolar modulation technique high) by pressing the foot pedal. When power is activated, the top portion of the expanded monopolar 1 panel becomes highlighted, as shown by screen 1948M. When the user is ready to test a second mode and power level of the monopolar 1 energy modality, he or she may tap the button within the expanded monopolar 1 panel corresponding to that mode and level (e.g. monopolar modulation technique low). This causes a second monopolar 1 test mode screen to appear.

Figure 82:
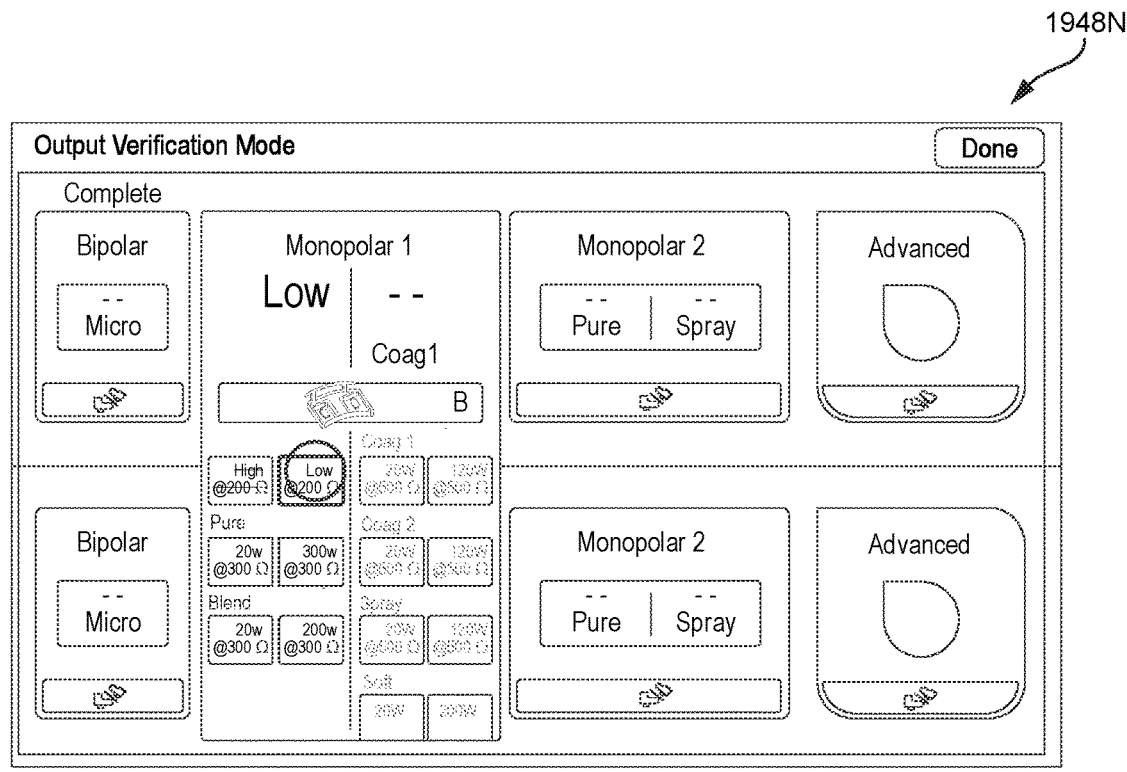
FIG. 82 is an illustrative graphical user interface second monopolar 1 test mode screen, in accordance with at least one aspect of the present disclosure.
Figure 83:
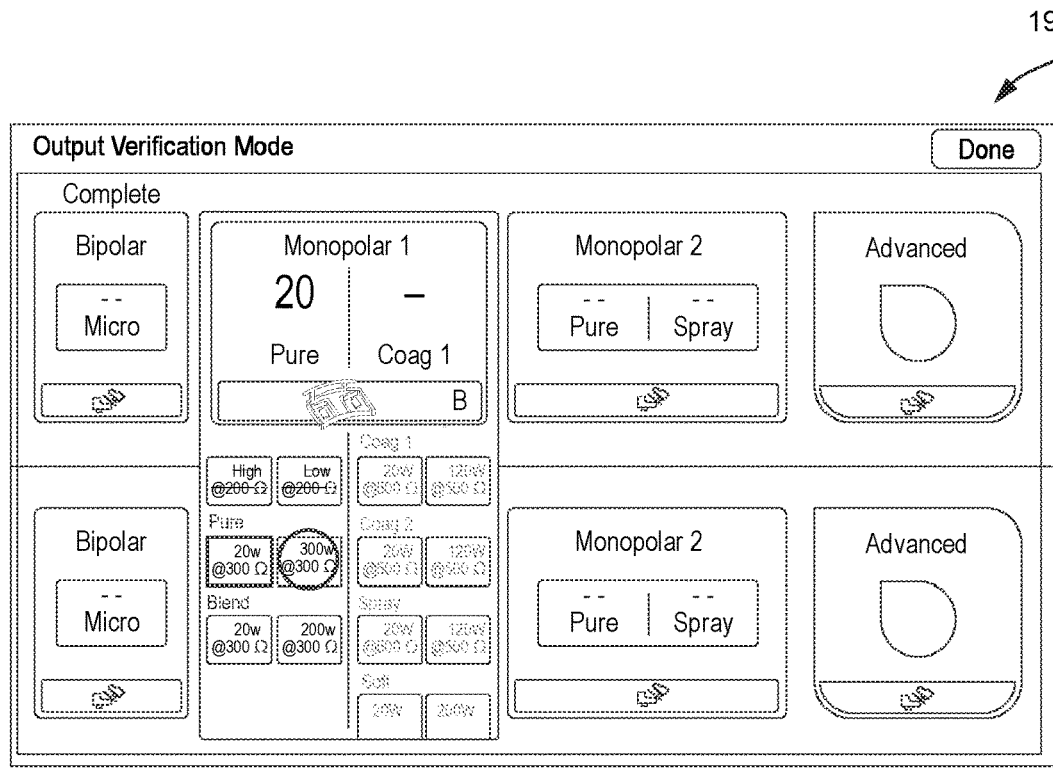
FIG. 83 is an illustrative graphical user interface third monopolar 1 test mode screen, in accordance with at least one aspect of the present disclosure.

FIG. 82 is an illustrative GUI second monopolar 1 test mode screen 1948N. Similar to the first monopolar 1 test mode screen 1948L, the second monopolar 1 test mode screen 1948N includes an expanded monopolar 1 panel that displays the available modes and power levels associated with the monopolar 1 energy modality that are to be tested. However, the text within the button corresponding to the first mode and power level tested now appears with strikethrough, indicated that testing at that setting has been completed. Further, the button corresponding to the second mode and power level to be tested (e.g., monopolar modulation technique low) is highlighted and the large text at the top of the expanded monopolar 1 panel now is updated (e.g., Low monopolar modulation technique). To test the second power level, the user proceeds similarly as explained above related to the first power level. Similarly, the user proceeds through each power level shown in the expanded monopolar 1 panel. For example, the third monopolar 1 test mode screen 1948P shown in FIG. 83 indicates that the user has tested the monopolar modulation technique High and Low settings, is currently testing the Pure 20w setting, and is ready to proceed to the Pure 300w setting. After testing all monopolar 1 settings, the user may remove the ESU analyzer leads from the ports corresponding to the monopolar 1 energy modality. Removing the leads causes the modular energy system return to the output verification mode main screen. From the main screen, the user may proceed to test the monopolar 2 energy modality following similar steps to those described above.

Figure 84:
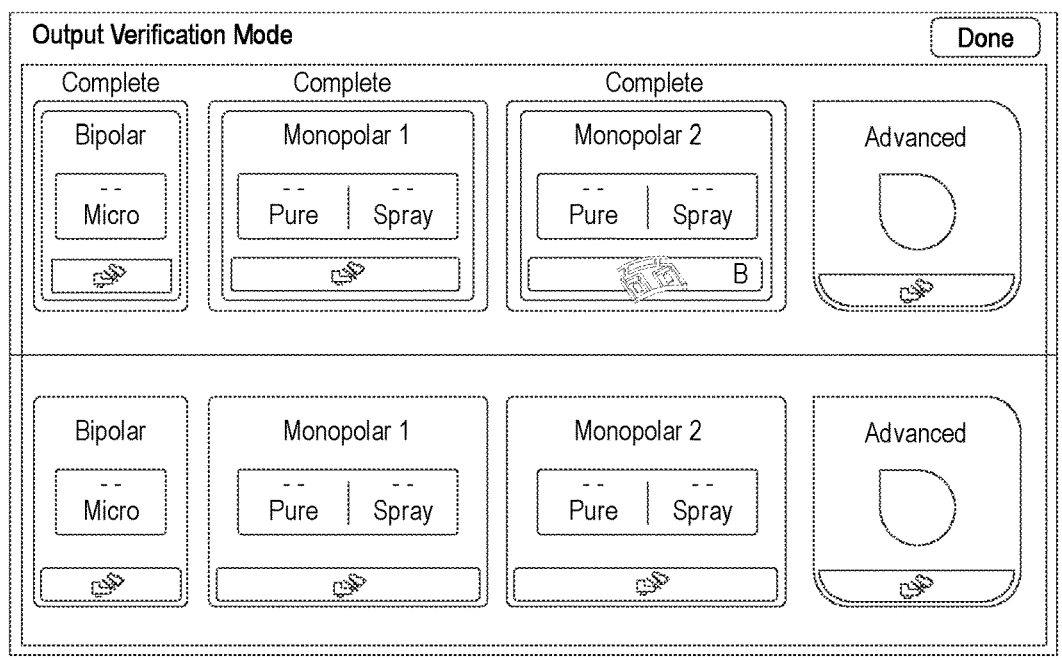
FIG. 84 is an illustrative graphical user interface output verification mode main screen, in accordance with at least one aspect of the present disclosure.

FIG. 84 is an illustrative GUI output verification mode main screen 1948Q. This screen shows the bipolar, monopolar 1, and monopolar 2 panels as highlighted. These highlighted panels indicate that output verification testing has been completed for the corresponding energy modalities. The user may begin output verification of the advanced energy modality by inserting the ESU analyzer leads into the corresponding ports of the output verification key. This causes an advanced energy: ultrasonic test mode screen to appear.

Figure 85:
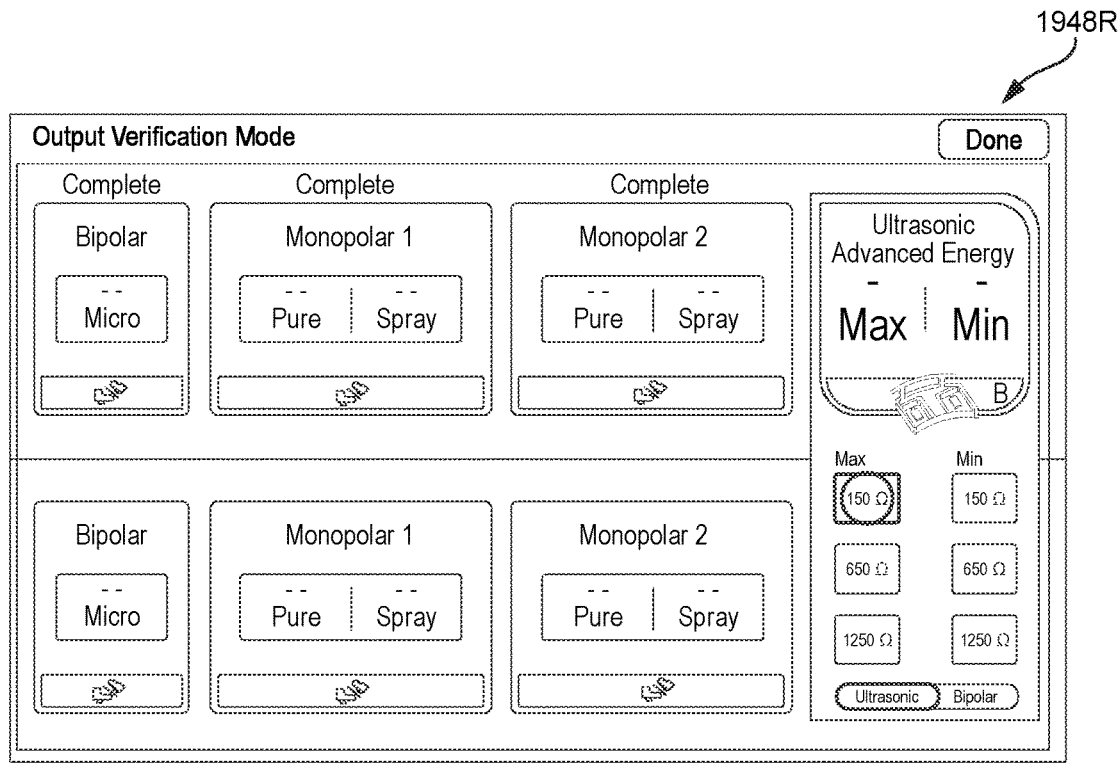
FIG. 85 is an illustrative graphical user interface first advanced energy: ultrasonic test mode screen, in accordance with at least one aspect of the present disclosure.

FIG. 85 is an illustrative GUI first advanced energy: ultrasonic test mode screen 1948R. Similar to the other test mode screens described above, screen 1948R includes an expanded advanced energy panel that displays the available testing modes and power levels associated with the advanced energy modality. Each of the buttons also displays the required ESU analyzer resistance level for each test. The button corresponding to the first power mode and power level to be tested (i.e. Ultrasonic Max at 150 ohms) is highlighted on screen 1948R. Further, that same mode and power level is displayed in large font at the top of the expanded advanced energy panel (i.e. Ultrasonic Max).

Figure 86:
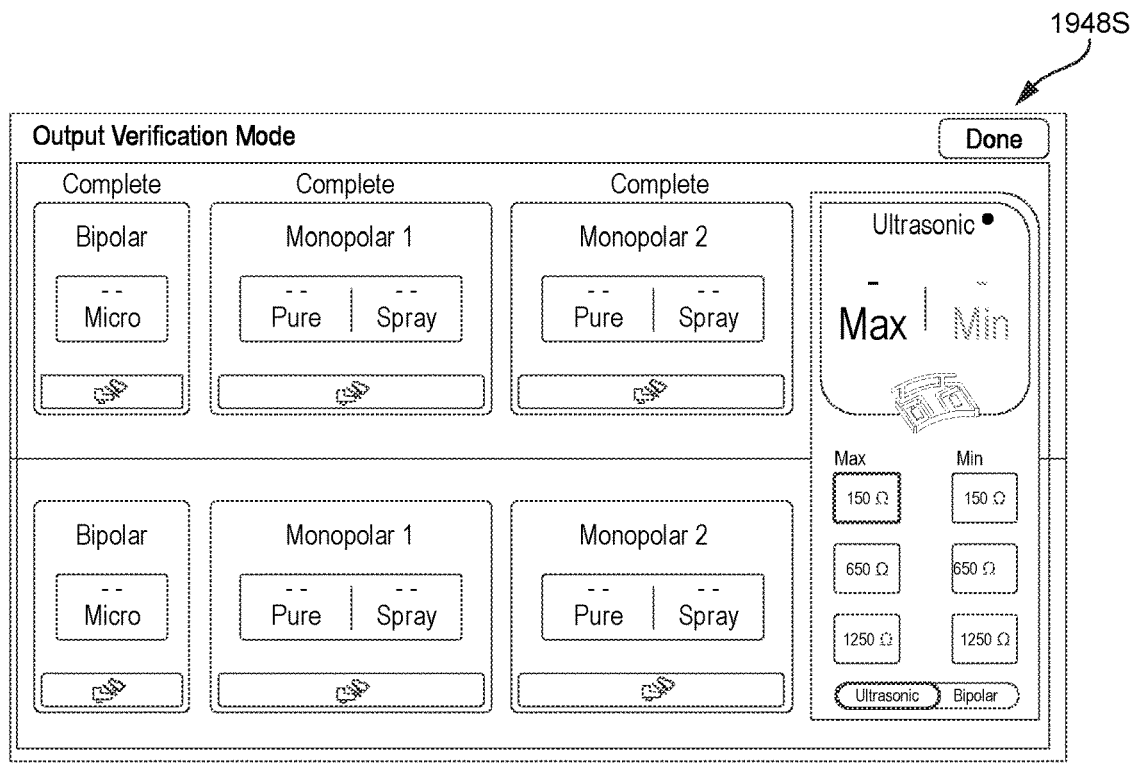
FIG. 86 is an illustrative graphical user interface first advanced energy:ultrasonic test mode screen, in accordance with at least one aspect of the present disclosure.
Figure 87:
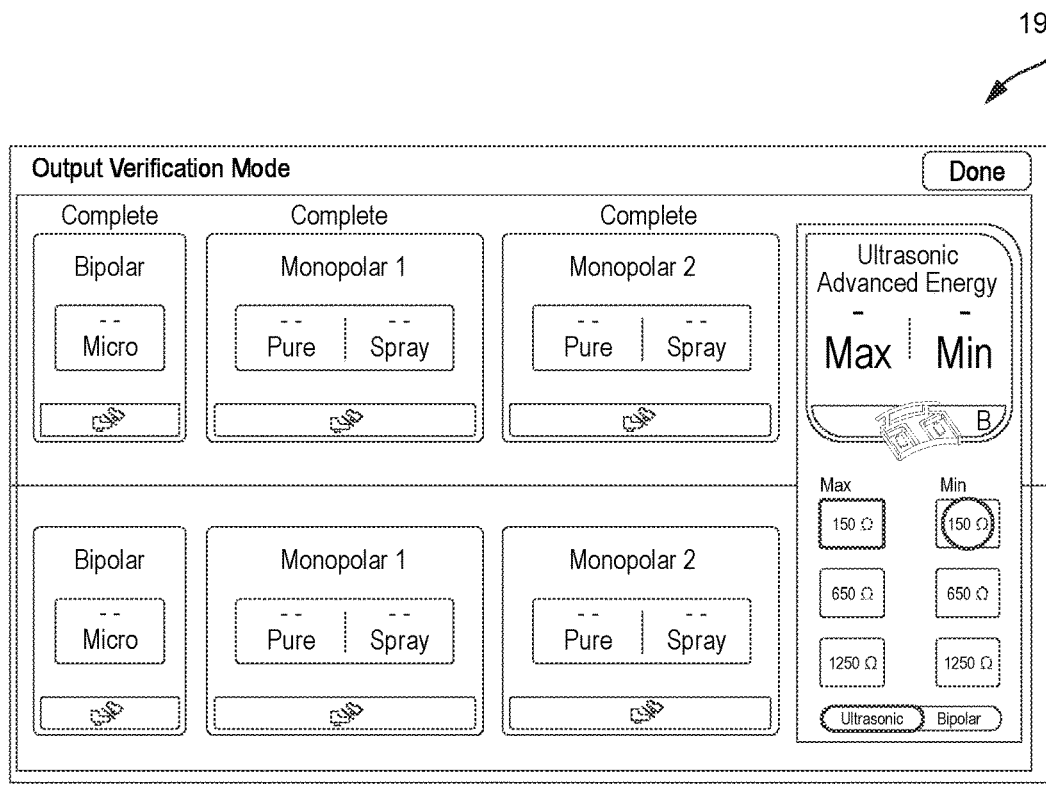
FIG. 87 is an illustrative graphical user interface advanced energy: ultrasonic test mode screen, in accordance with at least one aspect of the present disclosure.
Figure 88:
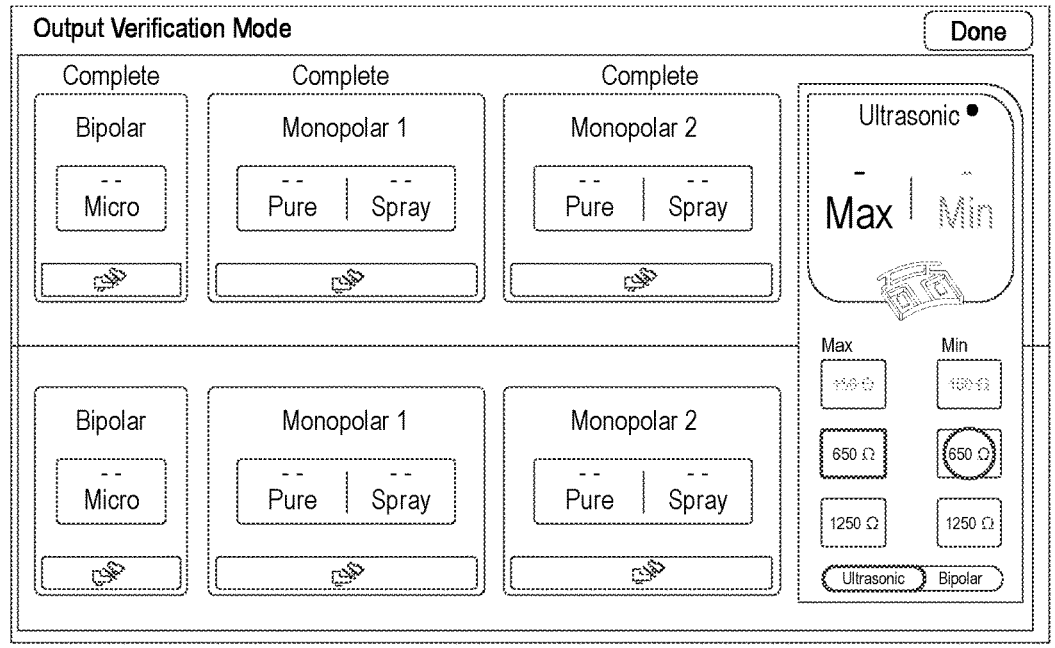
FIG. 88 is an illustrative graphical user interface third advanced energy:ultrasonic test mode screen, in accordance with at least one aspect of the present disclosure.

Referring now to the first advanced energy: ultrasonic test mode screen 1948S shown in FIG. 86, the user activates the advanced energy port at the first mode and power level (i.e. Ultrasonic Max) by pressing the foot pedal. When power is activated, the top portion of the expanded advanced energy panel becomes highlighted, as shown by screen 1948S. When the user is ready test a second mode and power level of the advanced energy modality, he or she may tap the button within the expanded advanced energy panel corresponding to that mode and level (e.g. Ultrasonic Min at 150 ohms), as illustrated by advanced energy: ultrasonic test mode screen 1948T of FIG. 87. This causes a second advanced energy: ultrasonic test mode screen to appear. To test the second power level, the user proceeds as explained above related to the first power level. Similarly, the user proceeds through each ultrasonic setting shown in the expanded advanced energy panel, adjusting the resistance of the ESU analyzer as required. For example, the third advanced energy: ultrasonic test mode screen 1948U shown in FIG. 88 indicates that the user has tested the ultrasonic max and min settings at 150 ohms, is currently testing the ultrasonic max setting at 650 ohms, and is ready to proceed to the ultrasonic min setting at 650 ohms. After testing all ultrasonic settings, the user may proceed to the bipolar setting of the advanced energy modality by tapping the toggle button at the bottom of the expanded advanced energy panel. This causes the expanded advanced energy panel to display all of the required output verification test settings for the advanced energy: bipolar modality. After the user has completed all of the required output verification testing related to the advanced energy modality, the user may remove the ESU analyzer leads from the output verification key. Removing the leads causes the modular energy system return to the output verification mode main screen.

Figure 89:
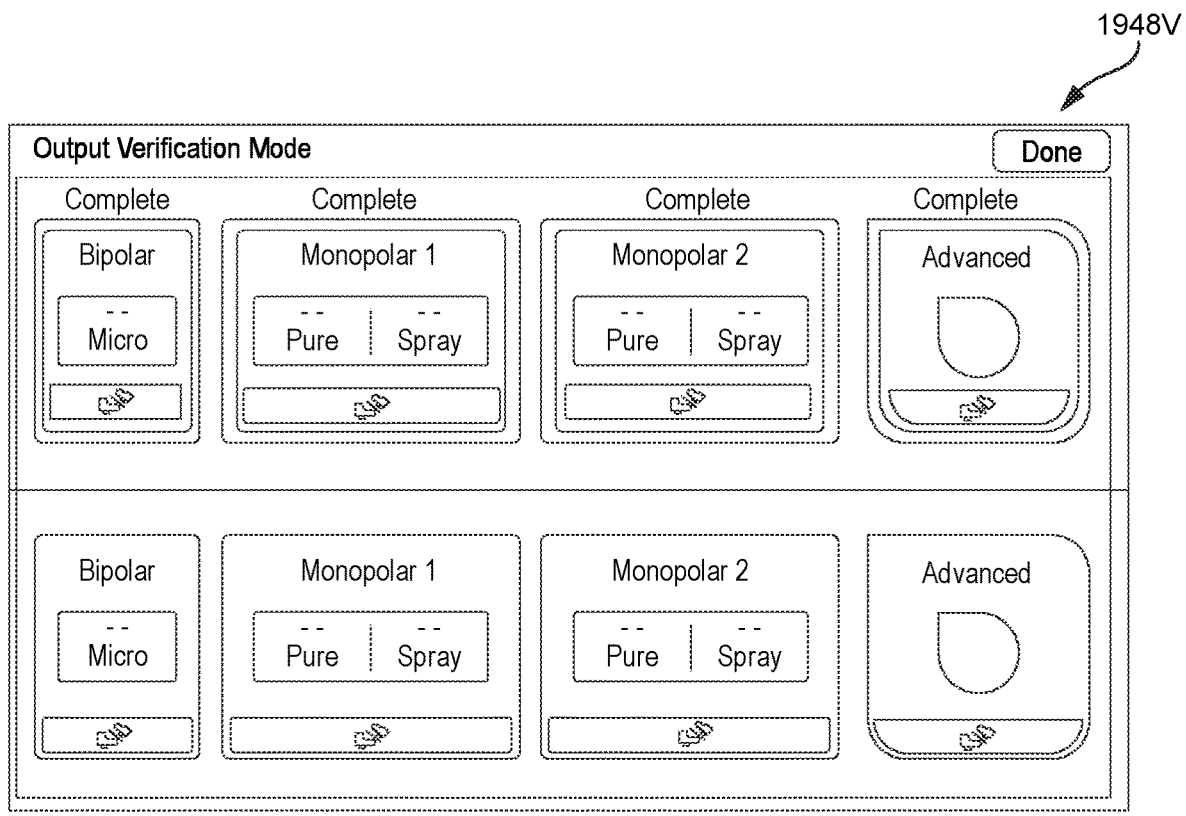
FIG. 89 is an illustrative graphical user interface output verification mode main screen, in accordance with at least one aspect of the present disclosure.

FIG. 89 is an illustrative GUI output verification mode main screen 1948V. This screen shows the bipolar, monopolar 1, monopolar 2, and advanced energy panels as highlighted. These highlighted panels indicate that output verification testing has been completed for all energy modalities of the first energy module (e.g. generator 1). The user may begin output verification of the second energy module (e.g. generator 2) by transferring the output verification key into the appropriate ports of the second module and inserting the ESU analyzer leads into the ports corresponding to the bipolar energy modality. The output verification process for the second energy module then proceeds similar to the description above.

Output Verification Key

As explained above, standard hospital procedure requires that output verification testing be performed on electrosurgical generators, often on an annual or semiannual basis. Typically, the output verification process involves connecting an electrosurgical unit (ESU) analyzer to various energy ports of the electrosurgical generator. Once the ESU analyzer is connected, users (e.g., biomedical technicians) cause the electrosurgical generator to activate the connected port at various modes and power settings while the ESU analyzer is set at various resistance levels. The user cycles through the different combinations of power and resistance levels and records the results. These results are used to determine whether the power output of the electrosurgical generator conforms with the manufacturer's specifications. However, some or all of the energy ports on typical electrosurgical generators are not compatible with wire leads associated with the ESU analyzer. Moreover, electrosurgical generators often do not include the necessary accessories to properly connect with the ESU analyzer. As a result, users need to "rig" up their own equipment and cables in order to create a makeshift connection to the ESU analyzer so that the output verification process can be completed. For example, FIG. 90 is a perspective view of an electrosurgical generator with a makeshift ESU analyzer connection. Electrosurgical generator 1950 includes various energy ports that need to be connected to leads of an ESU analyzer. Because the leads of the ESU analyzer are not compatible with the neutral electrode (NE) port of generator 1950, a makeshift connection 1952 has been created. In some cases, makeshift connection 1952 is "rigged" by cutting a return cable of the return pad and soldering a banana jack to the cable. Using devices such as makeshift connection 1952 may result in inaccurate output verification results. Further, these makeshift connections are a potential safety hazard to users when improperly "rigged." Therefore, there is a need for an adaptor that allows for safe and easy connection between the electrosurgical generator and the ESU analyzer.

In one aspect of the present disclosure, an output verification key that serves as an adaptor between the energy ports of an electrosurgical generator and the leads of an ESU analyzer is disclosed. A first side of the output verification key includes a connection that plugs into the neutral electrode port of the generator and a connection that plugs into the advanced energy port of the generator (e.g., neutral electrode port 2018 and combination energy port 2020 of energy module 2004 shown in FIG. 7A). A second side of the output verification key includes one port (i.e. neutral key port) that accepts a lead of the ESU analyzer to create a connection with the neutral electrode port of the generator. Therefore, when performing output verification testing of a monopolar energy modality of the generator, the user can easily plug a first ESU analyzer lead into the appropriate monopolar port of the generator (e.g., first monopolar port 2016*a* or second monopolar port 2016*b* shown in FIG. 7A) and plug the second lead into the neutral key port of the output verification key. The second side of the output verification key also includes four ports associated with the advanced energy (combination) port of the generator: a monopolar key port, a bipolar key port, an ultrasonic key port, and common key port. To test the monopolar modality of the advanced energy port, the user can easily plug the first ESU analyzer lead into the monopolar key port and plug the second ESU analyzer lead into the neutral key port. To test the bipolar modality of the advanced energy port, the user can easily plug the first ESU analyzer lead into the bipolar key port and plug the second ESU analyzer lead into the common key port. Finally, To test the ultrasonic modality of the advanced energy port, the user can easily plug the first ESU analyzer lead into the ultrasonic key port and plug the second ESU analyzer lead into the common key port. By including the ports and plugs described above, the output verification key beneficially serves as an adaptor that allows for safe and easy connection between the electrosurgical generator and the ESU analyzer during output verification.

FIG. 91 is a perspective view of an electrosurgical generator connected to an output verification key. Generator 1950 includes various energy ports that need to be connected to leads of an ESU analyzer for output verification, including a bipolar port, two monopolar ports, a neutral electrode port, and an advanced energy port (e.g., similar to bipolar port 2014, first monopolar port 2016*a*, second monopolar port 2016*b*, neutral electrode port 2018, combination energy port 2020 shown in FIG. 7A). An output verification key 1960 is plugged into the neutral electrode and advanced energy ports of generator 1950. Specifically, a neutral electrode plug on a first side of output verification key 1960 is connected to the neutral electrode port of generator 1950 and an advanced energy plug on the first side of output verification key 1960 is connected to the advanced energy port of generator 1950.

FIG. 92 is a perspective view of an illustrative output verification key. A first side of output verification key 1960 includes a neutral electrode plug 1962 and an advanced energy plug 1964. Neutral electrode plug 1962 connects to the neutral electrode port of generator 1950. Similarly, advanced energy plug 1964 connects to the advanced energy port of generator 1950. A second side of output verification key 1960 includes a neutral key port 1966, a monopolar key port 1968A, a bipolar key port 1968B, an ultrasonic key port 1968C, and common key port 1968D.

FIG. 93 is a perspective view of an alternative illustrative output verification key. In this example, output verification key 1970 includes a neutral electrode plug 1972 and an advanced energy plug 1974. Neutral electrode plug 1972 connects to the neutral electrode port of generator 1950. Similarly, advanced energy plug 1974 connects to the advanced energy port of generator 1950. Output verification key 1970 also includes a neutral key port 1976, a monopolar key port 1978A, a bipolar key port 1978B, an ultrasonic key port 1978C, and common key port 1978D. Additional views of output verification key 1970 are discussed below in FIGS. 94-97. Although some these figures are described as "top," "front," "back" views of output verification key 1970, these terms are only used to identify the relative angle from which the output verification key 1970 is depicted and are not intended to limit the directionality associated with the output verification key 1970 in any way.

FIG. 94 is a top view of the output verification key shown in FIG. 93. Viewing output verification key 1970 from this angle, the neutral electrode plug 1972 and advanced energy plug 1974, as well as the neutral key port 1976, monopolar key port 1978A, and common key port 1978D are depicted.

FIG. 95 is a front view of the output verification key shown in FIG. 93. Viewing output verification key 1970 from this angle, the neutral key port 1976, monopolar key port 1978A, bipolar key port 1978B, ultrasonic key port 1978C, and common key port 19678D are depicted.

FIG. 96 is a back view of the output verification key shown in FIG. 93. Viewing output verification key 1970 from this angle, the neutral electrode plug 1972 and advanced energy plug 1974 are depicted.

FIG. 97 is an alternate perspective view of the output verification key shown in FIG. 93. Viewing output verification key 1970 from this angle, the neutral electrode plug 1972 and advanced energy plug 1974, as well as the neutral key port 1976, monopolar key port 1978A, bipolar key port 1978B, ultrasonic key port 1978C, and common key port 1978D are depicted.

EXAMPLES

Various aspects of the surgical procedurelization via modular energy system described herein are set out in the following examples.

Example 1: A modular energy system for use in a surgical environment comprising: an energy module configured to generate at least one energy modality for driving an electrosurgical and/or ultrasonic surgical instrument connected thereto; a header module communicably coupled to the energy module, the header module comprising a display screen capable of rendering a graphical user interface (GUI); wherein the GUI is configured to display a plurality of steps that correspond with actions performed by a user while operating the modular energy system.

Example 2: The modular energy system according to Example 1 wherein the plurality of steps displayed by the GUI are steps of a predetermined procedural checklist; the steps of the predetermined procedural checklist corresponding with steps of a surgical procedure.

Example 3: The modular energy system according to any one or more of Examples 1 through 2 wherein the GUI is further configured to sequentially display each step of the predetermined procedural checklist as the user performs the surgical procedure, the GUI displaying each step until the user provides an input to the modular energy system indicting the step is complete.

Example 4: The modular energy system according to any one or more of Examples 1 through 3 further comprising a storage device configured to record event data related to operation of the energy module during the surgical procedure; wherein the event data is organized in an event log based on the step of the predetermined procedural checklist that was displayed by the GUI while the event was recorded.

Example 5: The modular energy system according to any one or more of Examples 1 through 4 wherein the display screen further comprises a touch screen; and wherein the touch screen is configured to detect the input indicating that each step is complete.

Example 6: The modular energy system according to any one or more of Examples 1 through 5 further comprising a microphone; wherein the input indicating that each step is complete is a voice command that is captured by the microphone.

Example 7: The modular energy system according to any one or more of Examples 1 through 6 wherein the GUI is configured to skip a step of the predetermined checklist when the user provides an input to the modular energy system.

Example 8: The modular energy system of any one or more of Examples 1 through 7 wherein the plurality of steps displayed by the GUI are steps of a procedural checklist that correspond with steps of a surgical procedure; wherein each step of the procedural checklist is input by the user upon a completion of each step of the surgical procedure.

Example 9: The modular energy system according to Example 8 wherein the display screen further comprises a touch screen; and wherein the touch screen in configured to the detect the steps of the procedural checklist input by the user.

Example 10: The modular energy system according to any one or more of Examples 8 through 9 further comprising a microphone; wherein the microphone is configured to detect the steps of the procedural checklist input by the user.

Example 11: The modular energy system according to any one or more of Examples 1 through 10 wherein the GUI is further configured to display an instrument usage pattern based on the event data.

Example 12: The modular energy system according to any one or more of Examples 1 through 11 wherein the instrument usage pattern compares an event recorded during a specific step of a first surgical procedure performed by a first user with an event recorded during the same specific step of a plurality of surgical procedures performed by the first user.

Example 13: The modular energy system according to any one or more of Examples 1 through 12 wherein the instrument usage pattern compares an event recorded during a specific step of a first surgical procedure performed by a first user with events recorded during the same specific step of a plurality of surgical procedures performed by a plurality of users.

Example 14: The modular energy system according to any one or more of Examples 1 through 13 wherein the instrument usage pattern comprises an average transection time, a number of transactions, an average instrument power level, and a number of instrument exchanges.

Example 15: The modular energy system according to any one or more of Examples 1 through 14 wherein the GUI is further configured to display the event log.

Example 16: The modular energy system according to any one or more of Examples 1 through 15 where the event log displayed by the GUI comprises: an event log main screen, the event log main screen comprising data related to the operation of the energy module during a plurality of surgical procedures, the data related to the operation of the energy module during the plurality of surgical procedures comprising: a date of each procedure; a time of each procedure; a duration of each procedure; a description of each procedure; and a details button corresponding to each procedure; and an event log details modal screen corresponding to each procedure comprised in the event log main screen; wherein the event log details modal screen for each procedure is accessed by selecting the details button corresponding to the procedure, the event log details modal screen for each procedure comprising: an energy modality used during the procedure; a mode of the energy modality; a power level of the energy modality; and an activation time of the energy modality.

Example 17: The modular energy system according to any one or more of Examples 1 through 16 wherein the event log details modal screen further comprises: an error description of the energy modality used during the procedure; and an error state information pop-up window; wherein the error state information pop up window is accessed by selecting the error description.

Example 18: The modular energy system according to any one or more of Examples 1 through 17 wherein the system is configured to export the event log to an external source.

Example 19: The modular energy system according to any one or more of Examples 1 through 18 wherein the plurality of steps displayed by the GUI are steps of an output verification process.

Example 20: The modular energy system according to Example 19 wherein at least one of the steps of the output verification process displayed by the GUI comprises: a power level and mode setting to be tested for the at least one energy modality, and instructions that prompt the user to adjust a resistance setting of an electrosurgical unit analyzer; wherein the energy module is further configured to activate the at least one energy modality at the power level and mode setting to be tested based on an input from the user.

Example 21: The modular energy system according to any one or more of Examples 19 through 20 wherein at least one of the steps of the output verification process displayed by the GUI comprises instructions that prompt the user to insert an output verification key into at least one port of the energy module.

Example 22: The modular energy system according to any one or more of Examples 19 through 21 wherein at least one of the steps of the output verification process displayed by the GUI comprises instructions that prompt the user to insert leads of the electrosurgical unit analyzer into at least one port of the energy module.

Example 23: The modular energy system according to any one or more of Examples 19 through 22 wherein the GUI displays a first step of the output verification process when the user inserts an output verification key into at least one port of the energy module.

Example 24. The modular energy system of Example 19 wherein the GUI does not display a next power level and mode setting to be tested until the user provides an input to the system indicating that the resistance setting of the electrosurgical unit analyzer has been adjusted.

Example 25: The modular energy system according to any one or more of Examples 19 through 24 wherein the output verification key comprises: a first side comprising: a neutral electrode plug that connects to a neutral electrode port of the energy module; and an advanced energy plug that connects to an advanced energy port of the energy module; and a second side comprising: a neutral key port that accepts a lead of an electrical surgical unit analyzer to create a connection with the neutral electrode port; a monopolar key port that accepts a lead of an electrical surgical unit analyzer to create a connection with a monopolar energy modality of the advanced energy port; a bipolar key port that accepts a lead of an electrical surgical unit analyzer to create a connection with a bipolar energy modality of the advanced energy port; and an ultrasonic key port that accepts a lead of an electrical surgical unit analyzer to create a connection with an ultrasonic energy modality of the advanced energy port.

Example 26: An output verification key device comprising: a first side comprising: a neutral electrode plug that connects to a neutral electrode port of the energy module: an advanced energy plug that connects to an advanced energy port of the energy module; and a second side comprising: a neutral key port that accepts a lead of an electrical surgical unit analyzer to create a connection with the neutral electrode port; a monopolar key port that accepts a lead of an electrical surgical unit analyzer to create a connection with a monopolar energy modality of the advanced energy port; a bipolar key port that accepts a lead of an electrical surgical unit analyzer to create a connection with a bipolar energy modality of the advanced energy port; and an ultrasonic key port that accepts a lead of an electrical surgical unit analyzer to create a connection with an ultrasonic energy modality of the advanced energy port.

Example 27: A modular energy system for use in a surgical environment comprising: an energy module configured to generate at least one energy modality for driving an electrosurgical and/or ultrasonic surgical instrument connected thereto; a header module communicably coupled to the energy module, the header module comprising a display screen capable of rendering a graphical user interface (GUI); a storage device configured to record event data related to operation of the energy module; wherein the modular energy system is able to detect which events of the event data are related to a surgical procedure based on a detection of a predetermined series of events; and wherein the event data is organized in an event log based on the detection of events related to the surgical procedure.

Example 28: The modular energy system according to Example 27 wherein the predetermined series of events comprise: connecting the electrosurgical and/or ultrasonic surgical instrument to the energy module; activating the connected electrosurgical and/or ultrasonic surgical instrument; and disconnecting the electrosurgical and/or ultrasonic surgical instrument from the energy module.

Example 29: The modular energy system according to any one or more of Examples 27 through 28 wherein the GUI is further configured to display the event log.

Example 30: The modular energy system according to any one or more of Examples 27 through 29 where the event log displayed by the GUI comprises: an event log main screen, the log main screen comprising event data related to a plurality of surgical procedures, the data related the plurality of surgical procedures comprising; a date of each procedure; a time of each procedure; a duration of each procedure; a description of each procedure; and a details button corresponding to each procedure; an event log details modal screen corresponding to each procedure comprised in the event log main screen; herein the event log details modal screen for each procedure is accessed by selecting the details button corresponding to the procedure, the event log details modal screen for each procedure comprising: an energy modality used during the procedure; a mode of the energy modality; a power level of the energy modality; and an activation time of the energy modality.

Example 31: The modular energy system according to any one or more of Examples 27 through 30 wherein the event log details modal screen further comprises: an error description of the energy modality used during the procedure; and an error state information pop-up window; wherein the error state information pop up window is accessed by selecting the error description.

Example 32: The modular energy system according to any one or more of Examples 27 through 31 wherein the system is configured to export the event log to an external source.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. A modular energy system for use in a surgical environment comprising:
an energy module configured to generate at least one energy modality for driving an electrosurgical and/or ultrasonic surgical instrument connected thereto;
a header module communicably coupled to the energy module, the header module comprising a display screen capable of rendering a graphical user interface (GUI);
wherein the GUI is configured to display a plurality of steps that correspond with actions performed by a user while operating the modular energy system;
wherein the plurality of steps displayed by the GUI comprises steps of an output verification process;
wherein the GUI displays a first step of the output verification process in response to the user inserting an output verification key into at least one port of the energy module, the first step being displayed prior to an energy being transferred to the energy module through the output verification key.

2. The modular energy system of claim 1 wherein the plurality of steps displayed by the GUI are steps of a predetermined procedural checklist; the steps of the predetermined procedural checklist corresponding with steps of a surgical procedure.

3. The modular energy system of claim 2 wherein the GUI is further configured to sequentially display each step of the predetermined procedural checklist as the user performs the surgical procedure, the GUI displaying each step until the user provides an input to the modular energy system indicting the step is complete.

4. The modular energy system of claim 3 further comprising a storage device configured to record event data related to operation of the energy module during the surgical procedure; wherein the event data is organized in an event log based on the step of the predetermined procedural checklist that was displayed by the GUI while the event was recorded.

5. The modular energy system of claim 4 wherein the GUI is further configured to display an instrument usage pattern based on the event data.

6. The modular energy system of claim 5 wherein the instrument usage pattern compares an event recorded during a specific step of a first surgical procedure performed by a first user with an event recorded during the same specific step of a plurality of surgical procedures performed by the first user.

7. The modular energy system of claim 5 wherein the instrument usage pattern compares an event recorded during a specific step of a first surgical procedure performed by a first user with events recorded during the same specific step of a plurality of surgical procedures performed by a plurality of users.

8. The modular energy system of claim 5 wherein the instrument usage pattern comprises an average transection time, a number of transactions, an average instrument power level, and a number of instrument exchanges.

9. The modular energy system of claim 4 wherein the GUI is further configured to display the event log.

10. The modular energy system of claim 9 where the event log displayed by the GUI comprises:
an event log main screen, the event log main screen comprising data related to the operation of the energy module during a plurality of surgical procedures, the data related to the operation of the energy module during the plurality of surgical procedures comprising:
a date of each procedure;
a time of each procedure;
a duration of each procedure;
a description of each procedure; and
a details button corresponding to each procedure; and
an event log details modal screen corresponding to each procedure comprised in the event log main screen; wherein the event log details modal screen for each procedure is accessed by selecting the details button corresponding to the procedure, the event log details modal screen for each procedure comprising:
an energy modality used during the procedure;
a mode of the energy modality;
a power level of the energy modality; and
an activation time of the energy modality.

11. The modular energy system of claim 10 wherein the event log details modal screen further comprises:
an error description of the energy modality used during the procedure; and
an error state information pop-up window;
wherein the error state information pop-up window is accessed by selecting the error description.

12. The modular energy system of claim 9 wherein the system is configured to export the event log to an external source.

13. The modular energy system of claim 3 wherein the display screen further comprises a touch screen; and
wherein the touch screen is configured to detect the input indicating that each step is complete.

14. The modular energy system of claim 3 further comprising a microphone;
wherein the input indicating that each step is complete is a voice command that is captured by the microphone.

15. The modular energy system of claim 3 wherein the GUI is configured to skip a step of the predetermined checklist when the user provides an input to the modular energy system to skip the step.

16. The modular energy system of claim 1 wherein the plurality of steps displayed by the GUI are steps of a procedural checklist that correspond with steps of a surgical procedure; wherein each step of the procedural checklist is input by the user upon a completion of each step of the surgical procedure.

17. The modular energy system of claim 16 wherein the display screen further comprises a touch screen; and
wherein the touch screen in configured to detect the steps of the procedural checklist input by the user.

18. The modular energy system of claim 16 further comprising a microphone;
wherein the microphone is configured to detect the steps of the procedural checklist input by the user.

19. The modular energy system of claim 1 wherein at least one of the steps of the output verification process displayed by the GUI comprises:
a power level and mode setting to be tested for the at least one energy modality, and
instructions that prompt the user to adjust a resistance setting of an electrosurgical unit analyzer;
wherein the energy module is further configured to activate the at least one energy modality at the power level and mode setting to be tested based on an input from the user.

20. The modular energy system of claim 19 wherein the GUI does not display a next power level and mode setting to be tested until the user provides an input to the system indicating that the resistance setting of the electrosurgical unit analyzer has been adjusted.

21. The modular energy system of claim 1 wherein at least one of the steps of the output verification process displayed by the GUI comprises instructions that prompt the user to insert leads of an electrosurgical unit analyzer into at least one port of the energy module.

22. The modular energy system of claim 1 wherein the output verification key comprises:
a first side comprising:
a neutral electrode plug that connects to a neutral electrode port of the energy module; and
an advanced energy plug that connects to an advanced energy port of the energy module; and
a second side comprising:
a neutral key port that accepts a lead of an electrical surgical unit analyzer to create a connection with the neutral electrode port;
a monopolar key port that accepts a lead of an electrical surgical unit analyzer to create a connection with a monopolar energy modality of the advanced energy port;
a bipolar key port that accepts a lead of an electrical surgical unit analyzer to create a connection with a bipolar energy modality of the advanced energy port; and
an ultrasonic key port that accepts a lead of an electrical surgical unit analyzer to create a connection with an ultrasonic energy modality of the advanced energy port.

23. An output verification key device comprising:
a first side comprising:
a neutral electrode plug that connects to a neutral electrode port of an energy module;
an advanced energy plug that connects to an advanced energy port of the energy module; and
a second side comprising:
a neutral key port that accepts a lead of an electrical surgical unit analyzer to create a connection with the neutral electrode port;
a monopolar key port that accepts a lead of an electrical surgical unit analyzer to create a connection with a monopolar energy modality of the advanced energy port;
a bipolar key port that accepts a lead of an electrical surgical unit analyzer to create a connection with a bipolar energy modality of the advanced energy port; and
an ultrasonic key port that accepts a lead of an electrical surgical unit analyzer to create a connection with an ultrasonic energy modality of the advanced energy port.

24. A modular energy system for use in a surgical environment comprising:
an energy module configured to generate at least one energy modality for driving an electrosurgical and/or ultrasonic surgical instrument connected thereto;
a header module communicably coupled to the energy module, the header module comprising a display screen capable of rendering a graphical user interface (GUI);
a storage device configured to record event data related to operation of the energy module;
wherein the modular energy system is able to detect which events of the event data are related to a surgical procedure based on a detection of a predetermined series of events;
wherein the event data is organized in an event log based on the detection of events related to the surgical procedure; and
wherein the predetermined series of events comprise:
connecting the electrosurgical and/or ultrasonic surgical instrument to the energy module;
activating the connected electrosurgical and/or ultrasonic surgical instrument; and
disconnecting the electrosurgical and/or ultrasonic surgical instrument from the energy module.

25. The modular energy system of claim 24 wherein the GUI is further configured to display the event log.

26. The modular energy system of claim 25 where the event log displayed by the GUI comprises:

an event log main screen, the log main screen comprising event data related to a plurality of surgical procedures, the data related the plurality of surgical procedures comprising;
- a date of each procedure;
- a time of each procedure;
- a duration of each procedure;
- a description of each procedure; and
- a details button corresponding to each procedure;

an event log details modal screen corresponding to each procedure comprised in the event log main screen; wherein the event log details modal screen for each procedure is accessed by selecting the details button corresponding to the procedure, the event log details modal screen for each procedure comprising:
- an energy modality used during the procedure;
- a mode of the energy modality;
- a power level of the energy modality; and
- an activation time of the energy modality.

27. The modular energy system of claim 26 wherein the event log details modal screen further comprises:
- an error description of the energy modality used during the procedure; and
- an error state information pop-up window;
- wherein the error state information pop-up window is accessed by selecting the error description.

28. The modular energy system of claim 24 wherein the system is configured to export the event log to an external source.

* * * * *